United States Patent
Huebner et al.

(10) Patent No.: US 6,727,273 B2
(45) Date of Patent: Apr. 27, 2004

(54) ESTROGEN RECEPTOR MODULATORS

(75) Inventors: Verena D. Huebner, Benicia, CA (US); Xiaodong Lin, Walnut Creek, CA (US); Ian James, Rowville (AU); Liya Chen, East Brunswick, NJ (US); Manoj Desai, Pleasant Hill, CA (US); Beata Krywult, Armadale (AU); Rajinder Singh, San Francisco, CA (US); Liang Wang, Lafayette, CA (US)

(73) Assignee: Chiron Corporation, Emeryville, CA (US)

( * ) Notice: Subject to any disclaimer, the term of this patent is extended or adjusted under 35 U.S.C. 154(b) by 0 days.

(21) Appl. No.: 09/954,039

(22) Filed: Sep. 18, 2001

(65) Prior Publication Data

US 2004/0034081 A9 Feb. 19, 2004

Related U.S. Application Data

(62) Division of application No. 09/369,747, filed on Aug. 6, 1999, now Pat. No. 6,291,505.
(60) Provisional application No. 60/095,772, filed on Aug. 7, 1998, and provisional application No. 60/095,773, filed on Aug. 7, 1998.

(51) Int. Cl.$^7$ .................... A61K 31/416; C07D 231/54
(52) U.S. Cl. .................................. 514/406; 548/359.1
(58) Field of Search ...................... 548/359.1; 514/406

(56) References Cited

U.S. PATENT DOCUMENTS

| 4,112,108 A | 9/1978 | Nadelson |
| 4,229,204 A | 10/1980 | Howe |

FOREIGN PATENT DOCUMENTS

| DE | 2441504 A1 | 8/1974 |
| DE | 31 19727 A1 | 5/1981 |
| DE | 4126543 A1 | 2/1993 |
| DE | 4230839 A1 | 3/1993 |
| DE | 44 08 084 A1 | 3/1994 |
| EP | 0 026 928 | 3/1980 |
| EP | 0442448 A2 | 2/1991 |
| EP | 0 623603 A1 | 10/1993 |
| FR | 2104932 | 8/1970 |
| WO | WO 96/25405 | 8/1996 |
| WO | WO 97/01551 | 1/1997 |
| WO | WO 00/71531 | 12/2000 |

OTHER PUBLICATIONS

Meisenheimer et al., "Uber Triaryl–isoxazole", Chemische Berichte, 1921, 3195:3206.

Krishna et al., "Synthesis and Physiological Activity of 3–Hydrxy–Pheny–5–Aryl Isoxazoles", Chemical Abstracts, 1973, 79(13):487.

Yamawaki et al., "Synthesis and biological Activity of the Metabolites of [3,4–Bis(4–Methoxyphenyl)–5–Isoxazyolyl] Acetic Acid", Chemical and Pharmaceutical Bulletin, 1988, 36(8):142–3146.

Kim et al., "Reactions of 5–Substituted 3–Alkyl–and 3–Aryl–Isoxazoles with Tetrasulfur Tetranitride Antimony Pentachloride Complex . . . Thiadiazoles and their Mechanism of Formation", Journal of the Chem. Soc. 1998, 14:2175–2180.

Mohan et al., "Search for Physiologically Active . . . Isoxazoles and their Physiological Activity", Chemical Abstracts, 1968, 69(11):4107.

Kasturi et al., "Reaction of Spironaphthalenones with Hydroxylamine Hydrochloride: Part IV", Tetrahedron, 1995, 51(10):3051–3060.

Amme, Omar et al., "Synthesis, binding affinities and uterotrophic . . . pyrone derivatives", XP–002136351, Eur J. Med Chem, 29:25–32, 1995.

Duncan et al., "The Preparation of N–Carboalkoxypyrazoles . . . and Phenylhydrazones," XP–002136350, J. Heterocyclic Chem., 24:555, 1987.

Fink et al, "Novel sstructural templates . . . syntthesis of estrogens," XP–000905542, Chemistry & Biology, 6:205–219 (Apr. 1999).

Wachter et al., "Tetrahydronaphthalenes: Influence of Heterocyclic . . . aroma and P450 17", XP–002099563, J. Med. Chem. 39:834–841, 1996.

Sun et al., "Novel Ligands that function as Selective . . . Estrogen Receptor–β", XP000908867, Endocrinology, vol. 140, 2:800–804, 1999.

Wrobel et al., "Conversion of 1–(O–Nitroaryl) Alkyl P–Tolysulfones into Isoxazoles", Heterocycles, 1995, 40(1):187–190.

*Primary Examiner*—Joseph K. McKane
*Assistant Examiner*—Rebecca Anderson
(74) *Attorney, Agent, or Firm*—James E. Austin; Steven W. Collier; Robert P. Blackburn

(57) ABSTRACT

Estrogen receptor-modulating pyrazole compounds are described in addition to methods and compositions for treating or preventing estrogen receptor-mediated disorders. The compounds described have been found to have unexpected and surprising activity in modulating estrogen receptor activity. Thus, the compounds of the present invention have utility in preventing or treating estrogen receptor-mediated disorders such as osteoporosis, breast and endometrial cancers, atherosclerosis, and Alzheimer's disease.

15 Claims, No Drawings

ESTROGEN RECEPTOR MODULATORS

1 CROSS REFERENCE TO RELATED U.S. PATENT APPLICATIONS

The present application is a divisional of Ser. No. 09/369,747 filed Aug. 6, 1999, now U.S. Pat. No. 6,291,505, which claims priority under 35 U.S.C. §119(e) from co-pending provisional U.S. patent application Ser. No. 60/095,772 filed Aug. 7, 1998, which is incorporated herein by reference in its entirety and for all purposes. Priority under 35 §119(e) is also claimed from co-pending provisional U.S. patent application Ser. No. 60/095,773, also filed on Aug. 7, 1998.

2 BACKGROUND OF THE INVENTION

2.1 Field of the Invention

The present invention relates to compounds that have biological activity with respect to estrogen receptors and to the use of such compounds to treat diseases and disorders related to estrogen receptor activity. More particularly, the present invention provides selective estrogen receptor modulators ("SERMs"). The present invention therefore relates to the fields of medicine, medicinal chemistry, biochemistry, and endocrinology.

2.2 Background

Estrogen is a hormone critical to normal human development and function. Although estrogen is the predominant "sex hormone" in women, in whom estrogen controls the development of female sex characteristics and the development and function of the reproductive system (Berkow, Beers et al. 1997), it is also found in men (Gustafsson 1998). Women produce estrogen primarily in the ovaries; however, estrogen affects a variety of physiological functions in women including body temperature regulation, maintenance of the vaginal lining, and preservation of bone density (Jordan 1998). In addition, estrogen provides additional effects that are related to its ability to modulate production of cholesterol in the liver, as demonstrated by the reduced occurrence of atherocsclerosis in women compared to men due in part to the reduction of low-density lipoprotein ("LDL") (Jordan 1998). Estrogen has also been implicated in delaying and/or reducing the severity of Alzheimer's Disease (Jordan 1998).

Failure to produce estrogen has profound physiological consequences in females. Failure to produce estrogen resulting from incomplete or absent ovary development (Turner's Syndrome) causes deficiencies in the skin, bone (e.g., severe osteoporosis), and other organs severely affecting the life of the afflicted individual (Dodge 1995). In normal women, estrogen production falls sharply upon the onset of menopause, usually at about 50 years of age. The effects of the loss of estrogen production include increased atherosclerotic deposits (leading to greatly increase incidence of heart disease), decreased bone density (osteoporosis), and fluctuations in body temperature among others (Jordan 1998). Often, the effects of reduced estrogen production are addressed by hormone replacement therapy (Dodge 1995; Berkow, Beers et al. 1997; Jordan 1998).

However, estrogen also has undesirable effects. In menopausal women, supplementation of estrogen is associated with alleviation of the above-described unwanted effects. But, administration of estrogen is also associated with increased risks for breast and endometrial cancer as well as blood clots (Jordan 1998). The increased risk of endometrial cancer can be addressed by the administration of progesterone (or its synthetic analog progestin) to reinitiate menstruation and thereby shed potentially malignant cells, but many older women find this undesirable (Jordan 1998). Breast cancer, however, is by far the greater risk of estrogen replacement therapy, affecting one woman in every 15 between the ages of 60 and 79 (Jordan 1998).

Thus, for a long time the treatment options for the serious health problems caused by a failure to produce estrogen were limited and entailed severe risks. However, the discovery that some agents acted as estrogen agonists in some tissues (e.g., bone) and as an antagonists in other tissues (e.g., breast) provided hope that more effective treatments for estrogen loss could be found (Gradishar and Jordan 1997; Gustafsson 1998; Jordan 1998; MacGregor and Jordan 1998). The best known of these so-called Selective Estrogen Receptor Modulators ("SERMs"), tamoxifen, has been demonstrated to have therapeutic utility in treating and preventing breast cancer and lowering LDL concentrations; yet, without significant reduction bone density (Jordan 1998; MacGregor and Jordan 1998). However, tamoxifen has been associated with endometrial cancer and venous blood clots (Jordan 1998; MacGregor and Jordan 1998). In addition, tumor resistance to tamoxifen can occur (MacGregor and Jordan 1998).

Tamoxifen has been followed recently by newer SERMs, in particular raloxifene, that promise to provide many of tamoxifen's benefits with fewer risks (Howell, Downey et al. 1996; Gradishar and Jordan 1997; Gustafsson 1998; Jordan 1998; Purdie 1999; Sato, Grese et al. 1999). These newer SERMs, including idoxifene (Nuttall, Bradbeer et al. 1998), CP-336,156 (Ke, Paralkar et al. 1998), GW5638 (Willson, Norris et al. 1997), LY353581 (Sato, Turner et al. 1998) are part of the second- and third generation of partial estrogen agonists/antagonists. In addition, a new generation of pure antiestrogens such as RU 58,688 (Van de Velde, Nique et al. 1994) have been reported. A large number of additional partial and pure estrogen agonist/antagonist compounds and treatment modalities have reported recently (Bryant and Dodge 1995; Bryant and Dodge 1995; Cullinan 1995; Dodge 1995; Grese 1995; Labrie and Merand 1995; Labrie and Merand 1995; Thompson 1995; Audia and Neubauer 1996; Black, Bryant et al. 1996; Thompson 1996; Cullinan 1997; Wilson 1997; Miller, Collini et al. 1999; Palkowitz 1999; Wilson 1999).

However, no one drug candidate has emerged to fill the needs of women who require the benefits of estrogen replacement to live productive lives and/or treatments for estrogen-dependent cancers. The efforts to develop better partial and pure estrogen agonists and antagonists has been aided by several recent developments, including the discovery that human estrogen receptor has at least two isoforms ("ERα" and "ERβ") and the crystal structure of ERa that have permitted high-resolution structure-acitivty relationship studies (Sadler, Cho et al. 1998). Recently, a study of the application of combinatorial synthetic methods combined with three-dimensional structure-activity analysis to develop SERMs having optimal therapeutic profiles was reported (Fink, Mortensen et al. 1999). That study examined several heterocyclic motifs (imidazoles, thiazoles, pyrazoles, oxazoles, and isoxazoles) and identified certain pyrazole motifs as being well suited for combinatorial development of SERMs. The relative binding effectiveness of the pyrazoles viz. the other motifs was based on its ability to carry four substituents in addition to polarity consideration (see p. 215). In particular, the study referred the capacity of the pyrazole motif to carry four substituents explained the binding effectiveness pyrazoles compared to the poor binding results found for the oxazole, thiazole, and isoxazole motifs.

However, despite these recent advances no drug candidate has emerged to fill the needs of women who require the benefits of estrogen replacement to live productive lives and/or treatments for estrogen-dependent cancers. The present invention addresses these and other needs.

3 SUMMARY OF THE INVENTION

The present invention provides pyrazole estrogen receptor agonist and antagonist compounds in addition to methods and compositions for treating or preventing estrogen receptor-mediated disorders. The compounds described herein have been found to have unexpected and surprising activity in modulating estrogen receptor activity. Thus, the compounds of the present invention have utility in preventing or treating estrogen receptor-mediated disorders such as osteoporosis, breast and endometrial cancers, atherosclerosis, and Alzheimer's disease.

In a first aspect, the present invention provides compounds having the structures:

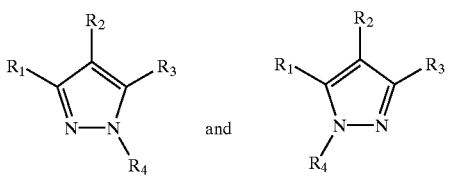

and their pharmaceutically acceptable salts. $R_1$ and $R_3$ are selected independently from the group consisting of optionally substituted aryl and aralkyl. $R_2$ is selected from the group consisting of hydrogen, halo, cyano, nitro, thio, amino, carboxyl, formyl, and optionally substituted loweralkyl, loweralkylcarbonyloxy, arylcarbonyloxy, heteroarylcarbonyloxy, cycloalkylcarbonyloxy, cycloheteroalkylcarbonyloxy, aralkycarbonyloxy, heteroaralkylcarbonyloxy, (cycloalkyl)alkylcarbonyloxy, (cycloheteroalkyl)alkylcarbonyloxy, loweralkylcarbonyl, arylcarbonyl, heteroarylcarbonyl, cycloalkylcarbonyl, cycloheteroalkylcarbonyl, aralkycarbonyl, heteroaralkylcarbonyl, (cycloalkyl)alkylcarbonyl, (cycloheteroalkyl)alkylcarbonyl, loweralkylaminocarbonyl, arylaminocarbonyl, aralkylaminocarbonyl, heteroarylaminocarbonyl, heteroaralkylaminocarbonyl, cycloalkylaminocarbonyl, (cycloalkyl)alkylaminocarbonyl, cycloheteroalkylaminocarbonyl, (cycloheteroallryl) alkylaminocarbonyl, loweralkylcarbonylamino, arylcarbonylamino, heteroarylcarbonylamino, cycloalkylcarbonylamino, cycloheteroalkylcarbonylamino, aralkylcarbonylamino, heteroaralkylcarbonylamino, (cycloalkyl)alkylcarbonylamino, (cycloheteroalkyl) alkylcarbonylamino, loweralkylamino, arylamino, aralkylamino, heteroarylamino, heteroaralkylamino, loweralkylsulfonyl, arylsulfonyl, heteroarylsulfonyl, cycloalkylsulfonyl, cycloheteroalkylsulfonyl, aralkylsulfonyl, heteroaralkylsulfonyl, (cycloalkyl) alkylsulfonyl, (cycloheteroalkyl)alkylsulfonyl, loweralkylsulfinyl, arylsulfinyl, heteroarylsulfinyl, cycloalkylsulfinyl, cycloheteroalkylsulfinyl, aralkylsulfinyl, heteroaralkylsulfinyl, (cycloalkyl)alkylsul finyl, (cycloheteroalkyl)alkylsulfmyl, loweralkyloxy, aryloxy, heteroaryloxy, cycloallcyloxy, cycloheteroalkyloxy, aralkyloxy, heteroaralkyloxy, (cycloalkyl)alkyloxy, and (cycloheteroalkyl)alkyloxy, loweralleylthio, arylthio, heteroarylthio, cycloalkylthio, cycloheteroalkylthio, aralkylthio, heteroaralkylthio, (cycloalkyl)alkylthio, (cycloheteroalkyl)alkylthio, loweralkylthiocarbonyl, arytthiocarbonyl; heteroarylthiocarbonyl, cycloalkylthiocarbonyl, cycloheteroalkylthiocarbonyl, aralkythiocarbonyloxythiocarbonyl, heteroaralkylthiocarbonyl, (cycloalkyl)allrylthiocarbonyl, (cycloheteroa(lcyl)alkylthiocarbonyl, loweralkyloxycarbonyl, aryloxycarbonyl, heteroaryloxycarbonyl, cycloalkyloxycarbonyl, cycloheteroallcyloxycarbonyl, aralkyoxycarbonyloxloxycarbonyl, heteroaralkyloxycarbonyl, (cycloalkyl)alkyloxycarbonyl, (cycloheteroalkyl)allryloxycarbonyl, iminoloweralkyl, iminocycloalkyl, iminocycloheteroalkyl, iminoarallcyl, iminoheteroaralkyl, (cycloalkyl)iminoalkyl, (cycloheteroalkyl)iminoalkyl, (cycloiminoalkyl)allcyl, (cycloiminoheteroalkyl)allcyl, oximinoloweralkyl, oximinocycloalkyl, oximinocycloheteroalkyl, oximinoaralkyl, oximinoheteroarallryl, (cycloallcyl) oximinoalkyl, (cyclooximinoallcyl)alkyl, (cyclooximinoheteroallryl)alkyl, and (cycloheteroalkyl) oximinoalkyl. $R_4$ is selected from the group consisting of hydrogen, carboxyl, formyl, and optionally substituted loweralkyl, aryl, aralkyl, heteroaryl, heteroaralkyl, cycloalkyl, cycloheteroalkyl, loweralkylcarbonyl, arylcarbonyl, heteroarylcarbonyl, cycloalkylcarbonyl, cycloheteroallcylcarbonyl, arallcycarbonyl, heteroaralkylcarbonyl, (cycloalkyl)allcylcarbonyl, (cycloheteroalkyl)alkylcarbonyl, loweralkylaminocarbonyl, arylaminocarbonyl, arallcylaminocarbonyl, heteroarylaminocarbonyl, heteroaralkylaminocarbonyl, cycloalkylaminocarbonyl, (cycloalkyl)alkylaminocarbonyl, cycloheteroalkylaminocarbonyl, (cycloheteroallryl) alkylaminocarbonyl, loweralkylsulfonyl, arylsulfonyl, heteroarylsulfonyl, cycloalkylsulfonyl, cycloheteroalkylsulfonyl, aralkylsulfonyl, heteroaralkylsulfonyl, (cycloalkyl)alkylsulfonyl, (cycloheteroalkyl)alkylsulfonyl, loweralkylsulfinyl, arylsulfinyl, heteroarylsulfinyl, cycloalkylsulfinyl, cycloheteroalkylsulfinyl, aralkylsulfinyl, heteroaralkylsulfinyl, (cycloalkyl)alkylsulfinyl, (cycloheteroalkyl)alkylsulfinyl, arylthiocarbonyl, heteroarylthiocarbonyl, cycloalkylthiocarbonyl, cycloheteroalkylthiocarbonyl, aralkythiocarbonyloxythiocarbonyl, heteroaralkylthiocarbonyl, (cycloalkyl) alkylthiocarbonyl, (cycloheteroalkyl)alkylthiocarbonyl, loweralkyloxycarbonyl, aryloxycarbonyl, heteroaryloxycarbonyl, cycloalkyloxycarbonyl, cycloheteroalkyloxycarbonyl, aralkyoxycarbonyloxloxycarbonyl, heteroaralkyloxycarbonyl, (cycloalkyl) alkyloxycarbonyl, (cycloheteroalkyl)alkyloxycarbonyl, carboxamidino, loweralkylcarboxamidino, arylcarboxamidino, aralkylcarboxamidino, heteroarylcarboxamidino, heteroaralkylcarboxamidino, cycloalkylcarboxamidino, cycloheteroalkylcarboxamindino.

In one embodiment of the invention having the generic structures shown above, $R_1$ and $R_3$ are selected independently from the group consisting of optionally substituted cycloalkyl, cycloheteroalkyl, (cycloalkyl)alkyl, and (cycloheteroalkyl)alkyl. Examples of such groups include without limitation cyclohexyl, piperidinyl, adamantyl, and quinuclidyl, each optionally substituted. Other examples include cyclohexylmethyl, 2-cyclohexylethyl, and adamantylmethyl, again, each optionally substituted. In other embodiments, $R_1$ and $R_3$ are selected independently from the group consisting of optionally substituted aryl, heteroaryl, aralkyl, and heteroaralkyl. More specific embodiments are those for which $R_1$ and $R_3$ are selected independently from the group consisting of optionally substituted heteroaryl and heteroaralkyl, such as pyridinyl, hydroxypyridyl, methoxypyridyl, pyridylmethyl, and the like.

More particular embodiments are those for which $R_1$ and $R_3$ are selected independently from the group consisting of optionally substituted aryl and arallryl. More particular embodiments include those wherein at least one of $R_1$ and $R_3$ is substituted with at least one hydroxyl, alkyloxy, aryloxy, thio, alkylthio, or arylthio group. Other more particular embodiments are those for which at least one of $R_1$ and $R_3$ is selected independently from the group consisting of phenyl, phenyloxyloweralkyl, and phenylloweralkyl and at least one of $R_1$ and $R_3$ is substituted with at least one hydroxyl, alkyloxy, aryloxy, thio, alkylthio, or arylthio group.

In some embodiments of the above-illustrated compounds, $R_2$ is selected from the group consisting of hydrogen, halo, and optionally substituted loweralkyl, haloloweralkyl, aryl, aralkyl, heteroaryl, heteroaralkyl, aryloxyalkyl, arylthioalkyl, arylcarbonyl, heteroarylcarbonyl, loweralkylcarbonyl, aminocarbonyl, arylaminocarbonyl, loweralkylaminocarbonyl, aralkylaminocarbonyl, (heterocycloloweralkyl)alkylaminocarbonyl, heteroarylaminocarbonyl, heteroaralkylaminocarbonyl, (cycloloweralkyl)aminocarbonyl, formyl, and alkenyl. More particular examples include those for which $R_2$ is selected from the group consisting of optionally substituted phenylcarbonyl, (heterocycloalkyl)loweralkyloxyphenylcarbonyl, hydroxyphenylcarbonyl, halophenylcarbonyl, phenylloweralkylaminocarbonyl, diloweralkyl-aminocarbonyl, phenylloweralkylaminocarbonyl, hydroxyphenyllowerlakylaminoc.arbonyl, cycloalkyl-aminocarbonyl, loweralkylphenylcarbonyl, haloloweralkylsulfonylloweralkyloxyphenylcarbonyl, and nitrophenylcarbonyl. Examples of $R_2$ substituents within such embodiments having useful properties include, but are not limited to, 4-(2-piperidin-1-ylethyloxy)phenylcarbonyl, 4-hydroxyphenylcarbonyl, (phenylmethyl)aminocarbonyl, 3-(2-oxopyrrolidin-1-yl)propylaminocarbonyl, di-n-butylaminocarbonyl, (4-hydroxyphenylmethyl)aminocarbonyl, (pyridin-3-ylmethyl)aminocarbonyl, (pyridin-2-ylmethyl)aminocarbonyl, dimethylamino-carbonyl, ethylaminocarbonyl, 4-(2-morpholinoethyloxy)phenylcarbonyl, 4-(3-dimethylaminopropyloxy)phenylcarbonyl, cyclopropylaminocarbonyl, cyclobutylaminocarbonyl, 4-(2-dimethylaminoethyloxy)phenylcarbonyl, 4-[2-(benzylmethylamino)ethyloxy]phenylcarbonyl, 4-(1-methylpiperdin-3-yhnethyloxy)phenylcarbonyl, 4-[2-(1-methylpyrrolidin-2-yl)ethyloxy]phenylcarbonyl, 4-[2-(4-methylpiperazin- 1 -yl)ethyloxy]phenylcarbonyl, 4-(1-methylpiperdin-4-ylmethyloxy)phenylcarbonyl, 2-chlorophenylcarbonyl, 3-chlorophenylcarbonyl, 4-chlorophenylcarbonyl, 3-nitrophenylcarbonyl, 4-nitrophenylcarbonyl, 3,4-dichlorophenylcarbonyl, 4-n-butylphenylcarbonyl, 3-hydroxyphenylcarbonyl, 2-hydroxyphenylcarbonyl, 4-methoxyphenylcarbonyl, 3-(2-piperidin-1-ylethyloxy)phenylcarbonyl, 3-(2-diethylaminoethyloxy)phenylcarbonyl, 3[2-(pyrrolidin-1-yl)ethyloxy]phenylcarbonyl, 3-(1-methylpiperdin-3-ylmethyloxy)phenylcarbonyl, and 3-(2-dimethylaminoethyloxy)phenylcarbonyl.

In another aspect, the present invention provides fused-ring pyrazoles having the structures:

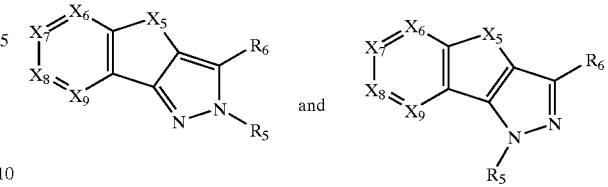

and their pharmaceutically acceptable salts. $X_5$ is $—(X_{10})_n{-}$, wherein n is an integer between 1 and 3 and $X_{10}$, for each value of n, is selected independently from the group consisting of oxygen, $—SO_x—$ where x is and integer between 0 and 2, nitrogen, nitrogen substituted with optionally substituted loweralkyl, aryl, aralkyl, heteroaryl, heteroaralkyl, arylcarbonyl, alkylcarbonyl, aralkylcarbonyl, heteroarylcarbonyl, heteroaralkylcarbonyl, and methylene or methine, each optionally substituted from the group consisting of halo, cyano, nitro, thio, amino, carboxyl, formyl, and optionally substituted loweralkyl, loweralkylcarbonyloxy, arylcarbonyloxy, heteroarylcarbonyloxy, cycloalkylcarbonyloxy, cycloheteroalkylcarbonyloxy, aralkycarbonyloxy, heteroaralkylcarbonyloxy, (cycloalkyl)alkylcarbonyloxy, (cycloheteroalkyl)alkylcarbonyloxy, loweralkylcarbonyl, arylcarbonyl, heteroarylcarbonyl, cycloalkylcarbonyl, cycloheteroalkylcarbonyl, aralkycarbonyl, heteroaralkylcarbonyl, (cycloalkyl)alkylcarbonyl, (cycloheteroalkyl)alkylcarbonyl, loweralkylaminocarbonyl, arylaminocarbonyl, aralkylaminocarbonyl, heteroarylaminocarbonyl, heteroaralkylaminocarbonyl, loweralkylcarbonylamino, arylcarbonylamino, heteroarylcarbonylamino, cycloalkylcarbonylamino, cycloheteroalkylcarbonylamino, aralkylcarbonylamino, heteroaralkylcarbonylamino, (cycloalkyl)alkylcarbonylamino, (cycloheteroalkyl)alkylcarbonylamino, loweralkylamino, arylamino, aralkylamino, heteroarylamino, heteroaralkylamino, loweralkylsulfonyl, arylsulfonyl, heteroarylsulfonyl, cycloalkylsulfonyl, cycloheteroalkylsulfonyl, aralkylsulfonyl, heteroaralkylsulfonyl, (cycloalkyl)alkylsulfonyl, (cycloheteroalkyl)alkylsulfonyl, loweralkylsulfinyl, arylsulfinyl, heteroarylsulfinyl, cycloalkylsulfinyl, cycloheteroalkylsulfinyl, aralkylsulfinyl, heteroaralkylsulfinyl, (cycloalkyl)alkylsulfinyl, (cycloheteroalkyl)alkylsulfinyl, loweralkyloxy, aryloxy, heteroaryloxy, cycloalkyloxy, cycloheteroalkyloxy, aralkyloxy, heteroaralkyloxy, (cycloalkyl)alkyloxy, and (cycloheteroalkyl)alkyloxy, loweralkylthio, arylthio, heteroarylthio, cycloalkylthio, cycloheteroalkylthio, aralkylthio, heteroaralkylthio, (cycloalkyl)alkylthio, (cycloheteroalkyl)alkylthio, loweralkylthiocarbonyl, arylthiocarbonyl, heteroarylthiocarbonyl, cycloalkylthiocarbonyl, cycloheteroalkylthiocarbonyl, aralkythiocarbonyloxlthiocarbonyl, heteroaralkyl-thiocarbonyl, (cycloalkyl)alkylthiocarbonyl, (cycloheteroalkyl)alkylthiocarbonyl, loweralkyl-oxycarbonyl, aryloxycarbonyl, heteroaryloxycarbonyl, cycloalkyloxycarbonyl, cycloheteroalkyloxycarbonyl, aralkyoxycarbonyloxloxycarbonyl, heteroarallcyl-oxycarbonyl, (cycloalkyl)alkyloxycarbonyl, (cycloheteroalkyl)alkyloxycarbonyl, iminoloweralkyl, iminocycloalkyl, iminocycloheteroalkyl, iminoaralkyl, iminoheteroaralkyl, (cycloalkyl)iminoalkyl, and (cycloheteroalkyl)iminoalkyl. $X_6$–$X_9$ are selected independently from the group consisting of oxygen, sulfur, sulfinyl, nitrogen, and optionally substituted methine. $R_5$ is selected from the group consisting of hydrogen, carboxyl, formyl, and optionally substituted loweralkyl, aryl, aralkyl, heteroaryl, heteroaralkyl, cycloalkyl, cycloheteroalkyl, loweralkylcarbonyl, arylcarbonyl, heteroarylcarbonyl, cycloalkylcarbonyl, cycloheteroalkylcarbonyl, aralkycarbonyl, heteroaralkylcarbonyl, (cycloalkyl)alkylcarbonyl, (cycloheteroalkyl)alkylcarbonyl, loweralkylaminocarbonyl, arylaminocarbonyl, aralkylaminocarbonyl, heteroarylaminocarbonyl, heteroaralkyiaminocarbonyl, cycloalkylaminocarbonyl, (cycloalkyl)alkylaminocarbonyl, cycloheteroalkyl-aminocarbonyl, (cycloheteroalkyl)alkylaminocarbonyl, loweralkylsulfonyl, arylsulfonyl, heteroarylsulfonyl, cycloallrylsulfonyl, cycloheteroalkylsulfonyl, aralkylsulfonyl, heteroaralkylsulfonyl, (cycloalkyl)alkylsulfonyl, (cycloheteroalkyl)alkylsulfonyl, loweralkylsulfinyl, arylsulfinyl, heteroarylsulfinyl, cycloalkylsulfinyl, cycloheteroalkylsulfinyl, aralkylsulfinyl, heteroaralkylsulfinyl, (cycloalkyl)alkylsulfinyl, (cycloheteroalkyl)alkylsulfinyl, arylthiocarbonyl, heteroarylthiocarbonyl, cycloalkylthiocarbonyl, cycloheteroalkylthiocarbonyl, aralkythiocarbonyl-oxythiocarbonyl, heteroaralkylthiocarbonyl, (cycloalkyl)alkylthiocarbonyl, (cycloheteroalkyl)alkylthiocarbonyl, loweralkyloxycarbonyl, aryloxycarbonyl, heteroaryloxycarbonyl, cycloalkyloxycarbonyl, cycloheteroalkyloxycarbonyl, aralkyoxycarbonyl-oxloxycarbonyl, heteroaralkyloxycarbonyl, (cycloalkyl)alkyloxycarbonyl, (cycloheteroalkyl)alkyloxycarbonyl, carboxamidino, loweralkylcarboxamidino, arylcarboxamidino, aralkylcarboxamidino, heteroarylcarboxamidino, heteroaralkylcarboxamidino, cycloalkylcarboxamidino, cycloheteroalkylcarboxamindino. $R_6$ is selected from the group consisting of optionally substituted loweralkyl, aryl, heteroaryl, cycloalkyl, cycloheteroalkyl, aralkyl, heteroaralkyl, (cycloalkyl)alkyl, and (cycloheteroalkyl)alkyl.

In some embodiments having the fused-ring structure shown above, n is 1 and $X_{10}$ is selected from the group consisting of nitrogen, optionally substituted nitrogen, and optionally substituted methylene or methine. In other embodiments, n is 1 and $X_{10}$ is selected from the group consisting of nitrogen, optionally substituted nitrogen, and optionally substituted methylene or methine and $R_6$ is selected from the group consisting of optionally substituted aryl, heteroaryl, arallcyl, and heteroaralkyl. In other more specific embodiments, $R_6$ includes at least one hydroxyl, thio, or optionally substituted loweralkyloxy, aryloxy, heteroaryloxy, loweralkylthio, arylthio, heteroarylthio, loweralkylcarbonyl, arylcarbonyl, or heteroarylcarbonyl moiety.

In other embodiments having the fused-ring structure shown above, n is 2 and each $X_{10}$ is selected independently from the group consisting of nitrogen, optionally substituted nitrogen, optionally substituted methylene, and optionally substituted methine. In some embodiments having these values for n and $X_{10}$, and $R_6$ is selected from the group consisting of optionally substituted aryl, heteroaryl, arallryl, and heteroaralkyl. In other more specific embodiments, $R_6$ includes at least one hydroxyl, thio, or optionally substituted lowerallcyloxy, aryloxy, heteroaryloxy, lowerallcylthio, arylthio, heteroarylthio, lowerallcylcarbonyl, arylcarbonyl, or heteroarylcarbonyl moiety.

Other embodiments include those as described above for which $R_5$ is selected from the group consisting of hydrogen and optionally substituted loweralkyl, aryl, aralkyl, heteroaryl, heteroaralkyl, cycloalkyl, cycloheteroalkyl, loweralkylcarbonyl, arylcarbonyl, heteroarylcarbonyl, cycloalkylcarbonyl, cycloheteroalkylcarbonyl, aralkycarbonyl, heteroaralkylcarbonyl, (cycloalkylalkylcarbonyl, (cycloheteroalkyl)alkylcarbonyl, loweralkylaminocarbonyl, arylaminocarbonyl, aralkylaminocarbonyl, heteroarylaminocarbonyl, heteroaralkylaminocarbonyl, cycloalkylaminocarbonyl, (cycloalkyl)alkylaminocarbonyl, cycloheteroalkyl-aminocarbonyl, (cycloheteroalkyl)alkylaminocarbonyl, loweralkylsulfonyl, arylsulfonyl, heteroarylsulfonyl, cycloalkylsulfonyl, cycloheteroalkylsulfonyl, aralkylsulfonyl, heteroaralkylsulfonyl, (cycloalkyl)alkylsulfonyl, and (cycloheteroalkyl)alkylsulfonyl.

In still other embodiments having the fused-ring structure shown above, $X_6$–$X_9$ are selected independently from the group consisting of nitrogen and optionally substituted methine, and in more particular embodiments, at least one of $X_6$–$X_9$ is methine substituted with a moiety selected from the group consisting of loweralkyloxy, aryloxy, heteroaryloxy, loweralkylthio, arylthio, heteroarylthio, loweralkylcarbonyl, arylcarbonyl, and heteroarylcarbonyl. In some embodiments, $X_7$ is methine substituted with hydroxy or loweralkyloxy. Further embodiments include the above-described characteristics of $X_6$–$X_9$, n, $R_5$, and $R_6$ in a variety of combinations.

In yet another aspect, the present invention provides the present invention provides methods for treating or preventing an estrogen receptor-mediated disorder in a human or animal subject in which an amount of an estrogen receptor-modulating compound of the invention that is effective to modulate estrogen receptor activity in the subject. Other embodiments provided methods for treating a cell or a estrogen receptor-mediated disorder in a human or animal subject, comprising administering to the cell or to the human or animal subject an amount of a compound or composition of the invention effective to modulate estrogen receptor activity in the cell or subject. Representative estrogen receptor-mediated disorders include, for example, osteoporosis, atheroschlerosis, estrogen-mediated cancers (e.g., breast and endometrial cancer), and Alzheimer's disease.

These and other aspects and advantages will become apparent when the Description below is read in conjunction with the accompanying Examples.

4 DESCRIPTION OF SOME EMBODIMENTS OF THE INVENTION

4.1 Definitions

4.1.1 Estrogen Receptor

"Estrogen Receptor" as defined herein refers to any protein in the nuclear receptor gene family that binds estrogen, including, but not limited to, any isoforms or deletion mutations having the characteristics just described. More particularly, the present invention relates to estrogen receptors) for human and non-human mammals (e.g., animals of veterinary interest such as horses, cows, sheep, and pigs, as well as household pets such as cats and dogs). Human estrogen receptors included in the present invention include the α- and (β-isoforms (referred to herein as "ERα" and "ERβ") in addition to any additional isoforms as recognized by those of skill in the biochemistry arts.

4.1.2 Estrogen Receptor Modulator

"Estrogen Receptor Modulator" refer herein to a compound that can act as an estrogen receptor agonist or antagonist of estrogen receptor having an $IC_{50}$ or $EC_{50}$ with respect to ERα and/or ERβ of no more than about 10 μM as determined using the ERα and/or ERβ transactivation assay described hereinbelow (Section 5.2.2.3). More typically, estrogen receptor modulators of the invention have $IC_{50}$ of $EC_{50}$ values (as agonists or antagonists) of not more than about 5 μM. Representative compounds of the present invention have been discovered to exhibit agonist or antagonist activity viz. estrogen receptor. Compounds of the present invention preferably exhibit an antagonist or agonist $IC_{50}$ or $EC_{50}$ with respect to ERα and/or ERβ of no more than about 5 μM, more preferably, no more than about 500 nM, even more preferably not more than about 1 nM, and most preferably, not more than about 500 μM, as measured in the ERα and/or ERβ transactivation assays. "$IC_{50}$" is that concentration of compound which reduces the activity of a target (e.g., ERα or ERβ) to half-maximal level. "$EC_{50}$" is that concentration of compound which provides half-maximum effect.

4.1.3 Selective Estrogen Receptor Modulator

A "Selective Estrogen Receptor Modulator" (or "SERM") is a compound that exhibits activity as an agonist or antagonist of an estrogen receptor (e.g., ERα or ERβ) in a tissue-dependent manner. Thus, as will be apparent to those of skill in the biochemistry and endocrinology arts, compounds of the invention that function as SERMs can act as estrogen receptor agonists in some tissues (e.g., bone, brain, and/or heart) and as antagonists in other tissue types, such as the breast and/or uterine lining.

4.1.4 Optionally Substituted

"Optionally substituted" refers to the replacement of hydrogen with a monovalent or divalent radical. Suitable substitution groups include, for example, hydroxyl, nitro, amino, imino, cyano, halo, thio, thioamido, amidino, oxo, oxamidino, methoxamidino, imidino, guanidino, sulfonamido, carboxyl, formyl, loweralkyl, haloloweralkyl, loweralkoxy, haloloweralkoxy, loweralkoxyalkyl, alkylcarbonyl, arylcarbonyl, aralkylcarbonyl, heteroarylcarbonyl, heteroaralkylcarbonyl, alkylthio, aminoalkyl, cyanoalkyl, and the like. The substitution group can itself be substituted. The group substituted onto the substitution group can be, for example, carboxyl, halo; nitro, amino, cyano, hydroxyl, loweralkyl, loweralkoxy, aminocarbonyl, —SR, thioamido, —$SO_3H$, —$SO_2R$ or cycloalkyl, where R is typically hydrogen, hydroxyl or loweralkyl. When the substituted substituent includes a straight chain group, the substitution can occur either within the chain (e.g., 2-hydroxypropyl, 2-aminobutyl, and the like) or at the chain terminus (e.g., 2-hydroxyethyl, 3-cyanopropyl, and the like). Substituted substitutents can be straight chain, branched or cyclic arrangements of covalently bonded carbon or heteroatoms.

4.1.5 Loweralkyl and Related Terms

"Loweralkyl" as used herein refers to branched or straight chain alkyl groups comprising one to ten carbon atoms that independently are unsubstituted or substituted, e.g., with one or more halogen, hydroxyl or other groups. Examples of loweralkyl groups include, but are not limited to, methyl, ethyl, propyl, isopropyl, n-butyl, t-butyl, n-hexyl, neopentyl, trifluoromethyl, pentafluoroethyl, and the like.

"Alkylenyl" refers to a divalent straight chain or branched chain saturated aliphatic radical having from 1 to 20 carbon atoms. Typical alkylenyl groups employed in compounds of the present invention are loweralkylenyl groups that have from 1 to about 6 carbon atoms in their backbone. "Alkenyl" refers herein to straight chain, branched, or cyclic radicals having one or more double bonds and from 2 to 20 carbon atoms. "Alkynyl" refers herein to straight chain, branched, or cyclic radicals having one or more triple bonds and from 2 to 20 carbon atoms.

The term "haloloweralkyl" refers to a loweralkyl radical substituted with one or more halogen atoms.

"Loweralkoxy" as used herein refers to RO— wherein R is loweralkyl. Representative examples of loweralkoxy groups include methoxy, ethoxy, t-butoxy, trifluoromethoxy and the like.

"Loweralkythio" as used herein refers to RS— wherein R is loweralkyl.

The term "alkoxyalkyl" refers to the group -$alk_1$-O-$alk_2$ where $alk_1$ is alkylenyl or alkenyl, and $alk_2$ is alkyl or alkenyl. The term "loweralkoxyalkyl" refers to an alkoxyalkyl where $alk_1$ is loweralkylenyl or loweralkenyl, and $alk_2$ is loweralkyl or loweralkenyl. The term "aryloxyalkyl" refers to the group -alkylenyl-O-aryl. The term "aralkoxyalkyl" refers to the group -alkylenyl-O-aralkyl, where aralkyl is a loweraralkyl.

"Cycloalkyl" refers to a mono- or polycyclic, loweralkyl substituent. Typical cycloalkyl substituents have from 3 to 8 backbone (i.e., ring) atoms in which each backbone atom is optionally substituted carbon. When used in context with cycloalkyl substituents, the term "polycyclic" refers herein to fused, non-fused cyclic carbon structures and spirocycles. Examples of cycloalkyl groups include, but are not limited to, cyclopropyl, cyclobutyl, cyclopentyl, cyclohexyl, adamantyl, bornyl, norbornyl, and the like.

The term "cycloheteroalkyl" refers herein to cycloalkyl substituents that have from 1 to 5, and more typically from 1 to 4 heteroatoms (i.e., non-carbon atoms such as nitrogen, sulfur, and oxygen) in the ring structure, with the balance of atoms in the ring being optionally substituted carbon. Representative heterocycloalkyl moieties include, for example, morpholino, piperazinyl, piperidinyl, pyrrolidinyl, methylpryolidinyl, pyrrolidinone-yl, and the like.

The terms "(cycloalkyl)alkyl" and "(cycloheteroalkyl) alkyl" refer to alkyl chains substituted with cycloalkyl and cycloheteroalkyl groups respectively.

The term "haloalkoxy" refers to an alkoxy radical substituted with one or more halogen atoms. The term "haloloweralkoxy" refers to a loweralkoxy radical substituted with one or more halogen atoms.

4.1.6 Halo

"Halo" refers herein to a halogen radical, such as fluorine, chlorine, bromine, or iodine.

4.1.7 Aryl and Related Terms

"Aryl" refers to monocyclic and polycyclic aromatic groups, or fused ring systems having at least one aromatic ring, having from 3 to 14 backbone carbon atoms. Examples of aryl groups include without limitation phenyl, naphthyl, dihydronaphtyl, tetrahydronaphthyl, and the like.

"Aralkyl" refers to an alkyl group substituted with an aryl group. Typically, aralkyl groups employed in compounds of the present invention have from 1 to 6 carbon atoms incorporated within the alkyl portion of the aralkyl group. Suitable aralkyl groups employed in compounds of the present invention include, for example, benzyl, picolyl, and the like.

4.1.8 Heteroaryl and Related Terms

The term "heteroaryl" refers herein to aryl groups having from one to four heteroatoms as ring atoms in an aromatic ring with the remainder of the ring atoms being aromatic or non-aromatic carbon atoms. When used in connection with aryl substituents, the term "polycyclic" refers herein to fused and non-fused cyclic structures in which at least one cyclic structure is aromatic, such as, for example, benzodioxozolo, naphthyl, and the like. Exemplary heteroaryl moieties employed as substituents in compounds of the present invention include pyridyl, pyrimidinyl, thiazolyl, indolyl, imidazolyl, oxadiazolyl, tetrazolyl, pyrazinyl, triazolyl, thiophenyl, furanyl, quinolinyl, purinyl, benzothiazolyl, benzopyridyl, and benzimidazolyl, and the like.

4.1.9 Amino and Related Terms

"Amino" refers herein to the group —NH$_2$. The term "loweralkylamino" refers herein to the group —NRR' where R and R' are each independently selected from hydrogen or loweralkyl. The term "arylamino" refers herein to the group —NRR' where R is aryl and R' is hydrogen, loweralkyl, aryl, or aralkyl. The term "aralkylamino" refers herein to the group —NRR' where R is aralkyl and R' is hydrogen, loweralkyl, aryl, or aralkyl. The terms "heteroarylamino" and heteroaralkylamino" are defined by analogy to arylamino and aralkylamino.

The term "aminocarbonyl" refers herein to the group —C(O)—NH$_2$. The terms "loweralkylaminocarbonyl", arylaminocarbonyl", "aralkylaminocarbonyl", "heteroarylaminocarbonyl", and "heteroaralkylaminocarbonyl" refer to —C(O)NRR' where R and R' independently are hydrogen and optionally substituted loweralkyl, aryl, aralkyl, heteroaryl, and heteroaralkyl respectively by analogy to the corresponding terms above.

4.1.10 Thio, Sulfonyl, Sulfinyl and Related Terms

The term "thio" refers to —SH. The terms "loweralkylthio", "arylthio", "heteroarylthio", "cycloalkylthio", "cycloheteroalkylthio", "aralkylthio", "heteroaralkylthio", "(cycloalkyl)alkylthio", and "(cycloheteroalkyl)alkylthio" refer to —SR, where R is optionally substituted loweralkyl, aryl, heteroaryl, cycloalkyl, cycloheteroalkyl, aralkyl, heteroaralkyl, (cycloalkyl)allcyl, and (cycloheteroalkyl)alkyl respectively.

The term "sulfonyl" refers herein to the group —SOZ—. The terms "loweralkylsulfonyl", "arylsulfonyl", "heteroarylsulfonyl", "cycloalkylsulfonyl", "cycloheteroalkylsulfonyl", "aralkylsulfonyl", "heteroaralkylsulfonyl", "(cycloalkyl)alkylsulfonyl", and "(cycloheteroalkyl)allcylsulfonyl" refer to —SO2R where R is optionally substituted loweralkyl, aryl, heteroaryl, cycloalkyl, cycloheteroalkyl, aralkyl, heteroaralkyl, (cycloalkyl)alkyl, and (cycloheteroalkyl)alkyl respectively.

The term "sulfinyl" refers herein to the group —SO—. The terms "loweralkylsulfinyl", "arylsulfinyl", "heteroarylsulfinyl", "cycloalkylsulfinyl", "cycloheteroalkylsulfinyl", "aralkylsulfinyl", "heteroaralkylsulfinyl", "(cycloalkyl)alkylsulfinyl", and "(cycloheteroalkyl)alkylsulfinyl" refer to —SOR where R is optionally substituted loweralkyl, aryl, heteroaryl, cycloalkyl, cycloheteroalkyl, aralkyl, heteroaralkyl, (cycloalkyl)alkyl, and (cycloheteroalkyl)alkyl respectively.

4.1.11 Formyl, Carboxyl, Carbonyl, Thiocarbonyl, and Related Terms

"Formyl" refers to —C(O)H.

"Carboxyl" refers to —C(O)OH.

"Carbonyl" refers to the divalent group —C(O)—. The terms "loweralkylcarbonyl", "arylcarbonyl", "heteroarylcarbonyl", "cycloalkylcarbonyl", "cycloheteroalkylcarbonyl", "aralkycarbonyl", "heteroaralkylcarbonyl", "(cycloalkyl)alkylcarbonyl", and "(cycloheteroalkyl)alkylcarbonyl" refer to —C(S)R, where R is optionally substituted loweralkyl, aryl, heteroaryl, cycloalkyl, cycloheteroalkyl, aralkyl, heteroaralkyl, (cycloalkyl)alkyl, and (cycloheteroalkyl)alkyl respectively.

"Thiocarbonyl" refers to the group —C(S)—. The terms "loweralkylthiocarbonyl", "arylthiocarbonyl", "heteroarylthiocarbonyl", "cycloalkylthiocarbonyl", "cycloheteroalkylthiocarbonyl", "aralkythiocarbonyloxlthiocarbonyl", "heteroaralkylthiocarbonyl", "(cycloalkyl)alkylthiocarbonyl", and "(cycloheteroalkyl)alkylthiocarbonyl" refer to —C(S)R, where R is optionally substituted loweralkyl, aryl, heteroaryl, cycloalkyl, cycloheteroalkyl, aralkyl, heteroaralkyl, (cycloalkyl)alkyl, and (cycloheteroalkyl)alkyl respectively.

"Carbonyloxy" refers generally to the group —C(O)—O—. The terms "loweralkylcarbonyloxy", "arylcarbonyloxy", "heteroarylcarbonyloxy", "cycloalkylcarbonyloxy", "cycloheteroalkylcarbonyloxy", "aralkycarbonyloxy", "heteroaralkylcarbonyloxy", "(cycloalkyl)alkylcarbonyloxy", "(cycloheteroalkyl)alkylcarbonyloxy" refer to —C(O)OR, where R is optionally substituted loweralkyl, aryl, heteroaryl, cycloalkyl, cycloheteroalkyl, aralkyl, heteroaralkyl, (cycloalkyl)alkyl, and (cycloheteroalkyl)alkyl respectively.

"Oxycarbonyl" refers to the group —O—C(O)—. The terms "loweralkyloxycarbonyl", "aryloxycarbonyl", "heteroaryloxycarbonyl", "cycloalkyloxycarbonyl", "cycloheteroalkyloxycarbonyl", "aralkyoxycarbonyloxloxycarbonyl", "heteroaralkyloxycarbonyl", "(cycloalkyl)alkyloxycarbonyl", "(cycloheteroalkyl)alkyloxycarbonyl" refer to —O—C(O)R, where R is optionally substituted loweralkyl, aryl, heteroaryl, cycloalkyl, cycloheteroalkyl, aralkyl, heteroaralkyl, (cycloalkyl)alkyl, and (cycloheteroalkyl)alkyl respectively.

"Carbonylamino" refers to the group NH—C(O)—. The terms "loweralkylcarbonylamino", "arylcarbonylamino", "heteroarylcarbonylamino", "cycloalkylcarbonylamino", "cycloheteroalkylcarbonylamino", "aralkylcarbonylamino", "heteroaralkylcarbonylamino", "(cycloalkyl)alkylcarbonylamino", and "(cycloheteroalkyl)alkylcarbonylamino" refer to —NH—C(O)R, where R is optionally substituted loweralkyl, aryl, heteroaryl, cycloalkyl, cycloheteroalkyl, aralkyl, heteroaralkyl, (cycloalkyl)alkyl, or (cycloheteroalkyl)alkyl respectively. In addition, the present invention includes N-substituted carbonylamino (—NR'C(O)R), where R' is optionally substituted loweralkyl, aryl, heteroaryl, aralkyl, or heteroaralkyl and R retains the previous definition.

4.1.12 Guanidino or Guanidyl

As used herein, the term "guanidino" or "guanidyl" refers to moieties derived from guanidino, H$_2$N—C(=NH)—NH$_2$. Such moieties include those bonded at the nitrogen atom carrying the formal double bond (the "2"-position of the guanidine, e.g., diaminomethyleneamino, (H$_2$N)$_2$C=NH—) and those bonded at either of the nitrogen atoms carrying a formal single bond (the "1" and/or "3"-positions of the guanidine, e.g., H$_2$N—C(=NH)—NH—). The hydrogen atoms at either nitrogen can be replaced with a suitable substituent, such as loweralkyl, aryl, or loweraralkyl.

4.1.13 Amidino

As used herein, the term "amidino" refers to the moieties R—C(=N)—NR'— (the radical being at the "N'" nitrogen) and R(NR')C=N— (the radical being at the "N$^{2}$" nitrogen), where R and R' can be hydrogen, loweralkyl, aryl, or loweraralkyl.

4.1.14 Imino and Oximino

The term "imino" refers to the group —C(=NR)—, where R can be hydrogen or optionally substituted loweralkyl, aryl, heteroaryl, or heteroaralkyl respectively. The terms "iminoloweralkyl", "iminocycloalkyl", "iminocycloheteroalkyl", "iminoaralkyl", "iminoheteroaralkyl", "(cycloalkyl)iminoalkyl", "(cycloiminoalkyl)alkyl", "(cycloiminoheteroalkyl)alkyl", and "(cycloheteroalkyl)iminoalkyl" refer to optionally substituted loweralkyl, cycloalkyl, cycloheteroalkyl, aralkyl, heteroaralkyl, (cycloalkyl)alkyl, and (cycloheteroalkyl)alkyl groups that include an imino group, respectively.

The term "oximino" refers to the group —C(=NOR)—, where R can be hydrogen ("hydroximino") or optionally substituted loweralkyl, aryl, heteroaryl, or heteroaralkyl respectively. The terms "oximinoloweralkyl", "oximinocycloalkyl", "oximinocycloheteroalkyl", "oximinoaralkyl", "oximinoheteroaralkyl", "(cycloalkyl)oximinoalkyl", "(cyclooximinoalkyl)alkyl", "(cyclooximinoheteroalkyl)alkyl", and (cycloheteroalkyl)oximinoalkyl" refer to optionally substituted loweralkyl, cycloalkyl, cycloheteroalkyl, aralkyl, heteroaralkyl, (cycloalkyl)alkyl, and (cycloheteroalkyl)alkyl groups that include an oximino group, respectively.

4.1.15 Methylene and Methine

The term "methylene" as used herein refers to an unsubstituted, monosubstituted, or disubstituted carbon atom having a formal $sp^3$ hybridization (i.e., —CRR'—, where R and R' are hydrogen or independent substituents).

The term "methine" as used herein refers to an unsubstituted or carbon atom having a formal $sp^2$ hybridization (i.e., —CR= or =CR—, where R is hydrogen a substituent).

4.2 Compounds of the Invention

The present invention provides compounds that have useful agonist and/or antagonist activity with respect to mammalian estrogen receptors in addition to compounds, compositions, and methods useful for treating estrogen receptor-mediated disorders in mammals. More particularly, the compounds of the present invention have been found to possess a surprising degree of activity with respect to the α- and β-isoforms of human estrogen receptor. Thus, the compounds, compositions, and methods described herein have utility in preventing and/or treating a wide variety of estrogen receptor-mediated disorders including, but not limited to, osteoporosis, breast cancer, uterine cancer, and congestive heart disease.

In a first aspect, the present invention provides compounds having the structures:

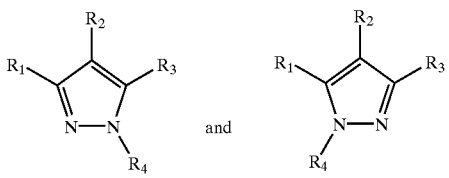

and their pharmaceutically acceptable salts. $R_1$ and $R_3$ are selected independently from the group consisting of optionally substituted loweralkyl, aryl, heteroaryl, cycloalkyl, cycloheteroalkyl, aralkyl, heteroaralkyl, (cycloalkyl)alkyl. $R_2$ is selected from the group consisting of hydrogen, halo, cyano, nitro, thio, amino, carboxyl, formyl, and optionally substituted loweralkyl, loweralkylcarbonyloxy, arylcarbonyloxy, heteroarylcarbonyloxy, cycloalkylcarbonyloxy, cycloheteroalkylcarbonyloxy, aralkycarbonyloxy, heteroaralkylcarbonyloxy, (cycloalkyl)alkylcarbonyloxy, (cycloheteroalkyl)alkylcarbonyloxy, loweralkylcarbonyl, arylcarbonyl, heteroarylcarbonyl, cycloalkylcarbonyl, cycloheteroalkylcarbonyl, aralkycarbonyl, heteroaralkylcarbonyl, (cycloalkyl)alkylcarbonyl, (cycloheteroalkyl)alkylcarbonyl, loweralkylaminocarbonyl, arylaminocarbonyl, aralkylaminocarbonyl, heteroarylaminocarbonyl, heteroaralkylaminocarbonyl, cycloalkylaminocarbonyl, (cycloalkyl)alkylaminocarbonyl, cycloheteroalkylaminocarbonyl, (cycloheteroalkyl)alkylaminocarbonyl, loweralkylcarbonylamino, arylcarbonylamino, heteroarylcarbonylamino, cycloalkylcarbonylamino, cycloheteroalkylcarbonylamino, aralkylcarbonylamino, heteroaralkylcarbonylamino, (cycloalkyl)alkylcarbonylamino, (cycloheteroalkyl)alkylcarbonylamino, loweralkylamino, arylamino, aralkylamino, heteroarylamino, heteroaralkylamino, loweralkylsulfonyl, arylsulfonyl, heteroarylsulfonyl, cycloalkylsulfonyl, cycloheteroalkylsulfonyl, aralkylsulfonyl, heteroaralkylsulfonyl, (cycloalkyl)alkylsulfonyl, (cycloheteroalkyl)alkylsulfonyl, loweralkylsulfinyl, arylsulfinyl, heteroarylsulfinyl, cycloalkylsulfinyl, cycloheteroalkylsulfinyl, aralkylsulfinyl, heteroaralkylsulfinyl, (cycloalkyl)alkylsulfinyl, (cycloheteroalkyl)alkylsulfinyl, loweralkyloxy, aryloxy, heteroaryloxy, cycloalkyloxy, cycloheteroalkyloxy, aralkyloxy, heteroaralkyloxy, (cycloalkyl)alkyloxy, and (cycloheteroalkyl)alkyloxy, loweralkylthio, arylthio, heteroarylthio, cycloalkylthio, cycloheteroalkylthio, aralkylthio, heteroaralkylthio, (cycloalkyl)alkylthio, (cycloheteroalkyl)alkylthio, loweralkylthiocarbonyl, arylthiocarbonyl, heteroarylthiocarbonyl, cycloalkylthiocarbonyl, cycloheteroalkylthiocarbonyl, aralkythiocarbonyloxythiocarbonyl, heteroaralkylthiocarbonyl, (cycloalkyl)alkylthiocarbonyl, (cycloheteroalkyl)alkylthiocarbonyl, loweralkyloxycarbonyl, aryloxycarbonyl, heteroaryloxycarbonyl, cycloalkyloxycarbonyl, cycloheteroalkyloxycarbonyl, aralkyoxycarbonyloxloxycarbonyl, heteroaralkyloxycarbonyl, (cycloalkyl)alkyloxycarbonyl, (cycloheteroalkyl)alkyloxycarbonyl, iminoloweralkyl, iminocycloalkyl, iminocycloheteroalkyl, iminoaralkyl, iminoheteroaralkyl, (cycloalkyl)iminoalkyl, (cycloheteroalkyl)iminoalkyl, (cycloiminoalkyl)alkyl, (cycloiminoheteroalkyl)alkyl, oximinoloweralkyl, oximinocycloalkyl, oximinocycloheteroalkyl, oximinoaralkyl, oximinoheteroaralkyl, (cycloalkyl)oximinoalkyl, (cyclooximinoalkyl)alkyl, (cyclooximinoheteroalkyl)alkyl, and (cycloheteroalkyl)oximinoalkyl. $R_4$ is selected from the group consisting of hydrogen, carboxyl, formyl, and optionally substituted loweralkyl, aryl, aralkyl, heteroaryl, heteroaralkyl, cycloalkyl, cycloheteroalkyl, loweralkylcarbonyl, arylcarbonyl, heteroarylcarbonyl, cycloalkylcarbonyl, cycloheteroalkylcarbonyl, aralkycarbonyl, heteroaralkylcarbonyl, (cycloalkyl)alkylcarbonyl, (cycloheteroalkyl)alkylcarbonyl, loweralkylaminocarbonyl, arylaminocarbonyl, aralkylaminocarbonyl, heteroarylaminocarbonyl, heteroaralkylaminocarbonyl, cycloalkylaminocarbonyl, (cycloalkyl)alkylaminocarbonyl, cycloheteroalkylaminocarbonyl, (cycloheteroalkyl)alkylaminocarbonyl, loweralkylsulfonyl, arylsulfonyl, heteroarylsulfonyl, cycloalkylsulfonyl, cycloheteroalkylsulfonyl, aralkylsulfonyl, heteroaralkylsulfonyl, (cycloalkyl)alkylsulfonyl, (cycloheteroalkyl)alkylsulfonyl, loweralkylsulfinyl, arylsulfinyl, heteroarylsulfinyl, cycloalkylsulfinyl, cycloheteroalkylsulfinyl, aralkylsulfinyl, heteroaralkylsulfinyl, (cycloalkyl)alkylsulfinyl, (cycloheteroalkyl)alkylsulfinyl, arylthiocarbonyl, heteroarylthiocarbonyl, cycloalkylthiocarbonyl, cycloheteroalkylthiocarbonyl, aralkythiocarbonyloxythiocarbonyl, heteroaralkylthiocarbonyl, (cycloalkyl)alkylthiocarbonyl, (cycloheteroalkyl)alkylthiocarbonyl, loweralkyloxycarbonyl, aryloxycarbonyl, heteroaryloxycarbonyl, cycloalkyloxycarbonyl, cycloheteroalkyloxycarbonyl, aralkyoxycarbonyloxloxycarbonyl, heteroaralkyloxycarbonyl, (cycloalkyl)alkyloxycarbonyl, (cycloheteroalkyl)alkyloxycarbonyl, carboxamidino, loweralkylcarboxamidino, arylcarboxamidino, aralkylcarboxamidino, heteroarylcarboxamidino, heteroaralkylcarboxamidino, cycloalkylcarboxamidino, cycloheteroalkylcarboxamindino.

In one embodiment of the invention having the generic structures shown above, $R_1$ and $R_3$ are selected independently from the group consisting of optionally substituted cycloalkyl, cycloheteroalkyl, (cycloalkyl)alkyl, and (cycloheteroalkyl)alkyl. Examples of such groups include without limitation cyclohexyl, piperidinyl, adamantyl, and quinuclidyl, each optionally substituted. Other examples include cyclohexyhnethyl, 2-cyclohexylethyl, and adamantylmethyl, again, each optionally substituted. In other embodiments, $R_1$ and $R_3$ are selected independently from the group consisting of optionally substituted aryl, heteroaryl, aralkyl, and heteroaralkyl. More specific embodiments are those for which $R_1$ and $R_3$ are selected independently from the group consisting of optionally substituted heteroaryl and heteroaralkyl, such as pyridinyl, hydroxypyridyl, methoxypyridyl, pyridylinethyl, and the like.

In another embodiment, $R_1$ and $R_3$ are selected independently from the group consisting of optionally substituted aryl and aralkyl. In some embodiments in which $R_1$ and $R_3$ are selected independently from the group consisting of optionally substituted aryl and aralkyl, at least one of $R_1$ and $R_3$ is substituted with at least one hydroxyl, alkyloxy, aryloxy, thio, alkylthio, or arylthio group. More specific embodiments are those wherein $R_1$ and $R_3$ are selected independently from the group consisting of optionally substituted aryl and aralkyl, at least one of $R_1$ and $R_3$ is substituted with at least one hydroxyl, alkyloxy, aryloxy, thio, alkylthio, or arylthio group, and at least one of $R_1$ and $R_3$ is selected independently from the group consisting of phenyl, phenyloxyloweralkyl, and phenylloweralkyl. In still more specific embodiments, at least one of $R_1$ and $R_3$ is selected independently from the group consisting of phenyl, phenyloxyloweralkyl, and phenylloweralkyl as just described and at least one of $R_1$ and $R_3$ is substituted optionally with a substituent selected from the group consisting of halogen, nitro, cyano, loweralkyl, halolowerlalkyl, loweralkyloxy, haloloweralkyloxy, carboxy, loweralkyloxycarbonyl, aryloxycarbonyl, (cycloloweralkyl)oxycarbonyl, aralkyloxycarbonyl, heteroaryloxycarbonyl, heteroaralkyloxycarbonyl, (heterocycloloweralkyl)oxycarbonyl, loweralkylsulfinyl, loweralkylsulfonyl, loweralkylthio, arylthio, loweralkylcarbonyloxy, arylcarbonyloxy, aralkylcarbonyloxy, heteroarylcarbonyloxy, heteroaralkylcarbonyloxy, (cycloloweralkyl)carbonyloxy, allrylsulfonylamino, (heterocycloloweralkyl)carbonyloxy, aminocarbonyl, loweraklylaminocarbonyl, arylaminocarbonyl, aralkylaminocarbonyl, heteroarylaminocarbonyl, and heteroaralkylaminocarbonyl. In further embodiments in which at least one of $R_1$ and $R_3$ is selected independently from the group consisting of phenyl, phenyloxyloweralkyl, and phenylloweralkyl as just described, at least one of $R_1$ and $R_3$ is substituted optionally with a substituent selected from the group consisting of halogen, nitro, cyano, loweralkyl, halolowerlalkyl, loweralkyloxy, halolowerlakyloxy, carboxy, loweralkylthio, aminocarbonyl, and loweralkylsulfinyl.

In other embodiments of the above-illustrated pyrazole derivatives of the invention, $R_2$ is selected from the group consisting of hydrogen, halo, and optionally substituted loweralkyl, haloloweralkyl, aryl, aralkyl, heteroaryl, heteroaralkyl, aryloxyalkyl, arylthioalkyl, arylcarbonyl, heteroarylcarbonyl, loweralkylcarbonyl, aminocarbonyl, arylaminocarbonyl, loweralkylaminocarbonyl, arallcylaminocarbonyl, (heterocycloloweralllcyl)allcylaminocarbonyl, heteroarylaminocarbonyl, heteroaralkylaminocarbonyl, (cycloloweralkyl) aminocarbonyl, formyl, and alkenyl. In some more specific embodiments, $R_2$ is selected from the group consisting of hydrogen and halo. In other more specific embodiments, $R_2$ is selected from the group consisting of optionally substituted phenyl, phenylloweralkyl, hydroxyphenyl, loweralkyloxyphenyl, haloloweralkylsulfonylloweralkyloxyphenyl, diloweralllrylaminoloweralllcyloxyphenyl, (cycloaminoloweralkyl)loweralkyloxyphenyl, and (heterocycloalkyl)loweralkyloxyphenyl. Examples of specific useful groups of this embodiment include without limitation 2-methyl-4-hydroxyphenyl, 2-aminocarbonyl-4-hydroxyphenyl, 4-methylsulfonylaminophenyl, 3-aminocarbonyl-4-hydroxyphenyl, 3-aminocarbonyl-4-methoxyphenyl, 3-chloro-4-hydroxyphenyl, 4-methylcarbonyloxyphenyl, 3-n-hexyl-4-hydroxyphenyl, 4-n-propylcarbonyloxyphenyl, 3-ethyl-4-hydroxyphenyl, 2-methylsulfinyl-4-hydroxyphenyl, 2-ethyl-4-hydroxyphenyl, 2-carboxy-4-hydroxyphenyl, 3-fluoro-4-hydroxyphenyl, 2-iodo-4-hydroxyphenyl, 2-n-butyl-4-hydroxyphenyl, 2-trifluoromethoxyphenyl, 4-methoxyphenyl, 2-hydroxyphenyl, 3-(phenylthio)-4-hydroxyphenyl, and 3-methylphenyl-4-hydroxyphenyl, and 4-fluorophenyl. Still other embodiments include those for which $R_2$ is selected from the group consisting of optionally substituted loweralkyl, haloloweralkyl, hydroxyalkyl, phenyloxyloweralkyl, hydroxyphenyloweralkyl, haloloweralkylsulfonylloweralkyl, and phenylthioloweralkyl. Examples of useful groups include without limitation 4-hydoxyphenyl, phenylinethyl, 4-hydroxyphenymethyl, 3-hydroxyphenylinethyl, 2-thin-4-hydroxyphenylinethyl, 2-(4-hydroxyphenyl)ethyl, phenyloxy)methyl.

Still more specific embodiments have the latter substituent pattern and $R_2$ is selected from the group consisting of optionally substituted phenylcarbonyl, (heterocycloalkyl) loweralkyloxyphenylcarbonyl, hydroxyphenylcarbonyl, halophenylcarbonyl, phenylloweralkylaminocarbonyl, diloweralkylaminocarbonyl, phenylloweralkylaminocarbonyl, hydroxyphenyllowerlkylaminocarbonyl, cycloalkylaminocarbonyl, loweralkylphenylcarbonyl, haloloweralkylsulfonylloweralkyloxyphenylcarbonyl, and nitrophenylcarbonyl. Examples of $R_2$ substituents within this embodiment having useful properties include, but are not limited to, 4-(2-piperidin-1-ylethyloxy)phenylcarbonyl, 4-hydroxyphenylcarbonyl, (phenylmethyl)aminocarbonyl, 3-(2-oxopyrrolidin-1-yl)propylaminocarbonyl, di-n butylaminocarbonyl, (4-hydroxyphenylinethyl) aminocarbonyl, (pyridin-3-ylmethyl)aminocarbonyl, (pyridin-2-ylmethyl)aminocarbonyl, dimethylaminocarbonyl, ethylaminocarbonyl, 4-(2-morpholinoethyloxy) phenylcarbonyl, 4(3-dimethylaminopropyloxy) phenylcarbonyl, cyclopropylaminocarbonyl, cyclobutylaminocarbonyl, 4-(2-dimethylaminoethyloxy)

phenylcarbonyl, 4-[2-(benzylmethylamino)ethyloxy]phenylcarbonyl, 4-(1-methylpiperdin-3-ylmethyloxy)phenylcarbonyl, 4-[2-(1-methylpyrrolidin-2-yl)ethyloxy]phenylcarbonyl, 4-[2-(4-methylpiperazin-1-yl)ethyloxy]phenylcarbonyl, 4-(1-methylpiperdin-4-ylmethyloxy) phenylcarbonyl, 2-chlorophenylcarbonyl, 3-chlorophenylcarbonyl, 4-chlorophenylcarbonyl, 3-nitrophenylcarbonyl, 4-nitrophenylcarbonyl, 3,4-dichlorophenylcarbonyl, 4-n-butylphenylcarbonyl, 3-hydroxyphenylcarbonyl, 2-hydroxyphenylcarbonyl, 4-methoxyphenylcarbonyl, 3-(2-piperidin-1-ylethyloxy)phenylcarbonyl, 3-(2-diethylaminoethyloxy)phenylcarbonyl, 3-[2-(pyrrolidin-1-yl)ethyloxy]phenylcarbonyl, 3-(1-methylpiperdin-3-ylmethyloxy)phenylcarbonyl, and 3-(2-dimethylaminoethyloxy)phenylcarbonyl.

In some embodiments for which $R_2$ is selected from the group consisting of optionally substituted phenylcarbonyl, (heterocycloalkyl)loweralkyloxyphenylcarbonyl, hydroxyphenylcarbonyl, halophenylcarbonyl, phenylloweralkylaminocarbonyl, diloweralkylaminocarbonyl, phenylloweralkylaminocarbonyl, hydroxyphenyllowerlakylaminocarbonyl, cycloalkylaminocarbonyl, loweralkylphenylcarbonyl, haloloweralkylsulfonylloweralkyloxyphenylcarbonyl, and nitrophenylcarbonyl as just described, $R_1$ and $R_3$ are selected independently from the group consisting of optionally substituted cycloalkyl, cycloheteroalkyl, (cycloalkyl)alkyl, and (cycloheteroalkyl)alkyl. More specific embodiments of these compounds include those for which $R_1$ and $R_3$ are selected independently from the group consisting of optionally substituted aryl, heteroaryl, aralkyl, and heteroaralkyl. Other more specific embodiments of compounds for which $R_2$ is selected from the group consisting of optionally substituted phenylcarbonyl, (heterocycloalkyl)loweralkyloxyphenylcarbonyl, hydroxyphenylcarbonyl, halophenylcarbonyl, phenylloweralkylaminocarbonyl, diloweralkylaminocarbonyl, phenylloweralkylaminocarbonyl, hydroxyphenyllowerlakylaminocarbonyl, cycloalkylaminocarbonyl, loweralkylphenylcarbonyl, haloloweralkylsulfonylloweralkyloxyphenylcarbonyl, and nitrophenylcarbonyl and $R_1$ and $R_3$ are selected independently from the group consisting of optionally substituted cycloalkyl, cycloheteroalkyl, (cycloalkyl)alkyl, and (cycloheteroalkyl)alkyl include those wherein $R_1$ and $R_3$ are selected independently from the group consisting of optionally substituted aryl and aralkyl. In other embodiments of this latter substitution pattern, at least one of $R_1$ and $R_3$ is substituted with at least one hydroxyl or thio group. Still more detailed embodiments for which $R_2$ is selected from the group consisting of optionally substituted phenylcarbonyl, (heterocycloalkyl)loweralkyloxyphenylcarbonyl, hydroxyphenylcarbonyl, halophenylcarbonyl, phenylloweralkylaminocarbonyl, diloweralkylaminocarbonyl, phenylloweralkylaminocarbonyl, hydroxyphenyllowerlakylaminocarbonyl, cycloalkylaminocarbonyl, loweralkylphenylcarbonyl, haloloweralkylsulfonylloweralkyloxyphenylcarbonyl, and nitrophenylcarbonyl and $R_1$ and $R_3$ are selected independently from the group consisting of optionally substituted cycloalkyl, cycloheteroalkyl, (cycloalkyl)alkyl, and (cycloheteroalkyl)alkyl include those wherein $R_1$ and $R_3$ are selected independently from the group consisting of optionally substituted aryl and aralkyl. In other embodiments of this latter substitution pattern, at least one of $R_1$ and $R_3$ is substituted with at least one hydroxyl or thio group include those wherein at least one of $R_1$ and $R_3$ is selected independently from the group consisting of phenyl, phenyloxyloweralkyl, and phenylloweralkyl.

Still more detailed embodiments of the above-illustrated pyrazoles of the invention are those for which $R_2$ is selected from the group consisting of optionally substituted phenylcarbonyl, (heterocycloalkyl)loweralkyloxyphenylcarbonyl, hydroxyphenylcarbonyl, halophenylcarbonyl, phenylloweralkylaminocarbonyl, diloweralkylaminocarbonyl, phenylloweralkylaminocarbonyl, hydroxyphenyllowerlakylaminocarbonyl, cycloalkylaminocarbonyl, loweralkylphenylcarbonyl, haloloweralkylsulfonylloweralkyloxyphenylcarbonyl, and nitrophenylcarbonyl and $R_1$ and $R_3$ are selected independently from the group consisting of optionally substituted cycloalkyl, cycloheteroalkyl, (cycloalkyl)alkyl, and (cycloheteroalkyl)alkyl include those wherein $R_1$ and $R_3$ are selected independently from the group consisting of optionally substituted aryl and aralkyl, at least one of $R_1$ and $R_3$ is substituted with at least one hydroxyl or thio group, and at least one of $R_1$ and $R_3$ is selected independently from the group consisting of phenyl, phenyloxyloweralkyl, and phenylloweralkyl, and at least one of $R_1$ and $R_3$ is substituted optionally with a substituent selected from the group consisting of halogen, loweralkyl, halolowerlalkyl, loweralkyloxy, halolowerlakyloxy, carboxy, loweralkyloxycarbonyl, aryloxycarbonyl, (cycloloweralkyl)oxycarbonyl, aralkyloxycarbonyl, heteroaryloxycarbonyl, heteroaralkyloxycarbonyl, (heterocycloloweralkyl)oxycarbonyl, loweralkylsulfmyl, loweralkylsulfonyl, loweralkylthio, arylthio, loweralkylcarbonyloxy, arylcarbonyloxy, aralkylcarbonyloxy, heteroarylcarbonyloxy, heteroaralkylcarbonyloxy, (cycloloweralkyl)carbonyloxy, (heterocycloloweralkylxarbonyloxy, aminocarbonyl, loweraklylaminocarbonyl, arylaminocarbonyl, aralkylaminocarbonyl, heteroarylaminocarbonyl, and heteroaralkylaminocarbonyl. Yet more detailed embodiments are those pyrazoles having this substituent pattern wherein $R_4$ is selected from the group consisting of hydrogen and optionally substituted loweralkyl, aryl, aralkyl, heteroaryl, heteroaralkyl, cycloalkyl, cycloheteroalkyl, loweralkylcarbonyl, arylcarbonyl, heteroarylcarbonyl, cycloalkylcarbonyl, cycloheteroalkylcarbonyl, aralkycarbonyl, heteroaralkylcarbonyl, (cycloalkyl)alkylcarbonyl, (cycloheteroalkyl)alkylcarbonyl, loweralkylaminocarbonyl, arylaminocarbonyl, aralkylaminocarbonyl, heteroarylaminocarbonyl, heteroaralkylaminocarbonyl, cycloalkylaminocarbonyl, (cycloalkyl)alkylaminocarbonyl, cycloheteroalkylaminocarbonyl, (cycloheteroalkyl)alkylaminocarbonyl, loweralkylsulfonyl, arylsulfonyl, heteroarylsulfonyl, cycloalkylsulfonyl, cycloheteroalkylsulfonyl, aralkylsulfonyl, heteroaralkylsulfonyl, (cycloalkyl)alkylsulfonyl, and (cycloheteroalkyl)alkylsulfonyl.

In a second aspect, the present invention provide compounds having the general structures shown below:

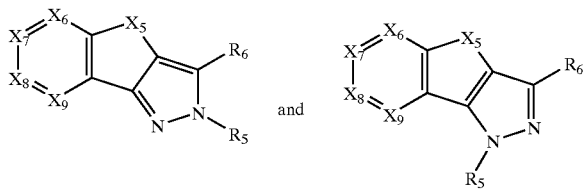

and their pharmaceutically acceptable salts. $X_5$ is —$(X_0)_n$ wherein n is an integer between 1 and 3 and $X_{10}$, for each value of n, is selected independently from the group consisting of oxygen, —$SO_x$,— where x is and integer between 0 and 2, nitrogen, nitrogen substituted with optionally substituted loweralkyl, aryl, aralkyl, heteroaryl, heteroaralkyl, arylcarbonyl, alkylcarbonyl, aralkylcarbonyl, heteroarylcarbonyl, heteroaralkylcarbonyl, and methylene or methine, each optionally substituted from the group consisting of halo, cyano, nitro, thio, amino, carboxyl, fornyl, and optionally substituted loweralkyl, loweralkylcarbonyloxy, arylcarbonyloxy, heteroarylcarbonyloxy, cycloalkylcarbonyloxy, cycloheteroalkylcarbonyloxy, aralkycarbonyloxy, heteroaralkylcarbonyloxy, (cycloalkyl)alkylcarbonyloxy, (cycloheteroalkyl)alkylcarbonyloxy, loweralkylcarbonyl, arylcarbonyl, heteroarylcarbonyl, cycloalkylcarbonyl, cycloheteroalkylcarbonyl, aralkycarbonyl, heteroaralkylcarbonyl, (cycloalkyl)alkylcarbonyl, (cycloheteroalkyl)alkylcarbonyl, loweralkylaminocarbonyl, arylaminocarbonyl, aralkylaminocarbonyl, heteroarylaminocarbonyl, heteroaralkylaminocarbonyl, loweralkylcarbonylamino, arylcarbonylamino, heteroarylcarbonylamino, cycloalkylcarbonylamino, cycloheteroalkylcarbonylamino, aralkylcarbonylamino, heteroaralkylcarbonylamino, (cycloalkyl)alkylcarbonylamino, (cycloheteroalkyl)alkylcarbonylamino, loweralkylamino, arylamino, aralkylamino, heteroarylamino, heteroaralkylamino, loweralkylsulfonyl, arylsulfonyl, heteroarylsulfonyl, cycloalkylsulfonyl, cycloheteroalkylsulfonyl, aralkylsulfonyl, heteroaralkylsulfonyl, (cycloalkyl)alkylsulfonyl, (cycloheteroalkyl)alkylsulfonyl, loweralkylsulfinyl, arylsulfinyl, heteroarylsulfinyl, cycloalkylsulfinyl, cycloheteroalkylsulfinyl, aralkylsulfinyl, heteroaralkylsulfinyl, (cycloalkyl)alkylsulfinyl, (cycloheteroalkyl)alkylsulfinyl, loweralkyloxy, aryloxy, heteroaryloxy, cycloalkyloxy, cycloheteroalkyloxy, aralkyloxy, heteroaralkyloxy, (cycloalkyl)alkyloxy, and (cycloheteroalkyl)alkyloxy, loweralkylthio, arylthio, heteroarylthio, cycloalkylthio, cycloheteroalkylthio, aralkylthio, heteroaralkylthio, (cycloalkyl)alkylthio, (cycloheteroalkyl)alkylthio, loweralkylthiocarbonyl, arylthiocarbonyl, heteroarylthiocarbonyl, cycloalkylthiocarbonyl, cycloheteroalkylthiocarbonyl, aralkythiocarbonyloxlthiocarbonyl, heteroaralkylthiocarbonyl, (cycloalkyl)alkylthiocarbonyl, (cycloheteroalkyl)alkylthiocarbonyl, loweralkyloxycarbonyl, aryloxycarbonyl, heteroaryloxycarbonyl, cycloalkyloxycarbonyl, cycloheteroalkyloxycarbonyl, aralkyoxycarbonyloxloxycarbonyl, heteroaralkyloxycarbonyl, (cycloalkyl)alkyloxycarbonyl, (cycloheteroalkyl)alkyloxycarbonyl, iminoloweralkyl, iminocycloalkyl, iminocycloheteroalkyl, iminoaralkyl, iminoheteroaralkyl, (cycloalkyl)iminoalkyl, and (cycloheteroalkyl)iminoallcyl. $X_6$–$X_9$ are selected independently from the group consisting of oxygen, sulfur, sulfinyl, nitrogen, and optionally substituted methine. $R_5$ is selected from the group consisting of hydrogen, carboxyl, formyl, and optionally substituted loweralkyl, aryl, aralkyl, heteroaryl, heteroaralkyl, cycloalkyl, cycloheteroalkyl, loweralkylcarbonyl, arylcarbonyl, heteroarylcarbonyl, cycloalkylcarbonyl, cycloheteroalkylcarbonyl, aralkycarbonyl, heteroaralkylcarbonyl, (cycloalkyl)alkylcarbonyl, (cycloheteroalkyl)alkylcarbonyl, loweralkylaminocarbonyl, arylaminocarbonyl, aralkylaminocarbonyl, heteroarylaminocarbonyl, heteroaralkylaminocarbonyl, cycloalkylaminocarbonyl, (cycloalkyl)alkylaminocarbonyl, cycloheteroalkylaminocarbonyl, (cycloheteroalkyl)alkylaminocarbonyl, loweralkylsulfonyl, arylsulfonyl, heteroarylsulfonyl, cycloalkylsulfonyl, cycloheteroalkylsulfonyl, aralkylsulfonyl, heteroaralkylsulfonyl, (cycloalkyl)alkylsulfonyl, (cycloheteroalkyl)alkylsulfonyl, loweralkylsulfinyl, arylsulfinyl, heteroarylsulfinyl, cycloalkylsulfinyl, cycloheteroalkylsulfinyl, aralkylsulfinyl, heteroaralkylsulfinyl, (cycloalkyl)alkylsulfinyl, (cycloheteroalkyl)alkylsulfinyl, arylthiocarbonyl, heteroarylthiocarbonyl, cycloalkylthiocarbonyl, cycloheteroalkylthiocarbonyl, aralkythiocarbonyloxythiocarbonyl, heteroaralkylthiocarbonyl, (cycloalkyl)alkylthiocarbonyl, (cycloheteroalkyl)alkylthiocarbonyl, loweralkyloxycarbonyl, aryloxycarbonyl, heteroaryloxycarbonyl, cycloalkyloxycarbonyl, cycloheteroalkyloxycarbonyl, aralkyoxycarbonyloxloxycarbonyl, heteroaralkyloxycarbonyl, (cycloalkyl)alkyloxycarbonyl, (cycloheteroalkyl)alkyloxycarbonyl, carboxamidino, loweralkylcarboxamidino, arylcarboxamidino, aralkylcarboxamidino, heteroarylcarboxamidino, heteroaralkylcarboxamidino, cycloalkylcarboxamidino, cycloheteroalkylcarboxamindino $R_6$ is selected from the group consisting of optionally substituted loweralkyl, aryl, heteroaryl, cycloalkyl, cycloheteroalkyl, aralkyl, heteroaralkyl, (cycloalkyl)alkyl, and (cycloheteroalkyl)alkyl.

Some embodiments of the present invention include those fused ring structures having the general form shown above for which n is 1 and $X_{10}$ is selected from the group consisting of nitrogen, optionally substituted nitrogen, and optionally substituted methylene or methine. Such embodiments will be recognized as including ring systems that are completely delocalized as well as ring systems that are not completely delocalized. More specific embodiments include those for which n is 1 and $X_{10}$ is selected from the group consisting of nitrogen, optionally substituted nitrogen, and optionally substituted methylene or methine and $R_6$ is selected from the group consisting of optionally substituted aryl, heteroaryl, aralkyl, and heteroaralkyl. Still more specific embodiments include those for which n is 1 and $X_{10}$ is selected from the group consisting of nitrogen, optionally substituted nitrogen, and optionally substituted methylene or methine and $R_6$ is optionally substituted aryl or aralkyl. Also included are embodiments of the above-illustrated fused-ring pyrazoles in which n is 1 and $X_{10}$ is selected from the group consisting of nitrogen, optionally substituted nitrogen, and optionally substituted methylene or methine, $R_6$ is optionally substituted aryl or aralkyl, and $R_6$ includes at least one hydroxyl, thio, or optionally substituted loweralkyloxy, aryloxy, heteroaryloxy, loweralkylthio, arylthio, heteroarylthio, loweralkylcarbonyl, arylcarbonyl, or heteroarylcarbonyl moiety.

In some embodiments for which n is 1 and $X_{10}$ is selected from the group consisting of nitrogen, optionally substituted nitrogen, and optionally substituted methylene or methine, $R_6$ is selected from the group consisting of optionally substituted aryl, heteroaryl, aralkyl, and heteroaralkyl, and $R_6$ includes at least one hydroxyl, thio, or optionally substituted loweralkyloxy, aryloxy, heteroaryloxy, loweralkylthio, arylthio, heteroarylthio, loweralkylcarbonyl, arylcarbonyl, or heteroarylcarbonyl moiety, $R_6$ is selected from the group consisting of phenyl, phenyloxyloweralkyl, and phenylloweralkyl. The present invention further includes compounds having these substituents wherein $R_6$ is further substituted optionally with a moiety selected from the group consisting of halogen, loweralkyl, halolowerlalkyl, loweralkyloxy, halolowerlakyloxy, carboxy, loweralkyloxycarbonyl, aryloxycarbonyl, (cycloloweralkyl)oxycarbonyl, aralkyloxycarbonyl, heteroaryloxycarbonyl, heteroaralkyloxycarbonyl, (heterocycloloweralkyl)oxycarbonyl, loweralkylsulfinyl, loweralkylsulfonyl, lowerallrylthio, arylthio, loweralkylcarbonyloxy, arylcarbonyloxy, aralkylcarbonyloxy, heteroarylcarbonyloxy, heteroaralkylcarbonyloxy, (cycloloweralkyl)carbonyloxy, (heterocycloloweralkyl)carbonyloxy, aminocarbonyl, loweraklylaminocarbonyl, arylaminocarbonyl, aralkylaminocarbonyl, heteroarylaminocarbonyl, and heteroaralkylaminocarbonyl.

The present invention also includes fused-ring pyrazole derivatives as illustrated above in which n is 1 and $X_{10}$ is selected from the group consisting of nitrogen, optionally substituted nitrogen, and optionally substituted methylene or methine, $R_6$ is selected from the group consisting of phenyl, phenyloxyloweralkyl, and phenylloweralkyl, $R_6$ includes at least one hydroxyl, thio, or optionally substituted loweralkyloxy, aryloxy, heteroaryloxy, loweralkylthio, arylthio, heteroarylthio, loweralkylcarbonyl, arylcarbonyl, or heteroarylcarbonyl moiety, $R_6$ is further substituted optionally with a moiety selected from the group consisting of halogen, loweralkyl, halolowerlalkyl, loweralkyloxy, halolowerlakyloxy, carboxy, loweralkyloxycarbonyl, aryloxycarbonyl, (cycloloweralkyl)oxycarbonyl, aralkyloxycarbonyl, heteroaryloxycarbonyl, heteroaralkyloxycarbonyl, (heterocycloloweralkyl)oxycarbonyl, loweralkylsulfinyl, loweralkylsulfonyl, loweralkylthio, arylthio, loweralkylcarbonyloxy, arylcarbonyloxy, aralkylcarbonyloxy, heteroarylcarbonyloxy, heteroaralkylcarbonyloxy, (cycloloweralkyl)carbonyloxy, (heterocycloloweralkyl)carbonyloxy, aminocarbonyl, loweraklylaminocarbonyl, arylaminocarbonyl, aralkylaminocarbonyl, heteroarylaminocarbonyl, and heteroaralkylaminocarbonyl, and $R_5$ is selected from the group consisting of hydrogen and optionally substituted loweralkyl, aryl, aralkyl, heteroaryl, heteroaralkyl, cycloalkyl, cycloheteroalkyl, loweralkylcarbonyl, arylcarbonyl, heteroarylcarbonyl, cycloalkylcarbonyl, cycloheteroalkylcarbonyl, aralkycarbonyl, heteroaralkylcarbonyl, (cycloalkyl)alkylcarbonyl, (cycloheteroalkyl)alkylcarbonyl, loweralkylaminocarbonyl, arylaminocarbonyl, aralkylaminocarbonyl, heteroarylaminocarbonyl, heteroaralkylaminocarbonyl, cycloalkylaminocarbonyl, (cycloalkyl)alkylaminocarbonyl, cycloheteroalkylaminocarbonyl, (cycloheteroalkyl)alkylaminocarbonyl, loweralkylsulfonyl, arylsulfonyl, heteroarylsulfonyl, cycloalkylsulfonyl, cycloheteroalkylsulfonyl, aralkylsulfonyl, heteroaralkylsulfonyl, (cycloalkyl)alkylsulfonyl, and (cycloheteroalkyl)alkylsulfonyl, Still other embodiments of the present invention include fused ring compounds of the general formula shown above for which n is 2 and each $X_{10}$ is selected independently from the group consisting of nitrogen, optionally substituted nitrogen, optionally substituted methylene, and optionally substituted methine. Again, these embodiments include fully aromatic and partly aromatic ring systems. More particular embodiments are those for which n is 2 and each $X_{10}$ is selected independently from the group consisting of nitrogen, optionally substituted nitrogen, optionally substituted methylene, and optionally substituted methine and $R_6$ is selected from the group consisting of optionally substituted aryl, heteroaryl, aralkyl, and heteroaralkyl. Still more particular embodiments having the structural pattern just described include those in which $R_6$ is optionally substituted aryl or aralkyl.

In other embodiments of the invention having the general fused ring structures shown for which n is 2 and each $X_{10}$ is selected independently from the group consisting of nitrogen, optionally substituted nitrogen, optionally substituted methylene, and optionally substituted methine, $R_6$ is selected from the group consisting of optionally substituted aryl, heteroaryl, aralkyl, and heteroaralkyl, more specifically wherein $R_6$ is optionally substituted aryl or aralkyl, are those for which $R_6$ includes at least one hydroxyl, thio, or optionally substituted loweralkyloxy, aryloxy, heteroaryloxy, loweralkylthio, arylthio, heteroarylthio, loweralkylcarbonyl, arylcarbonyl, or heteroarylcarbonyl moiety. More specific embodiments are those in which n, and $X_{10}$ have the values and identities just described, $R_6$ is selected from the group consisting of optionally substituted aryl, heteroaryl, aralkyl, and heteroaralkyl, more specifically $R_6$ is optionally substituted aryl or aralkyl, and $R_6$ includes at least one hydroxyl, thio, or optionally substituted loweralkyloxy, aryloxy, heteroaryloxy, loweralkylthio, arylthio, heteroarylthio, loweralkylcarbonyl, arylcarbonyl, or heteroarylcarbonyl moiety, wherein $R_6$ is selected from the group consisting of phenyl, phenyloxyloweralkyl, and phenylloweralkyl. More specific embodiments having this substituent pattern include those wherein $R_6$ is further substituted optionally with a moiety selected from the group consisting of halogen, loweralkyl, halolowerlalkyl, loweralkyloxy, haloloweralkyloxy, carboxy, loweralkyloxycarbonyll, aryloxycarbonyl, (cycloloweralkyl)oxycarbonyl, aralkyloxycarbonyl, heteroaryloxycarbonyl, heteroaralkyloxycarbonyl, (heterocycloloweralkyl)oxycarbonyl, loweralkylsulfinyl, loweralkylsulfonyl, loweralkylthio, arylthio, loweralkylcarbonyloxy, arylcarbonyloxy, aralkylcarbonyloxy, heteroarylcarbonyloxy, heteroaralkylcarbonyloxy, (cycloloweralkyl)carbonyloxy, (heterocycloloweralkyl)carbonyloxy, aminocarbonyl, loweraklylaminocarbonyl, arylaminocarbonyl, aralkylaminocarbonyl, heteroarylaminocarbonyl, and heteroaralkylaminocarbonyl. Still more specific embodiments include those for which n is 2 and each $X_{10}$ is selected independently from the group consisting of nitrogen, optionally substituted nitrogen, optionally substituted methylene, and optionally substituted methine, $R_6$ is selected from the group consisting of optionally substituted aryl, heteroaryl, aralkyl, and heteroaralkyl, more specifically $R_6$ is optionally substituted aryl or aralkyl, and $R_6$ includes at least one hydroxyl, thio, or optionally substituted loweralkyloxy, aryloxy, heteroaryloxy, loweralkylthio, arylthio, heteroarylthio, loweralkylcarbonyl, arylcarbonyl, or heteroarylcarbonyl moiety, wherein $R_6$ is selected from the group consisting of phenyl, phenyloxyloweralkyl, and phenylloweralkyl, more specifically wherein $R_6$ is further substituted optionally with a moiety selected from the group consisting of halogen, loweralkyl, halolowerlalkyl, loweralkyloxy, haloloworalkyl, carboxy, loweralkyloxycarbonyl, aryloxycarbonyl, (cycloloweralkyl)oxycarbonyl, aralkyloxycarbonyl, heteroaryloxycarbonyl, heteroaralkyloxycarbonyl, (heterocycloloweralkyl)oxycarbonyl, loweralkylsulfinyl, loweralkylsulfonyl, loweralkylthio, arylthio, loweralkylcarbonyloxy, arylcarbonyloxy, aralkylcarbonyloxy, heteroarylcarbonyloxy, heteroaralkylcarbonyloxy, (cycloloweralkyl)carbonyloxy, (heterocycloloweralkyl)carbonyloxy, aminocarbonyl, loweraklylaminocarbonyl, arylaminocarbonyl, aralkylaminocarbonyl, heteroarylaminocarbonyl, and heteroaralkylaminocarbonyl, and $R_5$ is selected from the group consisting of hydrogen and optionally substituted loweralkyl, aryl, aralkyl, heteroaryl, heteroaralkyl, cycloalkyl, cycloheteroalkyl, loweralkylcarbonyl, arylcarbonyl, heteroarylcarbonyl, cycloalkylcarbonyl, cycloheteroalkylcarbonyl, aralkycarbonyl, heteroaralkylcarbonyl, (cycloalkyl)alkylcarbonyl, (cycloheteroalkyl)alkylcarbonyl, loweralkylaminocarbonyl, arylaminocarbonyl, aralkylaminocarbonyl, heteroarylaminocarbonyl, heteroaralkylaminocarbonyl, cycloalkylaminocarbonyl, (cycloalkyl)alkylaminocarbonyl, cycloheteroalkylaminocarbonyl, (cycloheteroalkyl)alkylaminocarbonyl, loweralkylsulfonyl, arylsulfonyl, heteroarylsulfonyl, cycloalkylsulfonyl, cycloheteroalkylsulfonyl, aralkylsulfonyl, heteroaralkylsulfonyl, (cycloalkyl)alkylsulfonyl, and (cycloheteroalkyl)alkylsulfonyl.

In another embodiment, the present invention provides fused rings structures shown above in which $X_6$–$X_9$ are selected independently from the group consisting of nitrogen and optionally substituted methine. More particular embodiments are those for which at least one of $X_6$–$X_9$ is methine substituted with a moiety selected from the group consisting of loweralkyloxy, aryloxy, heteroaryloxy, loweralkylthio, arylthio, heteroarylthio, loweralkylcarbonyl, arylcarbonyl, and heteroarylcarbonyl. Still more particular fused ring embodiments are those for which $X_6$–$X_9$ are selected independently from the group consisting of nitrogen and optionally substituted methine, at least one of $X_6$–$X_9$ is methine substituted with a moiety selected from the group consisting of loweralkyloxy, aryloxy, heteroaryloxy, loweralkylthio, arylthio, heteroarylthio, loweralkylcarbonyl, arylcarbonyl, and heteroarylcarbonyl and $X_7$ is methine substituted with hydroxy or loweralkyloxy. Other more specific embodiments are those in which $X_6$–$X_9$ are selected independently from the group consisting of nitrogen and optionally substituted methine, at least one of $X_6$–$X_9$ is methine substituted with a moiety selected from the group consisting of loweralkyloxy, aryloxy, heteroaryloxy, loweralkylthio, arylthio, heteroarylthio, loweralkylcarbonyl, arylcarbonyl, and heteroarylcarbonyl, n is 1 and $X_{10}$ is selected from the group consisting of nitrogen, optionally substituted nitrogen, and optionally substituted methylene or methine.

Still more specific embodiments include those for which $X_6$–$X_9$, n, and $X_{10}$ have the values just defined and $R_6$ is selected from the group consisting of optionally substituted aryl, heteroaryl, aralkyl, and heteroaralkyl. In yet more specific embodiments, $X_6$–$X_9$, n and $X_{10}$ have the values just defined $R_6$ is selected from the group consisting of optionally substituted aryl, heteroaryl, aralkyl, and heteroaralkyl, and more particularly $R_6$ is optionally substituted aryl or aralkyl. Yet more specific embodiments are those for which $X_6$–$X_9$, n and $X_{10}$ have the values just defined $R_6$ is selected from the group consisting of optionally substituted aryl, heteroaryl, aralkyl, and heteroaralkyl, more particularly $R_6$ is optionally substituted aryl or aralkyl, and $R_6$ includes at least one hydroxyl, thio, or optionally substituted loweralkyloxy, aryloxy, heteroaryloxy, loweralkylthio, arylthio, heteroarylthio, loweralkylcarbonyl, arylcarbonyl, or heteroarylcarbonyl moiety. Other embodiments are those for which n and $X_{10}$ have the values just defined $R_6$ is selected from the group consisting of optionally substituted aryl, heteroaryl, aralkyl, and heteroaralkyl, more particularly $R_6$ is optionally substituted aryl or aralkyl, such that $R_5$ includes at least one hydroxyl, thio, or optionally substituted loweralkyloxy, aryloxy, heteroaryloxy, loweralkylthio, arylthio, heteroarylthio, loweralkylcarbonyl, arylcarbonyl, or heteroarylcarbonyl moiety, and further $R_6$ is selected from the group consisting of phenyl, phenyloxyloweralkyl, and phenylloweralkyl. Yet more particular embodiments having the latter substituent pattern are those in which $R_6$ is further substituted optionally with a moiety selected from the group consisting of halogen, loweralkyl, halolowerlalkyl, loweralkyloxy, halolowerlakyloxy, carboxy, loweralkyloxycarbonyl, aryloxycarbonyl, (cycloloweralkyl)oxycarbonyl, aralkyloxycarbonyl, heteroaryloxycarbonyl, heteroaralkyloxycarbonyl, (heterocycloloweralkyl)oxycarbonyl, loweralkylsulfinyl, loweralkylsulfonyl, loweralkylthio, arylthio, loweralkylcarbonyloxy, arylcarbonyloxy, aralkylcarbonyloxy, heteroarylcarbonyloxy, heteroaralkylcarbonyloxy, (cycloloweralkylcarbonyloxy, (heterocycloloweralkyl)carbonyloxy, aminocarbonyl, loweraklylaminocarbonyl, arylaminocarbonyl, aralkylaminocarbonyl, heteroarylaminocarbonyl, and heteroaralkylaminocarbonyl.

Still more particular embodiments having $X_6$–$X_9$ are selected independently from the group consisting of nitrogen and optionally substituted methine, at least one of $X_6$–$X_9$ is methine substituted with a moiety selected from the group consisting of loweralkyloxy, aryloxy, heteroaryloxy, loweralkylthio, arylthio, heteroarylthio, loweralkylcarbonyl, arylcarbonyl, and heteroarylcarbonyl, n is 1 and $X_{10}$ is selected from the group consisting of nitrogen, optionally substituted nitrogen, and optionally substituted methylene or methine, $R_6$ is selected from the group consisting of optionally substituted aryl, heteroaryl, aralkyl, and heteroaralkyl, more particularly $R_6$ is optionally substituted aryl or aralkyl, such that $R_6$ includes at least one hydroxyl, thio, or optionally substituted loweralkyloxy, aryloxy, heteroaryloxy, loweralkylthio, arylthio, heteroarylthio, loweralkylcarbonyl, arylcarbonyl, or heteroarylcarbonyl moiety, further such that $R_6$ is selected from the group consisting of phenyl, phenyloxyloweralkyl, and phenylloweralkyl and $R_6$ is further substituted optionally with a moiety selected from the group consisting of halogen, loweralkyl, halolowerlalkyl, loweralkyloxy, halolowerlakyloxy, carboxy, loweralkyloxycarbonyl, aryloxycarbonyl, (cycloloweralkyl)oxycarbonyl, aralkyloxycarbonyl, heteroaryloxycarbonyl, heteroaralkyloxycarbonyl, (heterocycloloweralkyl)oxycarbonyl, loweralkylsulfinyl, loweralkylsulfonyl, loweralkylthio, arylthio, loweralkylcarbonyloxy, arylcarbonyloxy, aralkylcarbonyloxy, heteroarylcarbonyloxy, heteroaralkylcarbonyloxy, (cycloloweralkyl)carbonyloxy, (heterocycloloweralkylcarbonyloxy, aminocarbonyl, loweraklylaminocarbonyl, arylaminocarbonyl, aralkylaminocarbonyl, heteroarylaminocarbonyl, and heteroaralkylaminocarbonyl, wherein $R_5$ is selected from the group consisting of hydrogen and optionally substituted loweralkyl, aryl, aralkyl, heteroaryl, heteroaralkyl, cycloalkyl, cycloheteroalkyl, loweralkylcarbonyl, arylcarbonyl, heteroarylcarbonyl, cycloalkylcarbonyl, cycloheteroalkylcarbonyl, aralkycarbonyl, heteroaralkylcarbonyl, (cycloalkyl)alkylcarbonyl, (cycloheteroalkyl)alkylcarbonyl, loweralkylaminocarbonyl, arylaminocarbonyl, aralkylaminocarbonyl, heteroarylaminocarbonyl, heteroaralkylaminocarbonyl, cycloalkylaminocarbonyl, (cycloalkyl)alkylaminocarbonyl, cycloheteroalkylaminocarbonyl, (cycloheteroalkyl) alkylaminocarbonyl, loweralkylsulfonyl, arylsulfonyl, heteroarylsulfonyl, cycloalkylsulfonyl, cycloheteroalkylsulfonyl, aralkylsulfonyl, heteroaralkylsulfonyl, (cycloalkyl)alkylsulfonyl, and (cycloheteroalkyl)alkylsulfonyl.

Yet other embodiments of the invention including the compounds of the general formula above are those in which $X_6$–$X_9$ are selected independently from the group consisting of nitrogen and optionally substituted methine, at least one of $X_6$–$X_9$ is methine substituted with a moiety selected from the group consisting of loweralkyloxy, aryloxy, heteroaryloxy, loweralkylthio, arylthio, heteroarylthio, loweralkylcarbonyl, arylcarbonyl, and heteroarylcarbonyl, n is 2 and each $X_{10}$ is selected independently from the group consisting of nitrogen, optionally substituted nitrogen, optionally substituted methylene, and optionally substituted methine. More specific embodiments are those in which $X_6$–$X_9$ are selected independently from the group consisting of nitrogen and optionally substituted methine, at least one of $X_6$–$X_9$ is methine substituted with a moiety selected from the group consisting of loweralkyloxy, aryloxy, heteroaryloxy, loweralkylthio, arylthio, heteroarylthio, loweralkylcarbonyl, arylcarbonyl, and heteroarylcarbonyl, n is 2 and each $X_{10}$ is selected independently from the group consisting of nitrogen, optionally substituted nitrogen, optionally substituted methylene, and optionally substituted methine, and $R_6$ is selected from the group consisting of optionally substituted aryl, heteroaryl, aralkyl, and heteroaralkyl. Still more specific embodiments include those for which $X_6$–$X_9$, n, and $X_{10}$ have the values just defined $R_6$ is selected from the group consisting of optionally substituted aryl, heteroaryl, aralkyl, and heteroaralkyl and, more particularly, $R_6$ is optionally substituted aryl or aralkyl. In yet more specific embodiments, $X_6$–$X_9$, n and $X_{10}$ have the values just defined $R_6$ is selected from the group consisting of optionally substituted aryl, heteroaryl, aralkyl, and heteroaralky, more particularly, $R_6$ is optionally substituted aryl or aralkyl, and $R_6$ includes at least one hydroxyl, thio, or optionally substituted loweralkyloxy, aryloxy, heteroaryloxy, loweralkylthio, arylthio, heteroarylthio, loweralkylcarbonyl, arylcarbonyl, or heteroarylcarbonyl moiety. Yet more specific embodiments are those for which $X_6$–$X_9$, n and $X_{10}$ have the values just defined $R_6$ is selected from the group consisting of optionally substituted aryl, heteroaryl, aralkyl, and heteoaralky, more particularly, $R_6$ is optionally substituted aryl or aralkyl, and $R_6$ includes at least one hydroxyl, thio, or optionally substituted loweralkyloxy, aryloxy, heteroaryloxy, loweralkylthio, arylthio, heteroarylthio, loweralkylcarbonyl, arylcarbonyl, or heteroarylcarbonyl moiety, such that $R_6$ is selected from the group consisting of phenyl, phenyloxyloweralkyl, and phenylloweralkyl, and $R_6$ is further substituted optionally with a moiety selected from the group consisting of halogen, loweralkyl, halolowerlalkyl, loweralkyloxy, halolowerlakyoxy, carboxy, loweralkyloxycarbonyl, aryloxycarbonyl, (cycloloweralkyl)oxycarbonyl, aralkyloxycarbonyl, heteroaryloxycarbonyl, heteroaralkyloxycarbonyl, (heterocycloloweralkyl) oxycarbonyl, loweralkylsulfinyl, loweralkylsulfonyl, loweralkylthio, arylthio, loweralkylcarbonyloxy, arylcarbonyloxy, aralkylcarbonyloxy, heteroarylcarbonyloxy, heteroaralkylcarbonyloxy, (cycloloweralkyl)carbonyloxy, (heterocycloloweralkyl) carbonyloxy, aminocarbonyl, loweraklylaminocarbonyl, arylaminocarbonyl, aralkylaminocarbonyl, heteroarylaminocarbonyl, and heteroaralkylaminocarbonyl. Yet other embodiments of the compounds having the fused ring structures shown above have the values $X_6$–$X_9$, n, $X_{10}$, and $R_6$ just described above and further $R_5$ is selected from the group consisting of hydrogen and optionally substituted loweralkyl, aryl, aralkyl, heteroaryl, heteroaralkyl, cycloalkyl, cycloheteroalkyl, loweralkylcarbonyl, arylcarbonyl, heteroarylcarbonyl, cycloalkylcarbonyl, cycloheteroalkylcarbonyl, aralkycarbonyl, heteroaralkylcarbonyl, (cycloalkyl)alkylcarbonyl, (cycloheteroalkyl)alkylcarbonyl, loweralkylaminocarbonyl, arylaminocarbonyl, aralkylaminocarbonyl, heteroarylaminocarbonyl, heteroaralkylaminocarbonyl, cycloalkylaminocarbonyl, (cycloalkyl)alkylaminocarbonyl, cycloheteroalkylaminocarbonyl, (cycloheteroalkyl) alkylaminocarbonyl, loweralkylsulfonyl, arylsulfonyl, heteroarylsulfonyl, cycloalkylsulfonyl, cycloheteroalkylsulfonyl, aralkylsulfonyl, heteroaralkylsulfonyl, (cycloalkyl)alkylsulfonyl, and (cycloheteroalkyl)alkylsulfonyl.

4.3 Synthesis of the Compounds of the Invention

The compounds of the present invention can be synthesized using techniques and materials known to those of skill in the art (Carey and Sundberg 1983; Carey and Sundberg 1983; Greene and Wuts 1991; March 1992). Starting materials for the compounds of the invention may be obtained using standard techniques and commercially available precursor materials, such as those available from Aldrich Chemical Co. (Milwaukee, Wis.), Sigma Chemical Co. (St. Louis, Mo.), Lancaster Synthesis (Windham, N.H.), Apin Chemicals, Ltd. (New Brunswick, N.J.), Ryan Scientific (Columbia, S.C.), Maybridge (Cornwall, England), Arcos (Pittsburgh, Pa.), and Trans World Chemicals (Rockville, Md.)

The procedures described herein for synthesizing the compounds of the invention may include one or more steps of protection and deprotection (e.g., the formation and removal of acetal groups) (Greene and Wuts 1991). In addition, the synthetic procedures disclosed below can include various purifications, such as column chromatography, flash chromatography, thin-layer chromatography ("TLC"), recrystallization, distillation, high-pressure liquid chromatography ("HPLC") and the like. Also, various techniques well known in the chemical arts for the identification and quantification of chemical reaction products, such as proton and carbon-13 nuclear magnetic resonance ($^1$H and $^{13}$C NMR), infrared and ultraviolet spectroscopy ("IR" and "UV"), X-ray crystallography, elemental analysis ("EA"). HPLC and mass spectroscopy ("MS") can be used for identification, quantitation and purification as well.

Scheme 1 is a general scheme for synthesis of pyrazoles.

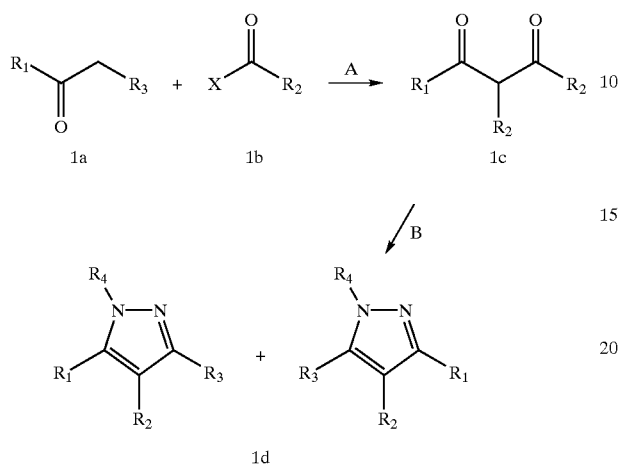

Step A is a Claisen-type condensation, in which X is a leaving group such as —OR (R=alkyl, aryl, arlkyl, heteroaryl, or heteroaralkyl), or halogen. When X is —OR and R is alkyl (e.g., X is methoxy or ethoxy) the reaction of 1a and 1b to produce 1c can be done using procedures known to those of skill in the organic chemistry arts (Tietze and Eicher 1989). When X is halogen, e.g., Cl, a typical procedure involves deprotonation of ketone 1a with a base such as lithium bis(trimethylsilyl)amide (LiHMDS) followed by addition of 1b. Suitable solvents for performing such reactions will be familiar to those of skill in the organic chemistry arts. Examples of suitable solvents include ether-type solvents such as tetrahydrofuran ("THF"), diethyl ether ($H_3CH_2COCH_2CH_3$), or aliphatic and aromatic hydrocarbon solvents such as cyclohexane ($C_6H_2$) and toluene ($C_7H_8$). Typical reaction temperatures range from $-78°$ C. to $+25°$ C. and the reaction times from 6 hours ("h") to 20 h. Step B is a cycloaddition reaction to form the pyrazole heterocycle. This can be done using the known Know pyrazole synthesis method. Typically, 1c, hydrazine ($NH_2NHR_4$) and catalytic amount of HCl (aq.) in ethanol are heated to reflux overnight. Removal of the solvent followed by routine extraction yields the crude material, which can be purified to afford pure compound 1d. If $R_1$ and $R_2$ are not identical, then a mixture of regioisomers is formed. In some cases, protecting groups have to be removed to obtain the desired compound (step not shown). Protection and deprotection will depend greatly on the chemical properties of the molecule and its functional groups; appropriate methods for protection and deprotection are well known in the organic chemistry arts (Greene and Wuts 1991). For example, when $R_1$ is methoxyphenyl, three methods can be used for demethylation: 1) reaction of aqueous hydrogen bromide (HBr) and glacial acetic acid with 1d with heating to 100–120° C. for 6 to 16 h; 2) reaction of ethane thiol, aluminum trichloride, and id in dichloroethane with stirring at room temperature ("rt") for 16 to 72 h; or 3) stirring boron tribromide with 1d in dichloromethane at room temperature overnight.

Scheme 2 describes an alternative method to synthesize compound 1c of Scheme 1.

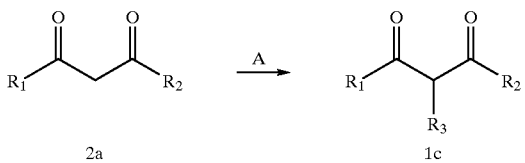

Step A above can be performed using various methods familiar to those of skill in the organic chemistry arts. For example, at least three well known methods can be used to convert 3a to 1c: 1) deprotonation of 3a with a base such as sodium hydride (NaH) in an aprotic solvent such as dimethylformamide ("DMF") or THF, followed by reaction of the resulting anion with an electrophile $R_3X$, wherein X is a leaving group such as halogen or MsO; or 2) compound 3a is reacted with $R_3X$, potassium carbonate and tetrabutylammonium bromide in DMF while stirring at rt $-100°$ C. for 6 to 24 h. If $R_3$ is paraalkyloxyphenyl, then a plumbate method can be applied (Craig, Holder et al. 1979; Pinhey, Holder et al. 1979).

Scheme 3 describes an alternative method to synthesize compound 1d in Scheme 1.

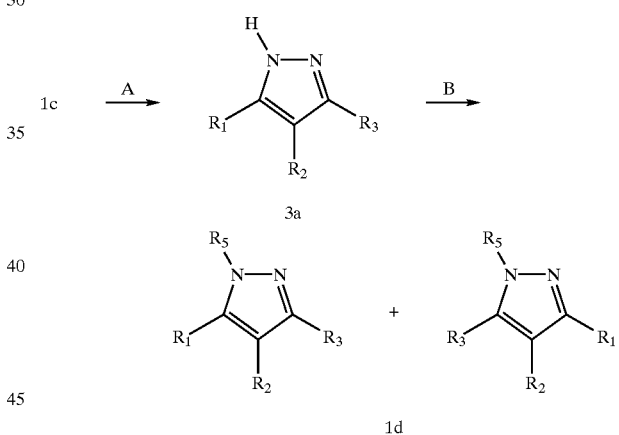

Pyrazole 3a was synthesized (Step A) by mixing diketone 1c with excess hydrazine and catalytic amount of a protonic acid such as HCl or acetic acid. The solvent can be ethanol, methanol, or DMSO; the reaction is usually performed at temperatures from 60–100° C. and completed within 18 h. Alkylation of 4a (Step B) can be carried out using known techniques, such as exemplified by the following two methods (both methods generate a mixture of regioisomers). In one method, a mixture of 3a, cesium carbonate and an alkylating agent $R_5X$ (wherein X=leaving group such as a halide or MsO) in DMF was heated to 100° C. overnight. A work-up under aqueous conditions, followed by extraction and purification (if necessary), affords the product 1d. In a second method 4a is deprotonated using 0 sodium hydride in DMF or THF, followed by addition of an electrophile such as an alkyl halide, sulfonyl chloride, or acyl chloride. The reaction is typically performed at a temperature between rt and 60° C. and completed within 16 h.

Scheme 4

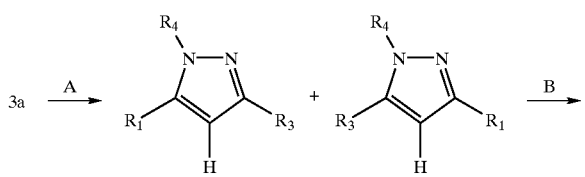

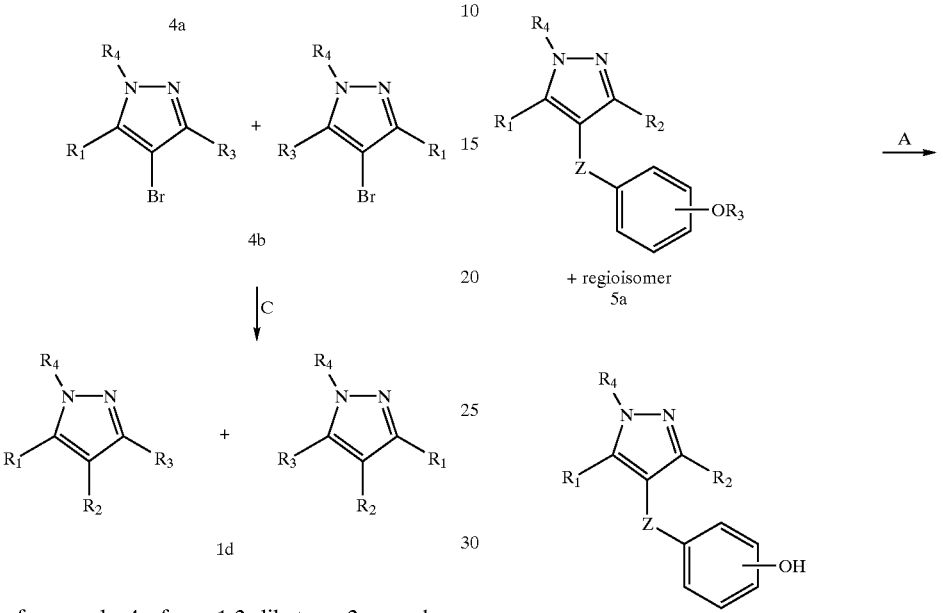

Formation of pyrazole 4a from 1,3-diketone 3a can be completed using the procedures described in Scheme 1 and in Scheme 3. Bromination of pyrazole 4a (Step B) can be performed by addition of bromine to a chloroform solution solution of 4a, at a reaction temperature from rt-55° C. from 0.5 to 2 h. A variety of $R_2$ substituents (Step C) can be introduced to 4-bromopyrazole 4b by known methods. For example, metal-halogen exchange followed by trapping the resulting anion with an electrophile can be used to attach $R_3$. This can be done, for example, by reaction of bromopyrazole 4b in THF solution at −78° C. with n-BuLi. The mixture is stirred at −78° C. for 1 h. The desired electrophile corresponding to $R_2$ is then added, and the reaction is warmed from 0° C.-rt over a period between 2 to 16 h. Suitable electrophiles include, but are not limited to, the following: alkyl halides, disulfides, iodine, N-chlorosuccinimide, tosyl nitrile, ethyl chloroformate, acid chlorides, carbon dioxide, dimethylformamide, aldehydes, Weinreb amides and sulfonyl chlorides. Alternatively, a 4-carboxypyrazole (i.e. $R_3$=—$CO_2$) can be obtained if carbon dioxide is used as the electrophile. The carboxylic acid can be further transformed to various esters, amides, and ketones. To form an amide at $R_2$, typical amide bond formation condition can be applied. For example, the corresponding carboxylic acid can be activated with 1-(3-dimethylaminopropyl)-3-ethylcarbodiimide ("EDC") HCl salt, 1-hydroxybenzotriazole ("HOBt"), and Hunig's base and mixed with a primary or secondary amine in THF or DMF. The reaction is complete in 6 to 16 hours at rt. Suzuki coupling can also be used to introduce aryl and alkenyl moieties at $R_3$ (Miyaura, Author et al. 1979; Miyaura and Suzuki 1979). The Ullmann reaction can be used to introduce aryloxy groups at $R_3$ (Knight; Semmelhack, Author et al. ). Moieties having C—N and C—O bonds at 4-position of pyrazole 4b can be achieved by applying palladium catalyzed coupling reactions (Palucki, Wolfe et al. 1996; Wolfe and Buchwald 1996; Wolfe, Wagaw et al. 1996).

Scheme 5 illustrates more specific modifications at 4-position of the pyrazole.

Starting material 5a can be synthesized by methods described above. The linker Z can be —$CH_2$—, —O—, —S—, —$SO_2$—, NR'R"—, —(C=O)—, —(C=NOR)—, or the aryl group can be attached to the pyrazole core directly. In the Scheme above, $R_3$ is a phenol protecting group which can be selectively removed (Greene and Wuts 1991). However, other suitable groups such as, but not limited to, thiols, protected thiols, amines, and the like can be synthesized using analogous methodologies. One specific methodology is described with respect to Scheme 6 below where Z is —$SO_2$— or —(C=O)— and Y is O, S, or N. The index n can be 1, 2, or 3, and $R_4$ is —NR'R" or —N(R') (C=O)R". In one example, sodium hydride was mixed with HY($CH_2$)$_n$$R_4$, to generate the nucleophile and added to 6a in THF or DMF solution at a temperature from between rt and 60° C. and completed within 2 to 8 h.

Scheme 6

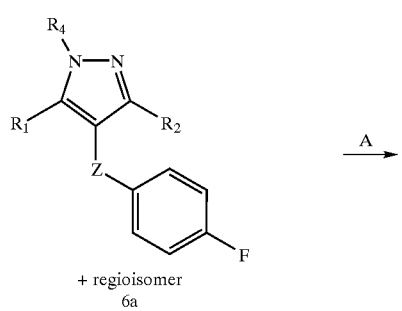
+ regioisomer
6a

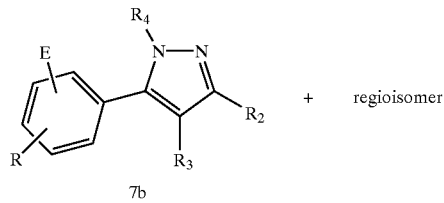
7b where E is alkyl, aryl, aralkyl, halo, cyano, amido, carboxy, sulfide, and sulfoxide. Starting material 7a can be synthesized according to methods described above. The functional group E is introduced using the methods described in Step C of Scheme 3 above. Modifications at the 4-position of the pyrazole can be made, for example, using the methods described with respect to Scheme 8.

Scheme 8

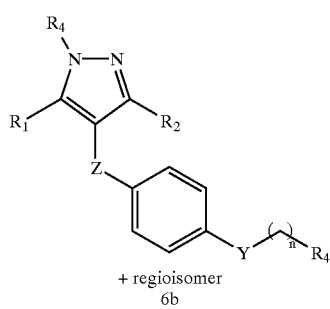
+ regioisomer
6b

Specific modifications at 5-position of the pyrazole can be performed using the methodologies described with Scheme 7 below:

Scheme 7

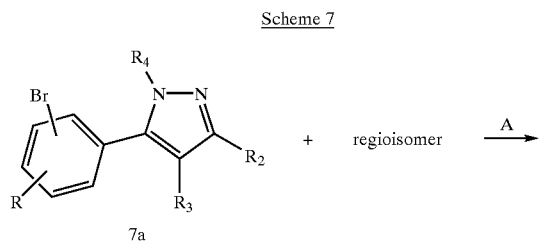
7a

Starting material 8a was synthesized according to methods described in Scheme 1. Bromination at the methyl position was performed using N-bromosuccinimide in carbon tetrachloride. Alkylation to form derivatives of 8c where R" is —OR, —SR or —NRR' can be conducted with appropriate nucleophile in a suitable solvent (e.g., DMF or THF) at temperatures ranging between rt and 100° C.

The procedures described above can be applied to solid phase methodologies as well. The actual implementation depends, of course, on the details of the desired products and starting materials. One example of a suitable methodology, where $R_1$ is hydroxyphenyl, is shown in Scheme 9.

Scheme 9

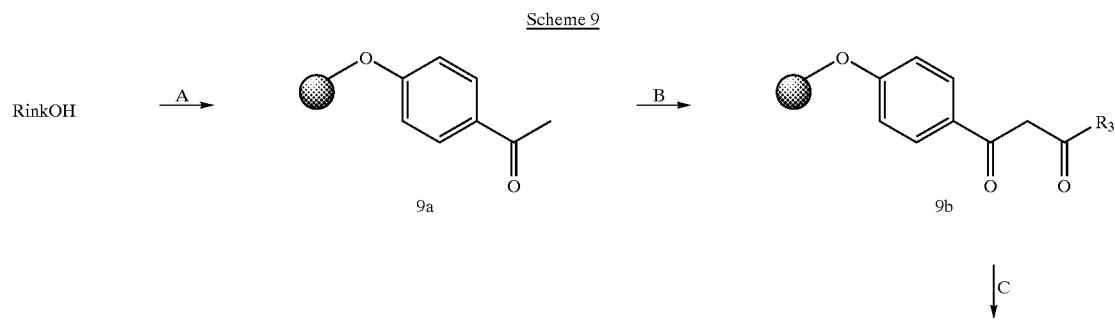

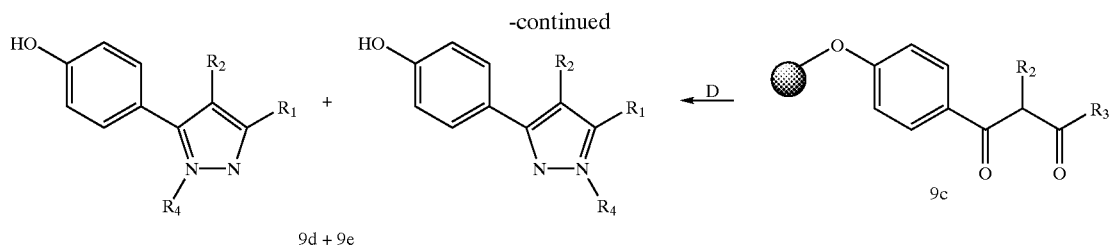

9d + 9e

9c

In step A, commercially available hydroxylated Rink resin (Calbiochem, La Jolla, Calif.) is reacted with mesyl chloride and Hünig's base in methylene chloride ($CH_2Cl_2$) at 0° C. with warming to room temperature over a two-hour period. Next, 4-hydroxyacetophenone and Hünig's base are reacted with the resin product in methylene chloride at room temperature overnight to provide resin-bound provides resin-bound ketone 9a. Reaction of the bound ketone with an ester bearing the $R_3$ substituent ($R_3CO_2R$) and base (e.g., potassium tert-butoxide, t-BuOK and dibenzo-18-crown-6) in a suitable solvent (e.g., THF) at 70° C. for six hours (Step B) provides diketone 9b. Deprotonation of 9b, using, e.g., tert-butyl ammonium iodide ("TBAI") under mild conditions (70° C. overnight) and the $R_2$ substituent bearing a suitable leaving group (e.g., halogen, tosylate, mesylate) provides 9c. Cyclization of 9c to form the desired pyrazole (resin-bound regioisomers 9d and 9e) can be performed by reaction of the bound diketone with $R_4NHNH_2$ and Hünig's base in a suitable solvent (e.g., dimethylsulfoxide, ("DMSO")) at 70° C. for fifteen hours. Cleavage from the resin can be performed under mild conditions (e.g., reaction with 5% trifluoroacetic acid. ("TFA") in methylene chloride) provides the final products 9d and 9e.

4.4 Biological Activity

The activities of the compounds of the invention to function as estrogen receptor agonists or antagonists can be determined using a wide variety of assays known to those having skill in the biochemistry, medicinal chemistry, and endochrinology arts. Several useful assays are described generally in this Section 4.4. Specific examples are described in Section 5.2 below.

4.4.1 Assays for Estrogen Receptor Modulating Activity In Vivo and Ex Vivo 4.4.1.1 Allen-Doisy Test for Estrogenicity This test (described in greater detail in Section 5.2.1.1 below) is used to evaluate a test compound for estrogenic activity, and, more specifically, the ability of a test compound to induce an estrogenic cornification of vaginal epithelium (Allen and Doisy 1923; Mühlbock 1940; Terenius 1971). Test compounds are formulated and administered subcutaneously to mature, ovariectomized female rats in test groups. In the third week after bilateral ovariectomy, the rats are primed with a single subcutaneous dose of estradiol to ensure maintenance of sensitivity and greater uniformity of response. In the fourth week, 7 days after priming, the test compounds are administered. The compounds are given in three equal doses over two days (evening of the first day and morning and evening of the second day). Vaginal smears are then prepared twice daily for the following three days. The extent of cornified and nucleated epithelial cells, as well as of leucocytes are evaluated for each of the smears.

4.4.1.2 Anti-Allen-Doisy Test for Anti-Estrogenicity

This test (described in greater detail in Section 5.2.1.2 below) is used to evaluate a test compound for antiestrogenic activity by observation of cornification of the vaginal epithelium of in ovariectornized rats after administration of a test compound (Allen and Doisy 1923; Mülhbock 1940; Terenius 1971). Evaluation of antiestrogenic activity is performed using mature female rats which, two weeks after bilateral ovariectomy, are treated with estradiol to induce a cornification of the vaginal epithelial. This was followed by administration of the test compound in a suitable formulation daily for 10 days. Vaginal smears are prepared daily, starting on the first day of test compound administration and proceeding until one day following the last administration of test compound. The extent of cornified and nucleated epithelial cells and leucocytes is evaluated for each of the smears as above.

4.4.1.3 Immature Rat Uterotrophic Bioassay for Estrogenicity and Anti-Estrogenicity Changes in uterine weight in response to estrogenic stimulation can be used to evaluate the estrogenic characteristics of test compounds on uterine tissues (Reel, Lamb et al. 1996; Ashby, Odum et al. 1997). In one example, described in Section 5.2.1.3 below, immature female rats having low endogenous levels of estrogen are dosed with test compound (subcutaneously) daily for 3 days. Compounds are formulated as appropriate for subcutaneous injection. As a control, 17-beta-estradiol is administered alone to one dose group. Vehicle control dose groups are also included in the study. Twenty-four hours after the last treatment, the animals are necropsied, and their uteri excised, nicked, blotted and weighed to. Any statistically significant increases in uterine weight in a particular dose group as compared to the vehicle control group demonstrate evidence of estrogenicity.

4.4.1.4 Estrogen Receptor Antagonist Efficacy in MCF-7 Xenograft Model

This test (described in detail in Section 5.2.1.4 below) is used to evaluate the ability of a compound to antagonize the growth of an estrogen-dependent breast MCF-7 tumor in vivo. Female Ncr-nu mice are implanted subcutaneously with an MCF-7 mammary tumor from an existing in vivo passage. A 17-(β-estradiol pellet is implanted on the side opposite the tumor implant on the same day. Treatment with test compound begins when tumors have reached a certain minimum size (e.g., 75–200 mg). The test compound is administered subcutaneously on a daily basis and the animals are subjected to daily mortality checks. Body weights and tumor volume are determined twice a week starting the first day of treatment. Dosing continues until the tumors reach 1,000 $mm^3$. Mice with tumors larger than 4,000 mg, or with ulcerated tumors, are sacrificed prior to the day of the study determination. The tumor weights of animals in the treatment group are compared to those in the untreated control group as well as those given the estradiol pellet alone.

4.4.1.5 OVX Rat Model

This model evaluates the ability of a compound to reverse the decrease in bone density and increase in cholesterol levels resulting from ovariectomy. One example of such a model is described in Section 5.2.1.5. Three-month old female rats are ovariectomized, and test compounds are administered daily by subcutaneous route beginning one day post-surgery. Sham operated animals and ovariectomized animals with vehicle control administered are used as control groups. After 28 days of treatment, the rats are weighed, the overall body weight gains obtained, and the animals euthanized. Characteristics indicative of estrogenic activity, such as blood bone markers (e.g., osteocalcin, bone-specific alkaline phosphatase), total cholesterol, and urine markers (e.g., deoxypyridinoline, creatinine) are measured in addition to uterine weight. Both tibiae and femurs are removed from the test animals for analysis, such as the measurement of bone mineral density. A comparison of the ovariectomized and test vehicle animals to the sham and ovariectomized control animals allows a determination of the tissue specific estrogenic/anti-estrogenic effects of the test compounds.

4.4.2 Assays for Estrogen Receptor Modulating Activity In Vitro 4.4.2.1 ERα/ERβ Binding Assays For evaluation of ERα/ERβ receptor binding affinity, a homogeneous scintillation proximity assay is used (described in Sections 5.2.2.1 and 5.2.2.2 below). 96-well plates are coated with a solution of either ERα or ERβ. After coating, the plates are washed with PBS. The receptor solution is added to the coated plates, and the plates are incubated. For library screening, [$^3$H]estradiol is combined with the test compounds in the wells of the 96-well plate. Non-specific binding of the radio-ligand is determined by adding estradiol to one of the wells as a competitor. The plates are gently shaken to mix the reagents and a sample from each of the wells is then transferred to the pre-coated ERα or ERβ plates. The plates are sealed and incubated, and the receptor-bound estradiol read directly after incubation using a scintillation counter to determine test compound activity. If estimates of both bound and free ligand are desired, supernatant can be removed and counted separately in a liquid scintillation counter.

4.4.2.2 ERα/ERβ Transactivation Assays

The estrogenicity of the compounds of the invention can be evaluated in an in vitro bioassay using Chinese hamster ovary ("CHO") cells that have been stably co-transfected with the human estrogen receptor ("hER"), the rat oxytocin promoter ("RO") and the luciferase reporter gene ("LUC") as described in Section 5.2.2.3 below. The estrogen transactivation activity (potency ratio) of a test compound to inhibit transactivation of the enzyme luciferase as mediated by the estrogen receptor is compared with a standard and the pure estrogen antagonist.

4.4.2.3 MCF-7 Cell Proliferation Assays

MCF-7 cells are a common line of breast cancer cells used to determine in vitro estrogen receptor agonist/antagonist activity (MacGregor and Jordan 1998). The effect of a test compound on the proliferation of MCF-7 cells, as measured by the incorporation of 5-bromo-2'-deoxyuridine ("BrdU") in a chemiluminescent assay format, can be used to determine the relative agonist/antagonist activity of the test compound. MCF-7 cells (ATCC HTB-22) are mainatined in log-phase culture. The cells are plated and incubated in phenol-free medium to avoid external sources of estrogenic stimulus (MacGregor and Jordan 1998). The test compound is added at varying concentrations to determine an $IC_{50}$- for the compound. To determine agonist activity, the assay system is kept free of estrogen or estrogen-acting sources. To determine antagonist activity, controlled amounts of estrogen are added.

4.5 Pharmaceutical Compositions

The compounds of the present invention can be used in the form of salts derived from inorganic or organic acids. These salts include, but are not limited to, the following: acetate, adipate, alginate, citrate, aspartate, benzoate, benzenesulfonate, bisulfate, butyrate, camphorate, camphorsulfonate, digluconate, cyclopentanepro-pionate, dodecylsulfate, ethanesulfonate, glucoheptanoate, glycerophosphate, hemi-sulfate, heptanoate, hexanoate, fumarate, hydrochloride, hydrobromide, hydroiodide, 2-hydroxyethanesulfonate, lactate, maleate, methanesulfonate, nicotinate, 2-napth-alenesulfonate, oxalate, pamoate, pectinate, sulfate, 3-phenylpropionate, picrate, pivalate, propionate, succinate, tartrate, thiocyanate, p-toluenesulfonate and undecanoate. Also, any basic nitrogen-containing groups can be quaternized with agents such as loweralkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulfuric acid, and phosphoric acid, and organic acids such as oxalic acid, maleic acid, succinic acid and citric acid. Basic addition salts can be prepared in situ during the final isolation and purification of the compounds of the invention, or separately by reacting carboxylic acid moieties with a suitable base such as the hydroxide, carbonate or bicarbonate of a pharmaceutically acceptable metal cation or with ammonia, or an organic primary, secondary or tertiary amine. Pharmaceutically acceptable salts include, but are not limited to, cations based on the alkali and alkaline earth metals, such as sodium, lithium, potassium, calcium, magnesium, aluminum salts and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. Other representative organic amines useful for the formation of base addition salts include diethylamine, ethylenediamine, ethanolamine, diethanolamine, piperazine and the like.

Compounds of the present invention can be administered in a variety of ways including enteral, parenteral and topical routes of administration. For example, suitable modes of administration include oral, subcutaneous, transdermal, transmucosal, iontophoretic, intravenous, intramuscular, intraperitoneal, intranasal, subdural, rectal, vaginal, and the like.

In accordance with other embodiments of the present invention, there is provided a composition comprising an estrogen receptor-modulating compound of the present invention, together with a pharmaceutically acceptable carrier or excipient.

Suitable pharmaceutically acceptable excipients include processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-(β-cyclodextrin, polyvinylpyrrolidinone, low melting waxes, ion exchange resins, and the like, as well as combinations of any two or more thereof. Other suitable pharmaceutically acceptable excipients are described in *Remington's Pharmaceutical Sciences*, Mack Pub. Co., New Jersey (1991), which is incorporated herein by reference.

Pharmaceutical compositions containing estrogen receptor modulating compounds of the present invention may be in any form suitable for the intended method of administration, including, for example, a solution, a suspension, or an emulsion. Liquid carriers are typically used in preparing solutions, suspensions, and emulsions. Liquid carriers contemplated for use in the practice of the present invention include, for example, water, saline, pharmaceutically acceptable organic solvent(s), pharmaceutically acceptable oils or fats, and the like, as well as mixtures of two or more thereof. The liquid carrier may contain other suitable pharmaceutically acceptable additives such as solubilizers, emulsifiers, nutrients, buffers, preservatives, suspending agents, thickening agents, viscosity regulators, stabilizers, and the like. Suitable organic solvents include, for example, monohydric alcohols, such as ethanol, and polyhydric alcohols, such as glycols. Suitable oils include, for example, soybean oil, coconut oil, olive oil, safflower oil, cottonseed oil, and the like. For parenteral administration, the carrier can also be an oily ester such as ethyl oleate, isopropyl myristate, and the like. Compositions of the present invention may also be in the form of microparticles, microcapsules, liposomal encapsulates, and the like, as well as combinations of any two or more thereof.

The compounds of the present invention may be administered orally, parenterally, sublingually, by inhalation spray, rectally, vaginally, or topically in dosage unit formulations containing conventional nontoxic pharmaceutically acceptable carriers, adjuvants, and vehicles as desired. Topical administration may also involve the use of transdermal administration such as transdermal patches or ionophoresis devices. The term parenteral as used herein includes subcutaneous injections, intravenous, intramuscular, intrasternal injection, or infusion techniques.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-propanediol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid can be useful in the preparation of injectables.

Suppositories for rectal or vaginal administration of the drug can be prepared by mixing the drug with a suitable nonirritating excipient such as cocoa butter and polyethylene glycols that are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, cyclodextrins, and sweetening, flavoring, and perfuming agents.

The compounds of the present invention can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and phosphatidyl cholines (lecithins), both natural and synthetic. Methods to form liposomes are known in the art (Prescott 1976).

While the compounds of the invention can be administered as the sole active pharmaceutical agent, they can also be used in combination with one or more other compound as described herein, and/or in combination with other agents used in the treatment and/or prevention of estrogen receptor-mediated disorders. Alternatively, the compounds of the present invention can be administered sequentially with one or more such agents to provide sustained therapeutic and prophylactic effects. Suitable agents include, but are not limited to, other SERMs as well as traditional estrogen agonists and antagonists. Representative agents useful in combination with the compounds of the invention for the treatment of estrogen receptor-mediated disorders include, for example, tamoxifen, 4-hydroxytamoxifen, raloxifene, toremifene, droloxifene, TAT-59, idoxifene, RU 58,688, EM 139, ICI 164,384, ICI 182,780, clomiphene, MER-25, DES, nafoxidene, CP-336,156, GW5638, LY139481, LY353581, zuclomiphene, enclomiphene, ethamoxytriphetol, delmadinone acetate, bisphosphonate, and the like. Other agents that can be combined with one or more of the compounds of the invention include aromatase inhibitors such as, but not limited to, 4-hydroxyandrostenedione, plomestane, exemestane, aminogluethimide, rogletimide, fadrozole, vorozole, letrozole, and anastrozole.

Still other agents useful for combination with the compounds of the invention include, but are not limited to antineoplastic agents, such as alkylating agents. Other classes of relevant antineoplastic agents include antibiotics, hormonal antineoplastics and antimetabolites. Examples of useful alkylating agents include alkyl sulfonates such as busulfan, improsulfan and piposulfan; aziridines, such as a benzodizepa, carboquone, meturedepa and uredepa; ethylenimines and methylinelamines such as altretamine, triethylenemelamine, triethylenephosphoramide, triethylenethiophosphoramide and trimethylolinelamine; nitrogen mustards such as chlorambucil, chlornaphazine, cyclophosphamide, estramustine, iphosphamide, mechlorethamine, mechlorethamine oxide hydrochloride, melphalan, novembichine, phenesterine, prednimustine, trofosfamide, and uracil mustard; nitroso ureas, such as carmustine, chlorozotocin, fotemustine, lomustine, nimustine, ranimustine, dacarbazine, mannomustine, mitobronitol, mitolactol and pipobroman. More such agents will be known to those having skill in the medicinal chemistry and oncology arts.

Additional agents suitable for combination with the compounds of the present invention include protein synthesis inhibitors such as abrin, aurintricarboxylic acid, chloramphenicol, colicin E3, cycloheximide, diphtheria toxin, edeine A, emetine, erythromycin, ethionine, fluoride, S-fluorotryptophan, fusidic acid, guanylyl methylene diphosphonate and guanylyl imidodiphosphate, kanamycin, kasugamycin, kirromycin, and O-methyl threonine, modeccin, neomycin, norvaline, pactamycin, paromomycine, puromycin, ricin, a-sarcin, shiga toxin, showdomycin, sparsomycin, spectinomycin, streptomycin, tetracycline, thiostrepton and trimethoprim. Inhibitors of DNA synthesis, including alkylating agents such as dimethyl sulfate, mitomycin C, nitrogen and sulfur mustards, MNNG and NMS; intercalating agents such as acridine dyes, actinomycins, adriamycin, anthracenes, benzopyrene, ethidium bromide, propidium diiodide-intertwining, and agents such as distamycin and netropsin, can also be combined with compounds of the present invention in pharmaceutical compositions. DNA base analogs such as acyclovir, adenine, (β-1-D-arabinoside, amethopterin, aminopterin, 2-aminopurine, aphidicolin, 8-azaguanine, azaserine, 6-azauracil, 2'-azido-2'-deoxynucleosides, 5-bromodeoxycytidine, cytosine, β-1-D-arabinoside, diazooxynorleucine, dideoxynucleosides, 5fluorodeoxycytidine, 5-fluorodeoxyuridine, 5-fluorouracil, hydroxyurea and 6-mercaptopurine also can be used in combination therapies with the compounds of the invention. Topoisomerase inhibitors, such as coumermycin, nalidixic acid, novobiocin and oxolinic acid, inhibitors of cell division, including colcemide, colchicine, vinblastine and vincristine; and RNA synthesis inhibitors including actinomycin D, α-amanitine and other fungal amatoxins, cordycepin (3'-deoxyadenosine), dichlororibofuranosyl benzimidazole, rifampicine, streptovaricin and streptolydigin also can be combined with the compounds of the invention to provide pharmaceutical compositions. Still more such agents will be known to those having skill in the medicinal chemistry and oncology arts.

In addition, the compounds of the present invention can be used, either singly or in combination as described above, in combination with other modalities for preventing or treating estrogen receptor-mediated diseases or disorders. Such other treatment modalities include without limitation, surgery, radiation, hormone supplementation, and diet regulation. These can be performed sequentially (e.g., treatment with a compound of the invention following surgery or radiation) or in combination (e.g., in addition to a diet regimen).

In another embodiment, the present invention includes compounds and compositions in which a compound of the invention is either combined with, or covalently bound to, a cytotoxic agent bound to a targeting agent, such as a monoclonal antibody (e.g., a murine or humanized monoclonal antibody). It will be appreciated that the latter combination may allow the introduction of cytotoxic agents into cancer cells with greater specificity. Thus, the active form of the cytotoxic agent (i.e., the free form) will be present only in cells targeted by the antibody. Of course, the compounds of the invention may also be combined with monoclonal antibodies that have therapeutic activity against cancer.

The additional active agents may generally be employed in therapeutic amounts as indicated in the PHYSICIANS' DESK REFERENCE (PDR) 53rd Edition (1999), which is incorporated herein by reference, or such therapeutically useful amounts as would be known to one of ordinary skill in the art. The compounds of the invention and the other therapeutically active agents can be administered at the recommended maximum clinical dosage or at lower doses. Dosage levels of the active compounds in the compositions of the invention may be varied to obtain a desired therapeutic response depending on the route of administration, severity of the disease and the response of the patient. The combination can be administered as separate compositions or as a single dosage form containing both agents. When administered as a combination, the therapeutic agents can be formulated as separate compositions that are given at the same time or different times, or the therapeutic agents can be given as a single composition.

4.6 Treatment of Estrogen Receptor-Mediated Disorders

In accordance with yet other embodiments, the present invention provides methods for treating or preventing an estrogen receptor-mediated disorder in a human or animal subject in which an amount of an estrogen receptor-modulating compound of the invention that is effective to modulate estrogen receptor activity in the subject. Other embodiments provided methods for treating a cell or a estrogen receptor-mediated disorder in a human or animal subject, comprising administering to the cell or to the human or animal subject an amount of a compound or composition of the invention effective to modulate estrogen receptor activity in the cell or subject. Preferably, the subject will be a human or non-human animal subject. Modulation of estrogen receptor activity detectable suppression or up-regulation of estrogen receptor activity either as compared to a control or as compared to expected estrogen receptor activity.

Effective amounts of the compounds of the invention generally include any amount sufficient to detectably modulate estrogen receptor activity by any of the assays described herein, by other activity assays known to those having ordinary skill in the art, or by detecting prevention or alleviation of symptoms in a subject afflicted with a estrogen receptor-mediated disorder.

Estrogen receptor-mediated disorders that may be treated in accordance with the invention include any biological or medical disorder in which estrogen receptor activity is implicated or in which the inhibition of estrogen receptor potentiates or retards signaling through a pathway that is characteristically defective in the disease to be treated. The condition or disorder may either be caused or characterized by abnormal estrogen receptor activity. Representative estrogen receptor-mediated disorders include, for example, osteoporosis, atheroschlerosis, estrogen-mediated cancers (e.g., breast and endometrial cancer), Turner's syndrome, benign prostate hyperplasia (i.e., prostate enlargement), prostate cancer, elevated cholesterol, restenosis, endometriosis, uterine fribroid disease, skin and/or vagina atrophy, and Alzheimer's disease. Successful treatment of a subject in accordance with the invention may result in the prevention, inducement of a reduction in, or alleviation of symptoms in a subject afflicted with an estrogen receptor-mediated medical or biological disorder. Thus, for example, treatment can result in a reduction in breast or endometrial tumors and/or various clinical markers associated with such cancers. Likewise, treatment of Alzheimer's disease can result in a reduction in rate of disease progression, detected, for example, by measuring a reduction in the rate of increase of dementia.

The amount of active ingredient that may be combined with the carrier materials to produce a single dosage form will vary depending upon the host treated and the particular mode of administration. It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy. The prophylactically or therapeutically effective amount for a given situation can be readily determined by routine experimentation and is within the skill and judgment of the ordinary clinician.

For exemplary purposes of the present invention, a prophylactically or therapeutically effective dose will generally be from about 0.1 mg/kg/day to about 100 mg/kg/day, preferably from about 1 mg/kg/day to about 20 mg/kg/day, and most preferably from about 2 mg/kg/day to about 10 mg/kg/day of a estrogen receptor-modulating compound of the present invention, which may be administered in one or multiple doses.

5 EXAMPLES

The following Examples are provided to illustrate certain aspects of the present invention and to aid those of skill in the art in the art in practicing the invention. These Examples are in no way to be considered to limit the scope of the invention in any manner.

5.1 Preparation of Compounds of the Invention
5.1.1 General Procedures

All reactions were carried out under nitrogen or argon atmosphere. All reagents obtained from commercial sources were used without further purification. Anhydrous solvents were obtained from commercial sources and used without further drying. Separation and purification of the products were carried out using any or combination of the following methods. Flash column chromatography was performed with silica gel, 200–400 mesh, 60 A (Aldrich Chemical Company, Inc., Milwaukee, Wis.) or a Flash 40 chromatography system and KP-Sil, 60 A (Biotage, Charlottesville, Va.). Typical solvents employed were dichloromethane (DCM), methanol (MeOH), ethyl acetate (EtOAc), and hexane (Hex). Preparative TLC was conducted using 20×20 cm plates coated with Merch-EM Type-60, GF-254 silica gel. Preparative HPLC was performed with Dynamax System using a C-18 reversed phase column (Ranin).

Compounds of the present invention were characterized by LC/MS using either Waters Micromass Platform LCZ system (ionization mode: electron spray positive; column: HP-Eclipse XDB-C18, 2×50 mm, buffer A: $H_2O$ with 0.1% trifluoroacetic acid (TFA), buffer B: acetonitrile (MeCN) with 0.1% TFA, elution gradient: 5–95% buffer over 5 minute period, flow rate: 0.8 mL/min) or HP 1100 Series LC/MSD system (ionization mode: electron spray positive; column: HP-Eclipse XDB-C18, 2×50 mm, buffer A: $H_2O$ with 0.1% TFA, buffer B: MeCN with 0.1% TFA, elution gradient: 5–95% buffer over 3.5 to 6 minute period, flow rate: 0.8 to 0.4 mL/min). Purity of the compounds was also evaluated by HPLC using a Waters Millennium chromatography system with a 2690 Separation Module (Milford, Mass.). The analytical columns were Alltima C-18 reversed phase, 4.6×250 mm from Alltech (Deerfield, Ill.). A gradient elution was used, typically starting with 5% MeCN/95% water and progressing to 100% MeCN over a period of 40 minuets. All solvents contained 0.1% TFA. Compounds were detected by ultraviolet light (LTV) absorption at 214 nm. Some of the mass spectrometric analysis was performed on a Fisons Electrospray Mass Spectrometer. All masses are reported as those of the protonated parent ions unless otherwise noted. Nuclear magnetic resonance (NMR) analysis was performed with a Varian 300 MHz NMR (Palo Alto, Calif.). The spectral reference was either TMS or the known chemical shift of the solvent. Proton NMR ($^1$H NMR) data are reported as follows: chemical shift (δ) in ppm, multiplicity (s=singlet, d=doublet, t=triplet, q=quartet, p=pentet, m=multiplet, dd=doublet of doublet, br=broad), coupling constant (Hz), integration and assignment. Melting points were determined on a Laboratory Devices MEL-TEMP apparatus (Holliston, Massachusetts) and are reported uncorrected.

Compound names were generated using NOMENCLATOR (ChemInnovation Software, Inc., San Diego, Calif.).

5.1.2 Synthesis of Estrogen Receptor-Modulating Pyrazoles
5.1.2.1 Synthesis of 4-[5-(Diphenylmethyl)-4-ethyl-1-methylpyrazol-3-yl]phenol This compound was synthesized based upon Scheme 1.

Step 1: To a solution of 4'-methoxybutyrylphenone (1.0 equiv.) in THF at −78° C. was added dropwise 1.5 equiv. of [$(CH_3)_2Si$], NLi. The solution was stirred for 1 h at −78° C., followed by addition of 1.2 equiv. of 2,2-diphenylacetyl chloride. The reaction mixture was stirred for 10 min at −78° C. and then for 22 h at rt, acidified with 10% citric acid, and extracted with EtOAc. The combined organic layers were washed with water and dried over $Na_2SO_4$. Removal of solvent in vacuo provided a crude solid which was purified by flash chromatography ($CH_2Cl_2$) to give product 2-ethyl-1-(4-methoxyphenyl)-4,4-diphenylbutane-1,3-dione.

Step 2: A mixture of the 1,3-diketone obtained in step 1 (1.0 equiv.), methyl hydrazine (1.5 equiv.), conc. HCl aq. (catalytic amount) and ethanol was heated to reflux overnight. Cooled to rt and removed solvent in vacuo. Water and ethyl acetate were added. The organic layer was separated, washed with dil. HCl, brine, dried, filtered and the solvent was concentrated in vacuo to give the pyrazole product.

Step 3: Demethylation was performed using as described in Scheme 1 to afford the final product.

ESMS m/z 369 (MH$^+$), $C_{25}H_{24}N_2O$=368 g/mol, HPLC purity=85%.

5.1.2.2 Synthesis of 4-[4-Ethyl-1-methyl-5-(2-phenylethyl)pyrazol-3-yl]phenol This compound was synthesized in the same manner as described in Section 5.1.2.1. In step 1, 3-phenylpropanoyl chloride and 4'-methoxybutyrylphenone were used to form the 1,3-diketone.

ESMS m/z 307 (MH$^+$), $C_{20}H_{22}N_{20}$=306 g/mol, HPLC purity=64%.

5.1.2.3 Synthesis of 4-(4-Ethyl-1-methyl-5-(2-thienyl)pyrazol-3-yl)phenol

This compound was synthesized in the same manner as described in Section 5.1.2.1. In step 1, thiophene-2-carbonyl chloride and 4'-methoxybutyrylphenone were used to form the 1,3-diketone.

ESMS m/z 285 (MH$^+$), $C_{16}H_{16}N_2O$=284 g/mol, HPLC purity=98%.

5.1.2.4 Synthesis of 4-[1-Methyl-5-(2-phenylethyl)-4-prop-2-enylpyrazol-3-yl]phenol This compound was synthesized based upon Scheme 1 and Scheme 3.

Step 1: Formation of 1,3-diketone. Same as step 1 in described in Section 5.1.2.1 using 4'-methoxyacetophenone and 3-phenylpropanoyl chloride as starting materials.

Step 2: Alkylation. A THF solution of the above 1,3-diketone (1.0 equiv.) was added dropwise to a suspension of sodium hydride (1.1 eq) in THF at 0° C. The mixture was stirred at rt for 30 min. followed by addition of allylbromide (1.1 equiv.). The reaction mixture was stirred at rt overnight, poured into saturated $NH_4Cl$ aq. and extracted with ether and DCM. The organic extracts were washed with brine, dried with $MgSO_4$ and concentrated in vacuo to give the product.

Step 3: Same as step 2 in Section 5.1.2.1.

Step 4: Demethylation was performed as described in Scheme 1 to afford the final product.

ESMS m/z 319 (MH$^+$), $C_{21}H_{22}N_2O$=318 g/mol, HPLC purity=80%.

5.1.2.5 Synthesis of 4-[1-Methyl-5-(phenoxymethyl)-4-prop-2-enylpyrazol-3-yl]phenol This compound was synthesized in the same manner as described in Section 5.1.2.4. In step 1, 2-phenoxyacetyl chloride and 4'-methoxyacetophenone were used to form the 1,3-diketone.

ESMS m/z 321 (MH$^+$), $C_{20}H_{22}N_2O_2$=320 g/mol, HPLC purity=60%.

5.1.2.6 Synthesis of 4-[3,5-bis(4-Hydroxyphenyl)-1-methylpyrazol-4-yl]phenol This compound was synthesized based upon Scheme I.

Step 1: To a solution of desoxyanisoin (1.0 equiv.) in THF at −78° C. was added dropwise 1.5 equiv. of $[(CH_3)_2Si]_2NLi$. The solution was stirred for 1 h at −78° C., followed by addition of 1.2 equiv. of p-anisoyl chloride. The reaction mixture was stirred for 10 min at −78° C. and then for 22 h at rt, acidified with 10% citric acid, and extracted with EtOAc. The combined organic layers were washed with water and dried over $Na_2SO_4$. Removal of solvent in vacuo provided a crude solid which was purified by flash chromatography ($CH_2Cl_2$) to give 1,2,3-tris(4-methoxyphenyl)propane-1,3-dione.

Step 2: A mixture of the 1,3-diketone obtained in step 1 (1.0 equiv.), methyl hydrazine (1.5 equiv.), conc. HCl aq. (catalytic amount) and ethanol was heated to reflux overnight. Cooled to rt and removed solvent in vacuo. Water and ethyl acetate were added. The organic layer was separated, washed with dil. HCl, brine, dried, filtered and the solvent was concentrated in vacuo to give the product 4-[4,5-bis(4-methoxyphenyl)-1-methylpyrazol-3-yl]-1-methoxybenzene.

Step 3: Demethylation was performed using Method 1 described in Scheme 1 to afford the final product.

ESMS m/z 359 (MH$^+$), $C_{22}H_{18}N_2O_3$=358 g/mol, HPLC purity=90%.

5.1.2.7 Synthesis of 4-[3,5-bis(4-Hydroxyphenyl)-1-phenylpyrazol-4-yl]phenol This compound was synthesized in the same manner as described in Section 5.1.2.6. In step 2, phenyl hydrazine was used as the reagent to form pyrazole.

ESMS m/z 421 (MH$^+$), $C_{27}H_{20}N_2O_3$=420 g/mol, HPLC purity=90%.

5.1.2.8 Synthesis of 4-[1-(4-Bromophenyl)-5-(4-hydroxyphenyl)-4-benzylpyrazol-3-yl]phenol This compound was synthesized based upon Scheme 1.

Step 1: To a solution of 1-(4-methoxyphenyl)-3-phenylpropan-1-one (1.0 equiv.) in THF at −78° C. was added dropwise 1.5 equiv. of $[(CH_3)_2Si]_2NLi$. The solution was stirred for 1 h at −78° C., followed by addition of 1.2 equiv. of p-anisoyl chloride. The reaction mixture was stirred for 10 min at −78° C. and then for 22 h at rt, acidified with 10% citric acid, and extracted with EtOAc. The combined organic layers were washed with water and dried over $Na_2SO_4$. Removal of solvent in vacuo provided a crude solid which was purified by flash chromatography ($CH_2Cl_2$) to give 1,3-bis(4-methoxyphenyl)-2-benzylpropane-1,3-dione.

Step 2: A mixture of the 1,3-diketone obtained in step 1 (1.0 equiv.), 4-bromophenyl hydrazine (1.5 equiv.), conc. HCl aq. (catalytic amount) and ethanol was heated to reflux overnight. Cooled to rt and removed solvent in vacuo. Water and ethyl acetate were added. The organic layer was separated, washed with dil. HCl, brine, dried, filtered and the solvent was concentrated in vacuo to give the product 1-[1-(4-bromophenyl)-3-(4-methoxyphenyl)-4-benzylpyrazol-5-yl]-4-methoxybenzene.

Step 3: Demethylation was performed as described in Scheme 1 to afford the final product.

$^1$H NMR (CDCl$_3$): δ 3.86 (2H, s), 6.67 (2H, d, J=8.8 Hz), 6.74 (2H, d, J=8.8 Hz), 6.88 (2H, d, J=8.8 Hz), 6.98 (2H, d, J=7.2 Hz), 7.05–7.09 (1H, m), 7.14 (4H, d, J=8.8 Hz), 7.36 (4H, d, J=8.8 Hz); ESMS m/z 497/499 (MH$^+$), $C_{28}H_{21}BrN_2O_2$=496/496 g/mol (1Br); HPLC purity=85%.

5.1.2.9 Synthesis of 4-[1-(4-Chloro-2-methylphenyl)-5-(4-hydroxyphenyl)-0-benzylpyrazol-3-yl]phenol This compound was synthesized in the same manner as described in Section 5.1.2.8. In step 2, 4-chloro-2-methylphenyl hydrazine was used to form the pyrazole heterocycle.

$^1$H NMR (CDCl$_3$): δ 2.02 (3H, s), 3.97 (2H, s), 6.60 (2H, d, J=8.8 Hz), 6.73 (2H, d, J=8.8 Hz), 6.86 (2H, d, J=8.8 Hz), 7.08–7.19 (6H, m), 7.21–7.26 (2H, m), 7.46 (2H, d, J=8.8 Hz); ESMS m/z 467/469 (MH+), $C_{29}H_{23}ClN_2O_2$=466 g/mol; HPLC purity=81%.

5.1.2.10 Synthesis of 4-[1-(3-Chlorophenyl)-5-(4-hydroxyphenyl)-4-benzylpyrazol-3-yl]phenol This compound was synthesized in the same manner as described in Section 5.1.2.8. In step 2, 3-chlorophenyl hydrazine was used to form the pyrazole heterocycle.

$^1$H NMR (CDCl$_3$): δ 3.95 (2H, s), 6.73 (2H, d, J=8.8 Hz), 6.78 (2H, d, J=8.8 Hz), 6.98 (2H, d, J=9.2 Hz), 7.05–7.18 (6H, m), 7.22 (2H, d, J=7.1 Hz), 7.46 (1H, t, J=2.1 Hz), 7.51 (2H, d, J=8.8 Hz); ESMS m/z 453/455 (MH+), $C_{28}H_{21}ClN_2O_2$=452 g/mol; HPLC purity=89%.

5.1.2.11 Synthesis of 4-[1-(4-Chlorophenyl)-5-(4-hydroxyphenyl)-4-benzylpyrazol-3-yl]phenol This compound was synthesized in the same manner as described in Section 5.1.2.8. In step 2, 4-chlorophenyl hydrazine was used to form the pyrazole heterocycle.

$^1$H NMR (CDCl$_3$): δ 3.97 (2H, s), 6.59 (2H, d, J=8.8 Hz), 6.73 (2H, d, J=8.8 Hz), 6.94 (2H, d, J=8.8 Hz), 7.11–7.18 (4H, m), 7.24–7.27 (3H, m), 7.34 (1H, dd, J=7.8, 3.5 Hz), 7.44 (1H, dd, J=6.8, 3.9 Hz), 7.48 (2H, d, J=8.8 Hz); ESMS m/z 453/455 (MH+), $C_{28}H_{21}ClN_2O_2$=452 g/mol; HPLC purity=86%.

5.1.2.12 Synthesis of 4-[3,4-bis(4-Hydroxyphenyl)-1-(2-methylphenyl)pyrazol-5-yl]phenol This compound was synthesized in the same manner as described in Section 5.1.2.6. In step 2, 2-methylphenyl hydrazine was used as the reagent to form pyrazole.

ESMS m/z 435 (MH$^+$), $C_{28}H_{24}N_2O_3$=434 g/mol, HPLC purity=90%.

5.1.2.13 Synthesis of 4-[3,4-bis(4-Hydroxyphenyl)-1-(3-fluorophenyl)pyrazol-5-yl]phenol This compound was synthesized in the same manner as described in Section 5.1.2.6. In step 2, 3-fluorophenyl hydrazine was used as the reagent to form pyrazole.

ESMS m/z 439 (MH$^+$), $C_{27}H_{19}FN_2O_3$=438 g/mol, HPLC purity=90%.

5.1.2.14 Synthesis of 4-[3,4-bis(4-Hydroxyphenyl)-1-(2-ethylphenyl)pyrazol-5-yl]phenol This compound was synthesized in the same manner as described in Section 5.1.2.6. In step 2, 2-ethylphenyl hydrazine was used as the reagent to form pyrazole.

ESMS m/z 449 (MH$^+$), $C_{29}H_{24}N_2O_3$=448 g/mol, HPLC purity=90%.

5.1.2.15 Synthesis of 4-[3,5-bis(4-Hydroxyphenyl)-1-(4-fluorophenyl)pyrazol-4-yl]phenol This compound was synthesized in the same manner as described in Section 5.1.2.6. In step 2, 4-fluorophenyl hydrazine was used as the reagent to form pyrazole.

ESMS m/z 439 (MH⁺), $C_{27}H_{19}FN_2O_3$=438 g/mol, HPLC purity=90%.

5.1.2.16 Synthesis of 4-[1-(2,4-Difluorophenyl)-3,4-bis(4-hydroxyphenyl)pyrazol-5-yl]phenol This compound was synthesized in the same manner as described in Section 5.1.2.6. In step 2, 2,4-difluorophenyl hydrazine was used as the reagent to form pyrazole.

ESMS m/z 457 (MH⁺), $C_{27}H_{18}F_2N_2O_3$=456 g/mol, HPLC purity=90%.

5.1.2.17 Synthesis of 4-{3,4-bis(4-Hydroxyphenyl)-1-[2-(trifluoromethyl)phenyl]pyrazol-5-yl}phenol This compound was synthesized in the same manner as described in Section 5.1.2.6. In step 2, 2-trifluoromethylphenyl hydrazine was used as the reagent to form pyrazole.

ESMS m/z 489 (MH⁺), $C_{28}H_{19}F_3N_2O$=488 g/mol, HPLC purity=85%.

5.1.2.18 Synthesis of 4-(3,4-bis(4-Hydroxyphenyl)-1-(2-fluorophenyl)pyrazol-5-yl]phenol This compound was synthesized in the same manner as described in Section 5.1.2.6. In step 2, 2-fluorophenyl hydrazine was used as the reagent to form pyrazole.

ESMS m/z 439 (MH⁺), $C_{27}H_{19}FN_2O_3$=438 g/mol, HPLC purity=80%.

5.1.2.19 Synthesis of 4-[3,4-bis(4-Hydroxyphenyl)-1-(3-methylphenyl)pyrazol-5-yl]phenol This compound was synthesized in the same manner as described in Section 5.1.2.6. In step 2, 3-methylphenyl hydrazine was used as the reagent to form pyrazole.

ESMS m/z 435 (MH⁺), $C_{28}H_{22}N_2O_3$=434 g/mol, HPLC purity=80%.

5.1.2.20 Synthesis of 4-[3,4-bis(4-Hydroxyphenyl)-1-(4-chloro-2-methylphenyl)pyrazol-5-yl]phenol This compound was synthesized in the same manner as described in Section 5.1.2.6. In step 2, 4-chloro-2methylphenyl hydrazine was used as the reagent to form pyrazole.

ESMS m/z 469 (MH⁺), $C_{28}H_{21}ClN_2O_3$=468 g/mol, HPLC purity=80%.

5.1.2.21 Synthesis of 4-[3,5-bis(4-Hydroxyphenyl)-1-(4-methylphenyl)pyrazol-4-yl]phenol This compound was synthesized in the same manner as described in Section 5.1.2.6. In step 2, 4-methylphenyl hydrazine was used as the reagent to form pyrazole.

ESMS m/z 435 (MH⁺), $C_{28}H_{22}N_2O_3$=434 g/mol, HPLC purity=80%.

5.1.2.22 Synthesis of 4-[1-(2,3-Dichlorophenyl)-3,4-bis(4-hydroxyphenyl)pyrazol-5-yl]phenol This compound was synthesized in the same manner as described in Section 5.1.2.6. In step 2, 2,3-dichlorophenyl hydrazine was used as the reagent to form pyrazole.

ESMS m/z 489 (MH⁺), $C_{27}H_{18}Cl_2N_2O_3$=490 g/mol, HPLC purity=80%

5.1.2.23 Synthesis of 4-(3,4-bis(4-Hydroxyphenyl)-1-(5-fluoro-2-methylphenyl)pyrazol-5-yl]phenol This compound was synthesized in the same manner as described in Section 5.1.2.6. In step 2, 5-tluoro-2methylphenyl hydrazine was used as the reagent to form pyrazole.

ESMS m/z 453 (MH⁺), $C_{28}H_{21}FN_2O_3$=452 g/mol, HPLC purity=low 5.1.2.24 Synthesis of 4-[3,4-bis(4-Hydroxyphenyl)-1-(2-chlorophenyl)pyrazol-5-yl]phenol This compound was synthesized in the same manner as described in Section 5.1.2.6. In step 2, 2-chlorophenyl hydrazine was used as the reagent to form pyrazole.

ESMS m/z 455 (MH⁺), $C_{27}H_{19}ClN_2O_3$=454 g/mol, HPLC purity=80%

5.1.2.25 Synthesis of 4-{3,4-bis(4-Hydroxyphenyl)-1-[4-(tert-butyl)phenyl]pyrazol-5-yl}phenol This compound was synthesized in the same manner as described in Section 5.1.2.6. In step 2, 4-t-butylphenyl hydrazine was used as the reagent to form pyrazole.

ESMS m/z 477 (MH⁺), $C_{31}H_{28}N_2O_3$=476 g/mol, HPLC purity=80%.

5.1.2.26 Synthesis of 4-[3,4-bis(4-Hydroxyphenyl)-1-(3-chlorophenyl)pyrazol-5-yl]phenol This compound was synthesized in the same manner as described in Section 5.1.2.6. In step 2, 3-chlorophenyl hydrazine was used as the reagent to forte pyrazole.

ESMS m/z 455 (MH⁺), $C_{27}H_{19}ClN_2O_3$=454 g/mol, HPLC purity=80%.

5.1.2.27 Synthesis of 4-[1-(2,4-Dichlorophenyl)-3,4-bis(4-hydroxyphenyl)pyrazol-5-yl]phenol This compound was synthesized in the same manner as described in Section 5.1.2.6. In step 2, 2,4-dichlorophenyl hydrazine was used as the reagent to form pyrazole.

ESMS m/z 490 (MH⁺), $C_{27}H_{18}ClN_2O_3$=489 g/mol, HPLC purity=80%.

5.1.2.28 Synthesis of 4-[3,5-bis(4-Hydroxyphenyl)-1-(4-chlorophenyl)pyrazol-4-yl]phenol This compound was synthesized in the same manner as described in Section 5.1.2.6. In step 2, 4-chlorophenyl hydrazine was used as the reagent to form pyrazole.

ESMS m/z 455 (MH⁺), $C_{27}H_{19}ClN_2O_3$=454 g/mol, HPLC purity=80%.

5.1.2.29 Synthesis of 4-[1-(2,6-Dichlorophenyl)-3,4-bis(4-hydroxyphenyl)pyrazol-5-yl]phenol This compound was synthesized in the same manner as described in Section 5.1.2.6. In step 2, 2,6-dichlorophenyl hydrazine was used as the reagent to form pyrazole.

ESMS m/z 490 (MH⁺), $C_{27}H_{18}Cl_2N_2O_3$=489 g/mol, HPLC purity=60%.

5.1.2.30 Synthesis of 4-[3,4-bis(4-Hydroxyphenyl)-1-(2,3-dimethylphenyl)pyrazol-5-yl]phenol This compound was synthesized in the same manner as described in Section 5.1.2.6. In step 2, 2,3-dimethylphenyl hydrazine was used as the reagent to form pyrazole.

ESMS m/z 449 (MH), $CZgH2qNZO3$=448 g/mol, HPLC purity=85%.

5.1.2.31 Synthesis of 4-[3,4-bis(4-Hydroxyphenyl)-1-(3-chloro-4-fluorophenyl)pyrazol-5-yl]phenol This compound was synthesized in the same manner as described in Section 5.1.2.6. In step 2, 3-chloro-4-fluorophenyl hydrazine was used as the reagent to form pyrazole.

ESMS m/z 473 (MH⁺), $C_{27}H_{18}ClFN_2O_3$=472 g/mol, HPLC purity=80%.

5.1.2.32 Synthesis of 4-{3,4-bis(4-Hydroxyphenyl)-1-[4-(trifluoromethoxy)phenyl]pyrazol-5-yl}phenol This compound was synthesized in the same manner as described in Section 5.1.2.6. In step 2, 4-tritluoromethoxyphenyl hydrazine was used as the reagent to form pyrazole.

ESMS m/z 505 (MH),=$C_{28}H_{19}F_3N_2O_4$ 504 g/mol, HPLC purity=85%.

5.1.2.33 Synthesis of 4-{3,4-bis(4-Hydroxyphenyl)-1-[4-(tritluoromethyl)phenyl]pyrazol-5-yl}phenol This compound was synthesized in the same manner as described in Section 5.1.2.6. In step 2, 4trifluoromethylphenyl hydrazine was used as the reagent to form pyrazole.

ESMS m/z 489 (MH⁺), $C_{28}H_{19}F_3N_2O_3$=488 g/mol, HPLC purity=80%.

5.1.2.34 Synthesis of 4-[3,5-bis(4-Hydroxyphenyl)-1-(4-iodophenyl)pyrazol-4-yl]phenol This compound was synthesized in the same manner as described in Section 5.1.2.6. In step 2, 4-iodophenyl hydrazine was used as the reagent to form pyrazole.

ESMS m/z 547 (MH$^+$), $C_{27}H_{19}IN_2O_3$=546 g/mol, HPLC purity=70%.

5.1.2.35 Synthesis of 4-{3,4-bis(4-Hydroxyphenyl)-1-[2-chloro-5-(trifluoromethyl)phenyl]pyrazol-5-yl}phenol This compound was synthesized in the same manner as described in Section 5.1.2.6. In step 2, 2-chloro-5-trifluoromethylphenyl hydrazine was used as the reagent to form pyrawle.

ESMS m/z 523 (MH$^+$), $C_{28}H_{18}ClF_3N_2O_3$=522 g/mol, HPLC purity=65%.

5.1.2.36 Synthesis of 4-3,4-bis(4-Hydroxyphenyl)-1-(1,3-dimethyl-5-nitropyrazol-4-yl)pyrazol-5-yl]phenol This compound was synthesized in the same manner as described in Section 5.1.2.6. In step 2, 1,3-dimethyl-5-nitropyrazole-4-ylhydrazine was used as the reagent to form pyrazole.

ESMS m/z 484 (MH$^+$), $C_{26}H_{21}N_5O_5$=483 g/mol, HPLC purity=60%.

5.1.2.37 Synthesis of 4-{3,4-bis(4-Hydroxyphenyl)-1-[5-chloro-3-(trifluoromethyl)(2-pyridyl)]pyrazol-5-yl}phenol This compound was synthesized in the same manner as described in Section 5.1.2.6. In step 2, 5-chloro-3-trifluoromethyl-2-pyridylhydrazine was used as the reagent to form pyrazole.

ESMS m/z 524 (MH$^+$), $C_{27}H_{17}ClF_3N_3O_3$;=523 g/mol, HPLC purity=80%.

5.1.2.38 Synthesis of 4-[3,4-bis(4-Hydroxyphenyl)-1-(1,4-dimethylpyrazolo[4,5-e]pyridin-6-yl)pyrazol-5-yl]phenol This compound was synthesized in the same manner as described in Section 5.1.2.6. In step 2, 1,4-dimethylpyrazolo[5,4-b]pyridine-6-ylhydrazine was used as the reagent to form pyrazole.

ESMS m/z 504 (MH$^+$), $C_{30}H_{25}N_5O_3$=503 g/mol, HPLC purity=85%.

5.1.2.39 Synthesis of 4-[3,5-bis(4-Hydroxyphenyl)-1-(6-methylpyridazin-3-yl)pyrazol-4-yl]phenol This compound was synthesized in the same manner as described in Section 5.1.2.6. In step 2, 6-methylpyridazine-3-ylhydrazine was used as the reagent to form pyrazole.

ESMS m/z 437 (MH$^+$), $C_{26}H_{20}N_4O_3$=436 g/mol, HPLC purity=70%.

5.1.2.40 Synthesis of 4-[3,4-bis(4-Hydroxyphenyl)-1-(6-chloro-2-fluorophenyl)pyrazol-5-yl]phenol This compound was synthesized in the same manner as described in Section 5.1.2.6. In step 2, 6-chloro-2-fluorophenyl hydrazine was used as the reagent to form pyrazole.

ESMS m/z 473 (MH$^+$), $C_{27}H_{18}ClFN_2O_3$=472 g/mol, HPLC purity=85%.

4-[1-(2-Fluorophenyl)-5-(4-methylphenyl)-4-benzylpyrazol-3-yl]phenol

This compound was synthesized in the same manner described in Section 5.1.2.8. In step 2, 2-fluorophenyl hydrazine was used to form the pyrazole heterocycle.

$^1$H NMR (CDCl$_3$): δ 4.11 (2H, s), 6.80 (2H, d, J=8.5 Hz), 6.93 (2H, d, J=8.5 Hz), 7.09 (2H, d, J=8.5 Hz), 7.19–7.24 (1H, m), 7.23 (2H, d, J=8.5 Hz), 7.27–7.32 (1H, m), 7.35 (1H, d, J=8.3 Hz), 7.38 (1H, d, J=8.3 Hz), 7.46–7.52 (1H, m), 7.55 (2H, d, J=8.3 Hz), 7.62 (1H, td, J=8.3, 1.6 Hz), 7.66 (1H, s); ESMS m/z 437 (MH$^+$), $C_{28}H_{21}FN_2O_2$=436 g/mol; HPLC purity=79%.

5.1.2.41 Synthesis of 3-{[3,5-bis(4-Hydroxyphenyl)-4-benzylpyrazolyl]methyl}phenol This compound was synthesized based upon Scheme 4.

Step I: To a solution of 1-(4-methoxyphenyl)-3-phenylpropan-1-one (1.0 equiv.) in THF at −78° C. was added dropwise 1.5 equiv. of [(CH$_3$)$_2$Si]$_2$NLi. The solution was stirred for 1 h at −78° C., followed by addition of 1.2 equiv. of p-anisoyl chloride. The reaction mixture was stirred for 10 min at −78° C. and then for 22 h at rt, acidified with 10% citric acid, and extracted with EtOAc. The combined organic layers were washed with water and dried over Na$_2$SO$_4$. Removal of solvent in vacuo provided a crude solid which was purified by flash chromatography (CH$_2$Cl$_2$) to give 1,3-bis(4-methoxyphenyl)-2-benzylpropane-1,3-dione.

Step 2: A mixture of the 1,3-diketone obtained in step 1 (1.0 equiv.), hydrazine (3.0 equiv.), conc. HCl aq. (catalytic amount) and ethanol was heated to reflux overnight. Cooled to rt and removed solvent in vacuo. Water and ethyl acetate were added. The organic layer was separated, washed with dil. HCl, brine, dried, filtered and the solvent was concentrated in vacuo to give the product 4-methoxy-1-[5-(4-methoxyphenyl)-4-benzylpyrazol-3-yl]benzene.

Step 3: Alkylation. Pyrazole obtained from the above step was dissolved in DMF. Cesium carbonate (6 equiv.) and 3'-methoxybenzyl bromide (4 equiv.) were added to the solution and the reaction was allowed to proceed at 90° C. for 3 days. EtOAc was added and the solution was washed with 10% citric acid (2×20 mL), 10% NaHCO$_3$ and brine. The organic layer was concentrated under reduced pressure and the resulting residue was taken up in 90% MeCN/H$_2$O and lyophilized. Purification was achieved by flash chromatography (EtOAc/petrol).

Step 4: Demethylation was performed as described in Scheme 1 to afford the final product.

$^1$H NMR (CDCl$_3$): δ 3.72 (2H, s), 5.05 (2H, s), 6.37 (1H, d, J=7.6 Hz), 6.46 (1H, s), 6.58 (1H, d, J=7.6 Hz), 6.65 (2H, d, J=7.6 Hz), 6.67 (2H, d, J=7.6 Hz), 6.87 (4H, d, J=7.8 Hz), 6.95–7.11 (4H, m), 7.26 (2H, d, J=7.8 Hz); ESMS m/z 449 (MH$^+$), $C_{29}H_{24}N_2O_3$=448 g/mol; HPLC purity=85%.

5.1.2.42 Synthesis of 1-[3,5-bis(4-Hydroxyphenyl)-4-benzylpyrazolyl]-4-(methylsulfonyl)benzene This compound was synthesized in the same manner described in Section 5.1.2.8. In step 2, 4methanesulfonylphenyl hydrazine was used to form the pyrazole heterocycle.

$^1$H NMR (CDCl$_3$): δ 2.89 (3H, s), 3.74 (2H, s), 6.59 (2H, d, J=8.6 Hz), 6.63 (2H, d, J=8.6 Hz), 6.79 (2H, d, J=8.6 Hz), 6.87 (2H, d, J=7.5 Hz), 6.96 (1H, t, J=6.8 Hz), 7.03 (2H, J=7.2 Hz), 7.28 (2H, d, J=8.6 Hz), 7.36 (2H, d, J=8.6 Hz), 7.65 (2H, d, J=8.6 Hz).; ESMS m/z 497 (MH+), $C_{29}H_{24}N_2O_{45}$=496 g/mol; HPLC purity=79%.

5.1.2.43 Synthesis of 4-[5-(4-Hydroxyphenyl)-1-(2,3,4,5,6-pentafluorophenyl)-4-benzylpyrazol-3-yl]phenol This compound was synthesized in the same manner described in Section 5.1.2.8. In step 2, 1,2,3,4,5-pentafluorophenyl hydrazine was used to form the pyrazole heterocycle.

$^1$H NMR (CDCl$_3$): δ 3.94 (2H, s), 6.69 (2H, d, J=8.8 Hz), 6.76 (2H, d, J=8.8 Hz), 6.99 (2H, d, J=7.9Hz), 7.06 (2H, d, J=7.2 Hz), 7.09 (2H, d, J=8.8 Hz), 7.16 (1H, t, J=7.2 Hz), 7.45 (2H, d, J=8.8 Hz); ESMS m/z 509 (MH+), $C_{28}H_{17}F_5N_2O_2$=508 g/mol; HPLC purity=83%.

5.1.2.44 Synthesis of $^1$4-{5-(4-Hydroxyphenyl)-4-benzyl-1-[4-(trifluoromethoxy)phenyl]pyrazol-3-yl}phenol This compound was synthesized in the same manner described in Section 5.1.2.8. In step 2, 4trifluoromethoxyphenyl hydrazine was used to form the pyrazole heterocycle.

¹H NMR (CDCl₃): δ 3.92 (2H, s), 6.71 (2H, d, J=8.8 Hz), 6.76 (2H, d, J=8.8 Hz), 6.96 (2H, d, J=8.1 Hz), 7.06 (2H, d, J=7.3 Hz), 7.09 (2H, d, J=8.8 Hz), 7.14 (1H, J=7.3 Hz), 7.20 (2H, d, J=8.1 Hz), 7.33 (2H, d, J=8.8 Hz), 7.49 (2H, d, J=8.8 Hz); ESMS m/z 503 (MH+), $C_{29}H_{21}F_3N_2O_3$=502 g/mol; HPLC purity=93%.

5.1.2.45 Synthesis of 4-[3,5-bis(4-Hydroxyphenyl)-1-(2-pyridyl)pyrazol-4-yl]phenol This compound was synthesized in the same manner as described in Section 5.1.2.6. In step 2, 2-pyridylhydrazine was used as the reagent to form pyrazole.

ESMS m/z 422 (MH⁺), $C_{26}H_{19}N_3O_3$=421 g/mol, HPLC purity=90%.

5.1.2.46 Synthesis of 4-[1-(2,4-Dimethylphenyl)-4-ethyl-5-(4-hydroxyphenyl)pyrazol-3-yl]phenol This compound was synthesized based upon Scheme 1.

Step 1: To a solution of 4'-methoxybutyrylphenone (1.0 equiv.) in THF at −78° C. was added dropwise 1.5 equiv. of [(CH₃)₂Si]₂NLi. The solution was stirred for 1 h at −78° C. followed by addition of 1.2 equiv. of p-anisoyl chloride. The reaction mixture was stirred for 10 min at −78° C. and then for 22 h at rt, acidified with 10% citric acid, and extracted with EtOAc. The combined organic layers were washed with water and dried over Na₂SO₄. Removal of solvent in vacuo provided a crude solid which was purified by flash chromatography (CH₂Cl₂) to give 1,3-bis(4-methoxyphenyl)-2-ethylpropane-1,3-dione.

Step 2: A mixture of the 1,3-diketone obtained in step 1 (1.0 equiv.), 2,4-dimethylphenyl hydrazine (1.5 equiv.), conc. HCl aq. (catalytic amount) and ethanol was heated to reflux overnight. Cooled to rt and removed solvent in vacuo. Water and ethyl acetate were added. The organic layer was separated, washed with dil. HCl, brine, dried, filtered and the solvent was concentrated in vacuo to give the product.

Step 3: Demethylation was performed as described in Scheme 1 to afford the final product.

ESMS m/z 385 (MH⁺), $C_{25}H_{24}N_2O_2$=384 g/mol, HPLC purity=80%.

5.1.2.47 Synthesis of 4-[4-Ethyl-5-(4-hydroxyphenyl)-1-(3-methylphenyl)pyrazol-3-yl]phenol This compound was synthesized in the same manner as described in Section 5.1.2.46. In step 2, 3-methylphenyl hydrazine was used as the reagent to form pyrazole.

ESMS m/z 371 (MH⁺), $C_{24}H_{22}N_2O_2$=370 g/mol, HPLC purity=95%.

5.1.2.48 Synthesis of 4-{4-Ethyl-5-(4-hydroxyphenyl)-1-[4-(methylethyl)phenyl]pyrazol-3-yl}phenol This compound was synthesized in the same manner described in Section 5.1.2.46. In step 2, 4-iso-propylphenyl hydrazine was used as the reagent to form pyrazole.

ESMS m/z 399 (MH⁺), $C_{26}H_{26}N_2O_2$=398 g/mol, HPLC purity=95%.

5.1.2.49 Synthesis of 4-[4-Ethyl-1-(3-fluorophenyl)-5-(4-hydroxyphenyl)pyrazol-3-yl]phenol This compound was synthesized in the same manner described in Section 5.1.2.46. In step 2, 3-fluorophenyl hydrazine was used as the reagent to form pyrazole.

ESMS m/z 375 (MU), $C_{23}H_{19}FN_2O_2$=374 g/mol, HPLC purity=95%.

5.1.2.50 Synthesis of 4-[4-Ethyl-1-(2-ethylphenyl)-5-(4-hydroxyphenyl)pyrazol-3-yl]phenol This compound was synthesized in the same manner described in Section 5.1.2.46. In step 2, 2-ethylphenyl hydrazine was used as the reagent to form pyrazole.

ESMS m/z 385 (MH⁺), $C_{25}H_{24}N_2O_2$=384 g/mol, HPLC purity=95%.

5.1.2.51 Synthesis of 4-[4-Ethyl-1-(4-fluorophenyl)-5-(4-hydroxyphenyl)pyrazol-3-yl]phenol This compound was synthesized in the same manner described in Section 5.1.2.46. In step 2, 4-fluorophenyl hydrazine was used as the reagent to form pyrazole.

ESMS m/z 375 (MH⁺) $C_{23}H_{19}FN_2O_2$=374 g/mol, HPLC purity=95%.

5.1.2.52 Synthesis of 4-[1-(2,4-Difluorophenyl)-4-ethyl-5-(4-hydroxyphenyl)pyrazol-3-yl]phenol This compound was synthesized in the same manner described in Section 5.1.2.46. In step 2, 2,4-difluorophenyl hydrazine was used as the reagent to form pyrazole.

ESMS m/z 393 (MH⁺) $C_{23}H_{18}F_2N_2O_2$=392 g/mol, HPLC purity=80%.

5.1.2.53 Synthesis of 4-{4-Ethyl-5-(4-hydroxyphenyl)-1-[2-(trifluoromethyl)phenyl]pyrazol-3-yl}phenol This compound was synthesized in the same manner described in Section 5.1.2.46. In step 2, 2-trifluoromethylphenyl hydrazine was used as the reagent to form pyrazole.

ESMS m/z 425 (MH⁺) $C_{24}H_{19}F_3N_2O_2$=424 g/mol, HPLC purity=90%.

5.1.2.54 Synthesis of 4-[4-Ethyl-1-(2-fluorophenyl)-5-(4-hydroxyphenyl)pyrazol-3-yl]phenol This compound was synthesized in the same manner described in Section 5.1.2.46. In step 2, 2-fluorophenyl hydrazine was used as the reagent to form pyrazole.

ESMS m/z 375 (MH⁺) $C_{23}H_{19}FN_2O_2$=374 g/mol, HPLC purity=85%.

5.1.2.55 Synthesis of 4-[4-Ethyl-5-(4-hydroxyphenyl)-1-(2-methylphenyl)pyrazol-3-yl]phenol This compound was synthesized in the same manner described in Section 5.1.2.46. In step 2, 2-methylphenyl hydrazine was used as the reagent to form pyrazole.

ESMS m/z 371 (MH⁺) $C_{24}H_{22}N_2O_2$=370 g/mol, HPLC purity=85%.

5.1.2.56 Synthesis of 4-[1-(3,5-Dichlorophenyl)-4-ethyl-5-(4-hydroxyphenyl)pyrazol-3-yl]phenol This compound was synthesized in the same manner described in Section 5.1.2.46. In step 2, 3,5-dichlorophenyl hydrazine was used as the reagent to form pyrazole.

ESMS m/z 426 (MH⁺) $C_{23}H_{18}Cl_2N_2O_2$=424 g/mol, HPLC purity=90%.

5.1.2.57 Synthesis of 4-[1-(4-Chloro-2-methylphenyl)-4-ethyl-5-(4-hydroxyphenyl)pyrazol-3-yl]phenol This compound was synthesized in the same manner described in Section 5.1.2.46. In step 2, 4-chloro-2methylphenyl hydrazine was used as the reagent to form pyrazole.

ESMS m/z 405 (MH⁺) $C_{24}H_{21}ClN_2O_2$=404 g/mol, HPLC purity=85%.

5.1.2.58 Synthesis of 4-[4-Ethyl-5-(4-hydroxyphenyl)-1-(4-methylphenyl)pyrazol-3-yl]phenol This compound was synthesized in the same manner described in Section 5.1.2.46. In step 2, 4-methylphenyl hydrazine was used as the reagent to form pyrazole.

ESMS m/z 371 (MH⁺) $C_{24}H_{22}N_2O_2$=370 g/mol, HPLC purity=80%.

5.1.2.59 Synthesis of 4-[1-(2,3-Dichlorophenyl)-4-ethyl-5-(4-hydroxyphenyl)pyrazol-3-yl]phenol This compound was synthesized in the same manner described in Section 5.1.2.46. In step 2, 2,3-dichlorophenyl hydrazine was used as the reagent to form pyrazole.

ESMS m/z 425 (MH⁺) $C_{23}H_{18}Cl_2N_2O_2$=424 g/mol, HPLC purity=85%.

5.1.2.60 Synthesis of 4-[1-(3,4-Dimethylphenyl)-4-ethyl-5-(4-hydroxyphenyl)pyrazol-3-yl]phenol This compound was synthesized in the same manner described in Section 5.1.2.46. In step 2, 3,4-dimethylphenyl hydrazine was used as the reagent to form pyrazole.

ESMS m/z 385 (MH$^+$) $C_{25}H_{24}N_2O_2$=384 g/mol, HPLC purity=95%.

5.1.2.61 Synthesis of 4-[4-Ethyl-1-(5-fluoro-2-methylphenyl)-5-(4-hydroxyphenyl)pyrazol-3-yl]phenol This compound was synthesized in the same manner described in Section 5.1.2.46. In step 2, 5-fluoro-2-methylphenyl hydrazine was used as the reagent to form pyrazole.

ESMS m/z 389 (MH$^+$) $C_{24}H_{21}FN_2O_2$=388 g/mol, HPLC purity=95%.

5.1.2.62 Synthesis of 4-[1-(2-Chlorophenyl)-4-ethyl-5-(4-hydroxyphenyl)pyrazol-3-yl]phenol This compound was synthesized in the same manner described in Section 5.1.2.46. In step 2, 2-chlorophenyl hydrazine was used as the reagent to form pyrazole.

ESMS m/z 391 (MH$^+$) $C_{23}H_{19}ClN_2O_2$=390 g/mol, HPLC purity=95%.

5.1.2.63 Synthesis of 4-{1-(4-(tert-Butyl)phenyl]-4-ethyl-5-(4-hydroxyphenyl)pyrazol-3-yl}phenol This compound was synthesized in the same manner described in Section 5.1.2.46. In step 2, 4-t-butylphenyl hydrazine was used as the reagent to form pyrazole.

ESMS m/z 413 (MH$^+$) $C_{27}H_{28}N_2O_2$=412 g/mol, HPLC purity=95%.

5.1.2.64 Synthesis of 4-[1-(3-Chlorophenyl)-4-ethyl-5-(4-hydroxyphenyl)pyrazol-3-yl]phenol This compound was synthesized in the same manner described in Section 5.1.2.46. In step 2, 3-chlorophenyl hydrazine was used as the reagent to form pyrazole.

ESMS m/z 391 (MH$^+$) $C_{23}H_{19}Cl_2N_2O_2$=390 g/mol, HPLC purity=90%.

5.1.2.65 Synthesis of 4-[1-(2,4-Dichlorophenyl)-4-ethyl-5-(4-hydroxyphenyl)pyrazol-3-yl]phenol This compound was synthesized in the same manner described in Section 5.1.2.46. In step 2, 2,4-dichlorophenyl hydrazine was used as the reagent to form pyrazole.

ESMS m/z 425 (MH$^+$) $C_{23}H_{18}Cl_2N_2O_2$=424 g/mol, HPLC purity=85%.

5.1.2.66 Synthesis of 4-[1-(3,4-Dichlorophenyl)-4-ethyl-5-(4-hydroxyphenyl)pyrazol-3-yl]phenol This compound was synthesized in the same manner described in Section 5.1.2.46. In step 2, 3,4-dichlorophenyl hydrazine was used as the reagent to form pyrazole.

ESMS m/z 425 (MH$^+$) $C_{23}H_{18}Cl_2N_2O_2$=424 g/mol, HPLC purity=85%.

5.1.2.67 Synthesis of 4-[1-(4-Chlorophenyl)-4-ethyl-5-(4-hydroxyphenyl)pyrazol-3-yl]phenol This compound was synthesized in the same manner described in Section 5.1.2.46. In step 2, 4-chlorophenyl hydrazine was used as the reagent to form pyrazole.

ESMS m/z 391 (MH$^+$) $C_{23}H_{19}ClN_2O_2$=390 g/mol, HPLC purity=80%.

5.1.2.68 Synthesis of 4-(1-(2,6-Dichlorophenyl)-4-ethyl-5-(4-hydroxyphenyl)pyrazol-3-yl]phenol This compound was synthesized in the same manner described in Section 5.1.2.46. In step 2, 2,5-dichlorophenyl hydrazine was used as the reagent to form pyrazole.

ESMS m/z 425 (MH$^+$) $C_{23}H_{18}Cl_2N_2O_2$=424 g/mol, HPLC purity=95%.

5.1.2.69 Synthesis of 4-[1-(2,3-Dimethylphenyl)-4-ethyl-5-(4-hydroxyphenyl)pyrazol-3-yl]phenol This compound was synthesized in the same manner described in Section 5.1.2.46. In step 2, 2,3-dimethylphenyl hydrazine was used as the reagent to form pyrazole.

ESMS m/z 385 (MH$^+$) $C_{25}H_{24}N_2O_2$=384 g/mol, HPLC purity=95%.

5.1.2.70 Synthesis of 4-[1-(3-Chloro-4-fluorophenyl)-4-ethyl-5-(4-hydroxyphenyl)pyrazol-3-yl]phenol This compound was synthesized in the same manner described in Section 5.1.2.46. In step 2, 3-chloro4fluorophenyl hydrazine was used as the reagent to force pyrazole.

ESMS m/z 409 (MH$^+$) $C_{23}H_{18}ClFN_2O_2$=408 g/mol, HPLC purity=99%.

5.1.2.71 Synthesis of 4-{4-Ethyl-5-(4-hydroxyphenyl)-1-[4-(trifluoromethoxy)phenyl]pyrazol-3-yl}phenol This compound was synthesized in the same manner described in Section 5.1.2.46. In step 2, 4-trifluoromethoxyphenyl hydrazine was used as the reagent to form pyrazole.

ESMS m/z 441 (MH$^+$) $C_{24}H_{19}F_3N_2O_3$=440 g/mol, HPLC purity=95%.

5.1.2.72 Synthesis of 4-{4-Ethyl-5-(4-hydroxyphenyl)-1-[4-(trifluoromethyl)phenyl]pyrazol-3-yl}phenol This compound was synthesized in the same manner described in Section 5.1.2.46. In step 2, 4-tritluoromethylphenyl hydrazine was used as the reagent to form pyrazole.

ESMS m/z 425 (MH$^+$) $C_{24}H_{19}F_3N_2O_2$=424 g/mol, HPLC purity=60%.

5.1.2.73 Synthesis of 4-[4-Ethyl-5-(4-hydroxyphenyl)-1-(4-iodophenyl)pyrazol-3-yl]phenol This compound was synthesized in the same manner described in Section 5.1.2.46. In step 2, 4-iodophenyl hydrazine was used as the reagent to form pyrazole.

ESMS m/z 482 (MH$^+$) $C_{23}H_{19}IN_2O_2$=481 g/mol, HPLC purity=60%.

5.1.2.74 Synthesis of 4-{1-[2-Chloro-5-(trifluoromethyl)phenyl]-4-ethyl-5-(4-hydroxyphenyl)pyrazol-3-yl}phenol This compound was synthesized in the same manner described in Section 5.1.2.46. In step 2, 2-chloro-5-trifluoromethylphenyl hydrazine was used as the reagent to form pyrazole.

ESMS m/z 459 (MH$^+$) $C_{24}H_{18}ClF_3N_2O_2$=458 g/mol, HPLC purity=95%.

5.1.2.75 Synthesis of 4-(1-(3,5-Dichloro(4-pyridyl))-4-ethyl-5-(4-hydroxyphenyl)pyrazol-3-yl]phenol This compound was synthesized in the same manner described in Section 5.1.2.46. In step 2, 3,5-dichloro-4-pyridylhydrazine was used as the reagent to form pyrazole.

ESMS m/z 427 (MH$^+$) $C_{22}H_{17}Cl_2N_3O_2$=426 g/mol, HPLC purity=85%.

5.1.2.76 Synthesis of 4-{4-Ethyl-5-(4-hydroxyphenyl)-1-[6-methyl-4-(trifluoromethyl)(2-pyridyl)]pyrazol-3-yl}phenol This compound was synthesized in the same manner described in Section 5.1.2.46. In step 2, 3-methyl-5-tritluoromethyl-2-pyridylhydrazine was used as the reagent to form pyrazole.

ESMS m/a 440 (MH$^+$) $C_{24}H_{20}F_3N_3O_2$=439 g/mol, HPLC purity=85%.

5.1.2.77 Synthesis of 4-[4-Ethyl-5-(4-hydroxyphenyl)-1-quinoxalin-2-ylpyrazol-3-yl]phenol This compound was synthesized in the same manner described in Section 5.1.2.46. In step 2, quinoxaline-2-ylhydrazine was used as the reagent to form pyrazole.

ESMS m/z 409 (MH$^+$) $C_{25}H_{20}N_4O_2$=408 g/mol, HPLC purity=70%.

5.1.2.78 Synthesis of 4-{1-[3,5-bis(Trifluoromethyl)phenyl]-4-ethyl-5-(4-hydroxyphenyl)pyrazol-3-yl}phenol This compound was synthesized in the same manner described in Section 5.1.2.46. In step 2, 3,5- ditrifluoromethylphenyl hydrazine was used as the reagent to form pyrazole.

ESMS m/z 493 (MH$^+$) $C_{25}H_{18}F_6N_2O_2$=492 g/mol, HPLC purity=80%.

5.1.2.79 Synthesis of 4-[3,5-bis(4-Hydroxyphenyl)-4-ethylpyrazolyl]benzenesulfonamide This compound was synthesized in the same manner described in Section 5.1.2.46. In step 2, 4-(methylsulfonyl)phenylhydrazine was used as the reagent to form pyrazole.

ESMS m/z 436 (MH$^+$) $C_{23}H_{21}N_3O_4S$=435 g/mol, HPLC purity=70%.

5.1.2.80 Synthesis of 4-[1-(1,3-Dimethyl-5-nitropyrazol-4-yl)-4-ethyl-3-(4-hydroxyphenyl)pyrazol-5-yl]phenol This compound was synthesized in the same manner described in Section 5.1.2.46. In step 2, 1,3-dimethyl-5nitropyrazole-4-ylhydrazine was used as the reagent to form pyrazole.

ESMS m/z 420 (MH$^+$) $C_{22}H_{21}N_5O_4$=419 g/mol, HPLC purity=70%.

5.1.2.81 Synthesis of 4-{1-[5-Chloro-3-(trifluoromethyl)(2-pyridyl)]-4-ethyl-5-(4-hydroxyphenyl)pyrazol-3-yl}phenol This compound was synthesized in the same manner described in Section 5.1.2.46. In step 2, 5-chloro-3trifluoromethyl-2-pyridylhydrazine was used as the reagent to form pyrazole.

ESMS m/z 460 (MH$^+$) $C_{23}H_{17}ClF_3N_3O_2$=459 g/mol, HPLC purity=85%.

5.1.2.82 Synthesis of 4-{1-[3-Chloro-5-(trifluoromethyl)(2-pyridyl)]-4-ethyl-5-(4-hydroxyphenyl)pyrazol-3-yl}phenol This compound was synthesized in the same manner described in Section 5.1.2.46. In step 2, 3-chloro-5trifluoromethyl-2-pyridylhydrazine was used as the reagent to form pyrazole.

ESMS m/z 460 (MH$^+$) $C_{23}H_{17}ClF_3N_3O_2$=459 g/mol, HPLC purity=85%.

5.1.2.83 Synthesis of 4-[4-Ethyl-5-(4-hydroxyphenyl)-1-(1,3,4-trimethylpyrazolo[4,5-e]pyridin-6-A)pyrazol-3-yl]phenol This compound was synthesized in the same manner described in Section 5.1.2.46. In step 2, 1,3,4-trimethylpyrazolo[5,4-b]pyridine-6-ylhydrazine was used as the reagent to form pyrazole.

ESMS m/z 440 (MH$^+$) $C_{26}H_{25}N_5O_2$=439 g/mol, HPLC purity=80%.

5.1.2.84 Synthesis of 4-[1-(6-Chloro-2-fluorophenyl)-4-ethyl-5-(4-hydroxyphenyl)pyrazol-3-yl]phenol This compound was synthesized in the same manner described in Section 5.1.2.46. In step 2, 2-chloro-6-fluorophenyl hydrazine was used as the reagent to form pyrazole.

ESMS m/z 409 (MH$^+$) $C_{23}H_{18}ClFN_2O_2$=408 g/mol, HPLC purity=85%.

5.1.2.85 Synthesis of 4-[4-Ethyl-5-(4-hydroxyphenyl)-1-(2-pyridyl)pyrazol-3-yl]phenol This compound was synthesized in the same manner described in Section 5.1.2.46. In step 2, 2-pyridylhydrazine was used as the reagent to form pyrazole.

ESMS m/z 358 (MH$^+$) $C_{22}H_{19}N_3O_2$=357 g/mol, HPLC purity=90%

5.1.2.86 Synthesis of 4-[4-Ethyl-1-(3-hexadecylthiophenyl)-5-(4-hydroxyphenyl)pyrazol-3-yl]phenol This compound was synthesized in the same manner described in Section 5.1.2.46. In step 2, 3-hexadecylthiophenylhydrazine was used as the reagent to form pyrazole.

ESMS m/z 613 (MH$^+$) $C_{39}H_{52}$=612 g/mol, HPLC purity=50%.

5.1.2.87 Synthesis of 4-[3,5-bis(4-Hydroxyphenyl)-1-(3-hexadecylthiophenyl)pyrazol-4-yl]phenol This compound was synthesized in the same manner described in Section 5.1.2.46. In step 2, 3hexadecylthiophenylhydrazine was used as the reagent to form pyrazole.

ESMS m/z 677 (MH$^+$) $C_{43}H_{52}N_2O_3S$=676 g/mol, HPLC purity=50%.

5.1.2.88 Synthesis of 4-{4-Ethyl-5-(4-hydroxyphenyl)-1-[(4-hydroxyphenyl)methyl]pyrazol-3-yl}phenol This compound was synthesized based upon Scheme 4.

Step 1: To a solution of 4'-methoxybutyryl phenone (1.0 equiv.) in THF at −78° C. was added dropwise 1.5 equiv. of [(CH$_3$)$_2$Si]$_2$NLi. The solution was stirred for 1 h at −78° C., followed by addition of 1.2 equiv. of p-anisoyl chloride. The reaction mixture was stirred for 10 min at −78° C. and then for 22 h at rt, acidified with 10% citric acid, and extracted with EtOAc. The combined organic layers were washed with water and dried over Na$_2$SO$_4$. Removal of solvent in vacuo provided a crude solid which was purified by flash chromatography (CH$_2$Cl$_2$) to give 1,3-bis(4-methoxyphenyl)-2-ethylpropane-1,3-dione.

Step 2: A mixture of the 1,3-diketone obtained in step 1 (1.0 equiv.), hydrazine (3.0 equiv.), conc. HCl aq. (catalytic amount) and ethanol was heated to reflux overnight. Cooled to rt and removed solvent in vacuo. Water and ethyl acetate were added. The organic layer was separated, washed with dil. HCl, brine, dried, filtered and the solvent was concentrated in vacuo to give the product 4-methoxy-1-[5-(4-methoxyphenyl)-4-benzylpyrazol-3-yl]benzene.

Step 3: Alkylation. Reaction was carried out in oven-dried glassware under nitrogen. Diketone (obtained from the above step) in DMF was added to a chilled suspension of NaH (1.1 equiv.) in DMF. The mixture was allowed to stir for 5 min after which the 4'-methoxybenzyl bromide was added (2.0 Oequiv.). The reaction was then allowed to stir over night at RT. Ethyl acetate was then added and the reaction was washed with 10% citric acid, 10% NaHCO$_3$ and brine. After drying over Na$_2$SO$_4$ the solvent was removed. Products required purification which was achieved with flash chromatography (10% EtOAc/petrol).

Step 4: Demethylation was performed as described in Scheme 1 to afford the final product.

$^1$H NMR (d$_6$-DMSO): δ 0.83 (3H, t, J=7.3 Hz), 2.38 (2H, q, J=7.3 Hz), 4.94 (2H, s), 6.58 (2H, d, J=8.4 Hz), 6.74 (2H, d, J=8.4 Hz), 6.76 (2H, d, J=8.4 Hz), 6.81 (2H, d, J=8.8 Hz), 7.05 (2H, d, J=8.4 Hz), 7.39 (2H, d, J=8.8 Hz); ESMS m/z 387 (MH$^+$), $C_{24}H_{22}N_2O_3$=386 g/mol; HPLC purity=96%.

5.1.2.89 Synthesis of 4-(4-Ethyl-5-(4-hydroxyphenyl)-1-{[4-(2-piperidylethoxy)phenyl]methyl}pyrazol-3-yl)phenol This compound was synthesized in the same manner as described in Section 5.1.2.88. In step 3, 4-(chloromethyl)-1(2-piperidylethoxy)benzene was used for alkylation.

$^1$H NMR (acetone): δ 0.93 (3H, t, J=7.4 Hz), 1.42–1.57 (1H, m), 1.72–2.05 (5H, m), 2.49 (2H, q, J=7.4 Hz), 3.07–3.18 (2H, m), 3.54–3.58 (2H, m), 3.62–3.71 (2H, m), 3.83 (3H, m), 4.44 (2H, t, J=5.1 Hz), 5.08 (2H, s), 6.82 (2H, d, J=7.8 Hz), 6.87 (2H, d, J=8.8 Hz), 6.92 (2H, d, J=8.6 Hz), 6.98 (2H, d, J=7.5 Hz), 7.10 (2H, d, J=8.2 Hz), 7.55 (2H, d, J=8.0 Hz); ESMS m/z 498 (MH+), $C_{31}H_{35}N_3O_3$=497 g/mol; HPLC purity=97.9%.

5.1.2.90 Synthesis of 4-{1-[(3-Chlorophenyl)methyl]-4-ethyl-5-(4-hydroxyphenyl)pyrazol-3-yl}phenol This compound was synthesized in the same manner described in Section 5.1.2.88. In step 3, 3'-chlorobenzyl chloride was used for alkylation.

$^1$H NMR (CDCl$_3$): δ 0.75 (3H, t, J=7.5 Hz), 2.30 (2H, q, J=7.5 Hz), 4.95 (2H, s), 6.67–6.73 (5H, m), 6.77–6.80 (1H, m), 6.87 (2H, dd, J=5.5, 1.6 Hz), 7.30 (2H, d, J=8.8 Hz); ESMS m/z 405 (NM+), C$_{24}$H$_{21}$ClN$_2$O$_2$=404 g/mol; HPLC purity=92.7%.

5.1.2.91 Synthesis of 4-{4-ethyl-1-[(4-Fluorophenyl)methylJ-S-(4-hydroxyphenyl)pyrazol-3-yl}phenol This compound was synthesized in the same manner described in Section 5.1.2.88. In step 3, 4'-fluorobenzyl chloride was used for alkylation.

$^1$H NMR (CDCl$_3$): δ 0.79 (3H, t, J=7.5 Hz), 2.33 (2H, q, J=7.5 Hz), 4.99 (2H, s), 6.71–6.84 (8H, m), 6.90 (2H, d, J=8.4 Hz), 7.34 (2H, d, J=8.4 Hz); ESMS m/z 389 (MH+) C$_{24}$H$_{21}$FN$_2$O$_2$=388 g/mol; HPLC purity=90.8%.

5.1.2.92 Synthesis of 4-{4-ethyl-5-(4-Hydroxyphenyl)-1-[(3-methylphenyl)methyl]pyrazol-3-yl}phenol This compound was synthesized in the same manner described in Section 5.1.2.88. In step 3, 3'-methylbenzyl chloride was used for alkylation.

$^1$H NMR (CDCl$_3$): δ 0.85 (3H, t, J=7.5 Hz), 2.18 (3H, s), 2.40 (2H, q, J=7.5 Hz), 5.04 (2H, s), 6.68 (1H, d, J=7.4 Hz), 6.71 (1H, s), 6.78 (2H, d, 8.0 Hz), 6.80 (2H, d, 8.0 Hz), 6.93 (1H, d, J=7.4 Hz), 6.97 (2H, d, J=8.8 Hz), 7.03 (1H, t, J=7.4 Hz), 7.39 (2H, d, J=8.8 Hz); ESMS m/z 385 (MH+), C$_{25}$H$_{24}$N$_2$O$_2$=384 g/mol; HPLC purity=87.6%.

5.1.2.93 Synthesis of 4-{4-ethyl-5-(4-Hydroxyphenyl)-1-[(4-nitrophenyl)methyl]pyrazol-3-yl}phenol This compound was synthesized in the same manner described in Section 5.1.2.88. In step 3, 4'-nitrobenzyl chloride was used for alkylation.

$^1$H NMR (CDCl$_3$): δ 0.60 (3H, t, J=7.5 Hz), 2.17 (2H, q, J=7.5 Hz), 4.93 (2H, s), 6.51 (2H, d, J=8.8 Hz), 6.54 (2H, d, J=8.8 Hz), 6.69 (2H, d, J=8.8 Hz), 6.80 (2H, d, J=8.8 Hz), 7.12 (2H, d, J=8.8 Hz), 7.77 (2H, d, J=8.8 Hz); ESMS m/z 416 (MH+), C$_{24}$H$_{21}$N$_3$O$_4$=415 g/mol; HPLC purity=83.5%.

5.1.2.94 Synthesis of 4-{4-ethyl-5-(4-Hydroxyphenyl)-1-[(3-phenoxyphenyl)methyl]pyrazol-3-yl}phenol This compound was synthesized in the same manner described in Section 5.1.2.88. In step 3, 3'-phenoxybenzyl chloride was used for alkylation.

$^1$H NMR (CDCl$_3$): δ 0.90 (3H, t, J=7.5 Hz), 2.38 (2H, q, J=7.5 Hz), 5.04 (2H, s), 6.43 (1H, m), 6.65 (1H, d, J=7.1 Hz), 6.73–6.87 (7H, m), 6.93 (2H, dd, J=8.6, 2.4 Hz), 7.01 (1H, t, J=7.2 Hz), 7.13 (1H, t, J=7.9 Hz, 7.19–7.25 (2H, m), 7.34 (2H, d, J=8.6 Hz); ESMS m/z 463 (MH+), C$_{30}$H$_{26}$N$_2$O$_3$=462 g/mol; HPLC purity=78.5%.

5.1.2.95 Synthesis of 2-[3,5-bis(4-Hydroxyphenyl)-4-ethylpyrazolyl]-1-(4-methylphenyl)ethan-1-one This compound was synthesized in the same manner described in Section 5.1.2.88. In step 3, 2-chloro-1-(4methylphenyl)ethan-1-one was used for alkylation.

$^1$H NMR (CDCl$_3$): δ 0.89 (3H, t, J=7.5 Hz), 2.32 (3H, s), 2.44 (2H, q, J=7.5 Hz), 5.30 (2H, s), 6.77 (2H, d, J=9.2 Hz), 6.80 (2H, d, J=9.2 Hz), 7.06 (2H, d, J=8.1 Hz), 7.18 (2H, d, J=8.8 Hz), 7.41 (2H, d, J=8.8 Hz), 7.69 (2H, d, J=8.1 Hz); ESMS m/z 413 (MH+), C$_{26}$H$_{24}$N$_2$O$_3$=412 g/mol; HPLC purity=90.8%.

5.1.2.96 Synthesis of 2-[3,5-bis(4-Hydroxyphenyl)-4-ethylpyrazolyl]-1-(4-fluorophenyl)ethan-1-one This compound was synthesized in the same manner described in Section 5.1.2.88. In step 3, 2-chloro-1-(4-fluorophenyl)ethan-1-one was used for alkylation.

$^1$H NMR (CDCl$_3$): δ 0.86 (3H, t, J=7.5 Hz), 2.41 (2H, q, J=7.5 Hz), 5.29 (2H, s), 6.74 (2H, d, J=8.8 Hz), 6.76 (2H, d, J=8.8 Hz), 7.02 (2H, d, J=8.6 Hz), 7.05 (2H, d, J=8.8 Hz), 7.36 (2H, d, J=8.8 Hz), 7.80 (2H, dd, J=8.8, 5.1 Hz); ESMS m/z 417 (MH+), C$_{25}$H$_{21}$FN$_2$O$_3$=416 g/mol; HPLC purity= 83.1%.

5.1.2.97 Synthesis of 1-(3,4-Dichlorophenyl)-2-[3,5-bis(4-hydroxyphenyl)4-ethylpyrazolyl]ethan-1-one This compound was synthesized in the same manner described in Section 5.1.2.88. In step 3, 2-chloro-1-(3,4-dichlorophenyl)ethan-1-one was used for alkylation.

$^1$H NMR (CDCl$_3$): δ 0.88 (1.5H, t, J=7.5 Hz), 0.96 (1.5H, t, J=7.5 Hz), 2.43 (1H, q, J=7.5 Hz), 2.52 (1H, q, J=7.5 Hz), 5.30 (1H, s), 6.77–6.86 (4H, m), 7.05 ($^1$H, d, J=8.8 Hz), 7.32 (2H, t, J=8.6 Hz), 7.46–7.53 (1.5H, m), 7.64 (0.5H, dd, J=8.4, 2.4 Hz), 7.78–7.88 (0.5H, m), 7.79–8.10 (0.5H, m); ESMS m/z 467 (MH+), C$_{25}$H$_{20}$Cl$_2$N$_2$O$_3$=466 g/mol; HPLC purity=82.7%.

5.1.2.98 Synthesis of 2-[3,5-bis(4-Hydroxyphenyl)-4-ethylpyrazolyl]-1-(2-hydroxyphenyl)ethan-1-one This compound was synthesized in the same manner described in Section 5.1.2.88. In step 3, 2-chloro-1-(2-methoxyphenyl)ethan-1-one was used for alkylation.

$^1$H NMR (CDCl$_3$): δ 0.89 (3H, t, J=7.5 Hz), 2.45 (2H, q, J=7.5 Hz), 3.67 (2H, s), 5.38 (1H, s), 6.76–6.90 (6H, m), 7.08 (2H, d, J=8.8 Hz), 7.39–7.44 (3H, m), 7.58 91H, dd, J=7.4, 2.5 Hz), 7.29–7.50 (3H, m), 7.69 (2H, d, J=8.8 Hz); ESMS m/z 415 (MH+), C$_{25}$H$_{22}$N$_2$O$_4$=414 g/mol; HPLC purity=90.7%.

5.1.2.99 Synthesis of 4-[4-ethyl-5-(4-Hydroxyphenyl)-1-benzylpyrazol-3-yl]phenol This compound was synthesized in the same manner described in Section 5.1.2.88. In step 3, benzylbromide was used for alkylation.

$^1$H NMR (CDCl$_3$): δ 0.86 (3H, t, J=7.5 Hz), 2.41 (2H, q, J=7.5 Hz), 5.10 (2H, s), 6.77 (2H, d, J=8.8 Hz), 6.80 (1H, d, J=8.8 Hz), 6.90 (2H, d, J=8.8 Hz), 6.97 (2H, d, J=8.8 Hz), 7.10–7.19 (3H, m), 7.40 (2H, d, J=8.8 Hz); ESMS m/z 371 (MH+), C$_{24}$H$_{22}$N$_2$O$_2$370 g/mol; HPLC purity=90.0%.

5.1.2.100 Synthesis of 2-[3,5-bis(4-Hydroxyphenyl)-4-ethylpyrazolyl]-1-(4-bromophenyl)ethan-1-one This compound was synthesized in the same manner described in Section 5.1.2.88. In step 3, 2-chloro-1-(4-bromophenyl)ethan-1-one was used for alkylation.

ESMS m/z 477/479 (MH+), C$_{25}$H$_{21}$BrN$_2$O$_3$=476/478 g/mol; HPLC purity 80.8%.

5.1.2.101 Synthesis of 4-(1-{[4-(tert-Butyl)phenyl]methyl}-4-ethyl-5-(4-hydroxyphenyl)pyrazol-3-yl)phenol This compound was synthesized in the same manner described in Section 5.1.2.88. In step 3, 4'-butylbenzyl chloride was used for alkylation.

$^1$H NMR (CDCl$_3$): δ 0.85 (3H, t, J=7.5 Hz), 1.19 (9H, s), 2.48 (2H, q, J=7.5 Hz), 5.05 (2H, s), 6.77 (2H, d, J=8.8 Hz), 6.79 (2H, d, J=8.9 Hz), 6.84 (2H, d, J=8.9 Hz), 6.99 (2H, d, J=8.9 Hz), 7.18 (2H, d, J=8.9 Hz), 7.38 (2H, d, J=8.9 Hz); ESMS m/z 427 (MH+), C$_{28}$H$_{30}$N$_2$O$_2$=426 g/mol; HPLC purity=86.1%.

5.1.2.102 Synthesis of 4-{2-[3,5-bis(4-Hydroxyphenyl)-4-ethylpyrazolyl]acetyl}benzenecarbonitrile This compound was synthesized in the same manner described in Section 5.1.2.88. In step 3, 2-chloro-1-(4cyanophenyl)ethan-1-one was used for allkylation.

$^1$H NMR (CDCl$_3$): δ 0.88 (3H, t, J=7.5 Hz), 2.44 (2H, q, J=7.5 Hz), 5.28 (2H, s), 6.78 (2H, d, J=8.8 Hz), 6.82 (2H, d, J=9.1 Hz), 7.04 (2H, d, J=9.6 Hz), 7.40 (2H, d, J=8.4 Hz), 7.69 (2H, d, J=8.8 Hz), 7.86 (2H, d, J=8.8 Hz); ESMS m/z 424 (MH+), C$_{26}$H$_{21}$N$_3$O$_3$=423 g/mol; HPLC purity=81.8%.

5.1.2.103 Synthesis of 2-[3,5-bis(4-Hydroxyphenyl)-4-ethylpyrazolyl]-1-(4-phenylphenyl)ethan-1-one This compound was synthesized in the same manner described in Section 5.1.2.88. In step 3, 2-chloro-1-(4-phenylphenyl)ethan-1-one was used for alkylation.

$^1$H NMR (CDCl$_3$): δ 0.89 (3H, t, J=7.5 Hz), 2.45 (2H, q, J=7.5 Hz), 5.38 (2H, s), 6.77 (2H, d, J=8.8 Hz), 6.81 (2H, d,

J=9.2 Hz), 7.08 (2H, d, J=8.8 Hz), 7.29–7.45 (5H, m), 7.54 (2H, d, J=8.8 Hz), 7.62 (2H, d, J=8.8 Hz), 7.86 (2H, d, J=8.4 Hz); ESMS m/z 475 (MH$^+$), C$_{31}$H$_{26}$N$_2$O$_3$=474 g/mol; HPLC purity=90.9%.

5.1.2.104 Synthesis of 2-[3,5-bis(4-Hydroxyphenyl)-4-ethylpyrazolyl]-1-(3-hydroxyphenyl)ethan-1-one This compound was synthesized in the same manner described in Section 5.1.2.88. In step 3, 2-chloro-1-(3-methoxyphenyl)ethan-1-one was used for allkylation.

$^1$H NMR (CDCl$_3$): δ 0.79 (3H, t, J=7.5 Hz), 2.33 (2H, q, J=7.5 Hz), 5.19 (2H, s), 6.66 (2H, d, J=8.8 Hz), 6.70 (2H, d, J=8.8 Hz), 6.87 ($^1$H, ddd, J=7.9, 2.6, 1.1 Hz), 6.96 (2H, d, J=8.6, 2.5 Hz), 7.07–7.16 (3H, m), 7.31 (2H, d, J=8.8 Hz); ESMS m/z 415 (MH+), C$_{25}$H$_{22}$N$_2$O$_4$=414 g/mol; HPLC purity=84.9%.

5.1.2.105 Synthesis of 4-[1-(2,4-Dimethylphenyl)-5-(4-hydroxyphenyl)-4-phenylpyrazol-3-yl]phenol This compound was synthesized based upon Scheme 1.

Step 1: To a solution of 1-(4-methoxyphenyl)-2-phenylethan-1-one (1.0 equiv.) in THF at −78° C. was added dropwise 1.5 equiv. of [(CH$_3$)$_2$Si]NLi. The solution was stirred for 1 h at −78° C., followed by addition of 1.2 equiv. of p-anisoyl chloride. The reaction mixture was stirred for 10 min at −78° C. and then for 22 h at rt, acidified with 10% citric acid, and extracted with EtOAc. The combined organic layers were washed with water and dried over Na$_2$SO$_4$. Removal of solvent in vacuo provided a crude solid which was purified by flash chromatography (CH$_2$Cl$_2$) to give 1,3-bis(4-methoxyphenyl)-2-phenylpropane-1,3-dione.

Step 2: A mixture of the 1,3-diketone obtained in step I (1.0 equiv.), 2,4-dimethylphenyl hydrazine (1.5 equiv.), conc. HCl aq. (catalytic amount) and ethanol was heated to reflux overnight. Cooled to rt and removed solvent in vacuo. Water and ethyl acetate were added. The organic layer was separated, washed with dil. HCI, brine, dried, filtered and the solvent was concentrated in vacuo to give the product.

Step 3: Demethylation was performed as described in Scheme 1 to afford the final product.

ESMS m/z 433 (MH$^+$), C$_{29}$H$_{24}$N$_2$O$_2$=432 g/mol, HPLC purity=90%.

5.1.2.106 Synthesis of 4-[5-(4-Hydroxyphenyl)-1-(3-methylphenyl)-4-phenylpyrazol-3-yl]phenol This compound was synthesized in the same manner as described in Section 5.1.2.105. In step 2, 3-methylphenyl hydrazine was used to form the pyrazole heterocycle.

ESMS m/z 419 (MH$^+$), C$_{28}$H$_{22}$N$_2$O$_2$=418 g/mol, HPLC purity=90%.

5.1.2.107 Synthesis of 4-{5-(4-Hydroxyphenyl)-1-[4-(methylethyl)phenyl]-4-phenylpyrazol-3-yl}phenol This compound was synthesized in the same manner described in Section 5.1.2.105. In step 2, 4-iso-propylphenyl hydrazine was used to form the pyrazole heterocycle.

ESMS m/z 447 (MH$^+$), C$_{30}$H$_{26}$N$_2$O$_2$=446 g/mol, HPLC purity=90%.

5.1.2.108 Synthesis of 4-[1-(3-Fluorophenyl)-5-(4-hydroxyphenyl)-4-phenylpyrazol-3-yl]phenol This compound was synthesized in the same manner described in Section 5.1.2.105. In step 2, 3-fluorophenyl hydrazine was used to form the pyrazole heterocycle.

ESMS m/z 423 (MH$^+$)C$_{27}$H$_{19}$FN$_2$O$_2$=422 g/mol, HPLC purity=90%.

5.1.2.109 Synthesis of 4-[1-(2-Ethylphenyl)-5-(4-hydroxyphenyl)-4-phenylpyrazol-3-yl]phenol This compound was synthesized in the same manner described in Section 5.1.2.105. In step 2, 2-ethylphenyl hydrazine was used to form the pyrazole heterocycle.

ESMS m/z 433 (MH$^+$), C$_{29}$H$_{24}$N$_2$O$_2$=432 g/mol, HPLC purity=90%.

5.1.2.110 Synthesis of 4-[1-(4-Fluorophenyl)-3-(4-hydroxyphenyl)-4-phenylpyrazol-5-yl]phenol This compound was synthesized in the same manner described in Section. 5.1.2.105. In step 2, 4-fluorophenyl hydrazine was used to form the pyrazole heterocycle.

ESMS m/z 423 (MH$^+$)C$_{27}$H$_{19}$FN$_2$O$_2$=422 g/mol, HPLC purity=90%.

5.1.2.111 Synthesis of 4-[1-(2,4-Difluorophenyl)-5-(4-hydroxyphenyl)-4-phenylpyrazol-3-yl]phenol This compound was synthesized in the same manner described in Section 5.1.2.105. In step 2, 2,4-difluorophenyl hydrazine was used to form the pyrazole heterocycle.

ESMS m/z 441 (MH$^+$)C$_{27}$H$_{18}$F$_2$N$_2$O$_2$=440 g/mol, HPLC purity=90%.

5.1.2.112 Synthesis of 4-{5-(4-Hydroxyphenyl)-4-phenyl-1-[2-(trifluoromethyl)phenyl]pyrazol-3-yl}phenol This compound was synthesized in the same manner described in Section 5.1.2.105. In step 2, 2trifluoromethylphenyl hydrazine was used to form the pyrazole heterocycle.

ESMS m/z 473 (MH$^+$)C$_{28}$H$_{19}$F$_3$N$_2$O$_2$=472 g/mol, HPLC purity=90%.

5.1.2.113 Synthesis of 4-[1-(2-Fluorophenyl)-5-(4-hydroxyphenyl)-4-phenylpyrazol-3-yl]phenol This compound was synthesized in the same manner described in Section 5.1.2.105. In step 2, 2-fluorophenyl hydrazine was used to form the pyrazole heterocycle.

ESMS m/z 423 (MH$^+$)C$_{27}$H$_{19}$FN$_2$O$_2$=422 g/mol, HPLC purity=90%.

5.1.2.114 Synthesis of 4-[5-(4-Hydroxyphenyl)-1-(2-methylphenyl)-4-phenylpyrazol-3-yl]phenol This compound was synthesized in the same manner described in Section 5.1.2.105. In step 2, 2-methylphenyl hydrazine was used to form the pyrazole heterocycle.

ESMS m/z 419 (MH$^+$)C$_{28}$H$_{22}$N$_2$O$_2$=418 g/mol, HPLC purity=90%.

5.1.2.115 Synthesis of 4-[1-(3,5-Dichlorophenyl)-5-(4-hydroxyphenyl)-4-phenylpyrazol-3-yl]phenol This compound was synthesized in the same manner described in Section 5.1.2.105. In step 2, 3,5-dichlorophenyl hydrazine was used to form the pyrazole heterocycle.

ESMS m/z 473 (MH$^+$)C$_{27}$H$_{18}$Cl$_2$N$_2$O$_2$=472 g/mol, HPLC purity=90%.

5.1.2.116 Synthesis of 4-[1-(4-Chloro-2-methylphenyl)-5-(4-hydroxyphenyl)-4-phenylpyrazol-3-yl]phenol This compound was synthesized in the same manner described in Section 5.1.2.105. In step 2, 4-chloro-2-methylphenyl hydrazine was used to form the pyrazole heterocycle.

ESMS m/z 453 (MH$^+$)C$_{28}$H$_{21}$ClN$_2$O$_2$=452 g/mol, HPLC purity=90%.

5.1.2.117 Synthesis of 4-[3-(4-Hydroxyphenyl)-1-(4-methylphenyl)-4-phenylpyrazol-5-yl]phenol This compound was synthesized in the same manner described in Section 5.1.2.105. In step 2, 4-methylphenyl hydrazine was used to form the pyrazole heterocycle.

ESMS m/z 419 (MH$^+$)C$_{28}$H$_{22}$N$_2$O$_2$=418 g/mol, HPLC purity=90%.

5.1.2.118 Synthesis of 4-[1-(2,3-Dichlorophenyl)-5-(4-hydroxyphenyl)-4-phenylpyrazol-3-yl]phenol This compound was synthesized in the same manner described in Section 5.1.2.105. In step 2, 2,3-dichlorophenyl hydrazine was used to form the pyrazole heterocycle.

ESMS m/z 473 (MH$^+$)C$_{27}$H$_{18}$Cl$_2$N$_2$O$_2$=472 g/mol, HPLC purity=90%.

5.1.2.119 Synthesis of 4-[1-(3,4-Dimethylphenyl)-5-(4-hydroxyphenyl)-4-phenylpyrazol-3-yl]phenol This compound was synthesized in the same manner described in Section 5.1.2.105. In step 2, 3,4-dimethylphenyl hydrazine was used to form the pyrazole heterocycle.

ESMS m/z 433 (MH$^+$)C$_{29}$H$_{24}$N$_2$O$_2$=432 g/mol, HPLC purity=90%.

5.1.2.120 Synthesis of 4-[1-(5-Fluoro-2-methylphenyl)-5-(4-hydroxyphenyl)-4-phenylpyrazol-3-yl]phenol This compound was synthesized in the same manner described in Section 5.1.2.105. In step 2, 5-fluoro2-methylphenyl hydrazine was used to form the pyrazole heterocycle.

ESMS m/z 437 (MH$^+$), C$_{28}$H$_{21}$FN$_2$O$_2$=436 g/mol, HPLC purity=90%.

5.1.2.121 Synthesis of 4-[1-(2-Chlorophenyl)-5-(4-hydroxyphenly)-4-phenylpyrazol-3-yl]phenol This compound was synthesized in the same manner described in Section 5.1.2.105. In step 2, 2-chlorophenyl hydrazine was used to form the pyrazole heterocycle.

ESMS m/z 439 (MH$^+$), C$_{27}$H$_{19}$ClN$_2$O$_2$=438 g/mol, HPLC purity=90%.

5.1.2.122 Synthesis of 4-[1-(3-Chlorophenyl)-5-(4-hydroxyphenyl)-4-phenylpyrazol-3-yl]phenol This compound was synthesized in the same manner described in Section 5.1.2.105. In step 2, 3-chloro phenyl hydrazine was used to form the pyrazole heterocycle.

ESMS m/z 439 (MH$^+$), C$_{27}$H$_{19}$ClN$_2$O$_2$=438 g/mol, HPLC purity=90%.

5.1.2.123 Synthesis of 4-[1-(2,4-Dichlorophenyl)-5-(4-hydroxyphenyl)-4-phenylpyrazol-3-yl]phenol This compound was synthesized in the same manner described in Section 5.1.2.105. In step 2, 2,4-dichlorophenyl hydrazine was used to form the pyrazole heterocycle.

ESMS m/z 473 (MH$^+$), C$_{27}$H$_{18}$Cl$_2$N$_2$O$_2$=472 g/mol, HPLC purity=90%.

5.1.2.124 Synthesis of 4-[1-(3,4-Dichlorophenyl)-5-(4-hydroxyphenyl)-4-phenylpyrazol-3-yl]phenol This compound was synthesized in the same manner described in Section 5.1.2.105. In step 2, 3,4-dichlorophenyl hydrazine was used to forth the pyrazole heterocycle.

ESMS m/z 473 (MH$^+$), C$_{27}$H$_{18}$Cl$_2$N$_2$O$_2$=472 g/mol, HPLC purity=90%.

5.1.2.125 Synthesis of 4-[1-(4-Chlorophenyl)-3-(4-hydroxyphenyl)-4-phenylpyrazol-5-yl]phenol This compound was synthesized in the same manner described in Section 5.1.2.105. In step 2, 4-chlorophenyl hydrazine was used to form the pyrazole heterocycle.

ESMS m/z 439 (MH$^+$), C$_{27}$H$_{19}$ClN$_2$O$_2$=438 g/mol, HPLC purity=90%.

5.1.2.126 Synthesis of 4-[1-(2,6-Dichlorophenyl)-5-(4-hydroxyphenyl)-4-phenylpyrazol-3-yl]phenol This compound was synthesized in the same manner described in Section 5.1.2.105. In step 2, 2,5-dichlorophenyl hydrazine was used to form the pyrazole heterocycle.

ESMS m/z 473 (MH$^+$), C$_{27}$H$_{18}$Cl$_2$N$_2$O$_2$=472 g/mol, HPLC purity=90%.

5.1.2.127 Synthesis of 4-[1-(2,3-Dimethylphenyl)-5-(4-hydroxyphenyl)-4-phenylpyrazol-3-yl]phenol This compound was synthesized in the same manner described in Section 5.1.2.105. In step 2, 2,3-dimethylphenyl hydrazine was used to form the pyrazole heterocycle.

ESMS m/z 433 (MH$^+$), C$_{29}$H$_{24}$N$_2$O$_2$=432 g/mol, HPLC purity=90%.

5.1.2.128 Synthesis of 4-[1-(3-Chloro-4-fluorophenyl)-5-(4-hydroxyphenyl)-4-phenylpyrazol-3-yl]phenol This compound was synthesized in the same manner described in Section 5.1.2.105. In step 2, 3-chloro-4-fluorophenyl hydrazine was used to form the pyrazole heterocycle.

ESMS m/z 457 (MH$^+$), C$_{27}$H$_{18}$ClFN$_2$O$_2$=456 g/mol, HPLC purity=90%.

5.1.2.129 Synthesis of 4-{5-(4-Hydroxyphenyl)-4-phenyl-1-[4-(trifluoromethoxy)phenyl]pyrazol-3-yl}phenol This compound was synthesized in the same manner described in Section 5.1.2.105. In step 2, 4-trifluoromethoxyphenyl hydrazine was used to form the pyrazole heterocycle.

ESMS m/z 489 (MH$^+$), C$_{28}$H$_{19}$F$_3$N$_2$O$_3$=488 g/mol, HPLC purity=90%.

5.1.2.130 Synthesis of 4-{5-(4-Hydroxyphenyl)-4-phenyl-1-[4-(trifluoromethyl)phenyl]pyrazol-3-yl}phenol This compound was synthesized in the same manner described in Section 5.1.2.105. In step 2, 4-trifluoromethylphenyl hydrazine was used to form the pyrazole heterocycle.

ESMS m/z 473 (MH$^+$), C$_{28}$H$_{19}$F$_3$N$_2$O$_2$=472 g/mol, HPLC purity=90%.

5.1.2.131 Synthesis of 4-[3-(4-Hydroxyphenyl)-1-(4-iodophenyl)-4-phenylpyrazol-5-yl]phenol This compound was synthesized in the same manner described in Section 5.1.2.105. In step 2, 4-iodophenyl hydrazine was used to form the pyrazole heterocycle.

ESMS m/z 531 (MH$^+$), C$_{27}$H$_{19}$IN$_2$O$_2$=530 g/mol, HPLC purity=90%.

5.1.2.132 Synthesis of 4-{1-[2-Chloro-5-(trifluoromethyl)phenyl]-5-(4-hydroxyphenyl)-4-phenylpyrazol-3-yl}phenol This compound was synthesized in the same manner described in Section 5.1.2.105. In step 2, 2-chloro5-trifluoromethylphenyl hydrazine was used to form the pyrazole heterocycle.

$^1$H NMR (DMSO-d$_6$): δ 6.56 (2H, d, J=8.61 Hz), 6.66 (2H, d, J=8.61 Hz), 6.91 (2H, d, J=8.6 lHz), 7.12 (2H, d, J=8.06 Hz), 7.19 (2H, d, J=8.6 Hz), 7.22–7.29 (3H, m), 8.08 (1H, s), 9.49 (1H, s), 9.61 (1H, s); ESMS m/z 507 (MH$^+$), C$_{28}$H$_{18}$ClF$_3$N$_2$O$_2$496 g/mol; HPLC purity=98.1%.

5.1.2.133 Synthesis of 4-[1-(3,5-Dichloro(4-pyridyl))-5-(4-hydroxyphenyl)-4-phenylpyrazol-3-yl]phenol This compound was synthesized in the same manner described in Section 5.1.2.105. In step 2, 3,5-dichloro-4-pyridyl hydrazine was used to form the pyrazole heterocycle.

ESMS m/z 474 (MH$^+$), C$_{26}$H$_{17}$Cl$_2$N$_3$O$_2$=473 g/mol, HPLC purity=90%.

5.1.2.134 Synthesis of 4-{5-(4-Hydroxyphenyl)-1-[6-methyl-4-(Trifluoromethyl)(2-pyridyl)]-4-phenylpyrazol-3-yl}phenol This compound was synthesized in the same manner described in Section 5.1.2.105. In step 2, 6-methyl-4-trifluoromethyl-2-pyridyl hydrazine was used to form the pyrazole heterocycle.

ESMS m/z 488 (MH$^+$), C$_{28}$H$_{20}$F$_3$N$_3$O$_2$=487 g/mol, HPLC purity=90%.

5.1.2.135 Synthesis of 4-[5-(4-Hydroxyphenyl)-4-phenyl-1-quinoxalin-2-ylpyrazol-3-yl]phenol This compound was synthesized in the same manner described in Section 5.1.2.105. In step 2, quinoxaline-2-ylhydrazine was used to form the pyrazole heterocycle.

ESMS m/z 457 (MH$^+$), C$_{29}$H$_{20}$N$_4$O$_2$=456 g/mol, HPLC purity=90%.

5.1.2.136 Synthesis of 4-{1-[3,5-bis(Trifluoromethyl)phenyl]-5-(4-hydroxyphenyl)-4-phenylpyrazol-3-yl}phenol This compound was synthesized in the same manner described in Section 5.1.2.105. In step 2, 3,5-ditrifluoromethylphenyl hydrazine was used to form the pyrazole heterocycle.

ESMS m/z 541 (MH$^+$), $C_{29}H_{18}F_6N_2O_2$=540 g/mol, HPLC purity=90%.

5.1.2.137 Synthesis of 4-{1-[1,3-Dimethyl-5-(nitromethyl)pyrazol-4-yl]-5-(4-hydroxyphenyl)-4-phenylpyrazol-3-yl}phenol This compound was synthesized in the same manner described in Section 5.1.2.105. In step 2, 3-dimethyl-5-nitropyrazole-4-ylhydrazine was used to form the pyrazole heterocycle.

ESMS m/z 482 (MH$^+$), $C_{27}H_{23}N_5O_4$=481 g/mol, HPLC purity=90%.

5.1.2.138 Synthesis of 4-{1-[5-Chloro-3-(trifluoromethyl)(2-pyridyl)]-5-(4-hydroxyphenyl)-4-phenylpyrazol-3-yl}phenol This compound was synthesized in the same manner described in Section 5.1.2.105. In step 2, 5-chloro-3-trifluoromethyl-2-pyridylhydrazine was used to form the pyrazole heterocycle.

ESMS m/z 508 (MH$^+$), $C_{27}H_{17}ClF_3N_3O_2$=507 g/mol, HPLC purity=90%.

5.1.2.139 Synthesis of 4-{1-[3-Chloro-5-(trifluoromethyl)(2-pyridyl)]-5-(4-hydroxyphenyl)-4-phenylpyrazol-3-yl}phenol This compound was synthesized in the same manner described in Section 5.1.2.105. In step 2, 3-chloro-5-trifluoromethyl-2-pyridylhydrazine was used to form the pyrazole heterocycle.

ESMS m/z 508 (MH$^+$), $C_{27}H_{17}ClF_3N_3O_2$=507 g/mol, HPLC purity=90%.

5.1.2.140 Synthesis of 4-[5-(4-Hydroxyphenyl)-4-phenyl-1-(1,3,4-trimethylpyrazolo[4,5-e]pyridin-6-yl)pyrazol-3-yl]phenol This compound was synthesized in the same manner described in Section 5.1.2.105. In step 2, 1,3,4-trimethylpyrazolo[5,4-b]pyridine-6-ylhydrazine was used to form the pyrazole heterocycle.

ESMS m/z 488 (MH$^+$), $C_{30}H_{25}N_5O_2$=487 g/mol, HPLC purity=90%.

5.1.2.141 Synthesis of 4-[3-(4-Hydroxyphenyl)-1-(6-methylpyridazin-3-yl)-4-phenylpyrazol-5-yl]phenol This compound was synthesized in the same manner described in Section 5.1.2.105. In step 2, 6-methylpyridazine-3-ylhydrazine was used to form the pyrazole heterocycle.

ESMS m/z 421 (MH$^+$), $C_{26}H_{20}N_4O_2$=420 g/mol, HPLC purity=90%.

5.1.2.142 Synthesis of 4-[1-(6-Chloro-2-fluorophenyl)-5-(4-hydroxyphenyl)-4-phenylpyrazol-3-yl]phenol This compound was synthesized in the same manner described in Section 5.1.2.105. In step 2, 6-chloro-2-fluorophenyl hydrazine was used to form the pyrazole heterocycle.

ESMS m/z 457 (MH$^+$), $C_{27}H_{18}ClFN_2O_2$=456 g/mol, HPLC purity=90%.

5.1.2.143 Synthesis of 4-[1,3-bis(4-Hydroxyphenyl)-4-ethylpyrazol-5-yl]phenol

This compound was synthesized in the same manner described in Section 5.1.2.46. In step 2, 4-methoxyphenyl hydrazine was used to form the pyrazole heterocycle.

ESMS m/z 373 (MH$^+$), $C_{23}H_{20}N_2O_3$=372 g/mol, HPLC purity=90%.

5.1.2.144 Synthesis of 4-[1,3-bis(4-Hydroxyphenyl)-4-phenylpyrazol-5-yl]phenol

This compound was synthesized in the same manner described in Section 5.1.2.105. In step 2, 4-methoxyphenyl hydrazine was used to form the pyrazole heterocycle.

ESMS m/z 421 (MH$^+$), $C_{27}H_{20}N_2O_3$=420 g/mol, HPLC purity=90%.

5.1.2.145 Synthesis of 4-[1,3,5-tris(4-Hydroxyphenyl)pyrazol-4-yl]phenol

This compound was synthesized in the same manner as described in Section 5.1.2.6. In step 2, 4-methoxyphenyl hydrazine was used to form the pyrazole heterocycle.

ESMS m/z 437 (MH$^+$), $C_{27}H_{20}N_2O_4$=436 g/mol, HPLC purity=90%.

5.1.2.146 Synthesis of 4-[1,3-bis(4-Hydroxyphenyl)pyrazol-5-yl]phenol

This compound was synthesized following procedures described in Scheme 1.

Step 1: To a solution of 4'-methoxyacetophenone (1.0 equiv.) in THF at −78° C. was added dropwise 1.5 equiv. of [(CH$_3$)$_2$Si]$_2$NLi. The solution was stirred for 1 h at −78° C., followed by addition of 1.2 equiv. of p-anisoyl chloride. The reaction mixture was stirred for 10 min at −78° C. and then for 22 h at rt, acidified with 10% citric acid, and extracted with EtOAc. The combined organic layers were washed with water and dried over Na$_2$SO$_4$. Removal of solvent in vacuo provided a crude solid which was purified by flash chromatography (CH$_2$Cl$_2$) to give 1,3-di(4-methoxyphenyl)propane-1,3-dione.

Step 2: A mixture of the 1,3-diketone obtained in step 1 (1.0 equiv.), 4-methoxyphenyl hydrazine (1.5 equiv.), conc. HCl aq. (catalytic amount) and ethanol was heated to reflux overnight. Cooled to rt and removed solvent in vacuo. Water and ethyl acetate were added. The organic layer was separated, washed with dil. HCl, brine, dried, filtered and the solvent was concentrated in vacuo to give the product 1-[1,5-bis(4-methoxyphenyl)pyrazol-3-yl]-4methoxybenzene.

Step 3: Demethylation was performed as described in Scheme 1 to afford the final product.

ESMS m/z 345 (MH$^+$), $C_{21}H_{16}N_2O_3$=344 g/mol, HPLC purity=90%.

5.1.2.147 Synthesis of 4-[4-ethyl-5-(4-Hydroxyphenyl)-1-methylpyrazol-3-yl]phenol This compound was synthesized in the same manner described in Section 5.1.2.46. In step 2, methylhydrazine was used to form the pyrazole heterocycle.

ESMS m/z 295 (MH$^+$), $C_{18}H_{18}N_2O_2$=294 g/mol, HPLC purity=98%.

5.1.2.148 Synthesis of 4-[4-ethyl-5-(4-Hydroxyphenyl)pyrazol-3-yl]phenol

This compound was synthesized in the same manner described in Section 5.1.2.46. In step 2, hydrazine was used to form the pyrazole heterocycle.

5.1.2.149 Synthesis of 3-(4-Hydroxyphenyl)-2,4,5-trihydrobenzo[g]1H-indazol-7-ol This compound was synthesized based upon Scheme 1.

Step 1: To a solution of 6-methoxy-1-tetralone (1.0 equiv.) in THF at −78° C. was added dropwise 1.5 equiv. of [(CH$_3$)$_2$Si]$_2$NLi. The solution was stirred for 1 h at −78° C., followed by addition of 1.2 equiv. of p-anisoyl chloride. The reaction mixture was stirred for 10 min at −78° C. and then for 22 h at rt, acidified with 10% citric acid, and extracted with EtOAc. The combined organic layers were washed with water and dried over Na$_2$SO$_4$. Removal of solvent in vacuo provided a crude solid which was purified by flash chromatography (CH$_2$Cl$_2$) to give 6-methoxy-2-[(4-methoxyphenyl)carbonyl]-2,3,4-trihydronaphthalen-1-one.

Step 2: A mixture of the 1,3-diketone obtained in step 1 (1.0 equiv.), hydrazine (1.5 equiv.), conc. HCl aq. (catalytic amount) and ethanol was heated to reflux overnight. Cooled to rt and removed solvent in vacuo. Water and ethyl acetate were added. The organic layer was separated, washed with dil. HCl, brine, dried, filtered and the solvent was concentrated in vacuo to give the pyrazole product.

Step 3: Demethylation was performed as described in Scheme 1 to afford the final product.

ESMS m/z 279 (MH$^+$), $C_{17}H_{14}N_2O_2$=278 g/mol; HPLC purity=85%.

5.1.2.150 Synthesis of 3-(4-Hydroxyphenyl)-2-methyl-2,4,5-trihydrobenzo[g]1H-indazol-7-ol This compound was synthesized in the same manner as described in Section 5.1.2.149. In step 2, methylhydrazine was used to form the pyrazole heterocycle.

ESMS m/z 293 (MH$^+$), $C_{18}H_{16}N_2O_2$=292 g/mol; HPLC purity=85%.

5.1.2.151 Synthesis of 3-(4-Hydroxyphenyl)-2-phenyl-2,4,5-trihydrobenzo[g]1H-indazol-7-ol This compound was synthesized in the same manner described in Section 5.1.2.149. In step 2, phenylhydrazine was used to form the pyrazole heterocycle.

ESMS m/z 355 (MH+), $C_{23}H_{18}N_2O_2$=354 g/mol; HPLC purity=85%.

5.1.2.152 Synthesis of 1-[3,5-bis(4-Hydroxyphenyl)-4-ethylpyrazolyl]-4-(methylsulfonyl)benzene This compound was synthesized in the same manner described in Section 5.1.2.46. In step 2, 4-methylsulfonylphenylhydrazine was used to form the pyrazole heterocycle.

$^1$H NMR (MeOH-d$_4$): δ 0.88 (3H, t, J=7.3 Hz), 2.51 (2H, q, J=7.2 Hz), 3.20 (3H, s), 6.75 (2H, d, J=8.6 Hz), 6.79 (2H, d, J=8.6 Hz), 7.00 (2H, d, J=8.8 Hz), 7.41 (2H, d, J=8.6 Hz), 7.45 (2H, d, J=8.8 Hz), 7.77 (2H, d, J=8.6 Hz); ESMS m/z 435 (MH+), $C_{24}H_{22}N_2O_4S$=434 g/mol; HPLC purity=91.4%.

5.1.2.153 Synthesis of 3-{[3,5-bis(4-Hydroxyphenyl)pyrazolyl]methyl}phenol

This compound was synthesized based upon Scheme 4.

Step 1: Same as Step 1 in Section 5.1.2.149.

Step 2: Same as Step 2 in Section 5.1.2.149 but using hydrazine to form pyrazole ring.

Step 3: Alkylation. Similar as step 3 in Section 5.1.2.41 using 3'-methoxybenzyl chloride as alkylating agent.

Step 4: Step 3: Demethylation was performed as described in Scheme 1 to afford the final product.

$^1$H NMR (Acetone-d$_6$): δ 0 5.24 (2H, s), 6.55 (2H, d, J=8.6 Hz), 6.56 (1H, s), 6.64 (1H, d, J=6.6 Hz), 6.81 (2H, d, J=8.4 Hz), 6.84 (2H, d, J=8.9 Hz), 7.05 (1H, t, J=8.6 Hz), 7.21 (2H, d, J=8.2Hz), 7.68 (2H, d, J=8.2 Hz); ESMS m/z 359 (MH+), $C_{22}H_{18}N_2O_3$=358 g/mol; HPLC purity 83.8%.

5.1.2.154 Synthesis of 1-[3,5-bis(4-Hydroxyphenyl)-4-methylpyrazolyl]-4-(methylsulfonyl)benzene This compound was synthesized based upon Scheme 1.

Step 1: To a solution of 4'-methoxypropylphenone (1.0 equiv.) in THF at −78° C. was added dropwise 1.5 equiv. of [(CH$_3$)$_2$Si]$_2$NLi. The solution was stirred for 1 h at −78° C., followed by addition of 1.2 equiv. of p-anisoyl chloride. The reaction mixture was stirred for 10 min at −78° C. and then for 22 h at rt, acidified with 10% citric acid, and extracted with EtOAc. The combined organic layers were washed with water and dried over Na$_2$SO$_4$. Removal of solvent in vacuo provided a crude solid which was purified by flash chromatography (CH$_2$Cl$_2$) to give 1,3-di(4-methoxyphenyl)-2-methyl-propane-1,3-dione.

Step 2: A mixture of the 1,3-diketone obtained in step 1 (1.0 equiv.), 4-methylsulfonylphenyl hydrazine (1.5 equiv.), conc. HCl aq. (catalytic amount) and ethanol was heated to reflux overnight. Cooled to rt and removed solvent in vacuo. Water and ethyl acetate were added. The organic layer was separated, washed with dil. HCl, brine, dried, filtered and the solvent was concentrated in vacuo to give the pyrazole product.

Step 3: Demethylation was performed as described in Scheme 1 to afford the final product.

ESMS m/z 421 (MH+), $C_{23}H_{20}N_2O_4S$=420 g/mol; HPLC purity=85%.

5.1.2.155 Synthesis of 1-[3,5-bis(4-Hydroxyphenyl)pyrazolyl]-4-(methylsulfonyl)benzene This compound was synthesized in the same manner as described in Section 5.1.2.146. In step 2, 4-methylsulfonylphenylhydrazine was used to form the pyrazole heterocycle.

$^1$H NMR (Methanol-d$_4$): δ 2.04 (3H, s), 6.68 (2H, d, J=8.9 Hz), 6.69 (1H, s), 6.74 (2H, d, J=8.8 Hz), 7.03 (2H, d, J=8.8 Hz), 7.48 (2H, d, J=8.9 Hz), 7.63 (2H, d, J=8.8 Hz), 7.85 (2H, d, J=8.8 Hz); ESMS m/z 407 (MH+), $C_{22}H_{18}N_2O_4S$=406 g/mol; HPLC purity=86.4%.

5.1.2.156 Synthesis of 3-{[3,5-bis(4-Hydroxyphenyl)-4-methylpyrazolyl]methyl}phenol This compound was synthesized based upon Scheme 4.

Step 1: Same as step 1 in Section 5.1.2.154.

Step 2: Similar as step 2 in Section 5.1.2.154 but using hydrazine to form pyrazole ring.

Step 3: Alkylation. Same as step 3 in example 51623 using 3'-methoxybenzyl bromide as alkylating agent.

Step 4: Demethylation was performed as described in Scheme 1 to afford the final product.

$^1$H NMR (methanol-d$_4$): δ 1.97 (3H, s), 5.07 (2H, s), 6.44 (1H, d, J=7.3 Hz), 6.50 (1H, s), 6.58 (1H, dd, J=8.2 Hz, 2.6 Hz), 6.81 (2H, d, J=8.6 Hz), 6.85 (2H, d, J=8.6 Hz), 6.98 (1H, t, J=7.9 Hz), 7.05 (2H, d, J=8.6 Hz), 7.53 (2H, d, J=8.8 Hz); ESMS m/z 372 (MH+), $C_{23}H_{20}N_2O_3$=372 g/mol; HPLC purity=95.0%.

5.1.2.157 Synthesis of 3-{[3,5-bis(4-Hydroxyphenyl)-4-ethylpyrazolyl]methyl}phenol This compound was synthesized in the same manner described in Section 5.1.2.88. In step 3, 3'-methoxybenzyl chloride was used as alkylating agent.

$^1$H NMR (acetone-d$_6$): δ 0.95 (3H, t, J=7.5 Hz), 2.53 (2H, d, J=7.5 Hz), 5.08 (2H, s), 6.48 (1H, d, J=8.2 Hz), 6.56 (1H, m), 6.65 (1H, dd, J=8.8 Hz, 3.6 Hz), 6.87 (2H, d, J=8.8 Hz), 6.91 (2H, d, J=8.8 Hz), 7.04 (1H, t, J=7.8 Hz), 7.11 (2H, d, J=8.6 Hz), 7.57 (2H, d, J=8.8 Hz); ESMS m/z 386 (MH+), $C_{24}H_{22}N_2O_3$=386 g/mol; HPLC purity=96.5%.

5.1.2.158 Synthesis of 8-[3,5-bis(4-Hydroxyphenyl)-4-ethylpyrazolyl]-N-butyl-N-methyloctanamide This compound was synthesized based upon Scheme 4.

Step 1 and 2: Same as corresponding steps in Section 5.1.2.88.

Step 3: Preparation of the alkyl halide 8-bromo-N-butyl-N-methyloctanamide. Using oven dried glassware under an inert atmosphere isobutylchloroformate (0.64 mL) was added dropwise to 8-bromooctanoic acid (1.00 g) and NMM (0.74 mL) in THF (10 mL) at −23° C. The solution was stirred for 3 minutes then N-methylbutylamine (0.8 mL) in THF (5 mL) was added. The solution was stirred at −23° C. for 30 minutes then at room temperature overnight. EtOAc (25 mL) added and the solution washed with 2M HCl (2×25 mL), NaHCO$_3$ solution (2×25 mL) and brine (25 mL). It was then dried (Na$_2$SO$_4$) and the solvent removed to give the product as a light yellow oil (1.60 g) which was used without further purification. ESMS m/z 292 (MH+), $C_{13}H_{26}BrNO$=291 g/mol.

Step 4: Allrylation. Unalkylated pyrazole (obtained from step 2, 1.0 equiv.) and alkyl bromide (obtained from step 3, 2.0 equiv.) were dissolved in DMF then $Cs_2CO_3$ (2.0 equiv.) added. The mixture was stirred at 100° C. overnight then EtOAc added. The solution was washed with 10% citric acid solution (2×), $NaHCO_3$ solution (2×), and brine, dried ($Na_2SO_4$) and the solvent removed to give a yellow solid. The crude product was purified by flash chromatography (50% EtOAc/petrol) to give a colourless oil (yield=40%).

Step 5: Demethylation was performed as described in Scheme 1 to afford the final product.

$^1$H NMR ($CDCl_3$): δ 0.72–0.81 (2H, m), 0.82–0.91 (6H, m), 0.93–1.62 (12H, m), 2.14–2.20 (2H, m), 2.43 (2H, q, J=7.5 Hz), 2.86 (1.5H, s), 2.89 (1.5H, s), 3.17 (1H, t, J=7.5 Hz), 3.31 (1H, t, J=7.5 Hz), 3.91 (2H, t, J=7.1 Hz), 6.78 (2H, d, J=8.6 Hz), 6.89 (2J=8.4 Hz), 7.08 (2H, d, J=8.8 Hz), 7.45 (2H, d, J=8.6 Hz); ESMS m/z 492 (MH+), $C_{30}H_{41}N_3O_3$= 491 g/mol; HPLC purity=99.0%.

5.1.2.159 Synthesis of 3-(4-Hydroxyphenyl)-2-methylindeno[3,2-c]pyrazol-6-ol

This compound was synthesized in the same manner as described in Section 5.1.2.150. In step 1, 5-methoxy-1-indanone and p-anisoyl chloride were used as starting materials.

ESMS m/z 279 (MH+), $C_{17}H_{14}N_2O_2$=278 g/mol; HPLC purity=95%.

5.1.2.160 Synthesis of 1-[1-Cyclobutyl-4-ethyl-5-(4-methoxyphenyl)pyrazol-3-yl]-4-methoxybenzene This compound was synthesized in the same manner described in Section 5.1.2.88. In step 3, chlorobutane was used as alkylating agent. Step 4 was not performed.

$^1$H NMR ($CDCl_3$): δ 0.93 (3H, , J=7.4 Hz), 1.59–1.67 (2H, m), 1.83 (2H, q, J=10.1 Hz), 2.19–2.26 (2H, m), 2.47 (2H, q, J=7.5 Hz), 3.83 (3H, s), 3.87 (3H, s), 6.96 (2H, d, J=8.6 Hz), 7.00 (2H, d, J=8.6 Hz), 7.21 (2H, d, 8.6 Hz), 7.65 (2H, d, J=8.6 Hz); ESMS m/z 363 (MH+), $C_{23}H_{26}N_2O_2$= 362 g/mol; HPLC purity=91.2%.

5.1.2.161 Synthesis of 4-[1,4-Diethyl-5-(4-hydroxyphenyl)pyrazol-3-yl]phenol

This compound was synthesized in the same manner described in Section 5.1.2.88. In step 3, chloroethane was used as alkylating agent.

$^1$H NMR (MeOH-$d_4$): δ 8 0.87 (3H, t, J=7.4 Hz), 1.24 (3H, t, J=7.1 Hz), 2.42 (2H, q, J=7.5 Hz), 3.95 (2H, q, J=7.1 Hz), 6.82 (2H, d, J=8.4 Hz), 6.89 (2H, d, J=8.4 Hz), 7.15 (2H, d, J=8.4 Hz), 7.38 (2H, d, J=8.4 Hz); ESMS m/z 309 (MH+), $C_{19}H_{20}N_2O_2$=308 g/mol; HPLC purity=89.3%.

5.1.2.162 Synthesis of 4-[4-Ethyl-5-(4-hydroxyphenyl)-1-propylpyrazol-3-yl]phenol This compound was synthesized in the same manner described in Section 5.1.2.88. In step 3, 1-chloropeopane was used as alkylating agent.

$^1$H NMR (MeOH-$d_4$): δ 0.77 (3H, t, J=7.3 Hz), 0.89 (3H, t, J=7.3 Hz), 1.69 (2H, q, J=7.3 Hz), 2.44 (2H, q, J=7.3 Hz), 3.90 (2H, t, J=7.3 Hz), 6.84 (2H, d, J=8.1 Hz), 6.91 (2H, d, J=8.1 Hz), 7.16 (2H, d, J=8.2 Hz), 7.4 (2H, d, J=8.2 Hz); ESMS m/z 323 (MH+), $C_{20}H_{22}N_2O_2$=322 g/mol; HPLC purity=88.5%.

5.1.2.163 Synthesis of 4-[1-butyl-4-ethyl-5-(4-Hydroxyphenyl)pyrazol-3-yl]phenol This compound was synthesized in the same manner described in Section 5.1.2.88. In step 3, 1-chlorobutane was used as allrylating agent.

$^1$H NMR (Acetone-$d_6$): δ 0.71 (3H, t, J=7.23 Hz), 0.86 (3H, t, J=7.5 Hz), 1.11 (2H, t, J=7.5 Hz), 1.61 (2H, t, J=7.23 Hz), 2.41 (2H, q, J=7.43 Hz), 3.85 (2H, t, J=7.23 Hz), 6.80 (2H, d, J=8.79 Hz), 6.91 (2H, d, J=8.59 Hz), 7.13 (2H, d, J=8.59 Hz), 7.48 (2H,d, J=8.79 Hz), 8.21 (1H, s), 8.55 (1H, s); ESMS m/z 337 (MH+), $C_{21}H_{24}N_2O_2$=336 g/mol; HPLC purity 81.1%.

5.1.2.164 Synthesis of 4-[4-Ethyl-5-(4-hydroxyphenyl)-1-(2-methylpropyl)pyrazol-3-yl]phenol This compound was synthesized in the same manner described in Section 5.1.2.88. In step 3, 1-chloro-2-methylpropane was used as alkylating agent.

$^1$H NMR (Acetone-$d_6$): δ 0.73 (6H, d, J=7.51 Hz), 0.93 (3H, t, J=7.5 Hz), 2.01 (1H, m), 2.08 (1H, m), 2.49 (2H, q, J=7.51 Hz), 3.72 (2H, d, J=7.33 Hz), 6.86 (2H, d, J=8.79 Hz), 6.96 (2H, d, J=7.9 Hz), 7.18 (2H, d, J=8.0 Hz), 7.54 (2H, d, J=8.2 Hz); ESMS m/z 337 (MH+), $C_{21}H_{24}N_2O_2$= 336 g/mol; HPLC purity=96.0%.

5.1.2.165 Synthesis of 4-[4-Ethyl-5-(4-hydroxyphenyl)-1-prop-2-enylpyrazol-3-yl]phenol This compound was synthesized in the same manner described in Section 5.1.2.88. In step 3, allyl bromide was used as alkylating agent.

$^1$H NMR (MeOH-$d_4$): δ 0.90 (3H, t, J=7.5 Hz), 2.46 (2H, q, J=7.5 Hz), 4.55 (2H, d, J=4.9 Hz), 4.79 (1H, d, J=17.2 Hz), 5.01 (1H, d, J=10.41 Hz), 5.85–5.78 (1H, m), 6.76 (2H, d, J=8.4 Hz), 6.81 (2H, d, J=8.41 Hz), 7.08 (2H, d, J=8.4 Hz), 7.32 (2H, d, J=8.4 Hz); ESMS m/z 321 (MH+), $C_{20}H_{20}N_2O_2$=320 g/mol; HPLC purity=91.2%.

5.1.2.166 Synthesis of 4-[1-(Cydohexylmethyl)-4-ethyl-5-(4-hydroxyphenyl)pyrazol-3-yl]phenol This compound was synthesized in the same manner described in Section 5.1.2.88. In step 3, chlorocyclohexylmethane was used as alkylating agent.

$^1$H NMR (Acetone-$d_6$): δ 6 0.92 (3H, t, J=7.33 Hz), 1.07–1.11 (3H, m), 1.51–1.62 (3H, m), 1.77–1.80 (1H, m), 2.49 (2H, q, J=7.51 Hz), 3.74 (2H, d, J=7.06 Hz), 6.86 (2H, d, J=8.79 Hz), 6.97 (2H, d, J=8.79 Hz), 7.17 (2H, d, J=8.61 Hz), 7.54 (2H, d, J=8.79 Hz); ESMS m/z 377 (MH+), $C_{24}H_{28}N_2O_2$=376 g/mol; HPLC purity=96.1%.

5.1.2.167 Synthesis of 4-[1-Cyclobutyl-4-ethyl-5-(4-hydroxyphenyl)pyrazol-3-yl]phenol This compound was synthesized in the same manner described in Section 5.1.2.88. In step 3, chlorobutane was used as alkylating agent.

$^1$H NMR (Acetone-$d_6$): δ 0.92 (3H, t, J=7.33 Hz), 1.67–1.77 (2H, m), 2.16–2.22 (2H, m), 2.48 (2H, q, J=7.33 Hz), 2.67 (2H, m), 4.54–4.58 (1H, m), 6.88 (2H, d, J=8.79 Hz), 6.97 (2H, d, J=8.61 Hz), 7.15 (2H, d, J=8.61 Hz), 7.57 (2H, d, J=8.79 Hz), 8.27 (1H, s), 8.61 (1H, s); ESMS m/z 335 (MH+), $C_{21}H_{22}N_2O_2$=334 g/mol; HPLC purity=89.6%.

5.1.2.168 Synthesis of 4-[1-cyclohexyl-4-ethyl-5-(4-Hydroxyphenyl)pyrazol-3-yl]phenol This compound was synthesized in the same manner described in Section 5.1.2.88. In step 3, chlorohexane was used as alkylating agent.

$^1$H NMR (Acetone-$d_6$): δ 0.92 (3H, t, J=7.33 Hz), 1.09–1.20 (3H, m), 1.59 (1H, s), 1.76–1.82 (4H, m), 1.93–1.97 (2H, m), 2.48 (2H, q, J=7.43 Hz), 3.83–3.89 (1H, m), 6.86 (2H, d, J=8.79 Hz), 6.97 (2H, d, J=8.60 Hz), 7.18 (2H, d, J=8.60 Hz), 7.54 (2H, d, J=8.60 Hz), 8.24 (1H, s), 8.60 (1H, s); ESMS m/z 363 (MH+), $C_{23}H_{26}N_2O_2$=362 g/mol; HPLC purity=

5.1.2.169 Synthesis of 4-[4-Ethyl-5-(4-hydroxyphenyl)-1-(2-morpholin-4-ylethyl)pyrazol-3-yl]phenol This compound was synthesized in the same manner described in Section 5.1.2.88. In step 3, N-(2-chloroethyl) morpholine was used as alkylating agent.

$^1$H NMR (Acetone-$d_2$): δ 0.86 (3H, t, J=7.51 Hz), 2.42 (2H, q, J=7.51 Hz), 2.61–2.78 (4H, m), 3.21 (4H, m), 4.03 (2H, t, J=7.51 Hz), 6.80 (2H, d, J=8.79 Hz), 6.89 (2H, d, J=8.61 Hz), 7.19 (2H, d, J=8.61 Hz), 7.43 (2H, d, J=8.79 Hz); ESMS m/z 394 (MH+), $C_{23}H_{27}N_3O_3$=393 g/mol; HPLC purity=91.8%.

5.1.2.170 Synthesis of 2-[3,5-bis(4-Hydroxyphenyl)-4-ethylpyrazolyl]acetamide

This compound was synthesized in the same manner described in Section 5.1.2.88. In step 3, 2-chloroacetamidewas used as alkylating agent.

$^1$H NMR (MeOH-d$_4$): δ 0.93 (3H, t, J=7.4 Hz), 2.50 (2H, q, J=7.4 Hz), 4.6 (2H, s), 6.84 (2H, d, J=8.4 Hz), 6.89 (2H, d, J=8.2 Hz), 7.21 (2H, d, J=8.4 Hz), 7.45 (2H, d, J=8.2 Hz); ESMS m/z 338 (MH+), $C_{19}H_{19}N_3O_3$=337 g/mol; HPLC purity=94.5%.

5.1.2.171 Synthesis of 1-[3,5-bis(4-Hydroxyphenyl)-4-ethylpyrazolyl]acetone

This compound was synthesized in the same manner described in Section 5.1.2.88. In step 3, chloroacetone was used as alkylating agent.

$^1$H NMR (Acetone-d$_6$): δ 0.95 (3H, t, J=7.43 Hz), 1.98 (3H, s), 2.52 (2H, q, J=7.62 Hz), 7.76 (2H, s), 6.88 (2H, d, J=8.79 Hz), 6.94 (2H, d, J=8.79 Hz), 7.16 (2H, d, J=8.79 Hz), 7.54 (2H, d, J=8.60 Hz), 8.31 (1H, s), 8.64 (1H, s); ESMS m/z 337 (MH+), $C_{20}H_{20}N_2O_3$=336 g/mol; HPLC purity=85.5%.

5.1.2.172 Synthesis of 4-[1-cyclopentyl-4-ethyl-5-(4-Hydroxyphenyl)pyrazol-3-yl]phenol This compound was synthesized in the same manner described in Section 5.1.2.88. In step 3, chloropentane was used as alkylating agent.

$^1$H NMR (Acetone-d$_6$): δ 0.82 (3H, t, J=7.43 Hz), 1.46 (3H, d, J=7.62 Hz), 2.38 (2H, q, J=7.43 Hz), 4.35 (2H, s), 5.24–5.31 (1H, m), 5.40–5.47 (1H, m), 6.76 (2H, d, J=8.60 Hz), 6.84 (2H, d, J=8.40 Hz), 7.08 (2H, d, J=8.60 Hz), 7.43 (2H, d, J=8.60 Hz), 8.17 (1H, s), 8.50 (1H, s); ESMS m/z 349 (MH+), $C_{22}H_{29}N_2O_2$=348 g/mol; HPLC purity=98.7%.

5.1.2.173 Synthesis of 4-[4-Ethyl-5-(4-hydroxyphenyl)-1-(methylethyl)pyrazol-3-yl]phenol This compound was synthesized in the same manner described in Section 5.1.2.88. In step 3, 2-chloropropane was used as alkylating agent.

$^1$H NMR (Acetone-d$_6$): δ 0.93 (3H, t, J=7.5 Hz), 1.41 (6H, d, J=6.78 Hz), 2.48 (2H, q, J=7.5 Hz), 4.34–4.37 (1H, m), 6.89 (2H, d, J=8.6 Hz), 6.99 (2H, d, J=8.8 Hz), 7.22 (2H, d, J=8.6 Hz), 7.59 (2H, d, J=8.8 Hz); ESMS m/z 323 (MH+), $C_{20}H_{22}N_2O_2$=322 g/mol; HPLC purity=83.8%.

5.1.2.174 Synthesis of 4-[1-Cycloheptyl-4-ethyl-5-(4-hydroxyphenyl)pyrazol-3-yl]phenol This compound was synthesized in the same manner described in Section 5.1.2.88. In step 3, chlorocycloheptane was used as alkylating agent.

$^1$H NMR (Acetone-d$_6$): δ 0.92 (3H, t, J=7.43 Hz), 1.16–1.25 (3H, m), 1.43 (4H, s), 1.64 (2H, m), 1.76 (2H, m), 2.02 (1H, m), 2.39 (2H, m), 3.97–3.99 (1H, m), 6.76 (2H, d, J=8.60 Hz), 6.87 (2H, d, J=8.40 Hz), 7.07 (2H, d, J=8.60 Hz), 7.45 (2H, d, J=8.60 Hz), 8.14 (1H, s), 8.51 (1H, s); ESMS m/z 377 (MH+), $C_{24}H_{28}N_2O_2$=376 g/mol; HPLC purity 97.9%.

5.1.2.175 Synthesis of 4-[1-(Cyclopropylmethyl)-4-ethyl-5-(4-hydroxyphenyl)pyrazol-3-yl]phenol This compound was synthesized in the same manner described in Section 5.1.2.88. In step 3, chlorocyclopropylmethane was used as alkylating agent.

$^1$H NMR (Acetone-d$_6$): δ 0.82 (3H, t, J=7.4 Hz), 1.46 (3H, d, J=7.6 Hz), 2.38 (2H, q, J=7.4 Hz), 4.35 (2H, s), 5.24–5.31 (1H, m), 5.40–5.47 (1H, m), 6.76 (2H, d, J=8.6 Hz), 6.84 (2H, d, J=8.4 Hz), 7.08 (2H, d, J=8.6 Hz), 7.43 (2H, d, J=8.6 Hz), 8.17 (1H, s), 8.50 (1H, s); ESMS: m/z 335 (MH+), $C_{21}H_{22}N_2O_2$=334 g/mol; HPLC purity=87.3%.

5.1.2.176 Synthesis of 3-(4-Hydroxyphenyl)-1-methylindeno[2,3-d]pyrazol-6-01

This compound is the regioisomer of the compound made in Section 5.1.2.159. The synthesis is identical. HPLC was used to isolate the two isomers.

ESMS m/z 279 (MH+), $C_{17}H_{14}N_2O_2$=278 g/mol; HPLC purity=90%.

5.1.2.177 Synthesis of 4-[4-Ethyl-5-(4-hydroxyphenyl)-1-phenylpyrazol-3-yl]phenol This compound was synthesized in the same manner described in Section 5.1.2.46. In step 2, phenyl hydrazine was used as the reagent to form pyrazole.

ESMS m/z 357 (MH$^+$), $C_{23}H_{20}N_2O_2$=356 g/mol, HPLC purity=90%.

5.1.2.178 Synthesis of 4-[5-(4-Hydroxyphenyl)-1,4-diphenylpyrazol-3-yl]phenol

This compound was synthesized in the same manner described in Section 5.1.2.105. In step 2, phenyl hydrazine was used as the reagent to form pyrazole.

ESMS m/z 405 (MH$^+$), $C_{27}H_{20}N_2O_2$=404 g/mol, HPLC purity=90%.

5.1.2.179 Synthesis of 2-{4-Ethyl-5-(4-hydroxyphenyl)-1-[2-(trifluoromethyl)phenyl]pyrazol-3-yl}phenol This compound was synthesized based upon Scheme 1. The procedures are same as described in Section 5.1.2.53. In step I, 4'-methyxobutyrylphenone and o-anisoyl chloride were used as starting materials.

ESMS m/z 425 (MH$^+$), $C_{24}H_{19}F_3N_2O_2$=424 g/mol, HPLC purity=90%.

5.1.2.180 Synthesis of 3-{4-Ethyl-5-(4-hydroxyphenyl)-1-[2-(trifluoromethyl)phenyl]pyrazol-3-yl}phenol The procedures are same as described in Section 5.1.2.53. In step I, 4'-methyxobutyrylphenone and m-anisoyl chloride were used as starting materials.

ESMS m/z 425 (MH$^+$), $C_{24}H_{19}F_3N_2O_2$=424 g/mol, HPLC purity=90%.

5.1.2.181 Synthesis of 3-[1-(4-Hydroxyphenyl)-3-(3-hydroxyphenyl)-4-methylpyrazol-5-yl]phenol This compound was synthesized based upon Scheme 1 and Scheme 3.

Step 1: Formation of 1,3-diketone. Same as Step 1 in Section 5.1.2.6 using 3'-methyxobutyrylphenone and m-anisoyl chloride were used as starting materials.

Step 2: Alkylation. A THF solution of the above 1,3-diketone (1.0 equiv.) was added dropwise to a suspension of sodium hydride (1. 1 eq) in THF at 0° C. The mixture was stirred at rt for 30 min. followed by addition of iodomethane (1.1 equiv.). The reaction mixture was stirred at rt overnight, poured into saturated NH$_4$Cl aq. and extracted with ether and DCM. The organic extracts were washed with brine, dried with MgSO$_4$ and concentrated in vacuo to give the product 1,3-bis(3-methoxyphenyl)-2-methylpropane-1,3-dione.

Step 3: Same as step 2 in Section 5.1.2.6. 4-methoxyphenyl hydrazine was used to form the pyrazole core.

Step 4: Demethylation was performed as described in Scheme 1 to afford the final product.

ESMS m/z 359 (MH$^+$), $C_{22}H_{18}N_2O_3$=358 g/mol; HPLC purity=90%.

5.1.2.182 Synthesis of 3-[3-(3-Hydroxyphenyl)-4-methyl-1-phenylpyrazol-5-yl]phenol This compound was synthesized in the same manner as described in Section 5.1.2.181. In step 3, phenyl hydrazine was used to form the pyrazole core.

ESMS m/z 343 (MH$^+$), $C_{22}H_{18}N_2O_2$=342 g/mol, HPLC purity=90%.

5.1.2.183 Synthesis of 3,5-bis(4-Hydroxyphenyl)-4-ethyl-1-(methylsulfonyl)pyrazole This compound was synthesized based upon Scheme 4.

Steps 1 and 2: Same as corresponding steps in Section 5.1.2.148.

Step 3: Sulfonylation. To a solution of methanesulfonyl chloride (2.0 equiv.) and dry pyridine (solvent) in a screw cap container was added the pyrazole (1.0 equiv., obtained from step 2). After dissolution by shaking, the resultant solution was heated in a sealed tube at 60–65° C. for 22.5 h. The solution obtained was concentrated in vacuo and the residue partitioned between ethyl acetate and water. The organic phase was separated, washed with 7% $NaHCO_3$ (2×), brine (2×), then dried ($Na_2SO_4$) and the solvent removed to give a dark brown oil. Crystallisation was induced by the addition of pet. spirits (40–60°, ca. 3 mL) and the solid obtained was ground, collected, then washed with cold ether (2×0.5 mL) and dried overnight in vacuo to give the sulfonamide as a brown powder (yield=33%).

Note that in some cases EtOAc/pet. Spirits were used for recrystallization.

Step 4: Demethylation. A solution of the above sulfonamide (1.0 equiv.) in dry DCM was treated with $AlCl_3$ (6.0 equiv.) and ethane thiol (6.0 equiv.) and stirred in a sealed container for 16 h. The reaction mixture was diluted with EtOAc and washed with 10% citric acid solution (2×), 7% $NaHCO_3$ (2×), brine, then dried ($Na_2SO_4$) and concentrated in vacuo to give a residue which was purified by flash column chromatography (EtOAc : pet. spirits 2:1) to afford product as an off-white solid (yield=43%).

$^1$H NMR ($D_6$-DMSO): δ 0.87 (3H, t, J=7.4 Hz, 2.39 (2H, q, J=7.5 Hz), 3.37 (3H, s), 6.84 (2H, d, J=8.4 Hz), 6.88 (2H, d, J=8.6 Hz), 7.22 (2H, d, J=8.4 Hz), 7.54 (2H, d, J=8.6 Hz), 9.70 (1H, s), 9.72 (1H, s); ESMS: m/z 359 (MH+), $C_{18}H_{18}N_2O_4S$=358 g/mol; HPLC purity=96.4%.

5.1.2.184 Synthesis of 1-{[3,5-bis(4-Hydroxyphenyl)-4-ethylpyrazolyl]sulfonyl}-2-chlorobenzene This compound was synthesized in the same manner as described in Section 5.1.2.183. In step 3, 2-chlorophenylsulfonyl chloride was used to form the sulfonamide.

$^1$H NMR ($D_6$-DMSO): δ 0.84 (3H, t, J=7.4 Hz), 2.37 (2H, q, J=7.5 Hz), 6.77 (2H, d, J=8.4 Hz), 6.84 (2H, d, J=8.4 Hz), 7.05 (2H, d, J=8.4 Hz), 7.41 (2H, d, J=8.6 Hz), 7.50 (1H, t, J=7.5 Hz), 7.70 (3H, m), 9.70 (1H, s), 9.75 (1H, s); ESMS: m/z 455 (MH+), $C_{23}H_{19}ClN_2O_4S$=454 g/mol; HPLC purity=94.2%.

5.1.2.185 Synthesis of 3,5-bis(4-Hydroxyphenyl)-4-ethyl-1-[(4-methylphenyl)sulfonyl]pyrazole This compound was synthesized in the same manner as described in Section 5.1.2.183. In step 3, p-toluenesulfonyl chloride was used to form the sulfonamide.

$^1$H NMR ($D_6$-DMSO): δ 0.77 (3H, t, J=7.4 Hz), 2.31 (2H, q, J=7.5 Hz), 2.37 (3H, s), 6.85 (4H, m), 7.08 (2H, d, J=8.6 Hz,), 7.40 (2H, d, J=8.1 Hz), 7.45 (2H, dd, J=6.7, 1.9 Hz), 7.54 (2H, d, J=8.4 Hz); ESMS: m/z 463 (MH+), $C_{26}H_{26}N_2O_4S$=461 g/mol; HPLC purity=94.2%.

5.1.2.186 Synthesis of 3-(4-Hydroxyphenyl)-2-methyl-2,4,5-trihydrobenzo[g]1 H-indazol-6-ol This compound was synthesized in the same manner described in Section 5.1.2.149. In step 1, 5-methoxy-1-tetralone was used to form 1,3-diketone. In step 2, methylhydrazine was used to form the pyrazole heterocycle.

ESMS m/z 293 (MH+), $C_{18}H_{16}N_2O_2$=292 g/mol, HPLC purity=90%.

5.1.2.187 Synthesis of 3-(4-Hydroxyphenyl)-2-methyl-2,4,5-trihydrobenzo[g]1H-indazol-8-ol This compound was synthesized in the same manner described in Section 5.1.2.149. In step 1, 7-methoxy-1-tetralone was used to form 1,3-diketone. In step 2, methylhydrazine was used to form the pyrazole heterocycle.

ESMS m/z 293 (MH+), $C_{18}H_{16}N_2O_2$=2 g/mol, HPLC purity=90%.

5.1.2.188 Synthesis of 3-(4-Hydroxyphenyl)-2-[2-(trifluoromethyl)phenyl]-2,4,5-trihydrobenzo[g]1H-indazol-8-ol This compound was synthesized in the same manner as described in Section 5.1.2.149. In step 2, 2-trifluoromethylphenyl hydrazine was used to form the pyrazole heterocycle.

ESMS m/z 423 (MH+), $C_{24}H_{17}F_3N_2O_2$=422 g/mol, HPLC purity=90%.

5.1.2.189 Synthesis of 4-{3-(4-Hydroxyphenyl)-1-[2-(trifluoromethyl)phenyl]pyrazol-5-yl}phenol This compound was synthesized in the same manner as described in Section 5.1.2.146. In step 2, 2-trifluoromethylphenyl hydrazine was used to form the pyrazole heterocycle.

ESMS m/z 397 (MH+), $C_{22}H_{15}F_3N_2O_2$=396 g/mol, HPLC purity=90%.

5.1.2.190 Synthesis of 3-(4-Hydroxyphenyl)-2,4,5-trihydrobenzo[g]1H-indazol-6-ol This compound was synthesized in the same manner described in Section 5.1.2.149. In step 1, 5-methoxy-1-tetralone was used to form 1,3-diketone.

ESMS m/z 279 (MH+), $C_{17}H_{14}N_2O_2$=278 g/mol, HPLC purity=90%.

5.1.2.191 Synthesis of 4-[1-Cyclopropyl-4-ethyl-5-(4-hydroxyphenyl)pyrazol-3-yl]phenol This compound was synthesized in the same manner described in Section 5.1.2.88. In step 3, chlorocyclopropane was used for alkylation.

$^1$H NMR (DMSO): δ 0.76 (2H, q, J=6.6 Hz), 0.88 (3H, t, J=7.3 Hz), 0.93–0.97 (2H, m), 2.42 (2H, q, J=7.5 Hz), 3.38–3.44 (1H, m), 6.79 (2H, d, J=8.8 Hz), 6.89 (2H, d, J=8.6 Hz), 7.25 (2H, d, J=8.4 Hz), 7.39 (2H, d, J=8.6 Hz), 9.39 (1H, s), 9.76 (1H, s); ESMS: m/z 321 (MH+), $C_{20}H_{20}N_2O_2$=320 g/mol; HPLC purity=80.1%.

5.1.2.192 Synthesis of 4-(1-{[3,5-bis(4-Hydroxyphenyl)-4-ethylpyrazolyl]methyl}-4-ethyl-3-(4-hydroxyphenyl)pyrazol-5-yl)phenol This compound was obtained as a side-product of product described in Section 5.1.2.191. HPLC was used for isolation.

$^1$H NMR (DMSO): δ 0.95 (6H, t, J=7.3 Hz), 2.50 (4H, q, J=7.3 Hz), 5.93 (2H, s), 6.89 (4H, d, J=8.6 Hz), 6.96 (4H, d, J=8.4 Hz), 7.43 (4H, d, J=8.4 Hz), 7.50 (4H, d, J=8.6 Hz), 9.54 (1H, s), 9.85 (2H, s); ESMS: m/z 57 (MH+), $C_{35}H_{32}N_4O_4$=572 g/mol; HPLC purity=85.6%

5.1.2.193 Synthesis of 2-Cyclobutyl-3-(4-hydroxyphenyl)-2,4,5-trihydrobenzo[g]1H-indazol-6-ol This compound was synthesized based upon Scheme 4.

Steps1 and 2: Same as corresponding steps in Section 5.1.2.190.

Step 3: Alkylation. Same as step 3 in Section 5.1.2.88 using chlorocyclobutane as alkylating agent.

Step 4: Demethylation was performed as described in Scheme 1 to afford the final product.

ESMS m/z 333 (MH+), $C_{21}H_{20}N_2O_2$=332 g/mol, HPLC purity=90%.

5.1.2.194 Synthesis of 4-[1-Cyclobutyl-4-ethyl-5-(4-methoxyphenyl)pyrazol-3-yl]phenol This compound is a derivative of the final product in Section 5.1.2.167. To an acetone solution of 4-[1-cyclobutyl-4-ethyl-5-(4-hydroxyphenyl)pyrazol-3-yl] phenol (1.0 equiv.) was added potassium carbonate (1.0 equiv.) and dimethylsulfate (1.0 equiv.). The mixture was stirred at rt overnight and routine work-up afforded a mixture of starting material, mono-methylated product and di-methylated product. HPLC isolation afforded the title compound which is an off-white powder after lyophilization.

$^1$H NMR (DMSO-d$_6$): δ 0.87 (3H, t, J=7.3 Hz), 1.62–1.73 (2H, m), 2.14–2.20 (2H, m), 2.41 (2H, q, J=7.5 Hz), 2.56–2.61 (2H, m), 3.82 (3H, s), 4.47–4.51 (1H, m), 6.82 (2H, d, J=8.6 Hz), 7.07 (2H, d, J=8.6 Hz), 7.24 (2H, d, J=8.6 Hz), 7.46 (2H, d, J=8.4 Hz), 9.44 (1H, s); ESMS: m/z 349 (MH+), $C_{22}H_{24}N_2O_2$=348 g/mol; HPLC purity=98%.

5.1.2.195 Synthesis of 4-[5-(4-Acetyloxyphenyl)-1-cyclobutyl-4-ethylpyrazol-3-yl]phenyl Acetate This compound is a derivative of the final product in Section 5.1.2.167. To a THF solution of 4-[1-cyclobutyl-4-ethyl-5-(4-hydroxyphenyl)pyrazol-3-yl]phenol was added acetyl chloride (3.0 equiv.) and pyridine (3.0 equiv.). The mixture was stirred at rt for 24 h, poured into cold NaHCO$_3$, extracted with EtOAc. The organic extracts were washed with beine, dried with NaSO$_4$ and concentrated in vacuo. Purification afforded the product as a white powder.

$^1$H NMR (CDCl$_3$): δ 0.89 (3H, t, J=7.3 Hz), 1.60–1.64 (1H, m), 1.65–1.78 (1H, m), 2.14–2.20 (2H, m), 2.25 (3H, s), 2.29 (3H, s), 2.44 (2H, q, J=7.5 Hz), 2.69–2.76 (2H, m), 4.46–4.51 (1H, m), 7.09 (2H, d, J=8.6 Hz), 7.15 (2H, d, J=8.6 Hz), 7.25 (2H, d, J=8.6 Hz), 7.66 (2H, d, J=8.8 Hz); ESMS: m/z 419 (MH+), $C_{25}H_{26}N_2O_4$=418 g/mol; HPLC purity=98%.

5.1.2.196 Synthesis of 4-[5-(4-Butanoyloxyphenyl)-1-cyclobutyl-4-ethylpyrazol-3-yl]phenyl Butanoate This compound is a derivative of the final product in Section 5.1.2.167. To a THF solution of 4-[1-cyclobutyl-4-ethyl-5-(4-hydroxyphenyl)pyrazol-3-yl]phenol was added butyryl chloride (3.0 equiv.) and pyridine (3.0 equiv.). The mixture was stirred at rt for 24 h, poured into cold NaHCO$_3$, extracted with EtOAc. The organic extracts were washed with brine, dried with Na$_2$SO$_4$ and concentrated in vacuo to give the product as a white powder.

$^1$H NMR (CDCl$_3$): δ 0.89 (3H, t, J=7.5 Hz), 0.99 (3H, t, J=7.3 Hz), 1.01 (3H, t, J=7.5 Hz), 1.56–1.67 (2H, m), 1.71–1.81 (4H, m), 2.13–2.21 (2H, m), 2.43 (2H, q, J=7.5 Hz), 2.50 (2H, t, J=7.3 Hz), 2.52 (2H, t, J=7.3 Hz), 2.68–2.82 (2H, m), 4.43–4.53 (1H, m) 7.08 (2H, d, J=8.8 Hz), 7.15 (2H d, J=8.6 Hz), 7.25 (2H, d J=8.8 Hz), 7.66 (2H, d, J=8.8 Hz); ESMS: m/z 475 (MH+), $C_{29}H_{34}N_2O_4$=474 g/mol; HPLC purity=98%.

5.1.2.197 Synthesis of 2-Cyclobutyl-3-(4-hydroxyphenyl)-2,4,5-trihydrobenzo[g]1H-indazol-7-ol This compound was synthesized in the same manner as in Section 5.1.2.193. In step 1, 6-methoxy-1-tetralone was used to make the 1,3-diketone.

ESMS m/z 333 (MH+), $C_{21}H_{20}N_2O_2$=332 g/mol, HPLC purity=70%.

5.1.2.198 Synthesis of 3-(4-Hydroxyphenyl)-2-[2-(trifluoromethyl)phenyl]-2,4,5-trihydrobenzo[g]1H-indazol-7-ol This compound was synthesized in the same manner described in Section 5.1.2.149. In step 2, 2-trifluoromethylphenyl hydrazine was used to form the pyrazole heterocycle.

ESMS m/z 423 (MH+), $C_{24}H_{17}F_3N_2O_2$=422 g/mol, HPLC purity=90%.

5.1.2.199 Synthesis of 4-{4-Ethyl-5-phenyl-1-[2-(trifluoromethyl)phenyl]pyrazol-3-yl}phenol This compound was synthesized based upon Scheme 1.

Step 1: Same as step 1 in Section 5.1.2.6. 4-methoxybutyrylphenone and benzoylchloride were used as starting materials.

Step 2: Same as step 2 in Section 5.1.2.6. 2-trifluoromethylphenyl hydrazine was used to form the pyrazole heterocycle.

Step 3: Demethylation was performed as described in Scheme 1 to afford the final product.

ESMS m/z 409 (MH+), $C_{24}H_{19}F_3N_2O$=408 g/mol, HPLC purity=99%.

5.1.2.200 Synthesis of 4-[4-Ethyl-3-(4-hydroxyphenyl)-5-methylpyrazolyl]phenol This compound was synthesized based upon Scheme 1.

Step 1: Same as step 1 in Section 5.1.2.6. 4-methoxybutyrylphenone and acetylchloride were used as starting materials.

Step 2: Same as step 2 in Section 5.1.2.6. 4-methoxyphenyl hydrazine was used to form the pyrazole heterocycle.

Step 3: Demethylation was performed asdescribed in Scheme 1 to afford the final product.

ESMS m/z 295 (MH+), $C_{18}H_{18}N_2O_2$=294 g/mol, HPLC purity=99%.

5.1.2.201 Synthesis of 3-(4-Hydroxyphenyl)-2-methyl-2-hydrobenzo[g]1H-indazol-6-ol This compound was synthesized based upon Scheme 1.

Step 1: Same as step 1 in Section 5.1.2.149. 5-methoxy-1-tetralone and p-anisoyl chloride were used as starting materials.

Step 2: Same as step 2 in Section 5.1.2.149. 4-methoxyphenyl hydrazine was used to form the pyrazole heterocycle.

Step 3: Oxidation with 2,3-dichloro-5,6-dicyano-1,4-benzoquinone (DDQ). To the above product in dry toluene was added DDQ (1.1 equiv.). The solution was refluxed overnight, quenched with sat. NaHCO$_3$, K$_2$CO$_3$ and extracted with CH$_2$Cl$_2$. The combined organic layers were dried over Mg$_2$SO$_4$ and evaporated in vacuo to give a solid residue. Purification with flash column chromatography yield product.

Step 4: Demethylation was performed as described for Step C in Scheme 1 to afford the final product.

Step 5: The product was purified by HPLC using a C$_{18}$ column (Reliasil-BDXC18, 10×50 mm, Ranin Dynamax) running a first buffer of H$_2$O/0.1% TFA and a second buffer of HCN/0.1% TFA through a gradient from 5–95% of the second buffer over a nine-minute period at a flow rate of ten ml/min.

ESMS m/z 291 (MH+), $C_{18}H_{14}N_2O_2$=290 g/mol, HPLC purity=70%.

5.1.2.202 Synthesis of 3-(4-Hydroxyphenyl)-2-methyl-2-hydrobenzo[g]1H-indazol-8-ol This compound was synthesized in the same manner as described in Section 5.1.2.201. In step 1, 7-methoxy-1-tetralone and p-anisoyl chloride were used as starting materials.

ESMS m/z 291 (MH+), $C_{18}H_{14}N_2O_2$=290 g/mol, HPLC purity=70%.

5.1.2.203 Synthesis of 3-(4-Hydroxphenyl)-2-[2-(trifluoromethyl)phenyl]-2-hydrobenzo[g]1H-indazol-7-ol This compound was synthesized in the same manner as Section 5.1.2.201. In step 1, 6-methoxy-1-tetralone and p-anisoyl chloride were used as starting materials. In step 2, 2-trifluoromethylphenyl hydrazine was used to form the pyrazole.

ESMS m/z 421 (MH$^+$), $C_{24}H_{15}F_3N_2O_2$=420 g/mol, HPLC purity=90%.

5.1.2.204 Synthesis of 2-Cyclobutyl-3-(4-hydroxyphenyl)-2-hydrobenzo[g]1H-indazol-7-ol This compound was synthesized based upon Scheme 4.

Steps 1, 2 and 3: Same as corresponding steps in Section 5.1.2.197.

Step 4: Oxidation with 2,3-dichloro-5,6-dicyano-1,4-benzoquinone (DDQ). Same as step 3 in Section 5.1.2.201.

Step 5: Demethylation was performed as described in Scheme 1 to afford the final product.

ESMS m/z 331 (MH$^+$), $C_{21}H_{18}N_2O_2$=330 g/mol, HPLC purity=60%.

5.1.2.205 Synthesis of 4-{4-Ethyl-3-(4-methoxyphenyl)-1-[2-(trifluoromethyl)phenyl]pyrazol-5-yl}phenol This compound is a derivative of the final product in Section 5.1.2.53. To an acetone solution of 4-{4-ethyl-5-(4-hydroxyphenyl)-1-[2-(trifluoromethyl)phenyl]pyrazol-3-yl}phenol (1.0 equiv.) was added potassium carbonate (1.0 equiv.) and dimethylsulfate (1.0 equiv.). The mixture was stirred at rt overnight and routine work-up afforded a mixture of starting material, mono-methylated product and di-methylated product. HPLC using a $C_{18}$ column (ReliasilBDXC18, 10×50 mm, Ranin Dynamax) running a first buffer of $H_2O$/0.1% TFA and a second buffer of HCN/0.1% TFA through a gradient from 5–95% of the second buffer over a nine-minute period at a flow rate of ten ml/min afforded the title compound as an off-white powder after lyophilization.

ESMS m/z 439 (MH$^+$), $C_{25}H_{21}F_3N_2O_2$=438 g/mol, HPLC purity=98%.

5.1.2.206 Synthesis of 4-{4-Ethyl-5-(4-methoxyphenyl)-1-[2-(trifluoromethyl)phenyl]pyrazol-3-yl}phenol This compound is the regioisomer of Section 5.1.2.205 and produced as described therein.

ESMS m/z 439 (MH$^+$), $C_{25}H_{21}F_3N_2O_2$=438 g/mol, HPLC purity=98%.

5.1.2.207 Synthesis of 4-{5-(4-Acetyloxyphenyl)-4-ethyl-1-[2-(trifluoromethyl)phenyl]pyrazol-3-yl}phenyl Acetate This compound is a derivative of the final product in Section 5.1.2.53. To a THF solution of 4-{4-ethyl-5-(4-hydroxyphenyl)-1-[2-(trifluoromethyl)phenyl]pyrazol-3-yl}phenol was added acetyl chloride (3.0 equiv.) and pyridine (3.0 equiv.). The mixture was stirred at rt for 24 h, poured into cold $NaHCO_3$, extracted with EtOAc. The organic extracts were washed with brine, dried with $Na_2SO_4$ and concentrated in vacuo. Purification afforded the product as a white powder.

ESMS m/z 509 (MH+), $C_{28}H_{23}F_3N_2O_4$=508 g/mol, HPLC purity=98%.

5.1.2.208 Synthesis of 4-{4-Ethyl-5-(4-hydroxyphenyl)-1-[2-(trifluoromethyl)phenyl]pyrazol-3-yl}phenyl Acetate This compound is a derivative of the final product in Section 5.1.2.53. To a THF solution of 4-{4-ethyl-5-(4-hydroxyphenyl)-1-[2-(trifluoromethyl)phenyl]pyrazol-3-yl}phenol was added acetyl chloride (1.0 equiv.) and pyridine (2.0 equiv.). The mixture was stirred at rt for 24 h, poured into cold $NaHCO_3$, extracted with EtOAc. The organic extracts were washed with brine, dried with $Na_2SO_4$ and concentrated in vacuo to give a mixture of starting material, mono-acylated product and di-acylated product. HPLC isolation using a $C_{18}$ column (Reliasil-BDXC18, 10×50 mm, Ranin Dynamax) running a first buffer of $H_2O$/0.1% TFA and a second buffer of HCN/0.1% TFA through a gradient from 5–95% of the second buffer over a nine-minute period at a flow rate of ten ml/min. and purification followed by lyophilization afforded the title product as a white powder.

ESMS m/z 467 (MH$^+$), $C_{26}H_{21}F_3N_2O_3$=466 g/mol, HPLC purity=98%.

5.1.2.209 Synthesis of 4-{4-Ethyl-3-(4-hydroxyphenyl)-1-[2-(trifluoromethyl)phenyl]pyrazol-5-yl}phenyl Acetate This compound is the regioisomer of Section 5.1.2.208. The synthesis and isolation procedures are the same as in that Section.

ESMS m/z 467 (MH$^+$), $C_{26}H_{21}F_3N_2O_3$=466 g/mol, HPLC purity=98%.

5.1.2.210 Synthesis of 4-{5-[4-(2,2-Dimethylpropanoyloxy)phenyl]-4-ethyl-1-[2-(trifluoromethyl)phenyl]pyrazol-3-yl}phenyl 2,2-dimethylpropanoate This compound is a derivative of the final product in Section 5.1.2.53. To a THF solution of 4-{4-ethyl-5-(4-hydroxyphenyl)-1-[2-(trifluoromethyl)phenyl]pyrazol-3-yl}phenol was added pivaloyl chloride (3.0 equiv.) and pyridine (3.0 equiv.). The mixture was stirred at rt for 24 h, poured into cold $NaHCO_3$, extracted with EtOAc. The organic extracts were washed with brine, dried with $Na_2SO_4$ and concentrated in vacuo. Purification by HPLC using a $C_{18}$ column (Reliasil-BDXC18, 10×50 mm, Ranin Dynamax) running a first buffer of $H_2O$/0.1% TFA and a second buffer of HCN/0.1% TFA through a gradient from 5–95% of the second buffer over a nine-minute period at a flow rate of ten ml/min afforded the product as a white powder.

ESMS m/z 593 (MH$^+$), $C_{34}H_{35}F_3N_2O_4$=592 g/mol, HPLC purity=98%.

5.1.2.211 Synthesis of 4-{4-Ethyl-5-(4-hydroxyphenyl)-1-[2-(trifluoromethyl)phenyl]pyrazol-3-yl}phenyl 2,2-Dimethylpropanoate This compound is a derivative of the final product in Section 5.1.2.53. To a THF solution of 4- {4-ethyl-5-(4-hydroxyphenyl)-1-[2-(trifluoromethyl)phenyl]pyrazol-3-yl}phenol was added pivaloyl chloride (1.0 equiv.) and pyridine (2.0 equiv.). The mixture was stirred at rt for 24 h, poured into cold $NaHCO_3$, extracted with EtOAc. The organic extracts were washed with brine, dried with $Na_2SO_4$ and concentrated in vacuo to give a mixture of starting material, mono-acylated product and di-acylated product. HPLC HPLC using a $C_{18}$ column (Reliasil-BDXC 18, 10×50 mm, Ranin Dynamax) running a first buffer of $H_2O$/0.1% TFA and a second buffer of HCN/0.1% TFA through a gradient from 5–95% of the second buffer over a nine-minute period at a flow rate of ten ml/min and purification followed by lyophilization afforded the title product as a white powder.

ESMS m/z 509 (MH$^+$), $C_{29}H_{27}F_3N_2O_3$ 508 g/mol, HPLC purity=98%.

5.1.2.212 Synthesis of 4-{4-ethyl-3-(4-Hydroxyphenyl)-1-[2-(trifluoromethyl)phenyl]pyrazol-5-yl}phenyl 2,2-Dimethylpropanoate This compound is the regioisomer of Section 5.1.2.211. The synthesis and isolation procedures are the same as in that Section.

ESMS m/z 509 (MH$^+$), $C_{29}H_{27}F_3N_2O_3$=508 g/mol, HPLC purity=98%.

5.1.2.213 Synthesis of 3-(4-Hydroxyphenyl)-1-methylbenzo[g]1H-indazol-6-ol

This compound is the regioisomer of Section 5.1.2.201. The synthesis and isolation procedures are the same as in Section 5.1.2.201.

ESMS m/z 291 (MH$^+$), $C_{18}H_{14}N_2O_2$=290 g/mol, HPLC purity=99%.

5.1.2.214 Synthesis of 3-(4-Hydroxyphenyl)-1-methylbenzo[g]1H-indazol-B-ol

This compound is the regioisomer of Section 5.1.2.202. The synthesis and isolation procedures are the same as in Section 5.1.2.202.

ESMS m/z 291 (MH$^+$), $C_{18}H_{14}N_2O_2$=290 g/mol, HPLC purity=97%.

5.1.2.215 Synthesis of 1-Cyclobutyl-3-(4-hydroxyphenyl)benzo[g]1H-indazol-7-ol

This compound is the regioisomer of Section 5.1.2.204. The synthesis and isolation procedures are the same as in Section 5.1.2.204.

ESMS m/z 291 (MH$^+$), $C_{18}H_{14}N_2O_2$=290 g/mol, HPLC purity=97%.

5.1.2.216 Synthesis of 4-[4-Bromo-1-cyclobutyl-5-(4-hydroxyphenyl)pyrazol-3-yl]phenol This compound was synthesized based upon Scheme 4.

Step 1: Formation of 1,3-diketones. Same as Step 1 in Section 5.1.2.146.

Step 2 and 3: Same as corresponding steps in Section 5.1.2.167.

Step 4: Bromination. To a solution of the above pyrazole (1.0 equiv.) in anhydrous $CHCl_3$ at reflux (70° C.) under argon was added dropwise bromine (1.01 equiv.) in anhydrous $CHCl_3$ solution. The mixture was stirred for 50 min at reflux, followed by addition of 10% $Na_2S_2O_3$ in saturated $NaHCO_3$ aqueous solution. The aqueous-organic solution was separated and the aqueous layer was extracted with $CH_2Cl_2$. The combined organic phases were dried over $Na_2SO_4$ and rotary evaporated to give a yellow solid that was washed with EtOAc to afford pale yellow solid as 1-[4-bromo-1-cyclobutyl-3-(4-methoxyphenyl)pyrazol-5-yl]-4-methoxybenzene.

Step 5: Demethylation was performed as described in Scheme 1 to afford the final product.

ESMS: m/z 385 (MH+), $C_{19}H_{17}BrN_2O_2$=385 g/mol; HPLC purity=91.6%.

5.1.2.217 Synthesis of 3,5-bis(4-Hydroxyphenyl)-1-cyclobutylpyrazol-4-yl 4-hydroxyphenyl Ketone This compound was synthesized based upon Scheme 4.

Step 1–4: Same as corresponding steps in Section 5.1.2.216.

Step 5: Acylation. To a solution of the above 4-bormopyrazole (1.0 equiv.) in anhydrous THF at −98° C. under argon was added n-BuLi (1.2 equiv., 1.6 M in hexane). The resultant solution was stirred for 1 h at −98° C. and then transferred dropwise to a solution of 4-allyoxybenzoyl chloride (1.2 equiv.) in THF at −78° C. through a double-tipped needle. The reaction mixture was stirred overnight at −78° C., diluted with water, and then acidified with 10% aqueous citric acid. The organic layer was dried over $Na_2SO_4$ and purified with flash chromatography ($CH_2Cl_2$) to give acylated product.

Step 6: Demethylation was performed as described in Scheme 1 to afford the final product.

ESMS: m/z 427 (MH+), $C_{26}H_{22}N_2O_4$=426 g/mol; HPLC purity=84.1%.

5.1.2.218 Synthesis of 3,5-bis(4-Methoxyphenyl)-1-cyclobutylpyrazol-4-yl 4-(2-piperidylethoxy)phenyl Ketone This compound was synthesized based upon Scheme 4 and Scheme 5.

Step 1–5: Same as corresponding steps in Section 5.1.2.217.

Step 6: Selective removal of allyl protecting group. A mixture of the above pyrazole (1.0 equiv.), pyrrolidine (20 equiv.), triphenylphosphine (0.05 equiv.) and tetrakis(tiphenylphosphine) palladium(0) (0.05 equiv.) in THF was heated to reflux overnight. The solution was concentrated in vacuo and the crude material was purified by flash column chromatography (ethyl acetate/hexane 1:3).

Step 7: Alkylation. A mixture of the phenol (1.0 equiv., obtained from step 6), 1-(2-chloroethyl)piperidine monohydrochloride (1.2 equiv.) cesium carbonate (2.5 equiv) in DMF (30 ml) was heated at 100° C. overnight. The solids were removed by filtration, the filtrate was concentrated in vacuo and the residue was taken up into ethyl acetate. The solution was washed with water, brine, dried over sodium sulfate, filtered and concentrated in vacuo to give the title compound.

ESMS: m/z 566 (MH+), $C_{35}H_{39}N_3O_4$=565 g/mol; HPLC purity=82.5%.

5.1.2.219 Synthesis of 3,5-bis(4-Hydroxyphenyl)-1-cyclobutylpyrazol-4-yl 4-(2-piperidylethoxy)phenyl Ketone This compound was synthesized based upon Scheme 4 and Scheme 5.

Step 1–7: Same as corresponding steps in Scheme 5.1.2.218.

Step 8: Demethylation was performed as described in Scheme 1 to afford the final product.

ESMS: m/z 538 (MH+), $C_{33}H_{35}N_3O_4$=537 g/mol; HPLC purity=88.1%.

5.1.2.220 Synthesis of 4-{4-Ethyl-3-(4-hydroxyphenyl)-1-[2-(trifluoromethyl) phenyl]pyrazol-5-yl}-2-fluorophenol This compound was synthesized in the same manner as Section 5.1.2.53. In step 1, 4'-methoxybutyrylphenone and 3-tluoro-4-methoxybenzoyl chloride were used as starting materials.

ESMS: m/z 443 (MH+), $C_{24}H_{18}F_4N_2O_2$=442 g/mol; HPLC purity=90%.

5.1.2.221 Synthesis of 4-{5-(4-Butanoyloxyphenyl)-4-ethyl-1-[2-(trifluoromethyl) phenyl]pyrazol-3-yl}phenyl Butanoate This compound is a derivative of the final product in Section 5.1.2.53. To a THF solution of 4-{4-ethyl-5-(4-hydroxyphenyl)-1-[2-(trifluoromethyl)phenyl]pyrazol-3-yl}phenol was added butyryl chloride (3.0 equiv.) and pyridine (3.0 equiv.). The mixture was stirred at rt for 24 h, poured into cold $NaHCO_3$, extracted with EtOAc. The organic extracts were washed with brine, dried with $Na_2SO_4$ and concentrated in vacuo. Purification afforded the product as a white powder.

ESMS: m/z 565 (MH$^+$), $C_{32}H_{31}F_3N_2O_4$=564 g/mol; HPLC purity=98%.

5.1.2.222 Synthesis of 4-[3-(4-Butanoyloxyphenyl)-4-ethyl-1-methylpyrazol-5-yl]phenyl Butanoate This compound is a derivative of the final product in Section 5.1.2.147. To a THF solution of 4-[4-ethyl-5-(4hydroxyphenyl)-1-methylpyrazol-3-yl]phenol was added butyryl chloride (3.0 equiv.) and pyridine (3.0 equiv.). The mixture was stirred at rt for 24 h, poured into cold $NaHCO_3$, extracted with EtOAc. The organic extracts were washed with brine, dried with $NaSO_4$ and concentrated in vacuo. Purification afforded the product as a white powder.

ESMS: m/z 435 (NM$^+$), $C_{26}H_{30}N_2O_4$=434 g/mol; HPLC purity=98%.

5.1.2.223 Synthesis of 4-[5-(4-Acetyloxyphenyl)-4-ethyl-1-methylpyrazol-3-y]phenyl Acetate This compound is a derivative of the final product in Section 5.1.2.147. To a THF solution of 4-[4-ethyl-5-(4-hydroxyphenyl)-1-methylpyrazol-3-yl]phenol was added acetyl chloride (3.0 equiv.) and pyridine (3.0 equiv.). The mixture was stirred at rt for 24 h, poured into cold $NaHCO_3$, extracted with EtOAc. The organic extracts were washed with brine, dried with $NaSO_4$ and concentrated in vacuo. Purification afforded the product as a white powder.

ESMS: m/z 379 (MH+), $C_{22}H_{22}N_2O_4$=378 g/mol; HPLC purity=98%.

5.1.2.224 Synthesis of 3,5-bis(4-Hydroxyphenyl)-1-[2-(trifluoromethyl)phenyl]pyrazol-4-yl 4-(2-piperidylethoxy)phenyl Ketone, Chloride This compound was synthesized in the same manner as Section 5.1.2.219. In Step 2, 2-trifluoromethylphenyl hydrazine was used to form the pyrazole heterocycle.

$^1$H NMR (d$_6$-DMSO): δ 8.89 (s, 1H), 8.79(s, 1H), 7.14–5.73 (m, 15H), 3.562 (broad t, 2H,), 2.64 (m, 4H), 2.15 (m, 2H), 0.89 (m, 6H); LC/MS m/z 628 (MH+), $C_{36}H_{32}F_3N_3O_4$=627 g/mol; purity=99%.

5.1.2.225 Synthesis of 4-{5-[4-(4-Butylcydohexylcarbonyloxy)phenyl]-1-cyclobutyl-4-ethylpyrazol-3-yl}phenyl 4butylcydohexanecarboxylate This compound is a derivative of product in Section 5.1.2.167. Pyrazole 4-[1-cyclobutyl-4-ethyl-5-(4-hydroxyphenyl)pyrazol-3-yl]phenol was dissolved in THF. To this solution was added EDC (1.5equiv.), DMAP (0.1equiv.), DIEA (1.5equiv.), and trans-4-n-butylcycloxehanoic acid (3equiv.) and the reaction was allowed to stir for 16 h at RT. Ethyl acetate was then added and the reaction was washed with 10% citric acid, 10% NaHCO$_3$, brine and dried (Na$_2$SO$_4$). After removing solvent the products (a mixture of bis-acylated and mono-acylated products) were isolated by flash chromatography (5–30%EtOAc/DCM).

$^1$H NMR (CDCl$_3$): δ 0.80–0.99 (13H, m), 1.13–1.28 (15H, m), 1.47–1.62 (4H, m), 1.72–1.86 (5H, m), 2.05–2.19 (6H, m), 2.37–2.49 (4H, m), 2.66–2.79 (2H, m), 4.41 (1H, pent., J=8.4 Hz), 7.06 (2H, d, J=8.8 Hz), 7.12 (2H, d, J=8.7 Hz), 7.23 (2H, d, J=8.7 Hz), 7.64 (2H, d, J=8.7 Hz); ESMS: m/z 667 (MH+), $C_{43}H_{58}N_2O_4$=666 g/mol.

5.1.2.226 Synthesis of 4-[1-Cyclobutyl-4-ethyl-5-(4-Hydroxyphenyl)pyrazol-3-yl]phenyl 4-butylcydohexanecarboxylate This compound is a derivative of the product described in Section 5.1.2.167. Synthetic procedure is same as Section 5.1.2.225. The mixture of product was isolated and purified by HPLC using a C$_{18}$ column (Reliasil-BDXC18, 10×50 mm, Ranin Dynamax) running a first buffer of H$_2$O/0.1% TFA and a second buffer of HCN/0.1% TFA through a gradient from 5–95% of the second buffer over a nine-minute period at a flow rate of ten ml/min.

$^1$H NMR (CDCl$_3$): δ 0.84–1.03 (8H, m), 1.16–1.31 (8H, m), 1.48–1.66 (4H, m), 1.74–1.89 (2H, m), 2.09–2.22 (4H, m), 2.40–2.51 (2H, m), 2.69–2.80 (2H, m), 4.50 (1H, pent., J=8.2 Hz), 5.26 (1H, s), 6.85 (2H, d, J=8.7 Hz), 7.09 (2H, d, J=8.7 Hz), 7.11 (2H, d, J=8.6 Hz), 7.64 (2H, d, J=8.8 Hz); ESMS: m/z 501 (MH+), $C_{23}H_{40}N_2O_3$=500 g/mol; HPLC purity=98.2%.

5.1.2.227 Synthesis of 4-[1-Cyclobutyl-4-ethyl-3-(4-hydroxyphenyl)pyrazol-5-yl]phenyl 4-butylcydohexanecarboxylate This compound is a derivative of product in Section 5.1.2.167. Synthetic procedure is same as Section 5.1.2.225. The mixture of product was isolated and purified by HPLC.

$^1$H NMR (CDCl$_3$): δ 0.85–1.04 (8H, m), 1.17–1.32 (8H, m), 1.49–1.66 (4H, m), 1.74–1.91 (2H, m), 2.10–2.23 (4H, m), 2.40–2.54 (2H, m), 2.72–2.84 (2H, m), 4.51 (1H, pent., J=8.2 Hz), 5.04 (1H, s), 6.84 (2H, d, J=8.8 Hz), 7.16 (2H, d, J=8.6 Hz), 7.27 (2H, d, J=8.7 Hz), 7.54 (2H, d, J=8.8 Hz); ESMS: m/z 501 (MH+), $C_{23}H_{40}N_2O_3$=500 g/mol; HPLC purity=98.8%.

5.1.2.228 Synthesis of 4-[1-Cyclobutyl-4-ethyl-5-(4-hydroxy-2-methylphenyl)pyrazol-3-yl]-3-methylphenol This compound was synthesized based upon Scheme 5. Synthetic procedure was same as for Section 5.1.2.167. In Step 1, 4'-methoxy-2'-methylacetophenone and 4-methoxy-2-methylbenzoyl chloride were used as starting materials.

ESMS: m/z 363 (MH+), $C_{23}H_{26}N_2O_2$=362 g/mol; HPLC purity=95%.

5.1.2.229 Synthesis of 4-{4-Ethyl-5-(4-hydroxy-2-methylphenyl)-1-[2-(trifluoromethyl)phenyl]pyrazol-3-yl}-3-methylphenol This compound was synthesized based upon Scheme 1. Synthetic procedure was same as for Section 5.1.2.53. In Step 1, 4'-methoxy-2'-methylacetophenone and 4-methoxy-2-methylbenzoyl chloride were used as starting materials.

ESMS: m/z 453 (MH+), $C_{26}H_{23}$ $F_3N_2O_2$=452 g/mol; HPLC purity=95%.

5.1.2.230 Synthesis of 4-[1-cyclobutyl-5-(4-Hydroxyphenyl)-4-propylpyrazol-3-yl]phenol This compound was synthesized based upon Scheme 1.

Step 1–3: Same as corresponding steps in Section 5.1.2.216.

Step 4: Alkylation. To a solution of 4-bromopyrazole (1 equiv., obtained from step 3) in THF at −78° C. was added nBuLi (1.1 equiv., 1.6 M in hexane). After the solution was stirred at −78° C. for 1.5 h, it was added dropwise into a solution of the bromopropane (1.2 equiv.) in THF at −78° C. After 15 min., the solution was allowed to warm to room temperature and stirred overnight. After quenching reaction with 1M HCl, the layers were separated and the aqueous layer extracted with EtOAc (×3). The combined organic layers were washed with saturated NaHCO$_3$ (×1) and brine, dried over Na$_2$SO$_4$, filtered and concentrated to afford a crude product mixture. Flash chromatography yielded the alkylated product.

Step 5: Demethylation was performed as described in Scheme 1 to afford the final product.

$^1$H NMR (CDCl$_3$/DMSO, 6:1): δ 0.36 (3H, t, J=7.2 Hz), 0.94–0.99 (2H, m), 1.27–1.34 (1H, m), 1.40–1.45 (1H, m), 1.81–1.89 (2H, m), 2.03–2.07 (2H, m), 2.35 (2H, m), 4.15–4.24 (1H, m), 6.52 (2H, d, J=8.8 Hz), 6.57 (2H, d, J=8.6 Hz), 6.73 (2H, d, J=8.6 Hz), 7.14 (2H, d, J=8.8 Hz), 8.55 (1H, s), 8.87 (1H, s); ESMS: m/z 349 (MH+), $C_{22}H_{24}N_2O_2$=348 g/mol; HPLC purity=84.9%.

4-[1-Cyclobutyl-5-(4-hydroxyphenyl)-4-prop-2-enylpyrazol-3-yl]phenol

This compound was synthesized in the same manner as Section 5.1.2.230. In step 4, allyl bromide was used for alkylation.

$^1$H NMR (CDCl$_3$/DMSO, 6:1): δ 1.78–1.91 (2H, m), 2.29–2.37 (2H, m), 2.73–2.83 (2H, m), 3.26–3.28 (2H, m), 4.67–4.73 (1H, m), 4.91 (1H, dd, J=17.1 Hz, 1.9 Hz), 5.03 (1H, dd, J=10.1 Hz, 1.9 Hz), 5.89–5.99 (1H, m), 6.95 (2H, d, J=8.8 Hz), 7.01 (2H, d, J=8.7 Hz), 7.25 (2H, d, J=8.8 Hz), 7.64 (2H, d, J=8.8 Hz); ESMS: m/z 347 (MH+), $C_{22}H_{22}N_2O_2$346 g/mol; HPLC purity=82.2%.

5.1.2.231 Synthesis of 4-[1-Cyclobutyl-5-(4-hydroxyphenyl)-4-methylpyrazol-3-yl]phenol This compound was synthesized in the same manner as Section 5.1.2.156. In step 3, chlorocyclobutane was used for alkylation.

$^1$H NMR (CDCl$_3$/DMSO, 6:1): δ 1.30–1.37 (1H, m), 1.44–1.51 (1H, m), 1.70 (3H, s), 1.86–1.93 (2H, m), 2.40–2.46 (2H, m), 4.24–4.33 (1H, m),6.55 (2H, d, J=8.8 Hz), 6.60 (2H, d, J=8.6 Hz), 6.76 (2H, d, J=8.8 Hz), 7.20 (2H, d, J=8.8 Hz), 8.55 (1H, s), 8.87 (1H, s); ESMS: m/z 321 (MH+), $C_{20}H_{20}N_2O_2$=320 g/mol; HPLC purity=86.2%.

5.1.2.232 Synthesis of 4-[1-Cyclobutyl-3-(4-hydroxyphenyl)-4-phenylpyrazol-5-yl]phenol This compound was synthesized in the same manner as Section 5.1.2.231. In step 1, 1-(4-methoxyphenyl)-2-phenylethan-1-one was used to make the 1,3-diketone.

$^1$H NMR (CDCl$_3$/DMSO, 6:1): δ 1.44–1.49 (1H, m), 1.59–1.62 (1H, m), 1.99–2.07 (2H, m), 2.58–2.64 (2H, m), 4.38–4.46 (1H, m), 6.48 (2H, d, J=8.8 Hz), 6.56 (2H, d, J=8.7 Hz), 6.72–6.77 (3H, m), 6.85–6.88 (2H, m), 7.04 (2H, d, J=8.8 Hz), 8.47 (1H, s), 8.82 (1H, s); ESMS: m/z 383 (MH+), C$_{25}$H$_{22}$N$_2$O$_2$=382 g/mol; HPLC purity=94.8%.

5.1.2.233 Synthesis of 4-[1-Cyclobutyl-5-(4-hydroxyphenyl)-4-benrylpyrazol-3-yl]phenol This compound was synthesized in the same manner as Section 5.1.2.231. In step 1, 1-(4-methoxyphenyl)-3phenylpropan-1-one was used to make the 1,3-diketone.

$^1$H NMR (CDCl$_3$/DMSO, 6:1): δ 1.30–1.37 (1H, m), 1.45–1.51 (1H, m), 1.87–1.94 (2H, m), 2.40–2.50 (2H, m), 3.46 (2H, s), 4.23–4.29 (1H, m), 6.41 (2H, d, J=8.6 Hz), 6.49 (2H, d, J=8.6 Hz), 6.64 (4H, t, J=8.6 Hz), 6.74 (1H, t, J=7.4 Hz), 6.80 (2H, t, J=7.6 Hz), 7.05 (2H, d, J=8.6 Hz), 8.50 (1H, s), 8.84 (1H, s); ESMS: m/z 397 (MH+), C$_{26}$H$_{24}$N$_2$O$_2$=396 g/mol; HPLC purity=91.5%.

5.1.2.234 Synthesis of 4-[1-Cyclobutyl-5-(4-hydroxyphenyl)-4-iodopyrazol-3-yl]phenol This compound was synthesized in the same manner as Section 5.1.2.216. In step 4, instead of bromination, iodonation was performed.

$^1$H NMR (CDCl$_3$/DMSO, 6:1): δ 1.26–1.33 (1H, m), 1.39–1.44 (1H, m), 1.82–1.89 (2H, m), 2.30–2.40 (2H, m), 4.22–4.31 (1H, m), 6.50 (2H, d, J=8.6 Hz), 6.56 (2H, d, J=8.8 Hz), 6.76 (2H, d, J=8.8 Hz), 7.30 (2H, d, J=8.6 Hz); ESMS: m/z 433 (MH+), C$_{19}$H$_{17}$IN$_2$O$_2$=432 g/mol; HPLC purity=81.3%.

5.1.2.235 Synthesis of 2-Cyclobutyl-3-(4-hydroxyphenyl)-4,5,6-trihydrobenzo[c]pyrazolo[4,3-a][7]annulen-8-of This compound was synthesized in the same manner as Section 5.1.2.197. In step 1, 7-methoxy-1-benzosuberone was used to form the 1,3-diketone.

$^1$H NMR (CDCl$_3$): δ 1.75–1.90 (3H, m), 2.16 (2H, pent, J=7 0 Hz), 2.37–2.46 (3H, m), 2.54 (2H, t, J=7.0 Hz), 2.68–2.79 (2H, m), 4.97–5.04 (1H, m), 6.83 (2H, dd, J=8.2, 2.5 Hz), 6.86 (1H, d, J=2.5 Hz), 6.91 (2H, d, J=8.6 Hz), 7.19 (1H, d, J=8.2 Hz), 7.50 (2H, d, J=8.7 Hz); ESMS: m/z 347 (MH+), C$_{22}$H$_{22}$N$_2$O$_2$=346 g/mol; HPLC purity=97.0%.

5.1.2.236 Synthesis of 1-Cyclobutyl-3-(4-hydroxyphenyl)-4,5,6-trihydrobenzo[c]pyrazolo[4,5-a][7]annulen-8-ol This compound is the regioisomer of Section 5.1.2.235. HPLC using a C$_{18}$ column (Reliasil-BDXC18, 10×50 mm, Ranin Dynamax) running a first buffer of H$_2$O/0.1% TFA and a second buffer of HCN/0.1% TFA through a gradient from 5–95% of the second buffer over a nine-minute period at a flow rate of ten ml/min was used for separation of the two regioisomers.

$^1$H NMR (CDCl$_3$): δ 1.70–1.86 (2H, m), 1.96–2.03 (2H, m), 2.26–2.34 (2H, m), 2.49 (2H, t, J=7.0 Hz), 2.68–2.74 (4H, m), 4.71–4.79 (1H, m), 6.71 (1H, d, J=2.5 Hz), 6.76 (1H, dd, J=8.4, 2.5 Hz), 6.96 (2H, d, J=8.6 Hz), 7.20 (2H, d, J=8.8 Hz), 7.77 (1H, d, J=8.4 Hz); ESMS: m/z 347 (MH+), C$_{22}$H$_{22}$N$_2$O$_2$=346 g/mol; HPLC purity=97.1%.

5.1.2.237 Synthesis of 2-[3,5-bis(4-Hydroxyphenyl)-1-cyclobutylpyrazol-4-yl]phenol This compound was synthesized based upon Scheme 4.

Step 1–4: Same as corresponding steps in Section 5.1.2.216.

Step 5: Suzuki coupling of the above 4-bromopyrazole with aryl boronic acid. Reaction was carried out under an atmosphere of nitrogen and solvents were degassed by bubbling nitrogen for 2 h prior to the reaction. Pd(PPh$_3$)$_4$ (0.04eq) in DMF was added to the 4-bromopyrazole (obtained from step 4) and 2-methoxyphenylboronic acid (or vinyltributyltin) (1.1 ec). Sodium carbonate (0.4 mL, 2M) was then added. The reaction was sealed and allowed to stand overnight at 90° C. Ethyl acetate (20 mL) was then added and the reaction was washed with water and brine. The organic fractions were filtered and concentrated under reduced pressure. Residues were lyophilised in 90% MeCN/H$_2$O. Purification of the compound was achieved by teturation with 60% MeCN/H$_2$O and HPLC purification.

Step 5: Demethylation was performed as described for Scheme 1.

$^1$H NMR (CDCl$_3$ & DMSO-d$_6$): δ 1.36–1.61 (2H, m), 1.95–2.06 (2H, m), 2.50–2.60 (2H, m), 4.41 (1H, pent, J=7.8 Hz), 6.36 (2H, d, J=8.6 Hz), 6.37 (1H, t, J=6.0Hz), 6.45 (2H, d, J=8.8 Hz), 6.48 (1H, d, J=6.0 Hz), 6.61 (1H, d, J=7.6 Hz), 6.71 (2H, d, J=8.6 Hz), 6.75 (1H, t, J=6.6 Hz), 7.06 (2H, d, J=8.4 Hz), , 7.32 (1H, s), 8.45 (1H, s), 8.76 (1H, s); ESMS m/z 399 (MH+), C$_{25}$H$_{22}$N$_2$O$_3$=398 g/mol; HPLC purity= 81.7%.

5.1.2.238 Synthesis of 4-[1-Cyclobutyl-3-(4-hydroxyphenyl)-4-(2-methylphenyl)pyrazol-5-yl]phenol This compound was synthesized in the same manner as Section 5.1.2.237. In step 5, 2-methylphenylboronic acid was used f6r coupling.

$^1$H NMR (CDCl$_3$ & DMSO-d$_6$): δ 1.25–1.58 (2H, m), 1.66 (3H, s), 2.02–2.15 (2H, m), 2.61–2.76 (2H, m), 4.49 (1H, pent, J=7.8 Hz), 6.44 (2H, d, J=8.0 Hz), 6.53 (2H, d, J=8.2 Hz), 6.68 (2H, d, J=8.0 Hz), 6.80–6.92 (4H, m), 7.03 (2H, d, J=8.2 Hz), 8.39 (1H, s), 8.74 (1H, s); ESMS m/z 397 (MH+), C$_{26}$H$_{24}$N$_2$O$_2$=396 g/mol; HPLC purity=94.6%.

5.1.2.239 Synthesis of 4-{4-[3,5-bis(Trifluoromethyl)phenyl]-1-cyclobutyl-3-(4-hydroxyphenyl)pyrazol-5-yl}phenol This compound was synthesized in the same manner as Section 5.1.2.237. In step 5, 3,5-ditrifluoromethyl-phenylboronic acid was used for coupling.

$^1$H NMR (CDCl$_3$ & DMSO-d$_6$): δ 1.51–1.76 (2H, m), 2.09–2.18 (2H, m), 2.61–2.72 (2H, m), 4.52 (1H, pent, J=7.9 Hz), 6.61 (2H, d, J=8.6 Hz), 6.71 (2H, d, J=8.2 Hz), 6.83 (2H, d, J=8.4 Hz), 7.07 (2H, d, J=8.4Hz), 7.24 (2H, s), 7.39 (1H, s); ESMS m/z 519 (MH+), C$_{27}$H$_{22}$F$_6$N$_2$O$_2$=518 g/mol; HPLC purity=84.7%.

5.1.2.240 Synthesis of 3-[3,5-bis(4-Hydroxyphenyl)-1-cydobutylpyrazol-4-yl]phenol This compound was synthesized in the same manner as Section 5.1.2.237. In step 5, 3-methoxyphenylboronic acid was used for coupling.

$^1$H NMR (CDCl$_3$ & DMSO-d$_6$): δ 1.24–1.47 (2H, m), 1.81–2.10 (2H, m), 2.41 (2H, pent, J=9.7 Hz), 4.23 (1H, pent, J=8.3 Hz), 6.05 (1H, d, J=7.6 Hz), 6.09 (1H, s), 6.17 (1H, d, J=8.2 Hz), 6.27 (2H, d, J=8.2 Hz), 6.37 (2H, d, J=8.0 Hz), 6.52 (1 H, d, J=7.8 Hz), 6.56 (2H, d, J=8.2 Hz), 6.87 (2H, d, J=8.2 Hz); ESMS m/z 399 (MH+), C$_{25}$H$_{22}$N$_2$O$_2$= 398 g/mol; HPLC purity=89.3%.

5.1.2.241 Synthesis of 4-{1-Cyclobutyl-3-(4-hydroxyphenyl)-4-[3-(trifluoromethyl)phenyl]pyrazol-5-yl}phenol This compound was synthesized in the same manner as Section 5.1.2.237. In step 5, 3-trifluoromethylphenylboronic acid was used for coupling.

$^1$H NMR (CDCl$_3$ & DMSO-d$_6$): δ 1.27–1.53 (2H, m), 1.86–1.97 (2H, m), 2.47 (2H, pent, J=9.9 Hz), 4.39 (1H, pent, J=8.4 Hz), 6.47 (2H, d, J=7.8 Hz), 6.55 (2H, d, J=7.8 Hz), 6.68 (2H, d, J=7.8 Hz), 6.82 (2H, d, J=8.2 Hz), 6.96 (2H, d, J=7.6 Hz), 7.07 (2H, d, J=8.2 Hz); MS m/z 451 (MH+), C$_{26}$H$_{21}$F$_3$N$_2$O$_2$=450 g/mol; HPLC purity=99.4%.

5.1.2.242 Synthesis of 4-{1-Cyclobutyl-3-(4-hydroxyphenyl)-4-[4-(trifluoromethyl)phenyl]pyrazol-5-yl}phenol This compound was synthesized in the same manner as Section 5.1.2.237. In step 5, 4-trifluoromethylphenylboronic acid was used for coupling.

$^1$H NMR (CDCl$_3$ & DMSO-d$_6$): δ 1.39–1.61 (2H, m), 1.96–2.04 (2H, m), 2.57 (2H, pent, J=9.9 Hz), 4.30 (1H, pent, J=8.3 Hz), 6.36 (2H, d, J=7.8 Hz), 6.46 (2H, d, J=7.6 Hz), 6.60 (2H, d, J=7.8 Hz), 6.80–6.91 (5H, m), 6.97 (1H, d, J=7.6 Hz); ESMS m/z 451 (MH+), C$_{26}$H$_{21}$F$_3$N$_2$O$_2$=450 g/mol; HPLC purity=92.2%.

5.1.2.243 Synthesis of 4-[1-Cyclobutyl-3-(4-hydroxyphenyl)-4-(2-thienyl)pyrazol-5-yl]phenol This compound was synthesized in the same manner as Section 5.1.2.237. In step 5, 2-thiophenylboronic acid was used for coupling.

$^1$H NMR (CDCl$_3$ & DMSO-d$_6$): δ 1.36–1.63 (2H, m), 1.94–2.03 (2H, m), 2.55 (2H, pent, J=9.8 Hz), 4.36 (1H, pent, J=9.0 Hz), 6.38 (1H, d, J=3.5 Hz), 6.48 (2H, d, J=8.2Hz), 6.56 (1H, t, J=5.1 Hz), 6.57 (2H, d, J=8.2 Hz), 6.78 (2H, d, J=8.2 Hz), 6.82 (1H, d, J=5.1 Hz), 7.09 (2H, d, J=8.4 Hz); ESMS m/z 399 (MH+), C$_{23}$H$_{20}$N$_2$O$_2$S=388 g/mol; HPLC purity=99.1%.

5.1.2.244 Synthesis of 4-[1-Cyclobutyl-3-(4-hydroxyphenyl)-4-(3-thienyl)pyrazol-5-ylJphenol This compound was synthesized in the same manner as Section 5.1.2.237. In step 5, 3-thiophenylboronic acid was used for coupling.

$^1$H NMR (CDCl$_3$ & DMSO-d$_6$): δ 1.30–1.56 (2H, m), 1.88–1.98 (2H, m), 2.50 (2H, pent, J=9.9 Hz), 4.31 (1H, pent, J=8.3 Hz), 6.36 (1H, dd, J=4.9, 1.2 Hz), 6.43 (1H, dd, J=3.0, 1.2 Hz), 6.44 (2H, dd, J=8.8, 1.2 Hz), 6.53 (2H, d, J=8.8 Hz), 6.70 (2H, d, J=8.4 Hz), 6.78 (1H, dd, J=4.9, MHz), 7.00 (2H, dd, J=8.8, 1.2 Hz); ESMS m/z 399 (MH+), C$_{23}$H$_{20}$N$_2$O$_2$S=388 g/mol; HPLC purity=82.9%.

5.1.2.245 Synthesis of 4-[1-Cyclobutyl-3-(4-hydroxyphenyl)-4-vinylpyrazol-5-yl)phenol This compound was synthesized in the same manner as Section 5.1.2.237. In step 5, vinylboronic acid was used for coupling.

$^1$H NMR (CDCl$_3$ & DMSO-d$_6$): δ 1.64–1.89 (2H, m), 2.19–2.29 (2H, m), 2.80 (2H, pent, J=9.8 Hz), 4.59 (1H, pent, J=8.4 Hz), 4.85 (1H, d, J=11.7 Hz), 4.99 (1H, d, J=17.7 Hz) 6.48 (1H, dd, J=18.0, 11.5 Hz), 6.92 (2H, d, J=7.6 Hz), 6.98 (2H, d, J=7.6 Hz), 7.16 (2H, d, J=8.0 Hz), 7.51 (2H, d, J=8.0 Hz), 8.90 (1H, s), 9.23 (1H, s); ESMS m/z 333 (MH+), C$_{21}$H$_{20}$N$_2$O$_2$=332 g/mol; HPLC purity 86.4%.

5.2 Biological Activity of Compounds of the Invention 5.2.1 In vivo Assays 5.2.1.1 Allen-Doisy Test for Estrogenicity This test is used to evaluate a test compound for estrogenic activity by observation of cornification of the vaginal epithelium of in ovariectornized rats after administration of a test compound (Allen and Doisy 1923; Miihlbock 1940; Terenius 1971).

Mature female Hsd/Cpb rats, having initial weights between about 150–200 g, were obtained from a commercial supplier (Harlan—CPB, Horst, The Netherlands). The rats were housed in housed in aluminium cages in a light- and temperature-controlled room (14 hours light/10 hours dark at 19° C.–23° C.). Four rats were housed per cage. The rats were provided free access to standard pelleted food and to tap water. After a period of acclimatization (a few days) the rats were ovariectomized bilaterally under ether anaesthesia. Vaginal smears were taken over a period of 4–5 days. Rats showing positive smears were discarded.

The rats of each treatment group were housed in two juxtaposed cages. Each experiment consisted of 2+n groups of eight rats per group. Two reference groups received the reference compound (estradiol, 1, 3, 5 (10)-estratriene-3, 17-β-diol for subcutaneous "sc") administration; ethinylestradiol for oral administration); n groups received the test compound. For subcutaneous administration, between 0.1 pg and 0.2 pg total dose/rat (approx. 0.4–0.8 μ/kg total dose) was used. For oral administration, 0.008–0.016 mg total dose/rat (approx. 0.032–0.064 mg/kg total dose) was used. Vehicles used for sc administration were (in preferential order): arachis oil, arachis oil with 100 ml/l benzyl alcohol; gelatin (5.0 g/l) and mannitol (50 g/l) in water; methylcellulose (2.0 g/l) and NaCl, (9.0 g/l) in water; or any other suitable vehicle. For oral administration, the vehicles used were (in preferential order): gelatin (5.0 g/l) and mannitol (50 g/l) in water; methylcellulose (2.0 g/l) and NaCl, (9.0 g/l) in water; mulgofen (50 g/l) (sold under the tradename ELF 719, GAF) and NaCl (9.0 g/l) in water; or any other suitable vehicle.

Three weeks after ovariectomy, the rats were primed with a single sc dose of 1 μg estradiol (in 0.1 ml arachis oil) to ensure maintenance of sensitivity and greater uniformity of response. In the fourth week, 7 days after priming, (preferably on a Monday), the reference or test compound was administered in 3 equal doses, one in the afternoon of the first day of treatment, and two (one in the morning and one in the afternoon) of the second day of treatment. Compound doses were chosen based on extrapolations of in vitro data obtained in the CHO-transactivation (Section ) and/or binding assays for estrogen receptor using known estrogen agonists and antagonists. For sc administration, the reference compound (estradiol) was administered in total doses of 0.1–0.2 □g/rat. Test compounds were usually administered in total doses of 0.01–1.0 mg/rat. Each total sc dose was divided equally over three administrations, each in a dose volume of 0.25 ml. For oral administration, the reference compound (ethinylestradiol) was administered in total doses of 0.008–0.016 mg/rat. Test compounds are usually administered in total doses of 0.01–1.0 mg/rat. Each total oral dose was divided equally over 3 administrations, each in a dose volume of 0.25 ml. For expression of doses per kg, an average body weight of 250 g was assumed. Vaginal smears were taken in the afternoon of the third day, in the morning and afternoon of the fourth day, and in the morning of the fifth day of the treatment week. Additional vaginal smears were taken on succeeding days (in the morning) until the estrogenic response was complete. The vaginal smears were made on microscope slides. The slides were dried and fixed with 96% ethanol, and stained for about twenty minutes with Giemsa solution (Merck, Darmstadt, Germany), that had been diluted 1:10 with tap water, washed thoroughly under tap water, then dried. The percentage of cornified and nucleated epithelial cells was estimated for each smear was evaluated under microscope observation (60×). The rats were allowed to rest for one week (week five of the experiment). The experiment was then repeated, with priming on the sixth week and administration and observation during the seventh week, as described. The rats were then euthanized under deep anesthesia or with $CO_2/O_2$ gas.

The developmental phase of the vaginal epithelium for each rat was evaluated using a scale from "a"–"g" determined as follows (Table 1). The vaginal sequence of normal non-ovariectomized rats with a 4-day estrous cycle is: diestrus→diestrus→proestrus→estrus. The usual phases observed in the mornings of the 4-day estrous cycle using the scale in Table I are therefore a, a, e, and g, respectively. The phases b, c, d and f are intermediates.

TABLE 1

| Percentage of Leucocytes | Percentage of Nucleated Epithelial Cells | Percentage of Cornified Epithelial Cells | Developmental Phase |
| --- | --- | --- | --- |
| >67% | — | — | a. diestrus |
| 5–50% | >50% | — | b. late diestrus |
| <5% | >50% | — | e. proestrus |
| <5% | — | >50% | f. estrus |
| <5% | <5% | >90% | g. estrus |
| 5–67% | — | >50% | d. metestrus |
| 33–67% | — | <50% | c. late metestrus |

The number of rats with a positive response is a measure for the estrogenic activity of the test compound. The interpretation of the results was made as shown in Table 2.

TABLE 2

| Percentage of Rats Showing a Positive Response | Conclusion |
| --- | --- |
| 0% | inactive |
| 1%–50% | weakly active |
| >50% | active |

5.2.1.2 Anti-Allen-Doisy Test for Anti-Estrogenicity

This test is used to evaluate a test compound for anti-estrogenic activity when administered in the presence of estrogen (Allen and Doisy 1923; Jongh and Laqueur 1938; Miihlbock 1940; Emmens, Cox et al. 1959). More specifically, the ability of the test compound to counteract the estrogenic cornification of vaginal epithelium is determined.

Mature female Cpb rats, having initial weights between about 150–200 g, were obtained from a commercial supplier (CPB-TNO, Zeist, The Netherlands). The rats were housed in housed in aluminium cages in a light- and temperature-controlled room (14 hours light/10 hours dark at 21° C.–23° C.). Four rats were housed per cage. The rats were provided free access to standard pelleted food and to tap water. After a period of acclimatization (a few days) the rats were ovariectomized bilaterally under ether anaesthesia. Vaginal smears were taken over a period of 4–5 days. Rats showing positive smears were discarded.

The rats of each treatment group were housed in two juxtaposed cages. Each experiment consisted of 1+n groups of eight rats per group. One reference group received the reference compound (nafoxidine HCl); n groups received the test compound. For oral administration, 0.25 mg/rat/day (approx. 1.44 mg/kg/day) was used. Vehicles used for sub-cutaneous ("sc") administration were (in preferential order): arachis oil, arachis oil with 10% benzyl alcohol; gelatin (0.5%) and mannitol (5%) in water; and methylcellulose (0.2%) and NaCl (9.0%) in water. For oral administration, the vehicles used were (in preferential order): gelatin (0.5%) and mannitol (5%) in water; methylcellulose (0.2%) and NaCl (9.0%) in water; and mulgofen (5%) (sold under the tradename ELF 719, GAF) and NaCl (0.9%) in water.

Two weeks after ovariectomy, the rats were primed with a single sc dose of 0.2 µg estradiol (in 0.1 ml arachis oil) administered daily for ten days to ensure maintenance of sensitivity and greater uniformity of response. Administration of estradiol was followed immediately by administration of test compound or vehicle. Test compounds were administered at 1.0 mg/rat. For sc administration, the dose volume was 0.1 ml; for oral administration, the dose volume was 0.25 ml. Vaginal smears were taken daily throughout the administration period. The vaginal smears were made on microscope slides. The slides were dried and fixed with 96% ethanol, and stained for about twenty minutes with Giemsa solution (Merck, Darmstadt, Germany), that had been diluted 1:10 with tap water, washed thoroughly under tap water, then dried. The percentage of cornified and nucleated epithelial cells was estimated for each smear was evaluated under microscope observation (60×). Following the experiment, rats were euthanized under deep anesthesia or with $CO_2/O_2$ gas.

The developmental phase of the vaginal epithelium for each rat was evaluated using a scale from "a"–"g" determined as follows (Table 3). The vaginal sequence of normal non-ovariectomized rats with a 4-day estrous cycle is: diestrus→diestrus→proestrus→estrus. The usual phases observed in the mornings of the 4-day estrous cycle using the scale in Table 3 are therefore a, a, e, and g, respectively. The phases b, c, d and f are intermediates.

TABLE 3

| Percentage Of Leucocytes | Percentage of Nucleated Epithelial Cells | Percentage of Cornified Epithelial Cells | Developmental Phase |
| --- | --- | --- | --- |
| >67% | — | — | a. diestrus |
| 5–50% | >50% | — | b. late diestrus |
| <5% | >50% | — | e. proestrus |
| <5% | — | >50% | f. estrus |
| <5% | <5% | >90% | g. estrus |
| 5–33% | — | >50% | d. metestrus |
| 33–67% | — | <50% | c. late metestrus |

Smears showing any of phases e, f, or g were considered to be estrogenic (i.e., the vaginal epithelium showed cornification). The final result was expressed as a ratio of the number of smears showing estrogenic response to the total number of smears collected from the third day through the final day of the study. The number of rats with a positive response is a measure for the anti-estrogenic activity of the test compound. The interpretation of the results was made as shown in Table 4.

TABLE 4

| Percentage of Rats Showing a Positive Response | Conclusion |
| --- | --- |
| >70% | inactive |
| 35%–70% | weakly active |
| <35% | active |

5.2.1.3 Immature Rat Uterotrophic Bioassay for Estrogenicity and Anti-Estrogenicity Antiestrogenic activity is determined by the ability of a test compound to suppress the increase in uterine wet weight resulting from the administration of 0.2 μg 17-(β-estradiol ("$E_2$") per day. Any statistically significant decreases in uterine weight in a particular dose group as compared with the $E_2$ control group are indicative of anti-estrogenicity.

One hundred forty (140) female pups (19 days old) in the 35–50 g body weight range are selected for the study. On day 19 of age, when the pups weigh approximately 35–50 g, they are body weight-order randomized into treatment groups. Observations for mortality, morbidity, availability of food and water, general appearance and signs of toxicity are made twice daily. Pups not used in the study are euthanized along with the foster dams. Initial body weights are taken just prior to the start of treatment at day 19 of age. The final body weights are taken at necropsy on day 22 of age.

Treatment commences on day 19 of age and continues until day 20 and 21 of age. Each animal is given three subcutaneous ("sc") injections daily for 3 consecutive days. Three rats in each of the control and mid- to high-level dose test groups are anesthetized with a ketamine/xylazine mixture. Their blood is collected by exsanguination using a 22 gauge needle and 5 ml syringe flushed with 10 USP units sodium heparin/ml through the descending vena cava; and then transferred into a 5 ml green top plasma tube (sodium heparin (freeze-dried), 72 USP units). Plasma samples are collected by centrifugation, frozen at −70° C., and analyzed using mass spectrographic to determine the presence and amount of test compound in the serum. Blood chemistry is also analyzed to determine other blood parameters. The uteri from the rats are excised and weighed. The remaining rats are sacrificed by asphyxiation under $CO_2$. The uteri from these rats are excised, nicked, blotted to remove fluid, and weighed to the nearest 0.1 mg.

In order to determine whether the test compound significantly affected final body weight, a parametric one-way analysis of variance (ANOVA) is performed (SIGMASTAT version 2.0, available commercially from Jandel Scientific, San Rafael, Calif.). Estrogen agonist and antagonist activity is assessed by comparing uterine wet weights across treatment groups using a parametric ANOVA on loglo transformed data. The data are transformed to meet assumptions of normality and homogeneity of variance of the parametric ANOVA. The F value is determined and a Student—Newman-Kuels multiple range test is performed to determine the presence of significant differences among the treatment groups. The test compound is determined to act as a mixed estrogen agonist/antagonist if the test compound does not completely inhibit the 17 β-estradiol-stimulated uterotrophic response.

5.2.1.4 Estrogen Receptor Antagonist Efficacy in MCF-7 Xenograft Model

MCF-7 human mammary tumors from existing in vivo passages are implanted subcutaneously into 95 female Ncr-nu mice. A 17-β-estradiol pellet (Innovative Research of America) is implanted on the side opposite the tumor. Both implants are performed on the same day.

Treatment is started when the tumor sizes are between 75 mg and 200 mg. Tumor weight is calculated according to the formula for the volume of an ellipsoid, $$\frac{l \times w^2}{2}$$

where l and w are the larger- and smaller dimensions of the tumor and unit tumor density is assumed. The test compounds are administered BID: q7h×2, with one drug preparation per week. The test compounds are stored at +4° C. between injections. The dose of test compound is determined according to the individual animal's body weight on each day of treatment. Gross body weights are determined twice weekly, starting the first day of treatment. Mortality checks are performed daily. Mice having tumors larger than 4,000 mg, mice having ulcerated tumors, as and moribund mice are sacrificed prior to the day of study termination. The study duration is limited to 60 days from the day of tumor implantation but termination could occur earlier as determined to be necessary. Terminal bleeding of all surviving mice is performed on the last day of the experiment. Statistical analysis is performed on the data gathered, including mortality, gross individual and group average body weights at each weighing, individual tumor weights and median group tumor weight at each measurement, the incidence of partial and complete regressions and tumor-free survivors, and the calculated delay in the growth of the median tumor for each group.

5.2.1.5 OVX Rat Model

This model evaluates the ability of a compound to reverse the decrease in bone density and increase in cholesterol levels resulting from ovariectomy (Black, Author et al. 1994; Willson, Author et al. 1997). Three-month old female rats are ovariectomized ("ovx"), and test compounds are administered daily by subcutaneous route beginning one day post-surgery. Sham operated animals and ovx animals with vehicle control administered are used as control groups. After 28 days of treatment, the rats are weighed, the overall body weight gains obtained and the animals euthanized. Blood bone markers (e.g., osteocalcin and bone-specific alkaline phosphatase), total cholesterol, and urine markers (e.g., deoxypyridinoline and creatinine) are measured. Uterine wet weights are also obtained. Both tibiae and femurs are removed from the test animals for peripheral quantitative computed tomography scanning or other measurement of bone mineral density. Data from the ovx and test vehicle animals are compared to the sham and ovx control animals to determine tissue specific estrogenic/antiestrogenic effects of the test compounds.

5.2.2 In vitro Assays 5.2.2.1 ERα Binding Assays

ERa receptor (−0.2 mg/ml, Affinity Bioreagents) was diluted to about 2×10−3 mg/ml in phosphate-buffered saline ("PBS") at a pH of 7.4. Fifty microliters I of the ERα-PBS solution was then added to each the wells of a flashplate (Wallac SCINTISCTRIPS). The plates were sealed and stored in the dark at 4° C. for 16–18 hours.

The buffered receptor solution is removed just prior to use, and the plates were washed 3 times with 200 microliters per well of PBS. The washing was typically performed using a slow dispense of reagent into the wells to avoid stripping the receptor from the well surface.

For library screening, 150 microliters of 1 nM$^3$H-estradiol (New England Nuclear, Boston, Mass.) in 20 mM Tris-HCl, 1 mM EDTA, 10% glycerol, 6 mM monothioglycerol, SmM KCl, pH 7.8 was mixed with 50 microliters of the test compound (in same buffer) in a 96 well mictrotiter plate (Costar 3794), resulting in a final estradiol concentration of 0.6 nM. In addition, several dilutions of estradiol, centered on the $IC_{50}$ of 1–2 nM were also added to individual wells to generate a standard curve. The plates were gently shaken to mix the reagents. A total of 150 microliters from each of the wells is added to the corresponding wells of the pre-coated ERα plates. The plates were sealed (Packard #6005185) and the components in the wells were incubated either at room temperature for 4 hours or at 4° C. overnight. The receptor bound ligand was read directly after incubation using a scintillation counter (TRILUX, Wallac). The amount of receptor bound ligand was determined directly, i.e., without separation of bound from free ligand. If estimates of both bound and free ligand were required, the supernatant was removed from the wells, liquid scintillant added, and the wells counted separately in a liquid scintillation counter.

5.2.2.2 ERβ Binding Assays

ERβ receptor (~0.2 mg/ml, Affinity Bioreagents) was diluted to about $2 \times 10^{-3}$ mg/ml in phosphate-buffered saline ("PBS") at a pH of 7.4. Fifty microliters of the ERβ-PBS solution was then added to each the wells of a flashplate (Wallac SCINTISCTRIPS). The plates were sealed and stored in the dark at 4° C. for 16–18 hours. The buffered receptor solution is removed just prior to use, and the plates were washed 3 times with 200 microliters per well of PBS. The washing was typically performed using a slow dispense of reagent into the wells to avoid stripping the receptor from the well surface.

For library screening, 150 microliters of 1 nM $^3$H-estradiol (New England Nuclear, Boston, Mass.) in 20 mM Tris-HCl, 1 mM EDTA, 10% glycerol, 6 mM monothioglycerol, 5 mM KCI, pH 7.8 was mixed with 50 microliters of the test compound (in same buffer) in a 96 well mictrotiter plate (Costar 3794), resulting in a final estradiol concentration of 0.6 nM. In addition, several dilutions of estradiol, centered on the $IC_{50}$ of 1–2 nM were also added to individual wells to generate a standard curve. The plates were gently shaken to mix the reagents. A total of 150 microliters from each of the wells is added to the corresponding wells of the pre-coated ER(β plates. The plates were sealed (Packard #6005185) and the components in the wells were incubated at room temperature either for 4 hours or at 4° C. overnight. The receptor bound ligand was read directly after incubation using a scintillation counter (TRILUX, Wallac). The amount of receptor bound ligand was determined directly, i.e., without separation of bound from free ligand. If estimates of both bound and free ligand were required, the supernatant was removed from the wells, liquid scintillant added, and the wells counted separately in a liquid scintillation counter.

5.2.2.3 ERα/ERβ Transactivation Assays 5.2.2.3.1 Construction of Transfected CHO Cells The above-mentioned transfected CHO cells were derived from CHO KI cells obtained from the American Type Culture Collection ("ATCC", Rockville, Md.). The transfected cells were modified to contain the following four plasmid vectors: (1) pKCRE with DNA for the human estrogen receptor, (2) pAG-60-neo with DNA for the protein leading to neomycin resistance, (3) pRO-LUC with DNA for the rat oxytocin promoter and for firefly luciferase protein, and (4) $pDR_2$ with DNA for the protein leading to hygromycine resistance. All transformations with these genetically modified CHO cells were performed under rec-VMT containment according to the guidelines of the COGEM (Commissie Genetische Modificatie). Screening was performed either in the absence of estradiol (estrogenicity) or in the presence of estradiol (anti-estrogenicity).

Reagents

The following reagents were prepared using ultra pure water (milli-Q quality):

1. Culture Medium

Dulbecco's MEM/HAM F12 powder (12.5 g/l; Gibco, Paisley, UK) was dissolved in water. Sodium bicarbonate (2.5 grams/liter ("g/l")), L-glutamine (0.36 g/I) and sodium pyruvate ($5.5 \times 10^{-2}$ g/l) were added. This medium was supplemented with an aqueous mixture (0.50 ml/l medium) of ethanolamine (2.44 ml/l), sodium selenite (0.9 mg/l), and 2-mercaptoethanol (4.2 ml/l). The pH of the medium was adjusted to 7.0±0.1 with NaOH or HCl (1 mol/l), and the medium was sterilized by membrane filtration using a filter having 0.2 μm pores. The resulting serum-free culture medium was stored at 4° C.

2. Antibiotics Solution

Streptomycin sulfate (25 g; Mycofarm, Delft, The Netherlands) and sodium penicillin G (25 g; Mycofarm) were dissolved in 1 l water and sterilized by membrane filtration using a filter having 0.2 μm pores.

3. Defined Bovine Calf Serum Supplemented ("DBCSS")

DBCSS (Hyclone, Utah), sterilized by the manufacturer, was inactivated by heating for 30 min at 56° C. with mixing every 5 min. Aliquots of 50 ml and 100 ml were stored at −20° C.

4. Charcoal-Treated DBCSS ("cDBCSS")

Charcoal (0.5 g; Norit A) was washed with 20 ml water (3 times) and then suspended in 200 ml Tris buffer. For coating 0.05 g dextran (T70; Pharmacia, Sweden) is dissolved in a suspension that was stirred continuously for 3 hours at room-temperature. The resulting dextran-coated charcoal suspension was centrifuged for 10 min at 8,000 N/kg. The supernatant was removed and 100 ml DBCSS was added to the residue. The suspension was stirred for 30 min at 45° C. under aseptic conditions. Following stirring, the charcoal was removed by centrifugation for 10 min at 8000 N/kg. The supernatant was sterilized by membrane filtration using a first filter having a pore size of 0.8 μm followed by filtration with a second filter having a pore size of 0.2 μm. The sterilized, heat-inactivated cDBCSS was stored at −20° C.

5. Tris Buffer

Tromethamine ("Tris", 1.21 g; 10 mmol) was dissolved in approximately 950 ml water. The solution pH was adjusted to 7.4 using HCl (0.2 mol/l) and the volume raised to 1 l with additional water. This buffer was prepared fresh prior to use.

6. Luclite Substrate Solution

Luclite luminescence kit, developed for firefly luciferase activity measurements in microtiter plates was obtained from a commercial source (Packard, Meriden, Conn.). Ten milliliters of the above-described buffer solution was added to each flask of substrate.

Preparation of Transfected Cells

Under aseptic conditions, the above-described culture medium was supplemented with antibiotics solution (2.5 ml/l) and heat-inactivated cDBCSS (50 ml/l) to give complete medium. One vial of the above-described recombinant CHO cells was taken from the seed stock in liquid nitrogen and allowed to thaw in water at approximately 37° C. A Roux flask (80 cc) was inoculated with about $5 \times 10^5$ viable cells/ml in complete medium. The flask was flushed with 5% $CO_2$ in air until a pH of 7.2–7.4 resulted. The cells were subsequently incubated at 37° C. During this period, the complete medium was refreshed twice.

Following incubation the cell culture was trypsinized and inoculated at 1:10 dilution in a new flask (180 cc cell culturing) and at $5 \times 10^3$ cells with 100 μl complete medium per well in a 96-well white culture plate for transactivation assays. The 96 well plates were incubated over two days. The cells were grown as a monolayer at the bottoms of the wells and reached confluence after two days. After a cell culture period of 20 passages, new cells were taken from the seed stock in liquid nitrogen.

5.2.2.3.2 Assay of Compounds

Assay for Estrogenicity

Experiments were performed in groups of three blocks, each block in a separate microtiter plate. Each block included the following four groups Group Contents 1 One transactivation group of four wells, each containing ethanol and transfected cells. This group was used to estimate total transactivation.

2 One total transactivation group of four wells containing beta-estradiol ($1 \times 10^{-7}$ M) and transfected cells. This group was used to estimate total transactivation of cells.
3 Three standard groups of five wells each, containing five different concentrations of non-transfected and transfected cells.
4 Test or reference compound groups (n groups, $n5 \leq 21$) of three wells each, containing three different concentrations of test or reference compound and transfected cells.

Aliquots of ten ml of control, standard, test, and reference compounds were added by pipette into wells of the relevant groups as defined above. Each of the wells included 190 ml of complete medium.

Group Contents
1 Ethanol
2 Standard solution in ethanol ($10^{-9}$ M, to be raised to $10^{-6}$ M final concentration).
3 Standard solutions in ethanol ($0.47 \times 10^{-11}$ M, $0.95 \times 10^{-11}$ M, $1.95 \times 10^{-11}$ M, $3.9 \times 10^{-11}$ M, and $7.8 \times 10^{-11}$ M, to be raised to $0.47 \times 10^{-8}$ M, $0.95 \times 10^{-8}$ M, $1.95 \times 10^{-8}$ M, $3.9 \times 10^{-8}$ M, and $7.8 \times 10^{-8}$ M respectively).
4 Test or reference compound in six different concentrations $1 \times 10^{-5}$ M, $3.16 \times 10^{-6}$ M, $1 \times 10^{-6}$ M, $3.16 \times 10^{-7}$ M, $1 \times 10^{-7}$ M, $3.16 \times 10^{-8}$ M, respectively.

Assay for Anti-Estrogenicity

Experiments were performed in groups of three blocks, each block in a separate microtiter plate. Each block included the following four groups, each group containing estradiol, 1, 3, 5 (10)-estratriene-3, 17-(β-diol ($10^{-10}$ M) in the final reaction mixture.

Group Contents
1 One transactivation group of four wells, each containing ethanol and transfected cells. This group was used to estimate total transactivation.
2 One group of completely inhibited transactivation group of four wells containing ICl 164,384 ($10^{-6}$ M) and transfected cells. This group was used to estimate complete inhibition of transactivation.
3 Three standard groups of five wells each, containing five different concentrations of non-transfected and transfected cells.
4 Test or reference compound groups (n groups, $n \leq 21$) of three wells each, containing three different concentrations of test or reference compound and transfected cells.

Aliquots of ten μl of control, standard, test, and reference compounds were added by pipette into wells of the relevant groups as defined above. Each of the wells included 190 μl of complete medium.

Group Contents
1 Ethanol
2 Standard solution in ethanol ($10^{-9}$ M, to be raised to $10^{-6}$ M final concentration).
3 Standard solutions in ethanol ($0.47 \times 10^{-11}$ M, $0.95 \times 10^{-11}$ M, $1.95 \times 10^{-11}$ M, $3.9 \times 10^{-11}$ M, and $7.8 \times 10^{-11}$ M, to be raised to $0.47 \times 10^{-8}$ M, $0.95 \times 10^{-8}$ M, $1.95 \times 10^{-8}$ M, $3.9 \times 10^{-8}$ M, and $7.8 \times 10-8$ M respectively).
4 Test or reference compound in six different concentrations $1 \times 10^{-5}$ M, $3.16 \times 10^{-6}$ M, $1 \times 10^{-6}$ M, $3.16 \times 10^{-7}$ M, $1 \times 10^{-7}$ M, $3.16 \times 10^{-8}$ M, respectively.

The microtiter plates were shaken for at least 15 minutes to ensure dissolution of all compounds. Simultaneously, 100 μl estradiol, 1, 3, 5 (10)-estratriene-3, 17-(β-diol ($10^{-7}$ M) was added to 40 ml of complete medium, shaken, and equilibrated to 37° C. About 100 μl of this solution was added to microtiter white culture plates seeded the previous day with $10^4$ transfected cells in 100 μl of complete medium.

The microtiter white culture plates were gently shaken for at least 15 minutes and incubated for 16 h at 37° C. in the dark under a humidified atmosphere flushed with 5% $CO_2$ in air.

Finally, 200 μl of complete medium was removed from the microtiter culture plates, while 50 μl of LUCLITE substrate solution was added to the remaining 50 μl of medium and cells. After ten minutes cell, cell lysis was substantially complete. After sealing the top of the plate, luciferase activity was measured with a luminescence counter. Each sample was counted once for 2.5 s using a scintillation (luminescence) counter. All luminescence measurements were recorded on a teleprinter.

5.2.2.3.3 Evaluation of Responses

The counting figures are corrected to a standardized plate and converted into numbers of light flashes per second ("cps"). For each block (microtiter plate), the mean cps values for the total and non-specific transactivation groups were calculated. For each concentration of standard (separate for each well), test and reference compound, the percentage of transactivation activity relative to the maximum specific estradiol, 1, 3, 5 (10)-estratriene-3, 17β-diol transactivation activity was calculated using the formula:

cps (standard/test compound)−mean cps (non-specific transactivation)/cps (total transactivation)−mean cps (non-specific transactivation)×100

The percentage in the three blocks was evaluated statistically using the analysis of a 3-point parallel line assay in blocks. In order to meet better the requirements for this analysis, the percentages were replaced by their logit values. The log concentration-response curves for the standard, test, and reference compounds were tested for linearity; and the latter curves also for parallelism with the curve for the standard compound. If no significant curvature and no significant deviation from parallelism at the 0.01 levels were found; then the relative transactivation activity of the test compound with respect to estradiol, 1, 3, 5 (10)-estratriene-3, 17-(β-diol (potency ratio), together with the 95% confidence interval, was calculated. For antagonist assays, the relative inhibitory potency of transactivation activity of the test compound with respect to the standard antagonist, ICl 164,384 was calculated. For compounds showing significant agonist or antagonist activity in these initial screens, more accurate $EC_{50}$ values were determined by generating twelve-point curves with 3-fold dilutions of the compounds. In this case, the range of concentrations was selected based on the compound activity in the initial screens.

The following compounds of the invention were determined to be active (i.e., have agonist or antagonist values of $EC_{50} \leq 4 \times 10^{-6}$ M (ERα) and/or $EC_{50} \leq 4 \times 10^{-6}$ M (ERβ) against either or both ERα and ERβ:

4-[5(diphenylmethyl)-4-ethyl-1-methylpyrazol-3-yl]phenol, 4-[4-ethyl-1-methyl-5-(2-phenylethyl)pyrazol-3-yl]phenol, 4-(4-ethyl-1-methyl-5-(2-thienyl)pyrazol-3-yl)phenol, 4-[1-methyl-5-(2-phenylethyl)-4-prop-2-enylpyrazol-3yl]phenol, 4-[1-methyl-5-(phenoxymethyl)-4-prop-2-enylpyrazol-3-yl]phenol, 4-[3,5-bis(4-hydroxyphenyl)-1-methylpyrazol-4-yl]phenol, 4-[3,5-bis(4-hydroxyphenyl)-1-phenylpyrazol-4-yl]phenol, 4-[1-(4-bromophenyl)-5-(4hydroxyphenyl)-4-benzylpyrazol-3-yl]phenol, 4-[1-(4-chloro-2-methylphenyl)-5-(4-hydroxyphenyl)-4benzylpyrazol-3-yl]phenol, 4-[1-(2-chlorophenyl)-5-(4-hydroxyphenyl)-4-benzylpyrazol-3-yl]phenol,
4-[1-(3-chlorophenyl)-5-(4-hydroxyphenyl)-4-benzylpyrazol-3-yl]phenol,
4-[1-(4-chlorophenyl)-5-(4-hydroxyphenyl)-4-benzylpyrazol-3-yl]phenol,
4-[3,4-bis(4-hydroxyphenyl)-1-(2-methylphenyl)pyrazol-5-yl]phenol,
4-[3,4-bis(4hydroxyphenyl)-1-(3-fluorophenyl)pyrazol-5-yl]phenol,
4-[3,4-bis(4-hydroxyphenyl)-1-(2-ethylphenyl)pyrazol-5yl]phenol,
4-[3,5-bis(4-hydroxyphenyl)-1-(4-fluorophenyl)pyrazol-4-yl]phenol,
4-[1-(2,4-difluorophenyl)-3,4bis(4-hydroxyphenyl)pyrazol-5-yl]phenol,
4-{3,4-bis(4-hydroxyphenyl)-1-[2-(trifluoromethyl)phenyl]pyrazol-5yl}phenol,
4-[3,4-bis(4-hydroxyphenyl)-1-(2-fluorophenyl)pyrazol-5-yl]phenol,
4-[3,4-bis(4-hydroxyphenyl)-1-(3-methylphenyl)pyrazol-5-yl]phenol,
4-[3,4-bis(4-hydroxyphenyl)-1-(4-chloro-2-methylphenyl)pyrazol-5-yl]phenol,
4-[3,5-bis(4-hydroxyphenyl)-1-(4-methylphenyl)pyrazol-4-yl]phenol,
4-[1-(2,3-dichlorophenyl)-3,4-bis(4-hydroxyphenyl)pyrazol-5-yl]phenol,
4-[3,4-bis(4-hydroxyphenyl)-1-(5-fluoro-2-methylphenyl)pyrazol-5-yl]phenol,
4-[3,4-bis(4-hydroxyphenyl)-1-(2-chlorophenyl)pyrazol-5-yl]phenol,
4-{3,4-bis(4-hydroxyphenyl)-1-[4-(tertbutyl)phenyl]pyrazol-5-yl}phenol,
4-[3,4-bis(4-hydroxyphenyl)-1-(3-chlorophenyl)pyrazol-5-yl]phenol,
4-[1-(2,4dichlorophenyl)-3,4-bis(4-hydroxyphenyl)pyrazol-5-yl]phenol,
4-[3,5-bis(4-hydroxyphenyl)-1-(4chlorophenyl)pyrazol-4-yl]phenol,
4-[1-(2,6-dichlorophenyl)-3,4-bis(4-hydroxyphenyl)pyrazol-5-yl]phenol,
4-[3,4-bis(4-hydroxyphenyl)-1-(2,3-dimethylphenyl)pyrazol-5-yl]phenol,
4-[3,4-bis(4-hydroxyphenyl)-1-(3-chloro-4-fluorophenyl)pyrazol-5-yl]phenol,
4-{3,4-bis(4-hydroxyphenyl)-1-[4-(trifluoromethoxy)phenyl]pyrazol-5yl}phenol,
4-{3,4-bis(4-hydroxyphenyl)-1-[4-(trifluoromethyl)phenyl]pyrazol-5-yl}phenol,
4-[3,5-bis(4-hydroxyphenyl)-1-(4-iodophenyl)pyrazol-4-yl]phenol,
4-{3,4-bis(4-hydroxyphenyl)-1-[2-chloro-5(trifluoromethyl)phenyl]pyrazol-5-yl}phenol,
4-[3,4-bis(4-hydroxyphenyl)-1-(1,3-dimethyl-5-nitropyrazol-4yl)pyrazol-5-yl]phenol,
4-{3,4-bis(4-hydroxyphenyl)-1-[5-chloro-3-(trifluoromethyl)(2-pyridyl)]pyrazol-5yl}phenol,
4-[3,4-bis(4-hydroxyphenyl)-1-(1,4-dimethylpyrazolo[4,5-e]pyridin-6-yl)pyrazol-5-yl]phenol,
4-(3,5-bis(4-hydroxyphenyl)-1-(6-methylpyridazin-3-yl)pyrazol-4-yl]phenol,
4-[3,4-bis(4-hydroxyphenyl)-1-(6-chloro-2-fluorophenyl)pyrazol-5-yl]phenol,
4-[1-(2-fluorophenyl)-5-(4-methylphenyl)-4-benzylpyrazol-3-yl]phenol, 3-{[3,5-bis(4-hydroxyphenyl)-4-benzylpyrazolyl]methyl}phenol,
1-[3,5-bis(4-hydroxyphenyl)-4-benzylpyrazolyl]-4(methylsulfonyl)benzene,
4-[5-(4-hydroxyphenyl)-1-(2,3,4,5,6-pentafluorophenyl)-4-benzylpyrazol-3-yl]phenol,
4{5-(4-hydroxyphenyl)-4-benzyl-1-[4-(trifluoromethoxy)phenyl]pyrazol-3-yl}phenol,
4-[3,5-bis(4-hydroxyphenyl)-1-(2-pyridyl)pyrazol-4-yl]phenol,
4-[1-(2,4-dimethylphenyl)-4-ethyl-5-(4-hydroxyphenyl)pyrazol-3-yl]phenol,
4[4-ethyl-5-(4-hydroxyphenyl)-1-(3-methylphenyl)pyrazol-3-yl]phenol,
4-{4-ethyl-5-(4-hydroxyphenyl)-1-[4(methylethyl)phenyl]pyrazol-3-yl}phenol,
4-[4-ethyl-1-(3-fluorophenyl)-5-(4-hydroxyphenyl)pyrazol-3-yl]phenol,
4-[4-ethyl-1-(2-ethylphenyl)-5-(4-hydroxyphenyl)pyrazol-3-yl]phenol,
4-[4-ethyl-1-(4-fluorophenyl)-5-(4-hydroxyphenyl)pyrazol-3-yl]phenol,
4-[1-(2,4-difluorophenyl)-4-ethyl-5-(4-hydroxyphenyl)pyrazol-3-yl]phenol, 4-{4-ethyl-5-(4-hydroxyphenyl)-1-[2-(trifluoromethyl)phenyl]pyrazol-3-yl}phenol,
4-[4-ethyl-1-(2-fluorophenyl)-5-(4-hydroxyphenyl)pyrazol-3-yl]phenol,
4-[4-ethyl-5-(4-hydroxyphenyl)-1-(2-methylphenyl)pyrazol-3-yl]phenol, 4-[1-(3,5-dichlorophenyl)-4-ethyl-5-(4-hydroxyphenyl)pyrazol-3-yl]phenol,
4-[1-(4-chloro-2-methylphenyl)-4-ethyl-5-(4-hydroxyphenyl)pyrazol-3-yl]phenol,
4-[4-ethyl-5-(4-hydroxyphenyl)-1-(4-methylphenyl)pyrazol-3-yl] phenol,
4-[1-(2,3-dichlorophenyl)-4-ethyl-5-(4-hydroxyphenyl)pyrazol-3-yl]phenol,
4-[1-(3,4-dimethylphenyl)-4-ethyl-5-(4-hydroxyphenyl)pyrazol-3-yl]phenol,
4-[4-ethyl-1-(5-fluoro-2-methylphenyl)-5-(4-hydroxyphenyl)pyrazol-3yl]phenol,
4-[1-(2-chlorophenyl)-4-ethyl-5-(4-hydroxyphenyl)pyrazol-3-yl]phenol,
4-{1-[4-(tert-butyl)phenyl]-4-ethyl-5-(4-hydroxyphenyl)pyrazol-3-yl}phenol,
4-[1-(3-chlorophenyl)-4-ethyl-5-(4-hydroxyphenyl)pyrazol-3yl]phenol, 4-[1-(2,4-dichlorophenyl)-4-ethyl-5-(4-hydroxyphenyl)pyrazol-3-yl]phenol,
4-[1-(3,4-dichlorophenyl)-4-ethyl-5-(4-hydroxyphenyl)pyrazol-3-yl]phenol,
4-[1-(4-chlorophenyl)-4-ethyl-5-(4-hydroxyphenyl)pyrazol-3yl]phenol,
4-[1-(2,6-dichlorophenyl)-4-ethyl-5-(4-hydroxyphenyl)pyrazol-3-yl]phenol,
4-[1-(2,3-dimethylphenyl)-4-ethyl-5-(4-hydroxyphenyl)pyrazol-3-yl]phenol,
4-[1-(3-chloro-4-fluorophenyl)-4-ethyl-5-(4-hydroxyphenyl)pyrazol-3-yl]phenol,
4-[4-ethyl-5-(4-hydroxyphenyl)-1-5[4-(trifluoromethoxy)phenylpyrazol-3-yl]phenol, 4-{4-ethyl-5-(4-hydroxyphenyl)-1-[4-(trifluoromethyl)phenyl]pyrazol-3-yl}phenol, 4-[4-ethyl-5-(4-hydroxyphenyl)-1-(4-iodophenyl)pyrazol-3-yl]phenol, 4-{1-[2-chloro-5-(trifluoromethyl)phenyl]-4-ethyl-5-(4-hydroxyphenyl)pyrazol-3-yl}phenol, 4-[1-(3,5-dichloro(4-pyridyl))-4-ethyl-5-(4-hydroxyphenyl)pyrazol-3yl]phenol, 4-{4-ethyl-5-(4-hydroxyphenyl)-1-[6-methyl-4-(trifluoromethyl)(2-pyridyl)]pyrazol-3-yl}phenol 4-[4-ethyl-5-(4-hydroxyphenyl)-1-quinoxalin-2-ylpyrazol-3-yl]phenol, 4-{1-[3,5-bis(trifluoromethyl)phenyl]-4-ethyl-5(4-hydroxyphenyl)pyrazol-3-yl}phenol, 4-[3,5-bis(4-hydroxyphenyl)-4-ethylpyrazolyl]benzenesulfonamide, 4-[1-(1,3-dimethyl-5-nitropyrazol-4-yl)-4-ethyl-3-(4-hydroxyphenyl)pyrazol-5-yl]phenol, 4-{1-[5-chloro-3-(trifluoromethyl)(2-pyridyl)]-4-ethyl-5-(4-hydroxyphenyl) pyrazol-3-yl}phenol, 4-{1-[3-chloro-5-trifluoromethyl)(2-pyridyl)]-4-ethyl-5-(4-hydroxyphenyl) pyrazol-3-yl}phenol, 4-[4-ethyl-5-(4-hydroxyphenyl)-1(1,3,4-trimethylpyrazolo[4,5-e]pyridin-6-yl) pyrazol-3-yl]phenol, 4-[1-(6-chloro-2-fluorophenyl)-4-ethyl-5-(4-hydroxyphenyl)pyrazol-3-yl]phenol, 4-[4-ethyl-5-(4-hydroxyphenyl)-1-(2-pyridyl)pyrazol-3-yl]phenol, 4-[4-ethyl-1-(3-hexadecylthiophenyl)-5-(4-hydroxyphenyl)pyrazol-3-yl]phenol, 4-[3,5-bis(4-hydroxyphenyl)-1-(3-hexadecylthiophenyl)pyrazol-4-yl]phenol, 4-{4-ethyl-5-(4-hydroxyphenyl)-1-[(4-hydroxyphenyl)methyl]pyrazol-3yl}phenol, 4-(4-ethyl-5-(4-hydroxyphenyl)-1-{[4-(2-piperidylethoxy)phenyl]methyl}pyrazol-3-yl)phenol, 4-{1-[(3chlorophenyl)methyl]-4-ethyl-5-(4-hydroxyphenyl) pyrazol-3-yl}phenol, 4-{4-ethyl-1-[(4-fluorophenyl)methyl]-5(4-hydroxyphenyl)pyrazol-3-yl}phenol, 4-{4-ethyl-5-(4-hydroxyphenyl)-1-[(3-methylphenyl)methyl]pyrazol-3yl }phenol, 4-{4-ethyl-5-(4-hydroxyphenyl)-1-[(4-nitrophenyl)methyl]pyrazol-3-yl}phenol, 4-{4-ethyl-5-(4-hydroxyphenyl)-1-[(3-phenoxyphenyl)methyl]pyrazol-3-yl}phenol, 2-[3 ,5-bis(4-hydroxyphenyl)-4-ethylpyrazolyl]-1-(4-methylphenyl)ethan-1-one, 2-[3,5-bis(4-hydroxyphenyl)-4-ethylpyrazolyl]-1-(4-fluorophenyl)ethan-1-one, 1-(3,4-dichlorophenyl)-2-[3,5-bis(4-hydroxyphenyl)-4-ethylpyrazolyl]ethan-1-one, 2-[3,5-bis(4-hydroxyphenyl)-4-ethylpyrazolyl] - I-(2-hydroxyphenyl)ethan-1-one, 4-[4-ethyl-5-(4-hydroxyphenyl)-1-benzylpyrazol-3-yl]phenol, 2-[3,5-bis(4-hydroxyphenyl)-4-ethylpyrazolyl]-1-(4-bromophenyl)ethan-1-one, 4-(1-{[4-(tert-butyl)phenyl]methyl}4-ethyl-5-(4-hydroxyphenyl)pyrazol-3-yl)phenol, 4-{2-[3,5-bis(4-hydroxyphenyl)-4-ethylpyrazolyl]acetyl}benzenecarbonitrile, 2-[3,5-bis(4-hydroxyphenyl)-4-ethylpyrazolyl]-1-(4-phenylphenyl)ethan-1-one, 2-[3,5-bis(4-hydroxyphenyl)-4-ethylpyrazolyl]-1-(3-hydroxyphenyl)ethan-1-one, 4-[1- (2,4-dimethylphenyl)-5-(4-hydroxyphenyl)-4-phenylpyrazol-3-yl]phenol, 4-[5-(4-hydroxyphenyl)-1-(3-methylphenyl)-4-phenylpyrazol-3-yl]phenol, 4-{5-(4-hydroxyphenyl)-1-[4-(methylethyl)phenyl]-4-phenylpyrazol-3-yl}phenol, 4-[1-(3-fluorophenyl)-5-(4-hydroxyphenyl)-4-phenylpyrazol-3-yl]phenol, 4-[1-(2-ethylphenyl)-5-(4-hydroxyphenyl)-4-phenylpyrazol-3-yl]phenol, 4-[1-(4-fluorophenyl)-3-(4-hydroxyphenyl)-4-phenylpyrazol-5-yl]phenol, 4-[I1 (2,4-difluorophenyl)-5(4-hydroxyphenyl)-4-phenylpyrazol-3-yl]phenol, 4-{5(4-hydroxyphenyl)-phenyl-1-[2-(trifluoromethyl)phenyl]pyrazol-3-yl}phenol, 4-[1(2-fluorophenyl)-5-(4-hydroxyphenyl)-4phenylpyrazol-3-yl]phenol, 4-[5(4-hydroxyphenyl)-1-(2-methylphenyl)-4-phenylpyrazol-3-yl]phenol, 4-[1(3,5-ichlorophenyl)-5(4-hydroxyphenyl)-4-phenylpyrazol-3-yl]phenol, 4-[1-(4-chloro-2-methylphenyl)-5(4-hydroxyphenyl)-4-phenylpyrazol-3-yl]phenol, 4-[3-(4-hydroxyphenyl)-1-(4-methylphenyl)-4-phenylpyrazol-5-yl]phenol, 4-[1-(2,3-dichlorophenyl)-5-(4-hydroxyphenyl)-4-phenylpyrazol-3-yl]phenol, 4-[1-(3,4-dimethylphenyl)-5-(4-hydroxyphenyl)-4-phenylpyrazol-3-yl]phenol, 4-[1-(5-fluoro-2-methylphenyl)-5-(4-hydroxyphenyl)-4-phenylpyrazol-3-yl]phenol, 4-[1-(2-chlorophenyl)-5-(4-hydroxyphenyl)-4-phenylpyrazol-3yl]phenol, 4-[1-(3-chlorophenyl)-5-(4-hydroxyphenyl)-4-phenylpyrazol-3-yl]phenol, 4-[1-(2,4-dichlorophenyl)-5-(4-hydroxyphenyl)-4-phenylpyrazol-3-yl]phenol, 4-[1-(3,4-dichlorophenyl)-5-(4-hydroxyphenyl)-4-phenylpyrazol-3-yl]phenol, 4-[1-(4-chloroxyphenyl)-4-hydroxyphenyl-4-phenylpyrazol-5- yl]phenol, 4-[1-(2,6-dichlorophenyl)-5-(4-hydroxyphenyl)-4-phenylpyrazol-3-yl]phenol, 4-[1-(2,3-dimethylphenyl)-5-(4-hydroxyphenyl)-4-phenylpyrazol-3-yl]phenol, 4-[1-(3-chloro-4-fluorophenyl)-5-(4-hydroxyphenyl)-4-phenylpyrazol-3-yl]phenol, 4-{5-(4-hydroxyphenyl)-4-phenyl-1-[4-(trifluoromethoxy)phenyl]pyrazol-3-yl}phenol, 4-{5-(4-hydroxyphenyl)-4-phenyl-1-[4-(trifluoromethyl)phenyl]pyrazol-3-yl}phenol, 4-[3-(4-hydroxyphenyl)-1-(4-iodophenyl)-4-phenylpyrazol-5-yl]phenol, 4-{1-[2-chloro-5-(trifluoromethyl)phenyl]-5-(4-hydroxyphenyl)-4-phenylpyrazol-3-yl}phenol, 4-[1-(3,5-dichloro(4-pyridyl))-5-(4-hydroxyphenyl)-4-phenylpyrazol-3-yl]phenol, 4-{5-(4-hydroxyphenyl)-1-[6-methyl-4-(tri fluoromethyl)(2-pyridyl)]-4-phenylpyrazol-3-yl}phenol, 4-[5-(4-hydroxyphenyl)-4-phenyl-1-quinoxalin-2-ylpyrazol-3-yl]phenol,
4-{1-[3,5-bis(trifluoromethyl)phenyl]-5-(4-hydroxyphenyl)-4-phenylpyrazol-3-yl}phenol,
4-{1-[1,3-dimethyl-5-(nitromethyl)pyrazol-4-yl]-5-(4hydroxyphenyl)-4-phenylpyrazol-3-yl}phenol,
4-{1-[5-chloro-3-(trifluoromethyl)2-pyridyl)]-5-(4-hydroxyphenyl)-4-phenylpyrazol-3-yl}phenol,
4-{1-[3-chloro-5-(tri fluoromethyl)2-pyridyl)]-5-(4-hydroxyphenyl)-4-phenylpyrazol-3-yl}phenol,
4-[5-(4-hydroxyphenyl)-4-phenyl-1-(1,3,4-trimethylpyrazolo[4,5-e]pyridin-6-yl)pyrazol-3-yl]phenol,
4-[3-(4-hydroxyphenyl)-1-(6-methylpyridazin-3-yl)-4-phenylpyrazol-5yl]phenol,
4-[1-(6-chloro-2-fluorophenyl)-5-(4-hydroxyphenyl)-4-phenylpyrazol-3-yl]phenol,
4-[1,3-bis(4-hydroxyphenyl)-4-ethylpyrazol-5-yl]phenol,
4-[1,3-bis(4-hydroxyphenyl)-4-phenylpyrazol-5-yl]phenol, 4-[1,3,5-tris(4-hydroxyphenyl)pyrazol-4-yl]phenol,
4-[1,3-bis(4-hydroxyphenyl)pyrazol-5-yl]phenol, 4-[4-ethyl-5-(4-hydroxyphenyl)-1-methylpyrazol-3-yl]phenol,
4-[4-ethyl-5-(4-hydroxyphenyl)pyrazol-3-yl]phenol, 3-(4-hydroxyphenyl)-2,4,5-trihydrobenzo[g]1H-indazol-7-ol,
3-(4-hydroxyphenyl)-2-methyl-2,4,5-trihydrobenzo[g]1H-indazol-7-ol,
3-(4-hydroxyphenyl)-2-phenyl-2,4,5-trihydrobenzo[g]1H-indazol-7-ol,
1-[3,5-bis(4-hydroxyphenyl)4-ethylpyrazolyl]-4-(methylsulfonyl)benzene,
3-{[3,5-bis(4-hydroxyphenyl)pyrazolyl]methyl}phenol, 1-[3,5-bis(4-hydroxyphenyl)-4-methylpyrazolyl]-4-(methylsulfonyl)benzene,
1-[3,5-bis(4-hydroxyphenyl)pyrazolyl]-4 (methylsulfonyl)benzene,
3-{[3,5-bis(4-hydroxyphenyl)-4-methylpyrazolyl]methyl}phenol, 3-{[3,5-bis(4-hydroxyphenyl)-4-ethylpyrazolyl]methyl}phenol,
8-[3,5-bis(4-hydroxyphenyl)-4-ethylpyrazolyl]-N-butyl-N-methyloctanamide,
3-(4-hydroxyphenyl)-2-methylindeno[3,2-c]pyrazol-6-ol, 1-[1-cyclobutyl-4-ethyl-5-(4-methoxyphenyl)pyrazol-3-yl]-4-methoxybenzene, 4-[I,4-diethyl-5-(4-hydroxyphenyl)pyrazol-3-yl]phenol, 4-[4-ethyl-5-(4-hydroxyphenyl)-1-propylpyrazol-3-yl]phenol,
4-[1-butyl-4-ethyl-5-(4-hydroxyphenyl)pyrazol-3yl]phenol,
4-[4-ethyl-5-(4-hydroxyphenyl)-1-(2-methylpropyl)pyrazol-3-yl]phenol, 4-[4-ethyl-5-(4-hydroxyphenyl)-1-prop-2-enylpyrazol-3-yl]phenol,
4-[1-(cyclohexylinethyl)-4-ethyl-5-(4-hydroxyphenyl)pyrazol-3-yl]phenol,
4-[1-cyclobutyl-4-ethyl-5-(4-hydroxyphenyl)pyrazol-3-yl]phenol,
4-[1-cyclohexyl-4-ethyl-5-(4-hydroxyphenyl)pyrazol-3-yl]phenol,
4-[4-ethyl-5-(4-hydroxyphenyl)-1-(2-morpholin-4-ylethyl)pyrazol-3yl]phenol,
2-[3,5-bis(4-hydroxyphenyl)-4-ethylpyrazolyl] acetamide, 1-[3,5-bis(4-hydroxyphenyl)-4-ethylpyrazolyl]acetone,
4-[1-cyclopentyl-4-ethyl-5-(4-hydroxyphenyl)pyrazol-3-yl]phenol, 4-[4-ethyl-5-(4-hydroxyphenyl)-1-(methylethyl)pyrazol-3-yl]phenol,
4-[1-cycloheptyl-4-ethyl-5-(4-hydroxyphenyl)pyrazol-3yl]phenol,
4-[1-(cyclopropylmethyl)-4-ethyl-5-(4-hydroxyphenyl)pyrazol-3-yl]phenol,
3-(4-hydroxyphenyl)-1-methylindeno[2,3-d]pyrazol-6-ol,
4-[4-ethyl-5-(4-hydroxyphenyl)-1-phenylpyrazol-3-yl]phenol, 4-[5-(4-hydroxyphenyl)-1,4-diphenylpyrazol-3-yl]phenol, 2-{4-ethyl-5-(4-hydroxyphenyl)-1-[2-(trifluoromethyl)phenyl]pyrazol-3-yl}phenol, 3-{4-ethyl-5-(4-hydroxyphenyl)-1-[2-(trifluoromethyl)phenyl}pyrazol-3-yl}phenol,
3-[1-(4-hydroxyphenyl)-3-(3-hydroxyphenyl)-4-methylpyrazol-5-yl]phenol,
3-[3-(3-hydroxyphenyl)-4-methyl-1-phenylpyrazol-5-yl]phenol,
3,5-bis(4-hydroxyphenyl)-4-ethyl-1-(methylsulfonyl)pyrazole,
1-{[3,5-bis(4-hydroxyphenyl)-4-ethylpyrazolyl]sulfonyl}-2-chlorobenzene, 3,5-bis(4-hydroxyphenyl)-4-ethyl-1-[(4-methylphenyl)sulfonyl]pyrazole,
3-(4-hydroxyphenyl)-2-methyl-2,4,5-trihydrobenzo[g]1H-indazol-6-ol,
3-(4-hydroxyphenyl)-2-methyl-2,4,5-trihydrobenzo[g]1H-indazol-8-ol, 3-(4-hydroxyphenyl)-2-[2-(trifluoromethyl)phenyl]-2,4,5-trihydrobenzo[g] I H-indazol-8-ol,
4-{3-(4-hydroxyphenyl)-1-[2-(trifluoromethyl)phenyl]pyrazol-5-yl}phenol,
3-(4-hydroxyphenyl)-2,4,5-trihydrobenzo[g]1H-indazol-6-ol, 4-[1-cyclopropyl-4-ethyl-5-(4-hydroxyphenyl)pyrazol-3-yl]phenol,
4-(1-{[3,5-bis(4-hydroxyphenyl)-4-ethylpyrazolyl]methyl}-4-ethyl-3-(4-hydroxyphenyl)pyrazol-5-yl)phenol,
2-cyclobutyl-3-(4-hydroxyphenyl)-2,4,5-trihydrobenzo[g]1H-indazol-6-ol,
4-[1-cyclobutyl-4-ethyl-5-(4-methoxyphenyl)pyrazol-3-yl]phenol, 4-[5-(4-acetyloxyphenyl)-1-cyclobutyl-4-ethylpyrazol-3-yl]phenyl acetate,
4-[5-(4-butanoyloxyphenyl)-1-cyclobutyl-4-ethylpyrazol-3-yl]phenyl butanoate,
2-cyclobutyl-3-(4-hydroxyphenyl)-2,4,5-trihydrobenzo[g]1H-indazol-7-ol, 3-(4-hydroxyphenyl)-2-[2-(trifluoromethyl)phenyl]-2,4,5-trihydrobenzo[g] I H-indazol-7-ol,
4-{4-ethyl-5-phenyl-1-[2-(trifluoromethyl)phenyl]pyrazol-3-yl}phenol,
4-[4-ethyl-3-(4-hydroxyphenyl)-5-methylpyrazolyl]phenol, 3-(4-hydroxyphenyl)-2-methyl-2-hydrobenzo[g]1H-indazol-6-ol,
3-(4-hydroxyphenyl)-2-methyl-2-hydrobenzo[g]1H-indazol-8-ol,
3-(4-hydroxyphenyl)-2-[2-(trifluoromethyl)phenyl]-2-hydrobenzo[g]1H-indazol-7-ol,
2-cyclobutyl-3-(4-hydroxyphenyl)-2-hydrobenzo[g]1H-indazol-7-ol,
4-{4-ethyl-3-(4-methoxyphenyl)-1-[2-(trifluoromethyl)phenyl]pyrazol-5-yl}phenol,
4-{4-ethyl-5-(4-methoxyphenyl)-1-[2- (trifluoromethyl)phenyl]pyrazol-3-yl}phenol, 4-{5-(4-acetyloxyphenyl)-4-ethyl-1-[2-(trifluoromethyl) phenyl]pyrazol-3-yl}phenyl acetate, 4-{4-ethyl-5-(4-hydroxyphenyl)-1-[2(trifluoromethyl)phenyl]pyrazol-3-yl}phenyl acetate, 4-{4-ethyl-3-(4-hydroxyphenyl)-1-[2(trifluoromethyl)phenyl]pyrazol-5-yl}phenyl acetate, 4-{5-[4-(2,2-dimethylpropanoyloxy)phenyl]-4-ethyl-1-[2-(trifluoromethyl)phenyl]pyrazol-3-yl}phenyl 2,2-dimethylpropanoate, 4-{4-ethyl-5-(4-hydroxyphenyl)-I-[2(trifluoromethyl) phenyl]pyrazol-3-yl}phenyl 2,2-dimethylpropanoate, 4-{4-ethyl-3-(4-hydroxyphenyl)-1-[2-(trifluoromethyl)phenyl]pyrazol-5-yl}phenyl 2,2-dimethylpropanoate, 3-(4-hydroxyphenyl)-1-methylbenzo[g]1H-indazol-6-ol, 3-(4-hydroxyphenyl)-1-methylbenzo[g]1H-indazol-8-ol, 1-cyclobutyl-3-(4-hydroxyphenyl)benzo[g]1H-indazol-7-ol, 4-[4-bromo-1-cyclobutyl-5-(4-hydroxyphenyl)pyrazol-3-yl]phenol, 3,5-bis(4-hydroxyphenyl)-1-cyclobutylpyrazol-4-yl 4-hydroxyphenyl ketone, 3,5-bis(4-methoxyphenyl)-1-cyclobutylpyrazol-4-yl 4-(2-piperidylethoxy)phenyl ketone, 3,5-bis(4-hydroxyphenyl)-1-cyclobutylpyrazol-4-yl 4(2-piperidylethoxy)phenyl ketone, 4-{4-ethyl-3-(4-hydroxyphenyl)-1-[2-(tri fluoromethyl) phenyl]pyrazol-5-yl}-2-fluorophenol, 4-{5-(4-butanoyloxyphenyl)-4-ethyl-1-[2-(trifluoromethyl)phenyl]pyrazol-3-yl}phenyl butanoate, 4[3-(4-butanoyloxyphenyl)-4-ethyl-1-methylpyrazol-5-yl]phenyl butanoate, 4-[5-(4-acetyloxyphenyl)-4-ethyl-1-methylpyrazol-3-yl] phenyl acetate, 3,5-bis(4-hydroxyphenyl)-1-[2-(trifluoromethyl)phenyl] pyrazol-4-yl 4-(2-piperidylethoxy)phenyl ketone, chloride, 4-{5-[4-(4-butylcyclohexylcarbonyloxy) phenyl] -1-cyclobutyl-4ethylpyrazol-3-yl}phenyl 4-butylcyclohexanecarboxylate, 4-[1-cyclobutyl-4-ethyl-5-(4-hydroxyphenyl)pyrazol-3-yl]phenyl 4-butylcyclohexanecarboxylate, 4-[1-cyclobutyl-4-ethyl-3-(4-hydroxyphenyl)pyrazol-5-yl]phenyl 4-butylcyclohexanecarboxylate, 4-[-cyclobutyl-4-ethyl-5-(4-hydroxy-2-methylphenyl) pyrazol-3-yl]-3methylphenol, 4-{4-ethyl-5-(4-hydroxy-2-methylphenyl)-1-[2-(tri fluoromethyl)phenyl]pyrazol-3-yl}-3-methylphenol, 4-[1-cyclobutyl-5-(4-hydroxyphenyl)-4-propylpyrazol-3-yl]phenol, 4-[1-cyclobutyl-5-(4-hydroxyphenyl)-4-prop-2-enylpyrazol-3-yl]phenol, 4-[1-cyclobutyl-5-(4-hydroxyphenyl)-4-methylpyrazol-3yl]phenol, 4-[1-cyclobutyl-3-(4-hydroxyphenyl)-4-phenylpyrazol-5-yl]phenol, 4-[I-cyclobutyl-5-(4-hydroxyphenyl)-4-benzylpyrazol-3-yl]phenol, 4-[1-cyclobutyl-5-(4-hydroxyphenyl)-4-iodopyrazol-3-yl]phenol, 2-cyclobutyl-3-(4-hydroxyphenyl)-4,5,6-trihydrobenzo[c]pyrazolo[4,3-a][7]annulen-8-ol, and 1-cyclobutyl-3-(4-hydroxyphenyl)-4,5,6-trihydrobenzo[c]pyrazolo[4,5-a] [7]annulen-8-ol.

5.2.2.4 MCF-7 Cell Proliferation Assays

This assay determines the estrogen agonist/antagonist activity of a test compound by the effect of the test compound on the proliferation of MCF-7 cells as measured by the incorporation of 5-bromo-2'-deoxyuridine ("BrdU") in a chemiluminescent assay format.

MCF-7 cells (ATCC HTB-22) were maintained in log-phase culture using DMEM[HamF12 medium (v/v 1/1) that had been supplemented with 10% fetal bovine serum ("FBS"), at 37° C., and under at 5% $CO_2$ atmosphere. The cells were plated in a 96-well plate at a density of 7,000 cells per well. After 24 hours, the cells were further incubated in phenol red-free DMEM/HamF12 medium supplemented with 10% FBS that had been filtered with dextran-coated charcoal to deplete endogenous estrogen (DCC-FBS). The cells were incubated in this medium for an additional 24 hours, at which time either test compound at varying concentrations to determine the $IC_{50}$ for the compound. Each test compound was incubated with the cells either in the absence of estradiol (detection of estrogen agonist activity) or in the presence of 1 nM estradiol (detection of estrogen antagonist activity).

The cells were cultured in the presence of test compounds for 24 hours at 37° C. and under a 5% $CO_2$ atmosphere. Cell proliferation was detected by measuring the level of BrdU incorporation into DNA. This was accomplished using a commercially available reagent kit (Boeringer Mannheim/Roche). The assay was run according to the manufacturers direction. Ten microliters of BrDU labeling reagent, diluted according to the manufacturers directions, was added directly into each well, and incubation was continued for four hours. The culture media was then aspirated from the wells, and 100 $\mu$l of the fixing/denaturing agent from the kit was added. The cells were fixed for 30 minutes at room temperature. The plates were aspirated again, and 100 $\mu$l of peroxidase-labeled anti-BrdU antibody from the kit was added to each well. After one hour, the plates were washed six times with phosphate buffered saline ("PBS"), and 100 $\mu$l of SUPERSIGNAL (a chemilumiscent peroxidase substrate, Pierce Chemical) was added. The plates were shaken for ten minutes at room temperature, and the resulting chemiluminescent signals were counted using a TRI-LUX scintillation counter. Three compounds of the invention, 4-{4-ethyl-5-(4-hydroxyphenyl)-1-[2 (trifluoromethyl)phenyl]pyrazol-3-yl}phenol and 4-[1-cyclobutyl-4-ethyl-5-(4-hydroxyphenyl)pyrazol-3-yl] phenol, were tested using the above-described protocol and demonstrated activity at less than one hundred nanomolar concentrations.

Thus, the present invention will be seen to provide new compounds that have strong estrogen receptor-modulating action. These compounds can be employed in compositions and methods for treating estrogen receptor-mediated disorders, such as osteoporosis, breast and endometrial cancer, Alzheimer's disease, and atherosclerosis.

The disclosure above is for the purposes of illustration and not limitation. Those having skill in the arts relevant to the present invention (e.g., the organic chemistry, medicinal chemistry, endocrinology, and medical arts) will appreciate from the foregoing the present invention encompasses many additional embodiments of the invention that are not described explicitly, but which nevertheless are provided by the teachings of the present invention. Such additional embodiments include, but are not limited to, estrogen receptor-mediated diseases other than osteoporosis, breast and endometrial cancer, Alzheimer's disease, and atherosclerosis, that are preventable or treatable using the compounds, compositions, and methods of the invention. Still other aspects include compounds that can be designed, synthesized, and tested for therapeutic or prophylactic effect using the teachings of the foregoing disclosure.

6 Bibliography

The following references are incorporated herein by reference in their entirety and for all purposes.

Allen, F. and E. A. Doisy. 1923. "An Ovarian Hormone: Preliminary Report on its Localization, Extraction and Partial Purification, and Action in Test Animals." *J. Am. Med. Assn.* 81(10): 819–821.

Ashby, J., J. Odum, et al. 1997. *Reg. Toxocol. Pharm.* 25: 226–231.

Audia, J. E. and B. L. Neubauer. 1996. "Methods for Inhbiting Bone Loss". U.S. Pat. No.: 5,550,134. Aug. 27, 1996.

Berkow, R., M. H. Beers, et al. 1997. *The Merck Manual of Medical Information*. Whitehouse Station, Merck Research Laboratories.

Black, L. J. et al. 1994. *J. Clin. Invest.* 93: 63–69.

Black, L. J., H. U. Bryant, et al. 1996. "Sulfonate Derivatives of 3-Aroylbenzo[b]thiophenes". U.S. Pat. No. : 5,482,949. Jan. 9, 1996.

Bryant, H. U. and J. A. Dodge. 1995. "Method for the Treatment of Uterine Fibroid Disease". U.S. Pat. No. : 5,472,977. Dec. 5, 1995.

Bryant, H. U. and J. A. Dodge. 1995. "Methods for Lowering Serum Cholesterol and Inhibiting Smooth Muscle Cell Proliferation, Restenosis, Endometriosis, and Uterine Fibroid Disease". U.S. Pat. No. : 5,453,442. Sep. 26, 1995.

Carey, F. A. and R. J. Sundberg. 1983. *Advanced Organic Chemistry Part A: Structure and Mechanisms*. New York, Plenum.

Carey, F. A. and R. J. Sundberg. 1983. *Advanced Organic Chemistry Part B. Reactions and Synthesis*. New York, Plenum.

Craig, B. H., I. Holder, et al. 1979. *Aust. J. Chem.* 32: 1521–1530.

Cullinan, G. J. 1995. "Methods of Inhibiting Atrophy of the Skin and Vagina". U.S. Pat. No.: 5,461,064. Oct. 24, 1995.

Cullinan, G. J. 1997. "Methods of Inhibiting Atrophy of the Skin and Vagina". U.S. Pat. No.: 5,610,167. Mar. 11, 1997.

Dodge, J. A. 1995. "Methods of Inhibiting Turner's Syndrome". U.S. Pat. No. : 5,441,966. Aug. 15, 1995.

Emmens, C. W., R. F. Cox, et al. 1959. *Journal Endocrinology* 18: 372–380.

Fink, B. E., D. S. Mortensen, et al. 1999. "Novel Structural Templates for Estrogen-Receptor Ligands and Prospects for Combinatorial Synthesis of Estrogens." *Chemistry & Biology* 6(April 1999): 205 219.

Gradishar, W. J. and V. C. Jordan. 1997. "Clinical Potential of New Antiestrogens." *Journal of Clinical Oncology* 15(2): 840–852.

Greene, T. W. and P. G. M. Wuts. 1991. *Protective Groups in Organic Synthesis*. New York, John Wiley & Sons, Inc.

Grese, T. A. 1995. "Methods for Lowering Serum Cholesterol". U.S. Pat. No. : 5,446,071. Aug. 29, 1995.

Gustafsson, J.-A. 1998. "Therapeutic Potential of Selective Estrogen Receptor Modulators." *Current Opinion in Chemical Biology* 2: 508–511.

Howell, A., S. Downey, et al. 1996. "New Endocrine Therapies for Breast Cancer." *European Journal of Breast Cancer* 32A(4): 576–588.

Jongh, S. E. d. and E. Laqueur. 1938. "Die Eichung Oestrogener Stoffe". *Handbuch der biologischen Arbeitsmethoden, Abt. V. Teil* 3B. A. E. Berlin, Urban & Schwarzenberg: 1639–1666.

Jordan, V. C. 1998. "Designer Estrogens." *Scientific American*: 60–67.

Ke, H. Z., V. M. Paralkar, et al. 1998. "Effects of CP-336, 156, a New, Nonsteroidal Estrogen Agonist/Antagonist, on Bone, Serum Cholesterol, Uterus, and Body Composition in Rat Models." *Endocrinology* 139(4): 2068–2076.

Knight, D. *W. Comp. Org. Syn* 3: 499–507.

Labrie, F. and Y. Merand. 1995. "Anti-Estrogenic Compounds and Compositions". U.S. Pat. No. : 5,395,842. Mar. 7, 1995.

Labrie, F. and Y. Merand. 1995. "Therapeutic Antiestrogens". U.S. Pat. No. : 5,393,785. Feb. 28, 1995.

MacGregor, J. I. and V. C. Jordan. 1998. "Basic Guide to the Mechanisms of Antiestrogen Action." *Pharmacological Reviews* 50(2): 151–196.

March, J. 1992. *Advanced Organic Chemistry: Reactions, Mechanisms, and Structure*. New York, Wiley Interscience.

Miller, C. P., M. . Collini, et al. 1999. "2-Phenyl-I-[4-(Amino-1-yl-Alk-1-Ynyl)Benzyl]-1H-Indol-5-Ols as Estrogenic Agents". U.S. Pat. No.: 5,880,137. Mar. 9, 1999.

Miyaura, N. et al. 1979. *Tetrahedron Lett.*: 3437.

Miyaura, N. and A. Suzuki. 1979. *Chem. Commun.*: 866.

Miihlbock, O. 1940. *Acta Brev. Neerl. Physiol.* 10: 42–44.

Nuttall, M., E, J. N. Bradbeer, et al. 1998. "Idoxifene: A Novel Selective Estrogen Receptor Modulator Prevents Bone Loss and Lowers Cholesterol Levels in Ovariectomized Rats and Decreases Uterine Weight in Intact Rats." *Endocrinology* 139(1): 5224–5234.

Palkowitz, A. D. 1999. "Method of Treating Estrogen Dependent Cancers". U.S. Pat. No.: 5,856,340. Jan. 5, 1999.

Perkins, M., D. F. Beam, et al. 1988. *Organic Syntheses Collective Volumes*. W. A. Norland. New York, Wiley. VI: 278–281.

Pinhey, J. T., I. Holder, et al. 1979. *Aust. J. Chem* 32: 1561–1566.

Prescott. 1976. New York, Academic Press.

Purdie, D. W. 1999. "Therapeutic Application of Selective Estrogen Receptor Modulators." *Current Opinion in Oncologic, Endocrine & Metabolic Investigational Drugs* 1(1): 44–49.

Reel, J., J. Lamb, et al. 1996. *Fund. Appl. Toxicol.* 34: 288–305.

Sadler, B. R., S. J. Cho, et al. 1998. "Three-Dimensional Structure-Activity Relationship Study of Nonsteroidal Estrogen Receptor Ligands Using the Comparative Molecular Field Analysis/Cross-Validated $r^2$-Guided Region Selection Approach." *J. Med Chem.* 41: 2261–2267.

Sato, M., T. A. Grese, et al. 1999. "Emerging Therapies for the Prevention or Treatment of Postmenopausal Osteoporosis." *Journal of Medicinal Chemistry* 42(1): 1–24.

Sato, M., C. H. Turner, et al. 1998. "LY353381. HCl: A Novel Raloxifene Analog with Improved SERM Potency and Efficacy In Vivo." *The Journal of Pharmacology and Experimental Therapeutics* 287(1): I-7.

Semmelhack, M. F., T. W. Author, et al. *J. Am. Chem. Soc* 103: 6460.

Terenius, L. 1971. "The Allen-Doisy Test for Estrogens Reinvestigated." *Steroids*: 653–661.

Thompson, D. D. 1995. "Estrogen Agonists as Remedies for Prostate and Cardiovascular Diseases". U.S. Pat. No. : 5,441,986. Aug. 15, 1995.

Thompson, D. D. 1996. "Benzo-Thiophene Estrogen Agonists to Treat Prostatic Hyperplasia". U.S. Pat. No. : 5,589,482. Dec. 31, 1996.

Tietze, L.-F. and T. Eicher. 1989. *Reactions and Syntheses in the Organic Chemistry Laboratory*. Eng. University Science Books: 181.

Van de Velde, P., F. Nique, et al. 1994. "RU 58 688, a New Pure Antiestrogen Inducing a Regression of Human Mammary Carcinoma Implanted in Nude Mice." *J. Steroid Biochem. Molec. Biol.* 48(2/3): 187–196.

Wilson, T. M., et al. 1997. *Endocrinology* 138(9): 3901–3911.

Wilson, T. M., J. D. Norris, et al. 1997. "Dissection of the Molecular Mechanism of Action of GW5638, a Novel Estrogen Receptor Ligand, Provides Insights into the Role of Estrogen Receptor In Bone." *Endocrinology* 138(9): 3901–3911.

Wilson, T. M. 1997. "Non-Steroidal Ligands for the Estrogen Receptor". U.S. Pat. No. : 5,681,835. Oct. 28, 1997.

Wilson, T. M. 1999. "Non-Steroidal Ligands for the Estrogen Receptor". U.S. Pat. No. : 5,977,219. Mar. 2, 1999.

What is claimed:

1. A compound having the formula selected from the group consisting of:

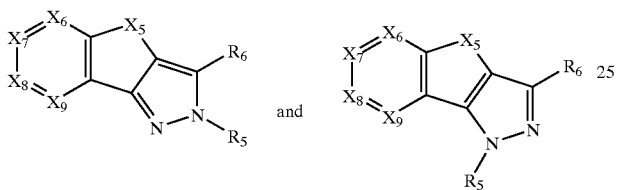

and their pharmaceutically acceptable salts, wherein:

$X_5$ is —$(X_{10})_n$—, wherein n is 2 and $X_{10}$ is methylene optionally substituted from the group consisting of halo, cyano, nitro, thio, amino, carboxyl, formyl, and optionally substituted loweralkyl, loweralkylcarbonyloxy, arylcarbonyloxy, heteroarylcarbonyloxy, cycloalkylcarbonyloxy, cycloheteroalkylcarbonyloxy, aralkycarbonyloxy, heteroaralkylcarbonyloxy, (cycloalkyl)alkylcarbonyloxy, (cycloheteroalkyl) alkylcarbonyloxy, loweralkylcarbonyl, arylcarbonyl, heteroarylcarbonyl, cycloalkylcarbonyl, cycloheteroalkylcarbonyl, aralkycarbonyl, heteroaralkylcarbonyl, (cycloalkyl)alkylcarbonyl, (cycloheteroalkyl)alkylcarbonyl, loweralkylaminocarbonyl, arylaminocarbonyl, aralkylaminocarbonyl, heteroarylaminocarbonyl, heteroaralkylaminocarbonyl, loweralkylcarbonylamino, arylcarbonylamino, heteroarylcarbonylamino, cycloalkylcarbonylamino, cycloheteroalkylcarbonylamino, aralkylcarbonylamino, heteroaralkylcarbonylamino, (cycloalkyl)alkylcarbonylamino, (cycloheteroalkyl) alkylcarbonylamino, loweralkylamino, arylamino, aralkylamino, heteroarylamino, heteroaralkylamino, loweralkylsulfonyl, arylsulfonyl, heteroarylsulfonyl, cycloalkylsulfonyl, cycloheteroalkylsulfonyl, aralkylsulfonyl, heteroaralkylsulfonyl, (cycloalkyl) alkylsulfonyl, (cycloheteroalkyl)alkylsulfonyl, loweralkylsulfinyl, arylsulfinyl, heteroarylsulfinyl, cycloallcylsulfmyl, cycloheteroalkylsulfinyl, aralkylsulfinyl, heteroaralkylsulfinyl, (cycloalkyl) alkylsulfinyl, (cycloheteroalkyl)alkylsulfinyl, loweralkyloxy, aryloxy, heteroaryloxy, cycloalkyloxy, cycloheteroalkyloxy, aralkyloxy, heteroaralkyloxy, (cycloalkyl)alkyloxy, and (cycloheteroalkyl)alkyloxy, loweralkylthio, arylthio, heteroarylthio, cycloalkylthio, cycloheteroalkylthio, aralkylthio, heteroarylthio, (cycloalkyl)alkylthio, (cycloheteroalkyl)alkylthio, loweralkylthiocarbonyl, arylthiocarbonyl, heteroarylthiocarbonyl, cycloalkylthiocarbonyl, cycloheteroalkylthiocarbonyl, aralkythiocarbonyloxlthiocarbonyl, heteroaralkylthiocarbonyl, (cycloalkyl)alkylthiocarbonyl, (cycloheteroalkyl) alkylthiocarbonyl, loweralkyloxycarbonyl, aryloxycarbonyl, heteroaryloxycarbonyl, cycloalkyloxycarbonyl, cycloheteroalkyloxycarbonyl, aralkyoxycarbonyloxloxycarbonyl, heteroaralkyloxycarbonyl, (cycloalkyl) alkyloxycarbonyl, (cycloheteroalkyl) alkyloxycarbonyl, iminoloweralkyl, iminocycloalkyl, iminocycloheteroalkyl, iminoaralkyl, iminoheteroaralkyl, (cycloalkyl)iminoalkyl, and (cycloheteroalkyl)iminoalkyl;

$X_6$–$X_9$ are each optionally substituted methine;

$R_5$ is selected from the group consisting of cycloalkyl, cycloalkylcarbonyl, and (cycloalkyl)alkylcarbonyl; and $R_6$ is selected from the group consisting of optionally substituted loweralkyl, aryl, heteroaryl, cycloalkyl, cycloheteroalkyl, aralkyl, heteroaralkyl, (cycloalkyl) alkyl, and (cycloheteroalkyl)alkyl.

2. The compound of claim 1, wherein $R_6$ is selected from the group consisting of optionally substituted aryl, heteroaryl, aralkyl, and heteroaralkyl.

3. The compound of claim 2, wherein $R_6$ is optionally substituted aryl or aralkyl.

4. The compound of claim 3, wherein $R_6$ includes at least one hydroxyl, thio, or optionally substituted loweralkyloxy, aryloxy, heteroaryloxy, loweralkylthio, arylthio, heteroarylthio, loweralkylcarbonyl, arylcarbonyl, or heteroarylcarbonyl moiety.

5. The compound of claim 4, wherein $R_6$ is selected from the group consisting of phenyl, phenyloxyloweralkyl, and phenylloweralkyl.

6. The compound of claim 5, wherein $R_6$ is further substituted optionally with a moiety selected from the group consisting of halogen, loweralkyl, halolowerlalkyl, loweralkyloxy, halolowerlakyloxy, carboxy, loweralkyloxycarbonyl, aryloxycarbonyl, (cycloloweralkyl) oxycarbonyl, aralkyloxycarbonyl, heteroaryloxycarbonyl, heteroaralkyloxycarbonyl, (heterocycloloweralkyl) oxycarbonyl, loweralkylsulfinyl, loweralkylsulfonyl, lowerallcylthio, arylthio, loweralkylcarbonyloxy, arylcarbonyloxy, aralkylcarbonyloxy, heteroarylcarbonyloxy, heteroaralkylcarbonyloxy, (cycloloweralkyl)carbonyloxy, (heterocycloloweralkyl) carbonyloxy, aminocarbonyl, loweraklylaminocarbonyl, arylaminocarbonyl, aralkylaminocarbonyl, heteroarylaminocarbonyl, and heteroaralkylaminocarbonyl.

7. The compound of claim 6, wherein $R_5$ is selected from the group consisting of cycloalkylcarbonyl and (cycloalkyl) alkylcylcarbonyl.

8. The compound of claim 1, wherein at least one of $X_6$–$X_9$ is methine substituted with a moiety selected from the group consisting of loweralkyloxy, aryloxy, heteroaryloxy, loweralkylthio, arylthio, heteroarylthio, loweralkylcarbonyl, arylcarbonyl, and heteroarylcarbonyl.

9. The compound of claim 8, wherein $X_7$ is methine substituted with hydroxy or loweralkyloxy.

10. A composition for use in treating an estrogen receptor-mediated disorder in a mammal, comprising a therapeutically effective amount of a compound of claim 1 in a pharmaceutically effective carrier.

11. A method for treating an estrogen receptor-mediated disorder in a mammal, comprising administering to such mammal a therapeutically effective amount of a compound of claim 1 in a pharmaceutically effective carrier.

12. The method of claim 11, wherein said disease is chosen from the group consisting of: osteoporosis, estrogendependent cancer, and estrogen-dependent illness.

13. A method for modulating the biological activity of an estrogen receptor, comprising exposing said estrogen receptor to a compound of claim 1 to modulate thereby the binding of said estrogen receptor to an associated estrogen receptor element.

14. The method of claim 13, wherein said estrogen receptor is the $\alpha$ isoform.

15. The method of claim 13, wherein said estrogen receptor is the $\beta$ isoform.

* * * * *